United States Patent
Carroll et al.

(10) Patent No.: US 8,859,596 B2
(45) Date of Patent: *Oct. 14, 2014

(54) COMPOUNDS AS CANNABINOID RECEPTOR LIGANDS

(75) Inventors: William A. Carroll, Evanston, IL (US); Michael J. Dart, Highland Park, IL (US); Jennifer M. Frost, Grayslake, IL (US); Steven P. Latshaw, Round Lake Beach, IL (US); Teodozyj Kolasa, Lake Villa, IL (US); Tongmei Li, Lake Bluff, IL (US); Sridhar Peddi, Grayslake, IL (US); Bo Liu, Waukegan, IL (US); Arturo Perez-Medrano, Grayslake, IL (US); Meena Patel, Green Oaks, IL (US); Xueqing Wang, Evanston, IL (US); Derek W. Nelson, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 552 days.

This patent is subject to a terminal disclaimer.

(21) Appl. No.: 12/560,893

(22) Filed: Sep. 16, 2009

(65) Prior Publication Data

US 2010/0069348 A1 Mar. 18, 2010

Related U.S. Application Data

(60) Provisional application No. 61/224,200, filed on Jul. 9, 2009, provisional application No. 61/097,378, filed on Sep. 16, 2008.

(51) Int. Cl.
*A61K 31/433* (2006.01)
*C07D 285/12* (2006.01)
*C07D 405/12* (2006.01)
*C07D 413/14* (2006.01)
*C07D 413/12* (2006.01)
*C07D 403/12* (2006.01)
*C07D 405/14* (2006.01)
*C07D 409/14* (2006.01)
*C07D 417/12* (2006.01)
*C07D 285/135* (2006.01)
*C07D 231/40* (2006.01)

(52) U.S. Cl.
CPC ............ *C07D 405/12* (2013.01); *C07D 413/14* (2013.01); *C07D 413/12* (2013.01); *C07D 403/12* (2013.01); *C07D 405/14* (2013.01); *C07D 409/14* (2013.01); *C07D 417/12* (2013.01); *C07D 285/135* (2013.01); *C07D 231/40* (2013.01)
USPC ........... 514/363; 548/125; 548/136; 548/139; 514/361

(58) Field of Classification Search
CPC ...................... A61K 31/433; C07D 285/12
USPC .................. 548/125, 136, 139; 514/361, 363
See application file for complete search history.

(56) References Cited

U.S. PATENT DOCUMENTS

| | | | |
|---|---|---|---|
| 3,843,683 A | 10/1974 | Bell | |
| 3,928,327 A | 12/1975 | Takamizawa et al. | |
| 4,885,295 A | 12/1989 | Bell | |
| 4,966,828 A | 10/1990 | Doenges et al. | |
| 4,973,587 A | 11/1990 | Ward et al. | |
| 4,978,664 A | 12/1990 | Bell | |
| 5,013,837 A | 5/1991 | Ward et al. | |
| 5,055,579 A | 10/1991 | Pawlowski et al. | |
| 5,250,498 A | 10/1993 | Andree et al. | |
| 5,468,722 A | 11/1995 | Shibata et al. | |
| 5,530,019 A | 6/1996 | Okada et al. | |
| 5,654,322 A * | 8/1997 | Hirata et al. | .................. 514/363 |
| 6,323,214 B1 | 11/2001 | Baraldi | |
| 6,358,992 B1 | 3/2002 | Pamukcu et al. | |
| 6,369,052 B1 | 4/2002 | Kellar et al. | |
| 6,559,186 B1 | 5/2003 | Campbell | |
| 7,511,013 B2 | 3/2009 | Molino et al. | |
| 7,514,068 B2 | 4/2009 | Tung | |
| 7,521,421 B2 | 4/2009 | Naicker et al. | |

(Continued)

FOREIGN PATENT DOCUMENTS

| | | |
|---|---|---|
| CA | 2587667 A1 | 5/2006 |
| DE | 1522361 A1 | 7/1969 |

(Continued)

OTHER PUBLICATIONS

Abreo et al., "Novel 3-Pyridyl Ethers with Subnanomolar Affinity for Central Neuronal Nicotonic Acetylcholine Receptors," J. Med. Chem, 1996, vol. 39 (4), pp. 817-825.

(Continued)

*Primary Examiner* — Golam M M Shameem
(74) *Attorney, Agent, or Firm* — Lisa V. Mueller; Michael Best & Friedrich LLP

(57) ABSTRACT

Disclosed herein are cannabinoid receptor ligands of formula (I)

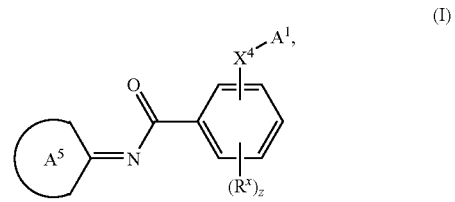

wherein $A^1$, $A^5$, $R^x$, $X^4$, and z are as defined in the specification. Compositions comprising such compounds, and methods for treating conditions and disorders using such compounds and compositions are also disclosed.

9 Claims, No Drawings

(56) References Cited

U.S. PATENT DOCUMENTS

| | | | |
|---|---|---|---|
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,560,456 | B2 | 7/2009 | Araki et al. |
| 7,560,481 | B2 | 7/2009 | Frost et al. |
| 7,674,912 | B2 | 3/2010 | Sams et al. |
| 7,683,084 | B2 | 3/2010 | Faghih et al. |
| 7,750,039 | B2 | 7/2010 | Frost et al. |
| 7,868,038 | B2 | 1/2011 | Nelson et al. |
| 7,872,006 | B2 * | 1/2011 | Moritani et al. ............ 514/236.5 |
| 7,872,033 | B2 * | 1/2011 | Carroll et al. ................. 514/372 |
| 7,875,639 | B2 * | 1/2011 | Florjancic et al. ............ 514/367 |
| 7,875,640 | B2 * | 1/2011 | Kolasa et al. ................. 514/370 |
| 7,985,768 | B2 | 7/2011 | Nelson et al. |
| 8,044,071 | B2 | 10/2011 | Carroll |
| 8,058,293 | B2 | 11/2011 | Kolasa et al. |
| 8,158,663 | B2 | 4/2012 | Carroll et al. |
| 8,173,687 | B2 | 5/2012 | Carroll et al. |
| 8,236,822 | B2 | 8/2012 | Wang et al. |
| 8,288,428 | B2 | 10/2012 | Wang et al. |
| 8,338,467 | B2 | 12/2012 | Kolasa et al. |
| 8,481,574 | B2 | 7/2013 | Meyer et al. |
| 8,492,371 | B2 | 7/2013 | Carroll et al. |
| 8,501,794 | B2 | 8/2013 | Carroll et al. |
| 8,586,596 | B2 | 11/2013 | Dart et al. |
| 2004/0023862 | A1 | 2/2004 | Smart et al. |
| 2004/0029040 | A1 | 2/2004 | Watanabe et al. |
| 2004/0034090 | A1 | 2/2004 | Barth et al. |
| 2004/0077617 | A1 | 4/2004 | Bennani et al. |
| 2004/0166539 | A1 | 8/2004 | Akhavan-Tafti et al. |
| 2004/0259912 | A1 | 12/2004 | Matsumoto et al. |
| 2005/0176713 | A1 | 8/2005 | Freyne et al. |
| 2006/0199817 | A1 | 9/2006 | Tasker et al. |
| 2007/0061360 | A1 | 3/2007 | Holcombe et al. |
| 2007/0155738 | A1 | 7/2007 | Steeneck et al. |
| 2008/0058335 | A1 | 3/2008 | Florjancic et al. |
| 2008/0058355 | A1 | 3/2008 | Westheim |
| 2008/0139635 | A1 | 6/2008 | Martin et al. |
| 2008/0242654 | A1 | 10/2008 | Kolasa et al. |
| 2008/0287510 | A1 | 11/2008 | Carroll et al. |
| 2008/0312435 | A1 | 12/2008 | Saito et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105305 | A1 | 4/2009 | Butlin et al. |
| 2009/0105306 | A1 | 4/2009 | Carroll et al. |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2010/0041720 | A1 | 2/2010 | Carroll et al. |
| 2010/0063022 | A1 | 3/2010 | Carroll et al. |
| 2010/0069349 | A1 | 3/2010 | Carroll et al. |
| 2010/0093814 | A1 | 4/2010 | Florjancic et al. |
| 2010/0216760 | A1 | 8/2010 | Frost |
| 2011/0065685 | A1 | 3/2011 | Frost et al. |
| 2011/0082116 | A1 | 4/2011 | Carroll et al. |
| 2011/0086832 | A1 | 4/2011 | Kolasa et al. |
| 2011/0086838 | A1 | 4/2011 | Nelson et al. |

FOREIGN PATENT DOCUMENTS

| | | |
|---|---|---|
| DE | 1772867 A1 | 6/1971 |
| DE | 2458933 A1 | 6/1975 |
| DE | 3533331 A1 | 3/1987 |
| EP | 412404 A2 | 2/1991 |
| EP | 568096 A1 | 11/1993 |
| EP | 0619316 A1 | 10/1994 |
| EP | 0639569 A1 | 2/1995 |
| EP | 1060734 A2 | 12/2000 |
| EP | 1219612 A1 | 7/2002 |
| EP | 1300401 A1 | 4/2003 |
| EP | 1640369 A1 | 3/2006 |
| EP | 1820504 A1 | 8/2007 |
| FR | 2796643 A1 | 1/2001 |
| JP | S57171986 A | 10/1982 |
| JP | 6345736 A | 12/1994 |
| WO | WO-9507271 A1 | 3/1995 |
| WO | WO-9531448 A1 | 11/1995 |
| WO | WO-9601591 A1 | 1/1996 |
| WO | WO-9700860 A1 | 1/1997 |
| WO | WO-9710223 A1 | 3/1997 |
| WO | WO-0063207 A1 | 10/2000 |
| WO | WO-0116138 A1 | 3/2001 |
| WO | WO-0128557 A1 | 4/2001 |
| WO | WO-0155139 A1 | 8/2001 |
| WO | WO-0155140 A1 | 8/2001 |
| WO | WO-0183422 A1 | 11/2001 |
| WO | WO-0242269 A1 | 5/2002 |
| WO | WO-02060447 A1 | 8/2002 |
| WO | WO-02102232 A2 | 12/2002 |
| WO | WO-03049741 A1 | 6/2003 |
| WO | WO-03097605 A1 | 11/2003 |
| WO | WO-2004050086 A1 | 6/2004 |
| WO | WO-2004110453 A1 | 12/2004 |
| WO | WO-2005023818 A2 | 3/2005 |
| WO | WO2005058887 A1 | 6/2005 |
| WO | WO-2005075464 A1 | 8/2005 |
| WO | WO-2005099353 A2 | 10/2005 |
| WO | WO-2005099353 A3 | 10/2005 |
| WO | WO-2005115972 A1 | 12/2005 |
| WO | WO-2005115986 A1 | 12/2005 |
| WO | WO-2006008754 A1 | 1/2006 |
| WO | WO2006051704 A1 | 5/2006 |
| WO | WO-2006051704 A1 | 5/2006 |
| WO | WO-2006070106 A1 | 7/2006 |
| WO | WO2006100208 A1 | 9/2006 |
| WO | WO-2007061360 A2 | 5/2007 |
| WO | WO2007140385 A2 | 12/2007 |
| WO | WO2007140439 A2 | 12/2007 |
| WO | WO2007140439 A3 | 1/2008 |
| WO | WO2007140385 A3 | 2/2008 |
| WO | WO-2008063781 A2 | 5/2008 |
| WO | WO-2008079687 A1 | 7/2008 |
| WO | WO-2008121558 A1 | 10/2008 |
| WO | WO-2008130953 A2 | 10/2008 |
| WO | WO2008144360 A1 | 11/2008 |
| WO | WO-2009009550 A1 | 1/2009 |
| WO | WO2009048936 A1 | 4/2009 |
| WO | WO2009067613 A1 | 5/2009 |
| WO | WO2009114566 A1 | 9/2009 |
| WO | WO-2010019547 A1 | 2/2010 |
| WO | WO-2010033543 A2 | 3/2010 |
| WO | WO-2010054024 A2 | 5/2010 |
| WO | WO-2010071783 A1 | 6/2010 |
| WO | WO-2010111573 A1 | 9/2010 |
| WO | WO-2010111574 A1 | 9/2010 |

OTHER PUBLICATIONS

Arevalo-Martin A. et al., "Therapeutic Action of Cannabinoids in a Murine Model of Multiple Sclerosis," Journal of Neuroscience, 2003, vol. 23 (7), pp. 2511-2516.

Benito C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, vol. 23 (35), pp. 11136-11141.

Bennett et al. "A peripheral mononeuropathy in rat that produces disorders of pain sensation like those seen in man", Pain, 1988, 33, 87-107.

Berge S. M., et al., "Pharmaceutical Salts," J Pharmaceutical Sciences, 1977, 66 (1), 1-19.

Blagojevic N. et al., "Topics in Dosimetry & Treatment Planning for Neutron Capture Therapy," 1994, vol. 23, Zamenhof R.G., Solares G.R. and Harling O.K., eds., Advanced Medical Publishing, Madison Wis, pp. 125-134.

Blake et al., "Studies with deuterated drugs," J. Pharm. Sci, 1975, vol. 64 (3), pp. 367-391.

(56) References Cited

OTHER PUBLICATIONS

Bouchard J. F et al., "Contribution of endocannabinoids in the endothelial protection afforded by ischemic preconditioning in the isolated rat heart," Life Sciences, 2003, vol. 72, pp. 1859-1870.
Boyle W. J. et al., "Osteoclast differentiation and activation," Nature, 2003, vol. 423, pp. 337-342.
Brennan T. J. et al., "Characterization of a rat model of incisional pain," Pain, 1996, vol. 64, pp. 493-501.
Brickner S. J. et al., "Synthesis and antibacterial activity of U-100592 and U-100766, two oxazolidinone antibacterial agents for the potential treatment of multidrug-resistant gram-positive bacterial infections," J Med Chem, 1976, vol. 39 (3), pp. 673.
Buckley N. E. et al., "Immunomodulation by cannabinoids is absent in mice deficient for the cannabinoid CB receptor," European Journal of Pharmacology, 2000, vol. 396, pp. 141-149.
Carlisle S. J. et al., "Differential expression of the CB2 cannabinoid receptor by rodent macrophages and macrophage-like cells in relation to cell activation," International Immunopharmacology, 2002, vol. 2, pp. 69.
Carrier E. J. et al., "Endocannabinoids in Neuroimmunology and Stress," Current Drug Targets CNS & Neurological Disorders, 2005, vol. 4, pp. 657-665.
Casanova M. L. et al., "Inhibition of skin tumor growth and angiogenesis in vivo by activation of cannabinoid receptors," Journal of Clinical Investigation, 2003, vol. 111, pp. 43-50.
Chaplan S. R. et al., "Quantitative assessment of tactile allodynia in the rat paw," Journal of Neuroscience Methods, 1994, vol. 53, pp. 55-63.
Cichewicz D. L. et al., "Synergistic interactions between cannabinoid and opioid analgesics," Life Sciences, 2004, vol. 74, pp. 1317-1324.
Clayton N., et al. , "CB1 and CB2 cannabinoid receptors are implicated in inflammatory pain," Pain, 2002, vol. 96, pp. 253-260.
Czajka D. M., "Effect of deuterium oxide on the reproductive potential of mice," Ann NY Acad Sci, 1960, vol. 84, pp. 770-779.
Czajka D. M., et al., "Physiological effects of deuterium on dogs", Am. J. Physiol, 1961, vol. 201, pp. 357-362.
Dixon W. J. et al., "Efficient analysis of experimental observations," Annual Review of Pharmacology and Toxicology, 1980, vol. 20, pp. 441-462.
Filippo C. D. et al., "Cannabinoid CB2 receptor activation reduces mouse myocardial ischemia-reperfusion injury: involvement of cytokine/chemokines and PMN," Journal of Leukocyte Biology, 2004, vol. 75, pp. 453-459.
Foster A.B., "Deuterium Isotope Effects in the Metabolism of Drugs and Xenobiotics: Implications for Drug Design" in: Advances in Drug Research, Harper, ed., 1985, vol. 14, Academic Press, pp. 2-36.
Galiégue et al., "Expression of central and peripheral cannabinoid receptors in human immune tissues and leukocyte subpopulations," European Journal of Biochemistry, 1995, vol. 232, pp. 54-61.
Greene T. W. et al., "Protective Groups in Organic Synthesis," 1999, Ed. 3, John Wiley & Sons, pp. 494-653.
Grotenhermen F. et al., "IACM 2nd Conference on Cannabinoids in Medicine," Expert Opinion in Pharmacotherapy, 2003, vol. 4 (12), pp. 2367-2371.
Hanus L. et al., "HU-308: A specific agonist for CB 2, a peripheral cannabinoid receptor," Proceedings of the National Academy of Science, 1999, vol. 96, pp. 14228-14233.
Hohmann A. G. et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.
Ibrahim M. M. et al., "Activation of CB2 cannabinoid receptors by AM1241 inhibits experimental neuropathic pain: Pain inhibition by receptors not present in the CNS," Proceedings of the National Academy of Science, 2003, vol. 100 (18), pp. 10529-10533.
Ibrahim M. M. et al., "CB2 cannabinoid receptor activation produces antinociception by stimulating peripheral release of endogenous opioids," Proceedings of the National Academy of Science, 2005, vol. 102 (8), pp. 3093-3098.

Ihenetu K. et al., "Inhibition of interleukin-8 release in the human colonic epithelial cell line HT-29 by cannabinoids," European Journal of Pharmacology, 2003, vol. 458, pp. 207-215.
Iupac Commission on Nomenclature of Organic Chemistry: Rules for the Nomenclature of Organic Chemistry Section E: Stereochemistry, Pure Appl Chem, 1976, 45, 13-30.
Joshi S. K., et al., "Comparison of Antinociceptive Actoins of Standard Analgesics in Attenuating Capsaicin and Nerve-Injury-Induced Mechanical Hypersensitivty," Neurosci, 2006, vol. 143, pp. 587-596.
Julien B et al., "Antifibrogenic Role of the Cannabinoid Receptor CB2 in the Liver," Gastroenterology, 2005, vol. 128, pp. 742-755.
Karsak M. et al, "Cannabinoid receptor type 2 gene is associated with human osteoporosis," Human Molecular Genetics, 2005, vol. 14 (22), pp. 3389-3396.
Kato et al., "Synthesis of Deuterated Mosapride Citrate," J. Labelled Comp. Radiopharmaceut, 1995, vol. 36 (10), pp. 927-932.
Kim S. H. et al., "An experimental model for peripheral neuropathy produced by segmental spinal nerve ligation in the rat," Pain, 1992, vol. 50 (3), pp. 355-363.
Kushner et al., "Pharmacological uses and perspectives of heavy water and deuterated compounds," Can J Physiol Pharmacol, 1999, vol. 77, pp. 79-88.
Lepicier P. et al., "Endocannabinoids protect the rat isolated heart against ischaemia," British Journal of Pharmacology, 2003, vol. 139, pp. 805-815.
Lizondo J. et al., "Linezolid: Oxazolidinone antibacterial", Drugs Fut, 1996, vol. 21 (11), pp. 116.
Lotersztajn S. et al., "Hepatic Fibrosis: Molecular Mechanisms and Drug Targets," Annual Review of Pharmacology and Toxicology, 2005, vol. 45, pp. 605-628.
Malan T. P. et al., "CB2 cannabinoid receptor-mediated peripheral antinociception," Pain, 2001, vol. 93, pp. 239-245.
Mallesham B. et al., "Highly efficient Cul-catalyzed coupling of aryl bromides with oxazolidinones using Buchwald's protocol: a short route to linezolid and toloxatone," Org Lett, 2003, vol. 5 (7), pp. 963-965.
Maresz K. et al., "Modulation of the cannabinoid CB2 receptor in microglial cells in response to inflammatory stimuli," Journal of Neurochemistry, 2005, vol. 95, pp. 437-445.
Mathison R. et al., "Effects of cannabinoid receptor-2 activation on accelerated gastrointestinal transit in lipopolysaccharide-treated rats," British Journal of Pharmacology, 2004, vol. 142, pp. 1247-1254.
McKallip R. J., et al., "Targeting CB2 cannabinoid receptors as a novel therapy to treat malignant lymphoblastic disease," Blood, 2002, vol. 15 (2), pp. 627-634.
Nackley A. G. et al., "Selective activation of cannabinoid CB2 receptors suppresses spinal fos protein expression and pain behavior in a rat model of inflammation," Neuroscience, 2003, vol. 119, pp. 747-757.
Ni X. et al., "Win 55212-2, a cannabinoid receptor agonist, attenuates leukocyte/endothelial interactions in an experimental autoimmune encephalomyelitis model," Multiple Sclerosis, 2004, vol. 10, pp. 158-164.
Patel J. J. et al., "Inhibition of guinea-pig and human sensory nerve activity and the cough reflex in guinea-pigs by cannabinoid (CB2) receptor activation," British Journal of Pharmacology, 2003, vol. 140, pp. 261-268.
Pertwee R. G., "Cannabinoids and multiple sclerosis," Pharmacology & Therapeutics, 2002, vol. 95, pp. 165-174.
Prescott et al., "Lipid Vesicles as Carriers for Introducing Biologically Active Materials into Cells," Methods in Cell Biology, 1976, vol. 14, Academic Press, pp. 33-71.
Quartilho A. et al., "Inhibition of Inflammatory Hyperalgesia by Activation of Peripheral CB2 Cannabinoid Receptors," Anesthesiology, 2003, vol. 99, pp. 955-960.
Ralston S. H., "Regulation of bone mass, bone loss and osteoclast activity by cannabinoid receptors," Nature Medicine, 2005, vol. 11, pp. 774-779.
Ramirez B. G. et al., "Prevention of Alzheimer's Disease Pathology by Cannabinoids: Neuroprotection Mediated by Blockade of Microglial Activation," Journal of Neuroscience, 2005, vol. 25 (8), pp. 1904-1913.

(56) References Cited

OTHER PUBLICATIONS

Ross WJ et al., Antianaphylactic agents. 1. 2-(Acylamino)oxazoles, J Med Chem., 1979, 22(4), 412-7.
Sanchez C. et al., "Inhibition of Glioma Growth in Vivo by Selective Activation of the CB2 Cannabinoid Receptor1," Cancer Research, 2001, vol. 61, pp. 5784-5789.
Steffens S. et al., "Low dose oral cannabinoid therapy reduces progression of atherosclerosis in mice," Nature, 2005, vol. 434, pp. 782-786.
Thomson J. F., "Physiological effects of D20 in mammals," Ann. New York Acad. Sci, 1960, vol. 84, pp. 736-744.
Valenzano K. J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, vol. 48, pp. 658-672.
Warhurst A. C. et al., "Interferon gamma induces differential upregulation of alpha and beta chemokine secretion in colonic epithelial cell lines," Gut, 1998, vol. 42, pp. 208-213.
Widdowson DA., Palladium catalysed Suzuki reactions of fluoroarenes, Chem Commun (Camb), 2003, vol. 5, 578-579.
Wright K. et al., "Differential Expression of Cannabinoid Receptors in the Human Colon: Cannabinoids Promote Epithelial Wound Healing," Gastroenterology, 2005, vol. 129, pp. 437-453.
Yoshihara S. et al., "Cannabinoid Receptor Agonists Inhibit Sensory Nerve Activation in Guinea Pig Airways," American Journal of Respiratory and Critical Care Medicine, 2004, vol. 170, pp. 941-946.
Yoshihara S. et al., "Endogenous Cannabinoid Receptor Agonists Inhibit Neurogenic Inflammations in Guinea Pig Airways," Allergy and Immunology, 2005, vol. 138, pp. 80-87.
Yoshihara S. et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.
Ambartsumova, et al., "Effect of Various Factors on the Reaction of 2-Aminobenzothiazoles with Propylene Oxide," Chemistry of Heterocyclic Compounds, 2002, vol. 38 (8), pp. 994-999.
Araki, et al., (2003): STN International HCAPLUS database, (Columbus, OH). Accession No. 2003-931334.
Baker, et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Benito, et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.
Beylot, et al., "In Vivo Studies of Intrahepatic Metabolic Pathways," Diabetes Metabolism, 1997, vol. 23 (3), pp. 251-257.
Bozidar, et al., "Transformations of 1,2,4-Thiadiazolo/2,3-X/ Azines," Heterocycles, 1987, vol. 26 (3), pp. 689-697.
Bozidar, et al., "Transformations of 1-(2-Chloropyridyl-3)-4-ethoxycarbonyland 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Dart, et al (2007): STN International HCAPLUS database, Columbus (OH), Accession No. 2007:1396538.
Final Office Action mailed Mar. 10, 2010 for U.S. Appl. No. 11/755,434, filed May 30, 2007.
Final Office Action mailed Mar. 24, 2011 for U.S. Appl. No. 11/755,434, filed May 30, 2007.
Final Office Action mailed Feb. 15, 2011for U.S. Appl. No. 12/10,969, filed May 15, 2008.
Florjancic, et al., (2009): Caplus Entry for WO2009067613, Accession No. 2009:649814.
Florjancic, et al., (2010): STN International HCAPLUS database, Columbus (OH), Accession No. 2010:478868.
Giron, D., "Applications of Thermal Analysis and Coupled Techniques in Pharmaceutical Industry," Journal of Thermal Analysis and Calorimetry, 2002, vol. 68, pp. 335-357.
Giron, D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Golech, S., et al., "Human Brain Endothelium: Coexpression and Function of Vannilloid and Endocannabinoid Receptors," Molecular Brain Research, 2004, vol. 132 (1), pp. 87-92.
Golub, et al., "Molecular Classification of Cancer: Class Discovery and Class Prediction by Gene Expression Monitoring," Science, 1999, vol. 286 (5439), pp. 531-537.
Gouldson, et al., "Mutational Analysis and Molecular Modeling of the Antagonist SR144528 Binding Site on the Human Cannabinoid CB2 Receptor; Figures 4 and 5," European Journal of Pharmacology, 2000, vol. 401 (1), pp. 17-25.
Hargreaves, et al., "A New and Sensitive Method for Measuring Thermal Nociception in Cutaneous Hyperalgesia," Pain, 1988.32 (1), pp. 77-88.
International Search Report for Application No. PCT/US07/069921, mailed on Nov. 27, 2007, 4 pages.
International Search Report for Application No. PCT/US08/063648, mailed on Aug. 13, 2008, 3 pages.
International Search Report for Application No. PCT/US2009/056179, mailed on Jun. 9, 2010, 4 pages.
International Search Report for Application No. PCT/US2009/057088, mailed on Oct. 5, 2010, 1 page.
International Search Report for Application No. PCT/US2009/068173, mailed on Feb. 5, 2010, 3 pages.
Kreutzberg, et al., "Microglia: A Sensor for Pathological Events in the CNS," Trends in Neuroscience, 1996, vol. 19, pp. 312-318.
Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Maligres, et al., "Stereocontrolled Preparation of a Nonpeptidal (-)-Spirobicyclic NK-1 Receptor Antagonist," Journal of Organic Chemistry, 2002, vol. 67 (4), pp. 1093-1101.
Manaka, et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.
Molina-Holgado, et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.
Non-Final Office Action mailed Jan. 27, 2011 for U.S. Appl. No. 12/274,105, filed Nov. 19, 2008.
Non-Final Office Action mailed Sep. 7, 2010 for U.S. Appl. No. 12/120,969, filed May 15, 2008.
Non-Final Office Action mailed Jan. 12, 2010 for U.S. Appl. No. 12/120,969, filed May 15, 2008.
Non-Final Office Action mailed Jun. 2, 2009 for U.S. Appl. No. 11/755,434, filed May 30, 2007.
Non-Final Office Action mailed Jun. 29, 2010 for U.S. Appl. No. 11/755,434, filed May 30, 2007.
Non-Final Office Action mailed Nov. 30, 2010 for U.S. Appl. No. 11/755,434, filed May 30, 2007.
Non-Final Office Action mailed Jun. 1, 2011for U.S. Appl. No. 12/554,445, filed Sep. 4, 2009.
Non-Final Office Action mailed Aug. 23, 2011for U.S. Appl. No. 12/639,173, filed Sep. 16, 2009.
Non-Final Office Action mailed Jun. 1, 2011for U.S. Appl. No. 12/560,897, filed Sep. 16, 2009.
Nunez, et al., "Cannabinoid CB2 Receptors Are Expressed by Perivascular Microglial Cells in the Human Brain: An Immunohistochemical Study," Synapse, 2004, vol. 53, pp. 208-213.
Ohta, et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.
Opposition filed by "Asociacion de Industrias Farmaceuticas Dominicanas Inc" for the Dominican Patent application Nr P2008-0060, 8 pages.
Radulescu, et al., "Actes Du Colloque Franco-Roumain De Chimie Appliquee, 3Rd, Bacau, Romania," 2004, pp. 117-120.

(56) References Cited

OTHER PUBLICATIONS

Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.
Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.
Ralston, S., "Genetic Determinants of Susceptibility to Osteoporosis," Current Opinion in Pharmacology, 2003, vol. 3, pp. 286-290.
Rautio, et al, "Prodrugs: Design and Clinical Applications," Nature Reviews Drug Discovery, 2008, vol. 7 (3), pp. 255-270.
Rodriquez-Spong, et al., "General Principles of Pharmaceutical Solid Polymorphism: A Supramolecular Perspective," Advanced Drug Delivery Reviews, 2004, vol. 56 (3), pp. 241-274.
Shilpi, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.
Smith, D., "Do Prodrugs Deliver?" Current Opinion in Drug Discovery and Development, 2007, vol. 10 (5), 550-559.
Souillac, et al, "Characterization of Delivery Systems, Differential Scanning Calorimetry," Encyclopedia of Controlled Drug Delivery, 1999, pp. 217-218.
Testa, B., "Prodrugs: Bridging Pharmacodynamic/Pharmacokinetic Gaps," Current Opinion in Chemical Biology, 2009, vol. 13 (3), pp. 338-344.
Walter, et al., "Cannabinoids and Neuroinflammation," British Journal of Pharmacology, 2004, vol. 141 (5), pp. 775-785.
Wang, et al., Drug Delivery: Principles and Applications, John Wiley & Sons, Inc., 2005, pp. 136-137.
Watkins, et al., "Glial Activation: A Driving Force for Pathological Pain," Trends in Neuroscience, 2001, vol. 24 (8), pp. 450-455.
Werbel, et al., "1-Alkyl-3-(3-alkyl-5-nitro-4-thiazolin-2-ylidene)ureasa and Related Compounds as Schistosomicides," Journal of Medicinal Chemistry, 1972, vol. 15 (9), pp. 955-963.
Weyer, et al., "Blutzuckersenkende Chinolin-8-Carboxamidoalkyl-Benzol Sulfonamid Derivate," Arzneimittel-Forschung, 1974, vol. 24 (3), pp. 269-275.
Williams, et al., "Renin Inhibitors Containing Conformationally Restricted P1-P1 Dipeptide Mimetics," Journal of Medicinal Chemistry, 1991, vol. 34 (3), pp. 887-900.
Zimmer, et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Sep. 14, 2011 for U.S. Appl. No. 12/274,105, filed Sep. 16, 2009.
Alfaro I., et al., "Dihydroaromatic Compounds in the Diels-Alder Reaction—III: In Situ Generation and Diels-Alder Reaction of Cyclohexa-1,3-Dienes," Tetrahedron, 1970, vol. 26, pp. 201-218.
Andreani, et al., "Ring-opened, etc," Collection of Czechoslovak Chemical Communications, 1999, vol. 64, pp. 299-312.
Ansell M.F., et al., "The Synthesis of (+/−)-10a-Homo-11a-CarbathromboxaneA1, a Stable Thromboxane a Analogue," Journal of Chemical Society Perkin Trans, 1984, pp. 1061-1068.
Atwood B.K., et al., "CB : Therapeutic Target-in-Waiting," Progress in Neuro-Psychopharmacology & Biological Psychiatry, 2012, vol. 38 (1), pp. 16-20.
Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.
Bartlett P.A., et al., "Chorismate Mutase Inhibitors: Synthesis and Evaluation of Some Potential Transition-State Analogues," Journal of Organic Chemistry, 1988, vol. 53, pp. 3195-3210.

Bermudez-Silva, et al., "Role of Cannabinoid CB2 Receptors in Glucose Homeostasis in Rats," European Journal of Pharmacology, 2007, vol. 565 (1-3), pp. 207-211.
Bruson H.A., et al., "Action of Sulfuric Acid upon Unsaturated Isothiocyanates: Mercaptothiazolines ," Journal of American Chemical Society, 2011, vol. 59 (10), pp. 2011-2013.
Cai, et al., Ex Parte Appeal No. 2011005302, decided Jul. 12, 2011.
Campbell V.A., et al., "Alzheimer's Disease; Taking the Edge off with Cannabinoids?," British Journal of Pharmacology, 2007, vol. 152 (5), pp. 655-662.
Caplus Entry for International Application Publication No. WO2008130953, Accessed Aug. 14, 2012, with Structures Relevant to Claim 25 as Filed Aug. 11, 2011.
Caplus Entry for International Application Publication No. WO2008130953, Accessed Aug. 14, 2012, with Structures Relevant to Claim 35 as Filed Aug. 11, 2011.
CAS Registry No. 1061668-81-2, which entered STN on Oct. 15, 2008.
Castejon P., et al., "A Convenient, Stereodivergent Approach to the Enantioselective Synthesis of N-Boc-Aminoalkyl Epoxides," Tetrahedron Letters, 1995, vol. 36 (17), pp. 3019-3022.
Chauhan M.S., "The Reaction of Some Heterocyclic Thiones with Ethyl Azidoformate," Canadian Journal of Chemistry, 1976, vol. 54 (24), pp. 3879-3883.
Chemical Abstracts Accession No. 1030770638, Jun. 26, 2008.
Cotarca L., et al., "Bis (trichloromethyl) Carbonate in Organic Synthesis," 1996, vol. 6, pp. 553-576.
Cross., et al., "Rules for the Nomenclature of Organic Chemistry, Section E: Stereochemistry," International Union of Pure and Applied Chemistry, 1976, vol. 45, pp. 11-30.
Database Registry [Online] Chemical Abstracts Service, Columbus, Ohio, US, Mar. 2, 2008, XP002687516, Database Accession No. 1006022-43-0.
Database Registry [Online] Chemical Abstracts Service, Columbus, Ohio, US, Mar. 2, 2008, XP002687517, Database Accession No. 1005993-02-1.
Database Registry [Online] Chemical Abstracts Service, Columbus, Ohio, US, Mar. 6, 2008, XP002687515, Database Accession No. 1006758-59-3.
Database Registry [Online] Chemical Abstracts Service, Columbus, Ohio, US, Mar. 7, 2008, XP002687514, Database Accession No. 1007004-94-5.
Database Registry [Online] Chemical Abstracts Service, Columbus, Ohio, US, Mar. 10, 2008, XP002687513, Database Accession No. 1007244-89-4.
Database Registry [Online] Chemical Abstracts Service, Columbus, Ohio, US, Feb. 29, 2008, XP002687518, Database Accession No. 1005931-81-6.
Dauben W.G., et al., "Organic Reactions at High Pressure Cycloadditions with Furans," Journal of the American Chemical Society, 1976, vol. 98 (7), pp. 1992-1993.
Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
Ebata et al., "Synthesis of Both Enantiomers of 4-Hexanolide and 4-Dodecanolide," Agriculture Biochemical, 1991, vol. 55 (6), pp. 1685-1686.
Eckert H., et al., "Triphosgene, a Crystalline Phosgene Substitute," Angewandte Chemie International Edition in English, 1987, vol. 26 (9), pp. 894-895.
European Search Report for Application No. EP12187944, mailed on Nov. 20, 2012, 7 pages.

(56) References Cited

OTHER PUBLICATIONS

Ex Parte Quayle Action mailed Oct. 12, 2012 for U.S. Appl. No. 13/160,952, filed Jun. 15, 2011.
Fattori D., et al. "The Demjanov and Tiffeneau-Demjanov One-Carbon Ring Enlargements of 2-Aminomethyl-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.
Final Office Action mailed Oct. 3, 2013 for U.S. Appl. No. 12/246,808, filed Oct. 7, 2008.
Final Office Action mailed Jul. 14, 2011 for U.S. Appl. No. 12/246,808, filed Oct. 7, 2008.
Final Office Action mailed Apr. 19, 2011 for U.S. Appl. No. 12/539,120, filed Aug. 11, 2009.
Final Office Action mailed Nov. 21, 2012 for U.S. Appl. No. 12/120,969, filed May 15, 2008.
Final Office Action mailed Apr. 23, 2013 for U.S. Appl. No. 12/967,275, filed Dec. 14, 2010.
Final Office Action mailed Dec. 28, 2011 for U.S. Appl. No. 12/639,173, filed Dec. 16, 2009.
Goerdeler J., et al., "Uber Isothiazole, VIII. Synthese von Sulfonylamino-isothiazolen and Sulfonyliminoisothiazolinen aus Sulfonylsenfolen," Chemische Berichte, 1969, vol. 102 (7), pp. 2273-2284.
Goodman A.J., et al., "CB2 Selective Sulfamoyl Benzamides; Optimization of the Amide Functionality," Bioorganic & Medicinal Chemistry Letters, 2009, vol. 19 (2), pp. 309-313.
Greene T.W., et al., in: Protective Groups in Organic Synthesis, 3rd Edition, John Wiley and Sons, Inc., 1999, Preface, Table of Contents, Abbreviations.
Hamuro Y., et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.
Horig H., et al., "From Bench to Clinic and Back: Perspective on the 1st IQPC Translational Research conference," Journal of Translational Medicine, 2004, vol. 2 (44).
Hutchins S.M., et al., "A General Method for the Solid Phase Synthesis of Ureas," Tetrahedron Letters, 1994, vol. 35 (24), pp. 4055-4058.
Hutchins S.M., et al., "A Strategy for Urea Linked Diamine Libraries," Tetrahedron Letters, 1995, vol. 36 (15), pp. 2583-2586.
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US08/079182, mailed on Apr. 13, 2010, 5 pages.
International Preliminary Report on Patentability and Written Opinion for Application No. PCT/US08/080253, mailed on Apr. 20, 2010, 6 pages.
International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/0087175, mailed on Jun. 23, 2009, 8 pages.
International Preliminary Report on Patentability and Written Opinion for Application No. PCT/US2007/069921, mailed on Dec. 3, 2008, 10 pages.
International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.
International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability and Written Opinion for Application No. PCT/US2010/028790, mailed on Sep. 27, 2008, 5 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report for Application No. PCT/US07/070029, mailed on Nov. 30, 2007, 3 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/060400, mailed on Oct. 17, 2008, 3 pages.
International Search Report for Application No. PCT/US08/069453, mailed on Sep. 25, 2008, 2 pages.
International Search Report for Application No. PCT/US08/079182, mailed on Dec. 15, 2008, 2 pages.
International Search Report for Application No. PCT/US08/080253, mailed on Mar. 3, 2009, 3 pages.
International Search Report for Application No. PCT/US2005/0046480, mailed on Apr. 18, 2006, 5 pages.
International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/063318, mailed on May 6, 2010, 3 pages.
International Search Report for Application No. PCT/US2010/028790, mailed Jul. 19, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.
Izdebski J., et al., "A New Convenient Method for the Synthesis of Symmetrical and Unsymmetrical N,N'-Disubstituted Ureas," Synthesis, 1989, pp. 423-425.

(56) References Cited

OTHER PUBLICATIONS

Jasys V.J., et al., "Preparation of Fluoroadamantane Acids and Amines: Impact of Bridgehead Fluorine Substitution on the Solution- and Solid-State Properties of Functionalized Adamantanes," Journal of the American Chemical Society, 2000, vol. 122, pp. 466-473.

Jhaveri M.D., et al., "Cannabinoid CB2 Receptor-Mediated Anti- Nociception in Models of Acute and Chronic Pain," Molecular Neurobiology, 2007, vol. 36 (1), pp. 26-35.

Katritzky A.R., et al., "A General Synthesis of Unsymmetrical Tetrasubstituted Ureas," Journal of Organic Chemistry, 1997, vol. 62 (11), pp. 4155-4158.

Kherjee S., et al., "Species Comparison and Pharmacological Characterization of Rat and Human Cb2 Cannabinoid Receptors," European Journal of Pharmacology, 2004, vol. 505 (1-3), pp. 1-9.

Khusnutdinov R.I., et al., "Chlorination of Adamantane and its Derivatives by Carbon Tetrachloride in the Presence of Manganese-, Vanadium-, and molybdenum-Containing Catalysts," Neftekhimiya, 2004, vol. 44 (2), pp. 148-155.

Knolker H.J., et al., "A Novel Method for the Synthesis of Isocyanates Under Mild Conditions," Angewandte Chemie International Edition in English, 1995, vol. 34 (22), pp. 2497-2500.

Knolker H.J., et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.

Kolasa., "Thiazolylidene Derivatives as Cannabinoid Receptor Ligands and Their Preparation" Accession No. 2008:1184581, Mar. 22, 2011.

Kruijtzer J., et al., "Approaches to the Synthesis of Ureapeptoid Peptidomimetics," Tetrahedron Letters, 1997, vol. 38 (30), pp. 5335-5338.

Kubinyi, "3D QSAR in Drug Design: Ligand Protein Interactions & Molecular Similarity, 800 pages," Springer, 1998, vol. 2-3, pp. 243-244.

Lamothe M., et al., "A Simple One-Pot Preparation of N,N'-unsymmetrical ureas from N-Boc Protected Primary Anilines and Amines," Synlett, 1996, vol. 6, pp. 507-508.

Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.

Leung M.K., et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.

Linn, et al., Journal of American Chemistry Society, 1963, 2032, vol. 85.

MacLennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.

Majer P., et al., "A Safe and Efficient Method for Preparation of N,"-Unsymmetrically Disubstituted Ureas Utilizing Triphosgene," Journal of Organic Chemistry, 1994, vol. 59, pp. 1937-1938.

Malan T.P., et al., "Inhibition of Pain Responses by Activation of CB(2) Cannabinoid Receptors," Chemistry and Physics of Lipids, 2002, vol. 121 (1-2), pp. 191-200.

Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.

Masciadri R., et al., "Regioselective Friedel_Crafts Alkylation of Anilines and Amino-Substituted Heteroarenes with Hexafluoroacetone Sesquihydrate," European Journal of Organic Chemistry, 2003, vol. 2003 (21), pp. 4286-4291.

Mayo clinic, Alzheimer's disease, [retrieved on Mar. 11, 2013]. Retrieved from the Internet< URL: http://www.mayoclinic.com/health/alzheimers-disease/DS00161/DSECTION=prevention>.

Meyers A.I., et al., "Oxazolines. XX. Synthesis of Achiral and Chiral Thiiranes and Olefins by Reaction of Carbonyl Compounds with 2-(Alkylthio)-2-oxazolines ," Journal of Organic Chemistry, 1976, vol. 41 (10), pp. 1735-1742.

Miyaura N., et al., ed., Topics in Current Chemistry: Cross-Coupling Reactions, Springer, 2002, Table of Contents.

Morii T., et al., "A General Strategy to Determine a Target DNA Sequence of a Short Peptide: Application to a [D]-Peptide," Journal American Chemical Society, 2002, vol. 124 (2), pp. 180-181.

Morissette S.L., et al., "High-throughput Crystallization: Polymorphs, Salts, Co-crystals and Solvates of Pharmaceutical Solids.," Advanced Drug Delivery Reviews, 2004, vol. 56 (3), pp. 275-300.

Mucke L., "Neuroscience: Alzheimer's Disease," Nature, 2009, vol. 461 (7266), pp. 895-897.

Negishi E., et al., eds., Handbook of Organopalladium Chemistry for Organic Synthesis, vol. 1, John Wiley & Sons, 2002, Table of Contents.

Nieuwenhuijzen J.W., et al., "Solid and Solution Phase Combinatorial Synthesis of Ureas," Tetrahedron Letters, 1998, vol. 39, pp. 7811-7814.

Non-Final Office Action mailed Mar. 9, 2012 for U.S. Appl. No. 12/732,428, filed Mar. 26, 2010.

Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.

Ozaki S., et al., "Recent Advances in Isocyanate Chemistry," Chemical Reviews, 1972, vol. 72 (5), pp. 457-496.

Padgett L.W., et al., "Recent Developments in Cannabinoid Ligands," Life Sciences, 2005, vol. 77 (14), pp. 1767-1798.

Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.

Rezoni G.E., et al., "Synthesis of 7-Carboxytricyclo[33103,7]nonan-3-ol," Journal of Organic Chemistry, 1983, vol. 48, pp. 5231-5236.

Sabnis R.W., et al., "2-Aminothiophenes by the Gewald Reaction," Journal of Heterocyclic Chemistry, 1999, vol. 36, pp. 333-345.

Schafer S.,et al., "Failure is an Option: Learning from Unsuccessful Proof-of-concept Trials," Drug Discovery Today, 2008, vol. 13 (21-22), pp. 913-916.

Schuart J., et al., "2-aminooxazoles And 2-iminooxazolines. 3. Selected Examples of a Homolog Series of 3 Substituted 2-imino-4-methyl-5-phenyloxazolines," Die Pharmazie, 1974, vol. 29 (3), pp. 170-172.

Scialdone M.A., et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.

Shultz D.A., et al., "Synthesis of Bis(semiquinone)s and their Electrochemical and Electron Paramagnetic Resonance Spectral Characterization," Journal of Organic Chemistry, 1998, vol. 63(25), pp. 9462-9469.

STN International HCAPLUS database Accession No. 2008:1184581, Columbus, Ohio, Lolasa et al, 2008.

Supplementary European Search Report for Application No. EP08837396, mailed on Jan. 16, 2012, 2 pages.

Supplementary European Search Report for Application No. EP08852528, mailed on Nov. 8, 2010, 2 pages.

Takeda K., et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.

Vasil'Eva V.F., et al., " Synthesis and Properties of 2-imino-3-benzyl-5-phenyl-1,3,4-oxadiazoline,"Caplus, 1970.

Viallet, et al., "2-Aminothiazoline, etc," 1980, CA 93:8074.

Vippagunta S.R., et al., "Crystalline Solids," Advanced Drug Delivery Reviews, 2001, vol. 48 (1), pp. 3-26.

Wermuth, "The practice of Medicinal chemistry," 2003, Chapters 9-10, 2nd edition,768 pages.

(56) References Cited

OTHER PUBLICATIONS

Whiteside G.T., et al., "The Role of the Cannabinoid Cb2 Receptor in Pain Transmission and Therapeutic Potential of Small Molecule CB2 Receptor Agonists," Current medicinal chemisty, 2007, vol. 14 (8), pp. 917-936.

Williams K., et al., "Central Nervous System Perivascular Cells Are Immunoregulatory Cells that Connect the CNS tith the Peripheral mune System," Journal Of Glia, 2001, vol. 36 (2), pp. 156-164.

Wu K.M., et al., "Regulatory Perspectives of Type II Prodrug Development and Time-Dependent Toxicity Management: Nonclinical Pharm/Tox Analysis and the Role of Comparative Toxicology," Toxicology, 2007, vol. 236 (1-2), pp. 1-6.

Yao B.B., et al., "In Vitro Pharmacological Characterization Of Am1241: A Protean Agonist At The Cannabinoid Cb2 Receptor," British Journal of Pharmacology, 2006, vol. 149 (2), pp. 145-154.

Notice of Allowance mailed Jan. 17, 2014 for U.S. Appl. No. 12/120,969, filed May 15, 2008.

Non-Final Rejection mailed Dec. 5, 2013 for U.S. Appl. No. 12/967,282, filed Dec. 14, 2010.

Office Action mailed Nov. 15, 2013 for European Application No. 05855099.7 filed Dec. 21, 2005.

Final Office Action mailed Mar. 14, 2014 for U.S. Appl. No. 12/970,480, filed Dec. 16, 2010.

Notice of Allowance mailed Apr. 14, 2014 for U.S. Appl. No. 12/967,282, filed Dec. 14, 2010.

Final Office Action mailed May 23, 2014 for U.S. Appl. No. 12/246,808, filed Oct. 7, 2008.

Notice of Allowance mailed Jun. 2, 2014 for U.S. Appl. No. 12/554,445, filed Sep. 4, 2009.

Notice of Allowance mailed Jun. 9, 2014 for U.S. Appl. No. 12/639,173, filed Dec. 16, 2009.

Notice of Allowance mailed Jun. 9, 2014 for U.S. Appl. No. 12/970,435, filed Dec. 16, 2010.

Notice of Allowance mailed May 14, 2014 for U.S. Appl. No. 12/274,105, filed Nov. 19, 2008.

Office Action mailed Jun. 30, 2014 for U.S. Appl. No. 12/970,480, filed Dec. 16, 2010.

\* cited by examiner

COMPOUNDS AS CANNABINOID RECEPTOR LIGANDS

This application claims priority to U.S. Patent Application Ser. No. 61/097,378 filed Sep. 16, 2008 and U.S. Patent Application Ser. No. 61/224,200 filed Jul. 9, 2009, which are incorporated herein by reference.

TECHNICAL FIELD AND BACKGROUND

The present application relates to compounds that are cannabinoid receptor ligands, compositions comprising such compounds, and methods of treating conditions and disorders using such compounds and compositions.

(−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-operative pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

Disclosed herein are compounds of formula (I)

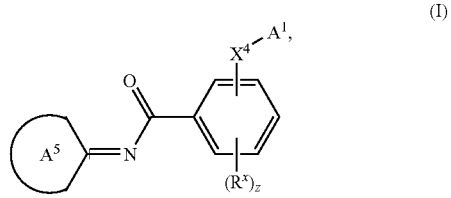

(I)

or pharmaceutically acceptable salts, solvates, prodrugs, salts of prodrugs, or any combination thereof, wherein $X^4$ is O, S, S(O), S(O)$_2$, or N(R$^{bx}$); wherein R$^{bx}$ is hydrogen, alkyl, haloalkyl, alkoxyalkyl, —C(O)O(alkyl), monocyclic cycloalkyl, —(CR$^{1c}$R$^{1d}$)$_{q3}$-(monocyclic cycloalkyl), or haloalkoxyalkyl; and $A^1$ is —N(R$^b$)C(O)R$^a$, —N(R$^b$)C(O)OR$^d$, —N(R$^b$)C(O)N(R$^b$)(R$^c$), —N(R$^b$)(R$^c$), or —N=C(R$^p$)(R$^q$); or $X^4$ and $A^1$ together is N=N(R$^{cx}$);

$A^3$ is C(O)R$^h$, —S(O)$_2$R$^e$, —C(O)N(R$^h$)$_2$, —C(S)N(R$^h$)$_2$, —S(O)$_2$N(R$^h$)$_2$, —C(=NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N(R$^h$)$_2$, —CN, —OR$^h$, or —N(R$^h$)$_2$;

each occurrence of R$^a$ and R$^c$, are each independently hydrogen, alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^b$, at each occurrence, is each independently hydrogen, alkyl, haloalkyl, alkoxyalkyl, monocyclic cycloalkyl, —(CR$^{1c}$R$^{1d}$)$_{q3}$-(monocyclic cycloalkyl), or haloalkoxyalkyl;

R$^d$, at each occurrence, is each independently alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^{cx}$ is alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^p$ is hydrogen, alkyl, haloalkyl, —(CR$^{1a}$R$^{1b}$)$_{q3}$-A$^3$, —C(O)OR$^d$, —C(O)R$^d$, G$^{1d}$, or —(CR$^{1a}$R$^{1b}$)$_{q3}$-G$^{1d}$;

R$^q$ is hydrogen, alkyl, haloalkyl, —N(R$^b$)(R$^c$), —(CR$^{1a}$R$^{1b}$)$_{q3}$-A$^3$, G$^{1d}$, or —(CR$^{1a}$R$^{1b}$)$_{q3}$-G$^{1d}$; or R$^p$ and R$^q$, together with the carbon atom to which they are attached, form a monocyclic 5-, 6-, 7-, or 8-membered ring, optionally substituted with 1, 2, 3, 4, or 5 substituents independently selected from the group consisting of oxo, alkyl, haloalkyl, and halogen;

$A^5$ represents formula (a), (b), (c), (d), or (e)

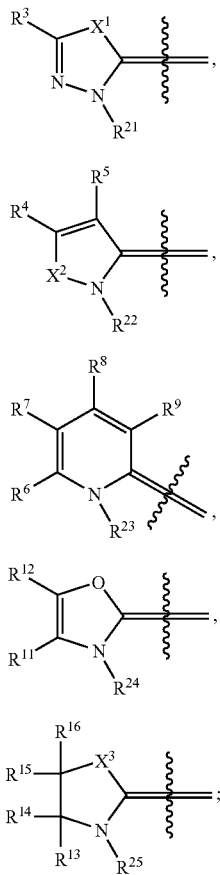

$G^{1d}$, at each occurrence, is independently a monocyclic heterocycle, a monocyclic heteroaryl, a phenyl, a monocyclic cycloalkyl, or a monocyclic cycloalkenyl; wherein $G^{1d}$ is optionally substituted with 1, 2, 3, or 4 substituents independently selected from the group consisting of —N(R$^h$)$_2$, —CN, oxo, alkyl, haloalkyl, alkoxy, haloalkoxy, halogen, and OH;

R$^e$, at each occurrence, is independently C$_1$-C$_4$ alkyl, C$_1$-C$_4$ haloalkyl, monocyclic cycloalkyl, monocyclic heterocycle, or —(CR$^{1c}$R$^{1d}$)$_{q3}$-(monocyclic cycloalkyl);

R$^f$, at each occurrence, is independently hydrogen, C$_1$-C$_4$ alkyl, C$_1$-C$_4$ haloalkyl, —(CR$^{1c}$R$^{1d}$)$_{q3}$—OR$^h$, monocyclic heterocycle, monocyclic cycloalkyl, or —(CR$^{1c}$R$^{1d}$)$_{q3}$-(monocyclic cycloalkyl);

R$^h$, at each occurrence, is independently hydrogen, C$_1$-C$_4$ alkyl, C$_1$-C$_4$ haloalkyl, monocyclic cycloalkyl, or —(CR$^{1c}$R$^{1d}$)$_{q3}$-(monocyclic cycloalkyl);

R$^{21}$, R$^{22}$, R$^{23}$, R$^{24}$, and R$^{25}$ are each independently alkyl, alkenyl, alkynyl, haloalkyl, —(CR$^{2a}$R$^{2b}$)$_{q4}$—OH, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q4}$—O-G$^{2a}$, —(CR$^{2a}$R$^{2b}$)$_{q4}$—O—(CR$^{2c}$R$^{2d}$)$_{q3}$-G$^{2a}$, —(CR$^{2a}$R$^{2b}$)$_{q5}$—C(O)—R$^a$, —(CR$^{2a}$R$^{2b}$)$_{q5}$—C(=N—OR$^f$)R$^a$, —(CR$^{2a}$R$^{2b}$)$_{q5}$—SO$_2$—R$^d$, —(CR$^{2a}$R$^{2b}$)$_{q5}$-G$^{2b}$, —(CR$^{2a}$R$^{2b}$)$_{q5}$—C(O)N(R$^h$)(R$^e$), or —(CR$^{2a}$R$^{2b}$)$_{q5}$—CN;

each occurrence of G$^{2a}$ is independently cycloalkyl, heterocycle, aryl, or heteroaryl;

G$^{2b}$ is a monocyclic ring selected from the group consisting of cycloalkyl, cycloalkenyl, thienyl, phenyl, furanyl, oxazolyl, isoxazolyl, oxadiazolyl, and heterocycle; wherein the heterocycle contains zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; each ring G$^{2b}$ is optionally fused with a monocyclic ring selected from the group consisting of benzo, cycloalkyl, cycloalkenyl, heterocycle and heteroaryl;

each occurrence of G$^{2a}$ and G$^{2b}$ are each independently unsubstituted or substituted with 1, 2, 3, 4, 5, or 6 substituents independently selected from the group consisting of oxo, alkyl, halogen, —OH, alkoxy, haloalkoxy, and haloalkyl;

$X^1$ is O or S;

$X^2$ is O, S, or N(R$^{10}$) wherein R$^{10}$ is alkyl, alkoxyalkyl, haloalkoxyalkyl, or haloalkyl;

$X^3$ is O or S;

R$^3$, R$^4$, R$^5$, R$^6$, R$^7$, R$^8$, R$^9$, R$^{11}$ and R$^{12}$ are each independently G$^3$, hydrogen, alkyl, alkenyl, alkynyl, —NO$_2$, —CN, halogen, —OR$^h$, —N(R$^h$)$_2$, —C(O)R$^h$, —C(O)O(R$^h$), haloalkyl, —(CR$^{3a}$R$^{3b}$)$_{q6}$—OR$^h$, —(CR$^{3a}$R$^{3b}$)$_{q6}$—N(R$^h$)$_2$, —(CR$^{3a}$R$^{3b}$)$_{q6}$—C(O)R$^h$, or —(CR$^{3a}$R$^{3b}$)$_{q6}$—C(O)O(R$^h$);

R$^{13}$ and R$^{14}$ are each independently G$^3$, hydrogen, alkyl, haloalkyl, or —(CR$^{3a}$R$^{3b}$)$_{q6}$—OR$^h$; or R$^{13}$ and R$^{14}$ taken together with the carbon atom to which they are attached form a monocyclic heterocycle ring or a monocyclic cycloalkyl ring, each of which is independently unsubstituted or substituted with 1, 2, 3, or 4 substituents selected from the group consisting of alkyl, OH, alkoxy, haloalkoxy, haloalkyl, and oxo;

R$^{15}$ and R$^{16}$ are each independently G$^3$, hydrogen, alkyl, haloalkyl, or —(CR$^{3a}$R$^{3b}$)$_{q6}$—OR$^h$; or R$^{15}$ and R$^{16}$ taken together with the carbon atom to which they are attached form a monocyclic cycloalkyl ring or a monocyclic heterocycle ring; each of which is independently unsubstituted or substituted with 1, 2, 3, or 4 substituents selected from the group consisting of alkyl, OH, alkoxy, haloalkoxy, haloalkyl, and oxo;

G$^3$, at each occurrence, is independently cycloalkyl, cycloalkenyl, aryl, heterocycle, or heteroaryl, wherein each G$^3$ is independently unsubstituted or substituted with 1, 2, 3 or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, =N—CN, =N—OR$^h$, oxo, —OR$^h$, —OC(O)R$^h$, —OC(O)N(R$^h$)$_2$, —S(O)$_2$R$^e$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^h$, —N(R$^h$)S(O)$_2$R$^e$, —N(R$^h$)C(O)O(R$^e$), and —N(R$^h$)C(O)N(R$^h$)$_2$;

R$^{1a}$, at each occurrence, is independently hydrogen, halogen, C$_1$-C$_4$ alkyl, or C$_1$-C$_4$ haloalkyl;

R$^b$, at each occurrence, is independently hydrogen, halogen, C$_1$-C$_4$ alkyl, C$_2$-C$_4$ alkenyl, C$_1$-C$_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$;

R$^{1c}$, R$^{1d}$, R$^{2a}$, R$^{2b}$, R$^{2c}$, R$^{2d}$, R$^{3a}$ and R$^{3b}$, at each occurrence, are each independently hydrogen, halogen, C$_1$-C$_4$ alkyl, or C$_1$-C$_4$ haloalkyl;

R$^x$ at each occurrence, is each independently G$^{1d}$, C$_1$-C$_4$ alkyl, C$_2$-C$_4$ alkenyl, C$_2$-C$_4$ alkynyl, halogen, C$_1$-C$_4$ haloalkyl, NO$_2$, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, or —(CR$^{1c}$R$^{1d}$)$_{q3}$—CN;

q4, at each occurrence, is independently 2, 3, 4, or 5;
q3, at each occurrence, is 1, 2 or, 3;

q5 and q6, at each occurrence, are each independently 1, 2, 3, 4, 5, or 6;

z is 0, 1, 2, 3, or 4; and the monocyclic cycloalkyl and the monocyclic heterocycle, as a substituent or as part of a substituent, of $R^{bx}$, $R^b$, $R^e$, $R^f$, and $R^h$, are each independently unsubstituted are substituted with 1, 2, 3, or 4 substituents independently selected from the group consisting of oxo, $C_1$-$C_4$ alkyl, halogen, OH, $C_1$-$C_4$ alkoxy, haloalkoxy, and $C_1$-$C_4$ haloalkyl;

with the proviso that when $X^4$ is $S(O)_2$, and $R^{21}$, $R^{22}$, $R^{23}$, or $R^{24}$ are each independently alkyl, alkynyl, haloalkyl, $-(CR^{2a}R^{2b})_{q4}$—O-alkyl, $-(CR^{2a}R^{2b})_{q4}$—OH, $-(CR^{2a}R^{2b})_{q5}$—C(O)-(monocyclic heterocycle), $-(CR^{2a}R^{2b})_{q5}$—C(O)N($R^b$)($R^c$), $-(CR^{2a}R^{2b})_{q5}$—CN, or $-(CR^{2a}R^{2b})_{q5}$-$G^{2b}$ wherein $G^{2b}$ is monocyclic cycloalkyl or phenyl;

then $A^1$ is not N(H)$_2$, N(H)(alkyl), or N(alkyl)$_2$.

Another aspect relates to pharmaceutical compositions comprising therapeutically effective amount of one or more compound(s) described herein or pharmaceutically acceptable salts or solvates thereof, in combination with one or more pharmaceutically acceptable carrier(s). Such compositions can be administered in accordance with methods described herein, typically as part of a therapeutic regimen for treatment or prevention of conditions and disorders related to cannabinoid (CB) receptor subtype CB$_2$. More particularly, the methods are useful for treating conditions related to pain such as, but not limited to, neuropathic pain, nociceptive pain, osteoarthritic pain, inflammatory pain, cancer pain, lower back pain, post operative pain, or eye pain; inflammatory disorders, immune disorders, neurological disorders, cancers of the immune system, respiratory disorders, obesity, diabetes, cardiovascular disorders, or for providing neuroprotection.

Further, provided herein is the use of present compounds or pharmaceutically acceptable salts or solvates thereof, in the manufacture of medicaments for the treatment of the disease or conditions described above, alone or in combination with one or more pharmaceutically acceptable carrier(s), particularly for the treatment of pain such as, but not limited to, neuropathic pain, nociceptive pain, osteoarthritic pain, inflammatory pain, cancer pain, lower back pain, post operative pain, or eye pain, or combinations thereof.

The compounds, compositions comprising the compounds, and methods for treating or preventing conditions and disorders by administering the compositions, or compounds or pharmaceutically acceptable salts or solvates thereof, are further described herein.

These and other objectives of the invention are described in the following paragraphs. These objectives should not be deemed to narrow the scope of the invention.

DETAILED DESCRIPTION

Compounds of formula (I) are disclosed

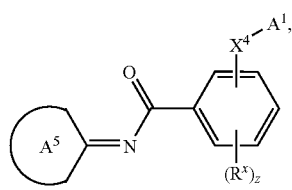

(I)

wherein $A^1$, $R^x$, $A^5$, $X^4$, and z are as defined above in the Summary and below in the Detailed Description. Compositions comprising such compounds and methods for treating conditions and disorders using such compounds and compositions are also disclosed.

In various embodiments, the compounds may contain variables that may occur more than one time in any substituent or in the formulae herein. Definition of a variable on each occurrence is independent of its definition at another occurrence. Further, combinations of substituents and variables are permissible only if such combinations result in stable compounds. Stable compounds are compounds that can be isolated from a reaction mixture.

A. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 10 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. The term "$C_1$-$C_4$ alkoxy" means an alkoxy group containing 1-4 carbon atoms. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylenyl group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "$C_1$-$C_4$ alkyl" and "$C_1$-$C_6$ alkyl" means a saturated, straight or branched chain hydrocarbon containing 1 to 4 carbon atoms and 1 to 6 carbon atoms respectively. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched chain hydrocarbon of 1 to 10 carbon atoms. Representative examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group of 2 to 4 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means an optionally substituted phenyl or an optionally substituted bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Non limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Non limiting examples of tricyclic-ring systems include tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms, each linking two non-adjacent carbon atoms of the ring system. Non limiting examples of the bicyclic cycloalkenyl groups include 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five, or six hydrogen atoms are replaced by halogen. The term "$C_1$-$C_4$ haloalkyl" means a haloalkyl group of 1-4 carbon atoms. Non limiting examples of haloalkyl include 4,4,4-trifluorobutyl, 4-fluorobutyl, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "haloalkoxy" as used herein, means an alkoxy group, as defined herein, in which one, two, three, four, five, or six hydrogen atoms are replaced by halogen. The term "$C_1$-$C_4$ haloalkoxy" means a haloalkoxy group of 1-4 carbon atoms. Non limiting examples of haloalkoxy include 2-fluoroethoxy, 2,2,2-trifluoroethoxy, trifluoromethoxy, and difluoromethoxy.

The term "haloalkoxyalkyl" as used herein, means a haloalkoxy group, as defined herein, appended to the parent moiety through an alkylenyl group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S, Non limiting examples of monocyclic heterocycles include azetidinyl (including, but not limited thereto, azetidin-2-yl, azetidin-3-yl), azepanyl (e.g. azepan-2-yl), aziridinyl, diazepanyl, 1,3-dioxanyl, 1,4-dioxanyl (including 1,4-dioxan-2-yl), 1,3-dioxolanyl (e.g. 1,3-dioxolan-4-yl), 1,3-dithiolanyl, dihydrofuranyl (including, but not limited to, 2,5-dihydrofuran-2-yl), 1,3-dithianyl, dihydroisozazolyl (including 4,5-dihydroisoxazol-5-yl), imidazolidinyl (including imidazolidin-1-yl), isothiazolinyl, isothiazolidinyl, isoxazolinyl, isoxazolidinyl, morpholinyl, oxadiazolinyl, oxadiazolidinyl, oxazolinyl, oxazolidinyl (e.g. 1,3-oxazolidin-4-yl, 1,3-oxazolidin-5-yl), oxetanyl (e.g. oxetan-3-yl, oxetan-2-yl), piperazinyl, piperidinyl (including, but not limited to, piperidin-2-yl), pyranyl, pyrazolinyl, pyrazolidinyl, pyrrolinyl, pyrrolidinyl (including pyrrolidin-2-yl, pyrrolidin-1-yl, pyrrolidin-3-yl), tetrahydrofuranyl (including, but not limited thereto, tetrahydrofuran-2-yl, tetrahydrofuran-3-yl), tetrahydropyranyl (including tetrahydro-2H-pyran-2-yl, tetrahydro-2H-pyran-3-yl, tetrahydro-2H-pyran-4-yl), tetrahydrothienyl (including tetrahydrothien-3-yl), tetrahydrothiopyranyl (e.g. tetrahydro-2H-thiopyran-4-yl), tetrahydrooxazolyl (including tetrahydrooxazol-5-yl), thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or by an alkenylene bridge of two, three, or four carbon atoms. Non limiting examples of bicyclic heterocycles include benzopyranyl, benzothiopyranyl, 2,3-dihydrobenzofuranyl, 2,3-dihydrobenzothienyl, azabicyclo[2.2.1]heptyl (including 2-azabicyclo[2.2.1]hept-2-yl), and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or by an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-admantane (2-oxatricyclo[3.3.1.1$^{3,7}$]decane). The monocyclic, bicyclic, and tricyclic heterocycles can be unsubstituted or substituted. The monocyclic, bicyclic, and tricyclic heterocycles are connected to the parent molecular moiety through any carbon atom or any nitrogen atom contained within the rings. The nitrogen and sulfur heteroatoms in the heterocycle rings may optionally be oxidized (e.g. 1,1-dioxidotetrahydrothienyl) and the nitrogen atoms may optionally be quarternized.

The term "heteroaryl" as used herein, means a monocyclic heteroaryl or a bicyclic heteroaryl. The monocyclic heteroaryl is a five- or six-membered ring containing at least one heteroatom selected from the group consisting of N, O, and S. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three, or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl (including pyridin-2-yl, pyridin-3-yl, pyridine-4-yl), pyridazinyl, pyrimidinyl, pyrazinyl (e.g. pyrazin-2-yl), pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen heteroatoms of the heteroaryl rings may optionally be oxidized, and are contemplated within the scope of the invention.

The term "heteroatom" as used herein, means a nitrogen, oxygen, or sulfur atom.

The term "oxo" as used herein, means a =O group.

B. COMPOUNDS

Compounds described herein have formula (I) as described above.

Particular values of variable groups in compounds of formula (I) are as follows. Such values may be used where appropriate with any of the other values, definitions, claims or embodiments defined hereinbefore or hereinafter.

In certain embodiments, the —X$^4$-A$^1$ group is situated on the carbon atom adjacent to the point of attachment to the carbonyl group of formula (I). Thus, contemplated but not limited thereto are compounds of formula (II)

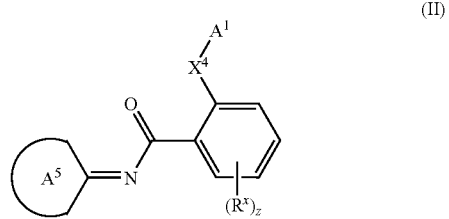

(II)

wherein A$^5$, X$^4$, A$^1$, R$^x$, and z are as described generally in the Summary and in the embodiments herein.

A$^5$ has values as described generally in the Summary. Thus, included but not limited thereto are compounds of formula (I) or (II) wherein A$^5$ has formula (a). Such compounds are represented by formula (Ia) and (IIa) respectively

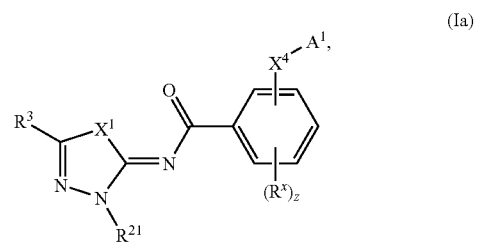

(Ia)

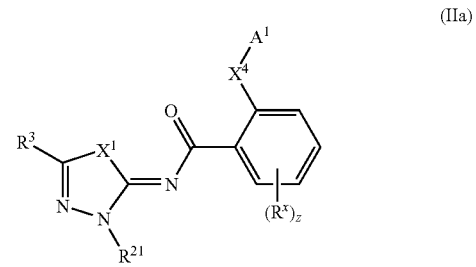

(IIa)

wherein R$^3$, R$^{21}$, X$^1$, X$^4$, A$^1$, R$^x$, and z are as described generally in the Summary and in the embodiments herein. For example, in certain embodiments, R$^3$ is G$^3$, hydrogen, alkyl, alkenyl, alkynyl, —CN, halogen, —OR$^h$, haloalkyl, —(CR$^{3a}$R$^{3b}$)$_{q6}$—OR$^h$, or —(CR$^{3a}$R$^{3b}$)$_{q6}$—N(R$^h$)$_2$, wherein G$^3$, R$^{3a}$, R$^{3b}$, q6, and R$^h$ are as described generally in the Summary and in the embodiments herein. R$^h$, for example, is hydrogen, C$_1$-C$_4$ alkyl, or C$_1$-C$_4$ haloalkyl. G$^3$, for example, is monocyclic cycloalkyl or monocyclic heterocycle, each of which is optionally substituted. In yet other embodiments, R$^3$ is alkyl (e.g. C$_1$-C$_4$ alkyl such as, but not limited thereto, isopropyl, tert-butyl), alkenyl, alkynyl, or a monocyclic cycloalkyl (e.g. optionally substituted cyclopropyl) that is optionally substituted as described generally in the Summary and in the embodiments herein. For example, the monocyclic cycloalkyl is optionally substituted with 1, 2, 3 or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, —CN, oxo, and —OR$^h$ (e.g. —OH, —O(C$_1$-C$_4$ alkyl)). In certain embodiments, R$^3$ is C$_1$-C$_4$ alkyl (such as, but not limited to, isopropyl or tert-butyl) or an optionally substituted monocyclic cycloalkyl (e.g. optionally substituted cyclopropyl). In certain embodiments, X$^1$ is S. In certain embodiments, X$^1$ is O.

Certain embodiments provide compounds of formula (I) or formula (II) wherein $A^5$ has formula (b). Accordingly, compounds included herein, but not limited to, have formula (Ib) or (IIb)

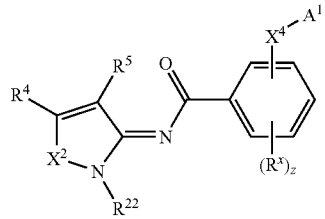
(Ib)

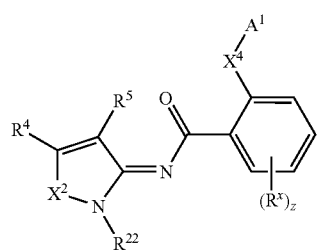
(IIb)

wherein $R^4$, $R^5$, $R^{22}$, $X^2$, $X^4$, $A^1$, $R^x$, and z are as described generally in the Summary and in the embodiments herein. For example, $X^2$ is $N(R^{10})$ wherein $R^{10}$ is $C_1$-$C_4$ alkyl. In certain embodiments, $X^2$ is $N(CH_3)$. In yet other embodiments, $X^2$ is O. $R^4$ and $R^5$, are each independently $G^3$, hydrogen, alkyl, alkenyl, alkynyl, —CN, halogen, —$OR^h$, haloalkyl, —$(CR^{3a}R^{3b})_{q6}$—$OR^h$, or —$(CR^{3a}R^{3b})_{q6}$—$N(R^h)_2$, wherein $G^3$, $R^{3a}$, $R^{3b}$, q6, and $R^h$ are as described generally in the Summary and in the embodiments herein. $R^h$, for example, is hydrogen, $C_1$-$C_4$ alkyl, or $C_1$-$C_4$ haloalkyl. $G^3$, for example, is monocyclic cycloalkyl or monocyclic heterocycle, each of which is optionally substituted. Examples of the optional substituents of $G^3$ include, but are not limited to $C_1$-$C_4$ alkyl, $C_2$-$C_4$ alkenyl, $C_2$-$C_4$ alkynyl, halogen, $C_1$-$C_4$ haloalkyl, —CN, oxo, and —$OR^h$ (e.g. —OH, —O($C_1$-$C_4$ alkyl)). In yet other embodiments, $R^4$ is alkyl (e.g. $C_1$-$C_4$ alkyl such as, but not limited thereto, tert-butyl, isopropyl), alkenyl, alkynyl, or an optionally substituted monocyclic cycloalkyl (e.g. optionally substituted cyclopropyl), and $R^5$ is hydrogen or halogen. In certain embodiments, $R^4$ is $C_1$-$C_4$ alkyl (such as, but not limited to, isopropyl or tert-butyl) or an optionally substituted monocyclic cycloalkyl (e.g. optionally substituted cyclopropyl), and $R^5$ is hydrogen.

Certain embodiments provide compounds of formula (I) or (II) wherein $A^5$ has formula (c). Accordingly, contemplated herein but not limited thereto are compounds of formula (Ic) or formula (IIc)

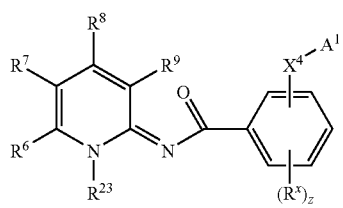
(Ic)

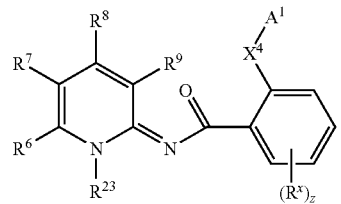
(IIc)

wherein $R^6$, $R^7$, $R^8$, $R^9$, $R^{23}$, $X^4$, $A^1$, $R^x$, and z are as described generally in the Summary and in the embodiments herein. For example, $R^6$, $R^7$, $R^8$, $R^9$ are each independently $G^3$, hydrogen, alkyl, alkenyl, alkynyl, —CN, halogen, —$OR^h$, haloalkyl, —$(CR^{3a}R^{3b})_{q6}$—$OR^h$, or —$(CR^{3a}R^{3b})_{q6}$—$N(R^h)_2$, wherein $G^3$, $R^{3a}$, $R^{3b}$, q6, and $R^h$ are as described generally in the Summary and in the embodiments herein. $R^h$, for example, is hydrogen, $C_1$-$C_4$ alkyl, or $C_1$-$C_4$ haloalkyl. $G^3$, for example, is monocyclic cycloalkyl or monocyclic heterocycle, each of which is optionally substituted. Examples of the optional substituents of $G^3$ include, but are not limited to $C_1$-$C_4$ alkyl, $C_2$-$C_4$ alkenyl, $C_2$-$C_4$ alkynyl, halogen, $C_1$-$C_4$ haloalkyl, —CN, oxo, and —$OR^h$ (e.g. —OH, —O($C_1$-$C_4$ alkyl)). In certain embodiments, one of $R^6$, $R^7$, $R^8$, and $R^9$ is hydrogen, alkyl (e.g. $C_1$-$C_4$ alkyl), alkenyl, alkynyl, or an optionally substituted monocyclic cycloalkyl (e.g. optionally substituted cyclopropyl), and the others are hydrogen or halogen. In certain embodiments, one of $R^6$, $R^7$, $R^8$, and $R^9$ is $C_1$-$C_4$ alkyl (such as, but not limited to, isopropyl or tert-butyl) or an optionally substituted monocyclic cycloalkyl (e.g. optionally substituted cyclopropyl), and the others are hydrogen.

Certain embodiments provide compounds of formula (I) or formula (II) wherein $A^5$ is formula (d). Accordingly, provided herein but not limited thereto are compounds of the formula (Id) or (IId)

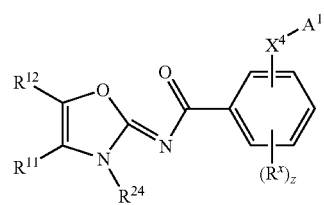
(Id)

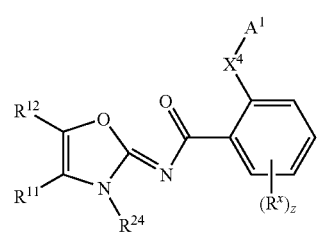
(IId)

wherein $R^{11}$, $R^{12}$, $R^{24}$, $X^4$, $A^1$, $R^x$, and z are as described generally in the Summary and in the embodiments herein. For example, $R^{11}$ and $R^{12}$ are each independently $G^3$, hydrogen, alkyl, alkenyl, alkynyl, —CN, halogen, —$OR^h$, haloalkyl, —$(CR^{3a}R^{3b})_{q6}$—$OR^h$, or —$(CR^{3a}R^{3b})_{q6}$—$N(R^h)_2$, wherein $G^3$, $R^{3a}$, $R^{3b}$, q6, and $R^h$ are as described generally in the Summary and in the embodiments herein. $R^h$, for example, is hydrogen, $C_1$-$C_4$ alkyl, or $C_1$-$C_4$ haloalkyl. $G^3$, for example, is monocyclic cycloalkyl or monocyclic heterocycle, each of which is optionally substituted. Examples of the optional substituents of $G^3$ include, but are not limited to $C_1$-$C_4$ alkyl, $C_2$-$C_4$ alkenyl, $C_2$-$C_4$ alkynyl, halogen, $C_1$-$C_4$ haloalkyl, —CN, oxo, and —$OR^h$ (e.g. —OH, —O($C_1$-$C_4$ alkyl)). In certain embodiments, $R^{12}$ is hydrogen, alkyl (e.g. $C_1$-$C_4$ alkyl such as, but not limited to, isopropyl, tert-butyl), alkenyl, alkynyl, or an optionally substituted monocyclic cycloalkyl (e.g. optionally substituted cyclopropyl), and $R^{11}$ is hydrogen, alkyl, or halogen. In certain embodiments, $R^{12}$ is $C_1$-$C_4$ alkyl (such as, but not limited to, isopropyl or tert-butyl) or an optionally substituted monocyclic cycloalkyl (e.g. optionally substituted cyclopropyl), and $R^{11}$ is hydrogen.

Certain embodiments provide compounds of formula (I) or (II) wherein $A^5$ is formula (e). Thus, included but not limited to are compounds of formula (Ie) or (IIe)

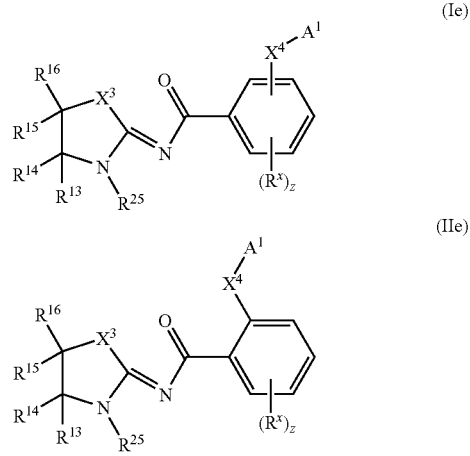

wherein $R^{13}$, $R^{14}$, $R^{15}$, $R^{16}$, $R^{25}$, $X^3$, $X^4$, $A^1$, $R^x$, and z are as described generally in the Summary and in the embodiments herein. For example, $R^{13}$, $R^{14}$, $R^{15}$, and $R^{16}$ are each independently $G^3$, hydrogen, alkyl, alkenyl, alkynyl, —CN, halogen, —$OR^h$, haloalkyl, —$(CR^{3a}R^{3b})_{q6}$—$OR^h$, or —$(CR^{3a}R^{3b})_{q6}$—$N(R^h)_2$, wherein $G^3$, $R^{3a}$, $R^{3b}$, q6, and $R^h$ are as described generally in the Summary and in the embodiments herein. $R^h$, for example, is hydrogen, $C_1$-$C_4$ alkyl, or $C_1$-$C_4$ haloalkyl. $G^3$, for example, is monocyclic cycloalkyl or monocyclic heterocycle, each of which is optionally substituted. Examples of the optional substituents of $G^3$ include, but are not limited to $C_1$-$C_4$ alkyl, $C_2$-$C_4$ alkenyl, $C_2$-$C_4$ alkynyl, halogen, $C_1$-$C_4$ haloalkyl, —CN, oxo, and —$OR^h$ (e.g. —OH, —O($C_1$-$C_4$ alkyl)). In certain embodiments, $R^{13}$, $R^{14}$, $R^{15}$, and $R^{16}$ are each independently hydrogen, alkyl (e.g. $C_1$-$C_4$ alkyl such as, but not limited to, methyl, isopropyl, tert-butyl), alkenyl, alkynyl, or an optionally substituted monocyclic cycloalkyl (e.g. optionally substituted cyclopropyl). In certain embodiments, $R^{15}$ and $R^{16}$ are each independently hydrogen or alkyl (e.g. methyl, isopropyl, tert-butyl) and $R^{13}$ and $R^{14}$ are hydrogen.

$R^{21}$, $R^{22}$, $R^{23}$, $R^{24}$, and $R^{25}$ of formula (I) (Ia), (Ib), (Ic), (Id), (Ie), (II) (IIa), (IIb), (IIc), (IId), or (IIe), are as described generally in the Summary and embodiments herein. For example, $R^{21}$, $R^{22}$, $R^{23}$, $R^{24}$, and $R^{25}$ are each independently alkyl (e.g. $C_1$-$C_6$ alkyl such as, but not limited to, n-butyl, isobutyl, n-propyl, n-pentyl), alkenyl, alkynyl, haloalkyl (e.g. $C_1$-$C_4$ haloalkyl), —$(CR^{2a}R^{2b})_{q4}$—O-alkyl, —$(CR^{2a}R^{2b})_{q4}$—O-haloalkyl, —$(CR^{2a}R^{2b})_{q4}$—O-$G^{2a}$, —$(CR^{2a}R^{2b})_{q4}$—O—$(CR^{2c}R^{2d})_{q3}$-$G^{2a}$, —$(CR^{2a}R^{2b})_{q5}$-$G^{2b}$, or —$(CR^{2a}R^{2b})_{q5}$—CN. In certain embodiments, $R^{21}$, $R^{22}$, $R^{23}$, $R^{24}$, and $R^{25}$ are each independently alkyl (e.g. $C_1$-$C_6$ alkyl such as, but not limited to, n-butyl, isobutyl, n-propyl, n-pentyl), alkenyl, alkynyl, haloalkyl (e.g. $C_1$-$C_4$ haloalkyl such as, but not limited to, 3,3,3-trifluoropropyl, 4,4,4-trifluorobutyl, 4-fluorobutyl), —$(CR^{2a}R^{2b})_{q4}$—O-alkyl (e.g. —$(CR^{2a}R^{2b})_{q4}$—O—$CH_3$), —$(CR^{2a}R^{2b})_{q4}$—O-haloalkyl, —$(CR^{2a}R^{2b})_{q5}$-$G^{2b}$, or —$(CR^{2a}R^{2b})_{q5}$—CN. In certain embodiments, $R^{21}$, $R^{22}$, $R^{23}$, $R^{24}$, and $R^{25}$ are each independently alkyl (e.g. $C_1$-$C_6$ alkyl such as, but not limited to, n-butyl, isobutyl, n-propyl, n-pentyl), haloalkyl (e.g. $C_1$-$C_4$ haloalkyl such as, but not limited to, 3,3,3-trifluoropropyl, 4,4,4-trifluorobutyl, 4-fluorobutyl), —$(CR^{2a}R^{2b})_{q5}$-$G^{2b}$, or —$(CR^{2a}R^{2b})_{q5}$—CN. In certain embodiments, $R^{21}$, $R^{22}$, $R^{23}$, $R^{24}$, and $R^{25}$ are each independently alkyl (e.g. $C_1$-$C_6$ alkyl such as, but not limited to, n-butyl, isobutyl, n-propyl, n-pentyl) or —$(CR^{2a}R^{2b})_{q5}$-$G^{2b}$, $R^{2a}$, $R^{2b}$, $R^{2c}$, $R^{2d}$, q3, q4, q5, $G^{2a}$, and $G^{2b}$ are as described generally in the Summary and in the embodiments herein. In certain embodiments, $R^{21}$, $R^{22}$, $R^{23}$, $R^{24}$, and $R^{25}$ are each independently alkyl (e.g. $C_1$-$C_6$ alkyl such as, but not limited to, n-butyl, isobutyl, n-propyl, n-pentyl) or haloalkyl (e.g. $C_1$-$C_4$ haloalkyl such as, but not limited to, 3,3,3-trifluoropropyl, 4,4,4-trifluorobutyl, 4-fluorobutyl). In certain embodiments, $R^{21}$, $R^{22}$, $R^{23}$, $R^{24}$, and $R^{25}$ are each independently alkyl (e.g. $C_1$-$C_6$ alkyl such as, but not limited to, n-butyl, isobutyl, n-propyl, n-pentyl). In other embodiments, $R^{21}$, $R^{22}$, $R^{23}$, $R^{24}$, and $R^{25}$ are each independently —$(CR^{2a}R^{2b})_{q5}$-$G^{2b}$, and $R^{2a}R^{2b}$, q5, and $G^{2b}$ are as described in the Summary and in embodiments herein. For example, $G^{2b}$ is an optionally substituted monocyclic ring selected from the group consisting of cycloalkyl, cycloalkenyl, thienyl, phenyl, furanyl, oxazolyl, isoxazolyl, oxadiazolyl, and a monocyclic heterocycle; wherein the monocyclic heterocycle contains zero or one double bond, one or two oxygen, and zero or one nitrogen as ring atoms. In certain embodiments, $G^{2b}$ is optionally substituted phenyl, optionally substituted monocyclic cycloalkyl (e.g. cyclopropyl, cyclobutyl, cyclopentyl, each of which is optionally substituted) or an optionally substituted monocyclic heterocycle containing zero or one double bond, one or two oxygen, and zero or one nitrogen as ring atoms. Examples of such optionally substituted monocyclic heterocycle rings include, but are not limited to, oxetanyl (e.g. oxetan-2-yl, oxetan-3-yl), oxazolidinyl (including 1,3-oxazolidin-4-yl), dihydroisoxazolyl (including 4,5-dihydroisoxazol-5-yl), tetrahydrofuranyl (including, but not limited to, tetrahydrofuran-2-yl and tetrahydrofuran-3-yl), tetrahydropyranyl (including but not limited to, tetrahydro-2H-pyran-2-yl, tetrahydropyran-2H-4-yl), 1,3-dioxalanyl (e.g. 1,3-dioxalan-4-yl), and 1,4-dioxanyl (including 1,4-dioxan-2-yl), each of these exemplary rings is optionally substituted In certain embodiments, $G^{2b}$ is optionally substituted tetrahydrofuranyl. In yet other embodiments, $G^{2b}$ is optionally substituted tetrahydrofuran-2-yl. Certain exemplary compounds include, but are not limited to, those of formula (I) (Ia), (Ib), (Ic), (Id), (Ie), (II) (IIa), (IIb), (IIc), (IId), or (IIe) wherein $G^{2b}$ is cyclopropyl, cyclobutyl, or cyclopentyl, each of which is optionally substituted. In certain embodiments, $G^{2b}$ is optionally substituted phenyl. Each of these exemplary rings of $G^{2b}$ is independently unsubstituted or substituted as described in the Summary and embodiments herein. For example, each can be unsubstituted or substituted with 1, 2, or 3 groups independently selected from the group consisting of alkyl such as, but not limited to, $C_1$-$C_4$ alkyl (e.g. methyl), halogen (e.g. F), haloalkyl, oxo, —OH, —O(alkyl) (including, but not limited to —$OCH_3$), and —O(haloalkyl). $R^{2a}$ and $R^{2b}$ are, for example, hydrogen or $C_1$-$C_4$ alkyl (e.g. methyl). q4, for example, is 2 or 3. q5, for example, is 1, 2, or 3. In certain embodiments, $R^{21}$, $R^{22}$, $R^{23}$, $R^{24}$, and $R^{25}$ are each independently —$(CH_2)$-$G^{2b}$ wherein $G^{2b}$ is as described generally in the Summary and in embodiments herein.

$A^1$ of formula (I) (Ia), (Ib), (Ic), (Id), (Ie), (II) (IIa), (IIb), (IIc), (IId), or (IIe), has values as described generally in the Summary and embodiments herein. For example, in certain embodiments, $A^1$ is —$N(R^b)C(O)R^a$, —$N(R^b)C(O)OR^d$, —$N(R^b)C(O)N(R^b)(R^c)$, or —$N=C(R^p)(R^q)$; wherein $R^a$, $R^b$, $R^c$, $R^d$, $R^p$, and $R^q$ are as described generally in the Summary and herein below.

One class of compounds of formula (I) (Ia), (Ib), (Ic), (Id), (Ie), (II) (IIa), (IIb), (IIc), (IId), or (IIe) is directed to those wherein $A^1$ is —$N(R^b)C(O)R^a$, —$N(R^b)C(O)OR^d$, or —$N(R^b)C(O)N(R^b)(R^c)$; wherein $R^a$, $R^b$, $R^c$, and $R^d$ are as disclosed in the Summary and herein. $R^b$ and $R^c$, for example, are each independently hydrogen or $C_1$-$C_4$ alkyl (e.g. methyl). $R^d$, for example, is $C_1$-$C_4$ alkyl (e.g. methyl, tert-butyl). $R^a$, for example, is $C_1$-$C_4$ alkyl (including but not limited to, methyl, ethyl, tert-butyl), haloalkyl, or $G^{1d}$; wherein $G^{1d}$ are as set forth in the Summary and herein. $G^{1d}$, for example, is optionally substituted phenyl or an optionally substituted monocyclic heteroaryl (including but not limited to, pyridinyl).

In certain embodiments, $A^1$ is —$N(R^b)(R^c)$ wherein $R^b$ and $R^c$ are as described generally in the Summary and herein. For example, $R^b$ is hydrogen or alkyl (e.g. $C_1$-$C_4$ alkyl such as, but not limited to, isopropyl, methyl, ethyl) and $R^c$ is alkyl (e.g. $C_1$-$C_4$ alkyl such as, but not limited to, tert-butyl, isopropyl, methyl, ethyl), —$(CR^{1a}R^{1b})_{q3}$-$G^{1d}$, or $G^{1d}$ wherein $R^{1a}$, $R^{1b}$, q3, and $G^{1d}$ are as set forth in the Summary and herein. For example, certain embodiments are directed to those wherein $G^{1d}$ is phenyl or monocyclic heteroaryl (including but not limited to, pyridinyl), each of which is optionally substituted as described in the Summary. $R^{1a}$ and $R^{1b}$ are, for example, each independently hydrogen or $C_1$-$C_4$ alkyl. In certain embodiments, $A^1$ is —$N(R^b)(R^c)$ wherein $R^b$ is hydrogen or $C_1$-$C_4$ alkyl and $R^c$ is $C_1$-$C_4$ alkyl.

In certain embodiments, $A^1$ is —$N=C(R^p)(R^q)$ wherein $R^p$ and $R^q$ are as described generally in the Summary and herein. For example, certain embodiments are directed to those wherein $R^p$ is alkyl (e.g. $C_1$-$C_4$ alkyl such as but not limited to, tert-butyl, isopropyl, methyl, ethyl), haloalkyl (e.g. $C_1$-$C_4$ haloalkyl such as, but not limited to, trifluoromethyl), —$C(O)OR^d$, —$C(O)R^d$, or $G^{1d}$; and $R^q$ is hydrogen, alkyl (e.g. $C_1$-$C_4$ alkyl such as but not limited to, methyl, ethyl, isopropyl), haloalkyl (e.g. $C_1$-$C_4$ haloalkyl such as, but not limited to, trifluoromethyl), or —$N(R^b)(R^c)$; wherein $R^d$, $G^{1d}$, $R^b$, and $R^c$ are as described in the Summary and embodiments herein. $R^d$, for example, is alkyl (e.g. $C_1$-$C_4$ alkyl such as but not limited to, methyl, ethyl). $G^{1d}$, for example, is phenyl, monocyclic heteroaryl (e.g. pyridinyl), or monocyclic cycloalkyl (e.g. cyclopropyl), each of which is optionally substituted as described in the Summary. $R^b$ and $R^c$, for example, are each independently hydrogen or alkyl (e.g. $C_1$-$C_4$ alkyl such as, but not limited to, methyl, ethyl).

In certain embodiments wherein $A^1$ is —$N=C(R^p)(R^q)$, $R^p$ and $R^q$, together with the carbon atom to which they are attached, form a monocyclic 5-, 6-, and 7-membered ring, optionally substituted as described in the Summary. For example, said monocyclic ring is azepanyl or cyclopentyl, each of which is optionally substituted.

$X^4$ has values as set forth in the Summary. For example, certain embodiments are directed to compounds wherein $X^4$ is O, $S(O)_2$, or $N(R^{bx})$. Other embodiments are directed to compounds wherein $X^4$ is O or $N(R^{bx})$. Yet certain embodiments are directed to those wherein $X^4$ is O. Certain embodiments are directed to those wherein $X^4$ is $S(O)_2$. Further embodiments are directed to those wherein $X^4$ is $N(R^{bx})$. $R^{bx}$ has values as set forth in the Summary and herein. For example, in certain embodiments, $R^{bx}$ is hydrogen, alkyl (e.g. methyl), or —$C(O)O(alkyl)$. In certain embodiments, $R^{bx}$ is hydrogen.

In certain embodiments, $X^4$ and $A^1$ together is $N=N(R^{cx})$ wherein $R^{cx}$ is as set forth in the Summary and embodiments herein. For example, certain classes of compounds are directed to those wherein $X^4$ and $A^1$ together is $N=N(R^{cx})$ and $R^{cx}$ is alkyl (e.g. $C_1$-$C_4$ alkyl such as, but not limited to, tert-butyl).

$R^x$ and z have values as described generally in the Summary and herein. In certain embodiments, z is 0, 1, or 2. Each occurrence of $R^x$ is, for example, independently $G^{1d}$, $C_1$-$C_4$ alkyl, $C_2$-$C_4$ alkenyl, $C_2$-$C_4$ alkynyl, halogen, $NO_2$, $C_1$-$C_4$ haloalkyl, —CN, —$OR^f$, —$C(O)OR^f$, or —$S(O)_2N(R^f)_2$ wherein $G^{1d}$ and $R^f$ are as described generally in the Summary. In certain embodiments, z is 1, and $R^x$ is $C_1$-$C_4$ haloalkyl (e.g. trifluoromethyl). In certain embodiments, $R^x$ is $C_1$-$C_4$ haloalkyl (e.g. trifluoromethyl), halogen, $NO_2$, —CN, —$C(O)OR^f$, —$S(O)_2N(R^f)_2$, or $C_1$-$C_4$ alkyl (e.g. methyl) wherein $R^f$ is as generally described in the Summary and herein. $R^f$, or example, is hydrogen or $C_1$-$C_4$ alkyl.

It is appreciated that the present invention contemplates compounds of formula (I) (Ia), (Ib), (Ic), (Id), (Ie), (II) (IIa), (IIb), (IIc), (IId), or (IIe) with combinations of the above embodiments, including particular, more particular and preferred embodiments.

For example, one aspect is directed to a group of compounds of formula (I) (Ia), (Ib), (Ic), (Id), (Ie), (II) (IIa), (IIb), (IIc), (IId), or (IIe) include, but not limited to, wherein $X^4$ is O, $S(O)_2$, or $N(R^{bx})$, and $R^{21}$, $R^{22}$, $R^{23}$, $R^{24}$, $R^{25}$ are each independently alkyl, alkenyl, alkynyl, haloalkyl, —$(CR^{2a}R^{2b})_{q4}$—O-alkyl, —$(CR^{2a}R^{2b})_{q4}$—O-haloalkyl, —$(CR^{2a}R^{2b})_{q4}$—O-$G^{2a}$, —$(CR^{2a}R^{2b})_{q4}$—O—$(CR^{2c}R^{2d})_{q3}$-$G^{2a}$, —$(CR^{2a}R^{2b})_{q5}$-$G^{2b}$, or —$(CR^{2a}R^{2b})_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O or $N(R^{bx})$, and $R^{21}$, $R^{22}$, $R^{23}$, $R^{24}$, $R^{25}$ are each independently alkyl, alkenyl, alkynyl, haloalkyl, —$(CR^{2a}R^{2b})_{q4}$—O-alkyl, —$(CR^{2a}R^{2b})_{q4}$—O-haloalkyl, —$(CR^{2a}R^{2b})_{q4}$—O-$G^{2a}$, —$(CR^{2a}R^{2b})_{q4}$—O—$(CR^{2c}R^{2d})_{q3}$-$G^{2a}$, —$(CR^{2a}R^{2b})_{q5}$-$G^{2b}$, or —$(CR^{2a}R^{2b})_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O, and $R^{21}$, $R^{22}$, $R^{23}$, $R^{24}$, $R^{25}$ are each independently alkyl, alkenyl, alkynyl, haloalkyl, —$(CR^{2a}R^{2b})_{q4}$—O-alkyl, —$(CR^{2a}R^{2b})_{q4}$—O-haloalkyl, —$(CR^{2a}R^{2b})_{q4}$—O-$G^{2a}$, —$(CR^{2a}R^{2b})_{q4}$—O—$(CR^{2c}R^{2d})_{q3}$-$G^{2a}$, —$(CR^{2a}R^{2b})_{q5}$-$G^{2b}$, or —$(CR^{2a}R^{2b})_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein $X^4$ is $N(R^{bx})$, and $R^{21}$, $R^{22}$, $R^{23}$, $R^{24}$, $R^{25}$ are each independently alkyl, alkenyl, alkynyl, haloalkyl, —$(CR^{2a}R^{2b})_{q4}$—O-alkyl, —$(CR^{2a}R^{2b})_{q4}$—O-haloalkyl, —$(CR^{2a}R^{2b})_{q4}$—O-$G^{2a}$, —$(CR^{2a}R^{2b})_{q4}$—O—$(CR^{2c}R^{2d})_{q3}$-$G^{2a}$, —$(CR^{2a}R^{2b})_{q5}$-$G^{2b}$, or —$(CR^{2a}R^{2b})_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein $X^4$ is $S(O)_2$, and $R^{21}$, $R^{22}$, $R^{23}$, $R^{24}$, $R^{25}$ are each independently alkyl, alkenyl, alkynyl, haloalkyl, —$(CR^{2a}R^{2b})_{q4}$—O-alkyl, —$(CR^{2a}R^{2b})_{q4}$—O-haloalkyl, —(CR$^{2a}$R$^{2b}$)$_{q4}$—O-G$^{2a}$, —(CR$^{2a}$R$^{2b}$)$_{q4}$—O—(CR$^{2c}$R$^{2d}$)$_{q3}$-G$^{2a}$, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ and A$^1$ together is N=N(R$^{cx}$), and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q4}$—O-G$^{2a}$, —(CR$^{2a}$R$^{2b}$)$_{q4}$—O—(CR$^{2c}$R$^{2d}$)$_{q3}$-G$^{2a}$, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, S(O)$_2$, or N(R$^{bx}$), and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O or N(R$^{bx}$), and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ is N(R$^{bx}$), and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ is S(O)$_2$, and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ and A$^1$ together is N=N(R$^{cx}$), and R$^{21}$, R$^{22}$, R$^{23}$, R$^{24}$, R$^{25}$ are each independently alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, S(O)$_2$, or N(R$^{bx}$), and R$^{21}$, R$^{22}$, R$^{23}$, R$^{24}$, R$^{25}$ are each independently alkyl or —(CR$^{2a}$R$^{2b}$)$_{q5}$-G$^{2b}$.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O or N(R$^{bx}$), and R$^{21}$, R$^{22}$, R$^{23}$, R$^{24}$, R$^{25}$ are each independently alkyl or —(CR$^{2a}$R$^{2b}$)$_{q5}$-G$^{2b}$.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, and R$^{21}$, R$^{22}$, R$^{23}$, R$^{24}$, R$^{25}$ are each independently alkyl or —(CR$^{2a}$R$^{2b}$)$_{q5}$-G$^{2b}$.

Other examples of a group of compounds of formula (I) (Ia), (Ib), (Ic), (Id), (Ie), (II) (IIa), (IIb), (IIc), (IId), or (IIe) include, but not limited to, wherein X$^4$ is N(R$^{bx}$), and R$^{21}$, R$^{22}$, R$^{23}$, R$^{24}$, R$^{25}$ are each independently alkyl or —(CR$^{2a}$R$^{2b}$)$_{q5}$-G$^{2b}$.

Other examples of a group of compounds of formula (I) (Ia), (Ib), (Ic), (Id), (Ie), (II) (IIa), (IIb), (IIc), (IId), or (IIe) include, but not limited to, wherein X$^4$ is S(O)$_2$, and R$^{21}$, R$^{22}$, R$^{23}$, R$^{24}$, R$^{25}$ are each independently alkyl or —(CR$^{2a}$R$^{2b}$)$_{q5}$-G$^{2b}$.

Other examples of a group of compounds of formula (I) (Ia), (Ib), (Ic), (Id), (Ie), (II) (IIa), (IIb), (IIc), (IId), or (IIe) include, but not limited to, wherein X$^4$ and A$^1$ together is N=N(R$^{cx}$), and R$^{21}$, R$^{22}$, R$^{23}$, R$^{24}$, R$^{25}$ are each independently alkyl or —(CR$^{2a}$R$^{2b}$)$_{q5}$-G$^{2b}$.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, S(O)$_2$, or N(R$^{bx}$), and R$^{21}$, R$^{22}$, R$^{23}$, R$^{24}$, R$^{25}$ are each independently alkyl or haloalkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O or N(R$^{bx}$), and R$^{21}$, R$^{22}$, R$^{23}$, R$^{24}$, R$^{25}$ are each independently alkyl or haloalkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, and R$^{21}$, R$^{22}$, R$^{23}$, R$^{24}$, R$^{25}$ are each independently alkyl or haloalkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is N(R$^{bx}$), and R$^{21}$, R$^{22}$, R$^{23}$, R$^{24}$, R$^{25}$ are each independently alkyl or haloalkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is S(O)$_2$, and R$^{21}$, R$^{22}$, R$^{23}$, R$^{24}$, R$^{25}$ are each independently alkyl or haloalkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ and A$^1$ together is N=N(R$^{cx}$), and R$^{21}$, R$^{22}$, R$^{23}$, R$^{24}$, R$^{25}$ are each independently alkyl or haloalkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, S(O)$_2$, or N(R$^{bx}$), and R$^{21}$, R$^{22}$, R$^{23}$, R$^{24}$, R$^{25}$ are each independently alkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O or N(R$^{bx}$), and R$^{21}$, R$^{22}$, R$^{23}$, R$^{24}$, R$^{25}$ are each independently alkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is O, and R$^{21}$, R$^{22}$, R$^{23}$, R$^{24}$, R$^{25}$ are each independently alkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is N(R$^{bx}$), and R$^{21}$, R$^{22}$, R$^{23}$, R$^{24}$, R$^{25}$ are each independently alkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ is S(O)$_2$, and R$^{21}$, R$^{22}$, R$^{23}$, R$^{24}$, R$^{25}$ are each independently alkyl.

Other examples of a group of compounds of formula (I) (Ia), (Ib), (Ic), (Id), (Ie), (II) (IIa), (IIb), (IIc), (IId), or (IIe) include, but not limited to, wherein X$^4$ and A$^1$ together is N=N(R$^{cx}$), and R$^{21}$, R$^{22}$, R$^{23}$, R$^{24}$, R$^{25}$ are each independently alkyl.

Other examples of a group of compounds of formula (I) (Ia), (Ib), (Ic), (Id), (Ie), (II) (IIa), (IIb), (IIc), (IId), or (IIe)

include, but not limited to, wherein $X^4$ is O, $S(O)_2$, or $N(R^{bx})$, and $R^{21}$, $R^{22}$, $R^{23}$, $R^{24}$, $R^{25}$ are each independently —$(CR^{2a}R^{2b})_{q5}$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O or $N(R^{bx})$, and $R^{21}$, $R^{22}$, $R^{23}$, $R^{24}$, $R^{25}$ are each independently —$(CR^{2a}R^{2b})_{q5}$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O, and $R^{21}$, $R^{22}$, $R^{23}$, $R^{24}$, $R^{25}$ are each independently —$(CR^{2a}R^{2b})_{q5}$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is $N(R^{bx})$, and $R^{21}$, $R^{22}$, $R^{23}$, $R^{24}$, $R^{25}$ are each independently —$(CR^{2a}R^{2b})_{q5}$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is $S(O)_2$, and $R^{21}$, $R^{22}$, $R^{23}$, $R^{24}$, $R^{25}$ are each independently —$(CR^{2a}R^{2b})_{q5}$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ and $A^1$ together is N=$N(R^{cx})$, and $R^{21}$, $R^{22}$, $R^{23}$, $R^{24}$, $R^{25}$ are each independently —$(CR^{2a}R^{2b})_{q5}$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O, $S(O)_2$, or $N(R^{bx})$, and $R^{21}$, $R^{22}$, $R^{23}$, $R^{24}$, $R^{25}$ are each independently —$(CH_2)$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O or $N(R^{bx})$, and $R^{21}$, $R^{22}$, $R^{23}$, $R^{24}$, $R^{25}$ are each independently —$(CH_2)$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is O, and $R^{21}$, $R^{22}$, $R^{23}$, $R^{24}$, $R^{25}$ are each independently —$(CH_2)$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is $N(R^{bx})$, and $R^{21}$, $R^{22}$, $R^{23}$, $R^{24}$, $R^{25}$ are each independently —$(CH_2)$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ is $S(O)_2$, and $R^{21}$, $R^{22}$, $R^{23}$, $R^{24}$, $R^{25}$ are each independently —$(CH_2)$-$G^{2b}$.

Other examples of a group of compounds of formula (I) (Ia), (Ib), (Ic), (Id), (Ie), (II) (IIa), (IIb), (IIc), (IId), or (IIe) include, but not limited to, wherein $X^4$ and $A^1$ together is N=$N(R^{cx})$, and $R^{21}$, $R^{22}$, $R^{23}$, $R^{24}$, $R^{25}$ are each independently —$(CH_2)$-$G^{2b}$.

Within each group of compounds of formula (I) (Ia), (Ib), (Ic), (Id), (Ie), (II) (IIa), (IIb), (IIc), (IId), or (IIe) described herein, the variables $A^1$, $R^{2a}$, $R^{2b}$, $R^{2c}$, $R^{2d}$, $R^{bx}$, $R^{cx}$, q3, q4, q5, $G^{2a}$, $G^{2b}$, $R^3$-$R^{16}$, $X^1$, $X^2$, $X^3$, $R^x$, and z have meanings as set forth in the Summary and the embodiments herein.

Thus, for certain group of compounds of formula (I) (Ia), (Ib), (Ic), (Id), (Ie), (II) (IIa), (IIb), (IIc), (IId), or (IIe) as described herein above, examples of a subgroup include, but are not limited to, those wherein $A^1$ is —$N(R^b)(R^c)$.

Yet other examples of a subgroup of compounds of formula (I) (Ia), (Ib), (Ic), (Id), (Ie), (II) (IIa), (IIb), (IIc), (IId), or (IIe) as described herein above include, but are not limited to, those wherein $A^1$ is —$N(R^b)C(O)R^a$, —$N(R^b)C(O)OR^d$, —$N(R^b)C(O)N(R^b)(R^c)$, or —N=$C(R^p)(R^q)$.

Yet other examples of a subgroup of compounds of formula (I) (Ia), (Ib), (Ic), (Id), (Ie), (II) (IIa), (IIb), (IIc), (IId), or (IIe) as described herein above include, but are not limited to, those wherein $A^1$ is —$N(R^b)C(O)R^a$, —$N(R^b)C(O)OR^d$, or —$N(R^b)C(O)N(R^b)(R^c)$.

Yet other examples of a subgroup of compounds of formula (I) (Ia), (Ib), (Ic), (Id), (Ie), (II) (IIa), (IIb), (IIc), (IId), or (IIe) as described herein above include, but are not limited to, those wherein $A^1$ is —N=$C(R^p)(R^q)$.

Within each group and subgroup of compounds of formula (I) (Ia), (Ib), (Ic), (Id), (Ie), (II) (IIa), (IIb), (IIc), (IId), or (IIe) as described herein above, the variables $R^a$, $R^b$, $R^c$, $R^d$, $R^p$, $R^q$, $R^{2a}$, $R^{2b}$, $R^{2c}$, $R^{2d}$, $R^{bx}$, $R^{cx}$, q3, q4, q5, $G^{2a}$, $G^{2b}$, $R^3$-$R^{16}$, $X^1$, $X^2$, $X^3$, $R^x$, and z have meanings as set forth in the Summary and the embodiments herein above. For example, in certain compounds, $R^{bx}$ is hydrogen, alkyl, or —C(O)O (alkyl). In certain embodiments, $R^{bx}$, for example, is hydrogen.

Exemplary compounds contemplated include, but are not limited to:

2-[(tert-butylamino)oxy]-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-{(2Z)-2-[(6-methylpyridin-2-yl)methylene]hydrazino}-5-(trifluoromethyl)benzamide;

tert-butyl 2-({[(2Z)-3-butyl-5-tert-butyl-1,3,4-thiadiazol-2(3H)-ylidene]amino}carbonyl)-4-(trifluoromethyl)phenoxycarbamate;

2-[(tert-butylamino)oxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-[(2Z)-3-butyl-5-tert-butyl-1,3,4-thiadiazol-2(3H)-ylidene]-2-[2-(4-fluorobenzoyl)hydrazino]-5-(trifluoromethyl)benzamide;

N-[(2Z)-3-butyl-5-tert-butyl-1,3,4-thiadiazol-2(3H)-ylidene]-2-[(isopropylamino)oxy]-5-(trifluoromethyl)benzamide;

2-[(tert-butylamino)oxy]-N-[(2Z)-3-butyl-5-(1-methylcyclopropyl)-1,3,4-thiadiazol-2(3H)-ylidene]-5-(trifluoromethyl)benzamide;

2-[(tert-butylamino)oxy]-N-[(3E)-5-tert-butyl-2-(cyclopropylmethyl)-1-methyl-1,2-dihydro-3H-pyrazol-3-ylidene]-5-(trifluoromethyl)benzamide;

2-[(tert-butylamino)oxy]-N-[(2Z)-5-tert-butyl-3-(tetrahydro-2H-pyran-2-ylmethyl)-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[(E)-tert-butyldiazenyl]-5-(trifluoromethyl)benzamide;

2-[(tert-butylamino)oxy]-N-[(3E)-2-butyl-5-tert-butyl-1-methyl-1,2-dihydro-3H-pyrazol-3-ylidene]-5-(trifluoromethyl)benzamide;

N-[(2Z)-3-butyl-5-tert-butyl-1,3,4-thiadiazol-2(3H)-ylidene]-5-(trifluoromethyl)-2-({[(1E)-1,2,2-trimethylpropylidene]amino}oxy)benzamide;

2-[(tert-butylamino)oxy]-N-[(2Z)-5-tert-butyl-3-(3-cyanopropyl)-1,3,4-thiadiazol-2(3H)-ylidene]-5-(trifluoromethyl)benzamide;

2-[(tert-butylamino)oxy]-N-[(2Z)-5-tert-butyl-3-isobutyl-1,3,4-thiadiazol-2(3H)-ylidene]-5-(trifluoromethyl)benzamide;

2-[(tert-butylamino)oxy]-N-[(2Z)-5-tert-butyl-3-[(2R)-tetrahydrofuran-2-ylmethyl]-1,3,4-thiadiazol-2(3H)-ylidene]-5-(trifluoromethyl)benzamide;

2-[(acetylamino)oxy]-N-[(2Z)-3-butyl-5-tert-butyl-1,3,4-thiadiazol-2(3H)-ylidene]-5-(trifluoromethyl)benzamide;

2-[(tert-butylamino)oxy]-N-[(3E)-5-tert-butyl-2-(cyclobutylmethyl)-1-methyl-1,2-dihydro-3H-pyrazol-3-ylidene]-5-(trifluoromethyl)benzamide;

2-[(tert-butylamino)oxy]-N-[(3E)-5-tert-butyl-1-methyl-2-(3,3,3-trifluoropropyl)-1,2-dihydro-3H-pyrazol-3-ylidene]-5-(trifluoromethyl)benzamide;

2-[(tert-butylamino)oxy]-N-[(2E)-1-butyl-4-tert-butylpyridin-2(1H)-ylidene]-5-(trifluoromethyl)benzamide;

2-[(tert-butylamino)oxy]-N-[(2Z)-5-tert-butyl-3-(2-methoxyethyl)-1,3,4-thiadiazol-2(3H)-ylidene]-5-(trifluoromethyl)benzamide;

N-[(3E)-2-butyl-5-tert-butyl-1-methyl-1,2-dihydro-3H-pyrazol-3-ylidene]-2-[(isopropylamino)oxy]-5-(trifluoromethyl)benzamide;

2-[(tert-butylamino)oxy]-N-[(2E)-1-butyl-5-tert-butylpyridin-2(1H)-ylidene]-5-(trifluoromethyl)benzamide;

2-[(tert-butylamino)oxy]-N-{(3E)-5-tert-butyl-1-methyl-2-[(2R)-tetrahydrofuran-2-ylmethyl]-1,2-dihydro-3H-pyrazol-3-ylidene}-5-cyanobenzamide;

2-[(tert-butylamino)oxy]-N-[(2Z)-3-butyl-5-tert-butyl-1,3,4-thiadiazol-2(3H)-ylidene]-5-chlorobenzamide;

2-[(tert-butylamino)oxy]-N-[(2Z)-5-tert-butyl-3-(cyclopropylmethyl)-1,3,4-thiadiazol-2(3H)-ylidene]-5-(trifluoromethyl)benzamide;

2-[(tert-butylamino)oxy]-N-[(2Z)-5-tert-butyl-3-(4,4,4-trifluorobutyl)-1,3,4-thiadiazol-2(3H)-ylidene]-5-(trifluoromethyl)benzamide;

2-[(tert-butylamino)oxy]-N-[(2Z)-5-tert-butyl-3-(cyclobutylmethyl)-1,3,4-thiadiazol-2(3H)-ylidene]-5-(trifluoromethyl)benzamide;

2-({[1-amino-2,2-dimethylpropylidene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-{[(1-methylethylidene)amino]oxy}-5-(trifluoromethyl)benzamide;

2-[(tert-butylamino)oxy]-N-{(3E)-5-tert-butyl-1-methyl-2-[(2R)-tetrahydrofuran-2-ylmethyl]-1,2-dihydro-3H-pyrazol-3-ylidene}-5-chlorobenzamide;

N-[(2Z)-3-butyl-5-tert-butyl-1,3,4-thiadiazol-2(3H)-ylidene]-2-{[(2,2-dimethylpropanoyl)amino]oxy}-5-(trifluoromethyl)benzamide;

2-[(tert-butylamino)oxy]-N-[(2Z)-3-butyl-5-tert-butyl-1,3,4-thiadiazol-2(3H)-ylidene]-4-(trifluoromethyl)benzamide;

N-[(2Z)-3-butyl-5-tert-butyl-1,3,4-thiadiazol-2(3H)-ylidene]-2-[(dimethylamino)oxy]-5-(trifluoromethyl)benzamide;

N-[(2Z)-3-butyl-5-tert-butyl-1,3,4-thiadiazol-2(3H)-ylidene]-5-(trifluoromethyl)-2-({[2,2,2-trifluoro-1-methylethylidene]amino}oxy)benzamide;

N-[(2Z)-3-butyl-5-tert-butyl-1,3,4-thiadiazol-2(3H)-ylidene]-2-(2-tert-butylhydrazino)-5-(trifluoromethyl)benzamide;

2-[(tert-butylamino)oxy]-N-[(2Z)-5-tert-butyl-3-(4-fluorobutyl)-1,3,4-thiadiazol-2(3H)-ylidene]-5-(trifluoromethyl)benzamide;

2-({[1-amino-2-methylpropylidene]amino}oxy)-N-[(2Z)-3-butyl-5-tert-butyl-1,3,4-thiadiazol-2(3H)-ylidene]-5-(trifluoromethyl)benzamide;

ethyl amino {[2-({[(2Z)-3-butyl-5-tert-butyl-1,3,4-thiadiazol-2(3H)-ylidene]amino}carbonyl)-4-(trifluoromethyl)phenoxy]imino}acetate;

2-[(tert-butylamino)oxy]-N-[(2Z)-5-tert-butyl-3-(oxetan-2-ylmethyl)-1,3,4-thiadiazol-2(3H)-ylidene]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-(trifluoromethyl)-2-({[(1E)-2,2,2-trifluoro-1-methylethylidene]amino}oxy)benzamide;

N-[(3E)-5-tert-butyl-2-(cyclopropylmethyl)-1-methyl-1,2-dihydro-3H-pyrazol-3-ylidene]-5-(trifluoromethyl)-2-({[(1E)-2,2,2-trifluoro-1-methylethylidene]amino}oxy)benzamide;

N-[(2Z)-3-butyl-5-tert-butyl-1,3,4-thiadiazol-2(3H)-ylidene]-2-({[(1E)-1-methyl-2-oxopropylidene]amino}oxy)-5-(trifluoromethyl)benzamide;

tert-butyl 2-[2-({[(2Z)-3-butyl-5-tert-butyl-1,3,4-thiadiazol-2(3H)-ylidene]amino}carbonyl)-4-(trifluoromethyl)phenyl]hydrazinecarboxylate;

2-({[amino(4-fluorophenyl)methylene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-(2-pyridin-2-ylhydrazino)-5-(trifluoromethyl)benzamide;

tert-butyl 2-[2-({[(2Z)-3-butyl-5-tert-butyl-1,3,4-thiadiazol-2(3H)-ylidene]amino}carbonyl)-4-(trifluoromethyl)phenyl]-1,2-dimethylhydrazinecarboxylate;

2-({[1-amino ethylidene]amino}oxy)-N-[(2Z)-3-butyl-5-tert-butyl-1,3,4-thiadiazol-2(3H)-ylidene]-5-(trifluoromethyl)benzamide;

2-({[1-aminopropylidene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[2-(1-methylethylidene)hydrazino]-5-(trifluoromethyl)benzamide;

2-({[amino(cyclopropyl)methylene]amino}oxy)-N-[(2Z)-3-butyl-5-tert-butyl-1,3,4-thiadiazol-2(3H)-ylidene]-5-(trifluoromethyl)benzamide;

2-{[azepan-2-ylideneamino]oxy}-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[(cyclopentylideneamino)oxy]-5-(trifluoromethyl)benzamide;

N-[(2Z)-3-butyl-5-tert-butyl-1,3,4-thiadiazol-2(3H)-ylidene]-2-(2-isonicotinoylhydrazino)-5-(trifluoromethyl)benzamide;

methyl 2-[2-({[(2Z)-3-butyl-5-tert-butyl-1,3,4-thiadiazol-2(3H)-ylidene]amino}carbonyl)-4-(trifluoromethyl)phenyl]hydrazinecarboxylate;

N-[(2Z)-3-butyl-5-tert-butyl-1,3,4-thiadiazol-2(3H)-ylidene]-2-[2-(2,2-dimethylpropanoyl)hydrazino]-5-(trifluoromethyl)benzamide;

N-[(3E)-2-butyl-5-tert-butyl-1-methyl-1,2-dihydro-3H-pyrazol-3-ylidene]-5-(trifluoromethyl)-2-({[(1E)-2,2,2-trifluoro-1-methylethylidene]amino}oxy)benzamide;

2-[(tert-butylamino)oxy]-N-[(3E)-2-(cyclopentylmethyl)-5-isopropyl-1-methyl-1,2-dihydro-3H-pyrazol-3-ylidene]-5-(trifluoromethyl)benzamide;

2-({[amino(pyridin-2-yl)methylene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[2-(pyridin-3-ylcarbonyl)hydrazino]-5-(trifluoromethyl)benzamide;

N-[(3E)-2-butyl-5-tert-butyl-1-methyl-1,2-dihydro-3H-pyrazol-3-ylidene]-2-[2-(2,2-dimethylpropanoyl)hydrazino]-5-(trifluoromethyl)benzamide;

N-[(3E)-2-butyl-5-tert-butyl-1-methyl-1,2-dihydro-3H-pyrazol-3-ylidene]-2-[2-(pyridin-3-ylcarbonyl)hydrazino]-5-(trifluoromethyl)benzamide;

N-[(3E)-2-butyl-5-tert-butyl-1-methyl-1,2-dihydro-3H-pyrazol-3-ylidene]-2-(2-isonicotinoylhydrazino)-5-(trifluoromethyl)benzamide;

2-[2-({[(2Z)-3-butyl-5-tert-butyl-1,3,4-thiadiazol-2(3H)-ylidene]amino}carbonyl)-4-(trifluoromethyl)phenyl]hydrazinecarboxamide;

2-(2-benzylhydrazino)-N-[(2Z)-3-butyl-5-tert-butyl-1,3,4-thiadiazol-2(3H)-ylidene]-5-(trifluoromethyl)benzamide;

2-({[amino(pyridin-4-yl)methylene]amino}oxy)-N-[(2Z)-3-butyl-5-tert-butyl-1,3,4-thiadiazol-2(3H)-ylidene]-5-(trifluoromethyl)benzamide;

2-({[amino(pyridin-3-yl)methylene]amino}oxy)-N-[(2Z)-3-butyl-5-tert-butyl-1,3,4-thiadiazol-2(3H)-ylidene]-5-(trifluoromethyl)benzamide;

tert-butyl (2E)-1-[2-({[(2Z)-3-butyl-5-tert-butyl-1,3,4-thiadiazol-2(3H)-ylidene]amino}carbonyl)-4-(trifluoromethyl)phenyl]-2-[(6-methylpyridin-2-yl)methylene]hydrazinecarboxylate; and N-[(2Z)-3-butyl-5-tert-butyl-1,3,4-thiadiazol-2(3H)-ylidene]-2-{(2E)-2-[(6-methylpyridin-2-yl)methylene]hydrazino}-5-(trifluoromethyl)benzamide;

or pharmaceutically acceptable salts or solvates thereof.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

C. BIOLOGICAL DATA (i) In Vitro Methods:

$CB_2$ and $CB_1$ Radioligand Binding Assays:

The $CB_1$ and $CB_2$ radioligand binding assays described herein are utilized to ascertain the affinity of compounds of the present application for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 µg/well for human $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 µL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP 55,940 ranging from 0.01 to 8 nM. Competition experiments were conducted with 0.5 nM [$^3$H] CP 55,940 and five concentrations (0.01 nM to 10 µM) of displacing ligands. The addition of 10 µM unlabeled CP 55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 µg/well for rat $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP 55,940 ranging from 0.01 to 8 nM. Competition experiments were conducted with 0.5 nM [$^3$H] CP 55,940 and five concentrations of displacing ligands selected from the range of 0.01 nM to 10 The addition of 10 µM unlabeled CP 55,940 (Tocris, Ellisville, Mo.) was used to assess nonspecific binding.

Compounds tested with the above assay have equilibrium dissociation constants (K) of less than about 1,000 nM, for example, less than about 400 nM, or less than about 200 nM, or less than about 100 nM.

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H]CP 55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP 55,940 and five concentrations (1 nM to 10 µM) of displacing ligands. The addition of 10 µM unlabeled CP 55,940 (Tocris, Ellisville, Mo.) was used to assess nonspecific binding. Compounds tested exhibit about 10×-1000× weaker binding affinity for $CB_1$ receptors than for $CB_2$. These results show that the compounds of the present application preferably bind to $CB_2$ receptors, therefore are selective ligands for the $CB_2$ receptor.

$CB_2$ and $CB_1$ Cyclase Functional Assays:

The cyclase functional assays were performed using the HitHunter™ cAMP assay kit from DiscoveRx (Fremont, Calif.) according to vendor's protocol. Briefly, HEK cells expressing $CB_2$ or $CB_1$ receptors (rat or human) were detached using cell dissociation buffer (Invitrogen, Carlsbad, Calif.), dispersed and placed in suspension at 10,000 cells per well in 96 well plates prior to the assay. Cell suspensions were incubated at 37° C. for 20 min with variable concentrations of test ligands and or 10 µM CP 55,940-positive control in the presence of a fixed concentration of forskolin (18 µM for rat $CB_2$ and 37 µM for rat $CB_1$) in Dulbescco's phosphate-buffered saline (Invitrogen, Carlsbad, Calif.) supplemented with bovine serum albumin (0.01% final concentration). The reactions were terminated by the addition of lysis buffer and the luminescence was detected following the procedure according to the manufacturer's instructions. $EC_{50}$ values were calculated using sigmoidal dose-response curve fitting from Prism (GraphPad). Compounds tested are more potent at activating $CB_2$ vs. $CB_1$ receptors in the described cyclase assays (Table 1).

TABLE 1

| Example | human CB$_2$ (K$_i$, nM) | rat CB$_2$ (K$_i$, nM) | rat CB$_2$ cyclase (EC$_{50}$, nM) | rCB$_1$ cyclase (EC$_{50}$, nM) |
| --- | --- | --- | --- | --- |
| 34 | 11 | 1.9 | 0.43 | >27000 |
| 35 | 185 | 20 | | |
| 141 | 0.32 | 2.3 | 1.12 | 273 |
| 142 | 24 | 9.4 | | >27000 |
| 144 | 0.6 | 0.8 | 0.22 | 415 |
| 145 | 16 | 2.5 | | |
| 146 | 54 | 14 | | |
| 147 | 1.7 | 0.7 | | |
| 148 | 6.2 | 15 | | |
| 149 | 77 | 5.5 | | |
| 150 | 216 | 283 | | |
| 151 | 4.3 | 1.2 | 0.13 | 938 |
| 152 | 29 | 31 | | |
| 153 | 10 | 3.2 | 0.24 | >27000 |
| 154 | 1.0 | 1.0 | 1.5 | 58 |
| 155 | 27 | 14 | | |
| 156 | 68 | 10 | | |
| 157 | 128 | 9.4 | | |
| 158 | 39 | 3.6 | | |
| 159 | 16 | 5.2 | | |
| 160 | 88 | 5.9 | | |
| 161 | 209 | 11 | | |
| 162 | 8.5 | 0.6 | | |
| 163 | 16 | 3.0 | | |
| 164 | 1.8 | 0.3 | 0.28 | 1020 |
| 165 | 2.8 | 0.8 | 0.93 | 925 |
| 166 | 65 | 43 | 3.14 | 6960 |
| 167 | 12 | 5.2 | | |
| 168 | 52 | 21 | | |
| 169 | 0.6 | 0.6 | | |
| 170 | 127 | 6.3 | | |
| 171 | 21 | 4.9 | | |
| 172 | 52 | 60 | 28 | >27000 |
| 174 | 6.2 | 1.1 | | |
| 175 | 5.3 | 2.9 | | |
| 176 | 6.1 | 1.7 | | |
| 177 | 15 | 7.3 | | |
| 178 | >1000 | 40 | | |
| 179 | >1000 | 288 | | |
| 180 | 18 | 11 | | |
| 181 | 1.0 | 1.7 | | |
| 182 | 21 | 7.0 | | |
| 183 | 32 | 5.6 | | |
| 184 | 279 | 35 | | |
| 185 | 16 | 3.6 | | |
| 186 | 5.1 | 2.7 | | |
| 187 | 247 | 120 | | |
| 188 | 2.5 | 0.9 | | |
| 189 | 1.6 | 4.9 | | |
| 190 | 1.7 | 3.2 | | |
| 191 | 0.8 | 0.9 | | |
| 192 | 0.7 | 0.7 | | |
| 193 | 0.4 | 0.5 | | |
| 194 | 12 | 40 | | |
| 196 | 18 | 4.1 | | |
| 197 | 1.1 | 0.7 | | |
| 198 | 0.4 | 1.7 | | |
| 199 | 2.5 | 2.2 | | |
| 200 | 0.7 | 1.3 | | |
| 201 | 47 | 5.2 | | |
| 202 | 43 | 36 | | |
| 203 | 68 | 33 | | |
| 204 | 87 | 13 | | |
| 205 | 44 | 43 | | |

(ii) In Vivo Data: Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incision Model of Postoperative Pain

A skin incision model of postoperative pain was measured using the procedures as described in Brennan et al., 1996, Pain, 64, 493. All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia is assessed as described below. To evaluate the anti-nociceptive effects, the vehicle or test compounds were administered i.p. or orally to the animals 90 minutes following skin incision. Tactile allodynia was assessed 30 minutes after compound administration.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441). A compound tested showed a statistically significant change in paw withdrawal latency versus a saline vehicle at less than about 300 micromoles/kg, for example, at less than about 100 micromoles/kg.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) was used to test the compounds of the present application The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds was also assessed in several control groups, including naive, sham-operated, and saline infused animals as well as in the contralateral paws of nerve-injured rats. Compounds tested showed a statistically significant change in paw withdrawal latency versus a saline vehicle at less than about 300 micromoles/kg, for example, at less than about 100 micromoles/kg.

Capsaicin-Induced Secondary Mechanical Hypersensitivity:

Rats were allowed to acclimate to the study room for 1 h. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were administered (i.p. or p.o.) 30 min before testing (150 min post-capsaicin).

Tactile allodynia was measured as described above. Compounds tested showed a statistically significant change in paw withdrawal latency versus a saline vehicle at less than about 300 micromoles/kg, for example, at less than about 100 micromoles/kg.

Sodium Iodoacetate-Induced Knee Joint Osteoarthritic Pain Model

Unilateral knee joint osteoarthritis was induced in the rats by a single intra-articular (i.a.) injection of sodium iodoacetate (3 mg in 0.05 mL sterile isotonic saline) into the right knee joint cavity under light isoflurane anesthesia using a 26 G needle. The dose of the sodium iodoacetate (3 mg/i.a. injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax)(gram force)/kg body weight for each animal. The analgesic effects of test compounds were determined 20 days following the i.a. injection of sodium iodoacetate. The vehicle control group for each compound being tested was assigned 0% whereas the age matched nave group was assigned as being 100% (normal). The % effect for each dose group was then expressed as % return to normalcy compared to the nave group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing may last for any time greater than one day. A typical duration of repeated daily dosing is about 5 days to about 12 days.

Compounds tested showed a statistically significant change in hind limb grip force strength versus a saline vehicle at less than about 300 μmoles/kg in the iodoacetate-induced model of osteoarthritic pain following a single dose, for example, at less than about 50 micromoles/kg in the iodoacetate-induced model of osteoarthritic pain following a single dose. Compounds tested also showed a statistically significant change in hind limb grip force strength versus a saline vehicle at less than about 30 μmoles/kg in the iodoacetate-induced model of osteoarthritic pain following repeated daily administration for 5 to 12 days, for example, at less than about 5 micromoles/kg in the iodoacetate-induced model of osteoarthritic pain following repeated daily administration for 5 to 12 days.

Chronic Constriction Injury Model of Neuropathic Pain

A model of chronic constriction injury-induced (CCI) neuropathic pain was produced in rats by following the method of Bennett and Xie (Pain, 1988, 33:87). Following sterilization and anesthetic procedures, a 1.5 cm incision was made dorsal to the pelvis, and the biceps femoris and gluteous superficialis (right side) were separated. The right common sciatic nerve was exposed/isolated, and loosely ligated by 4 ligatures of chromic gut (5-0) with <1 mm spacing using hemostats and forceps. The wound was sutured (layer of muscle closed with 6.0 absorbable sutures, and the skin closed with wound clips or tissue glue. The animals were allowed to recover on a warming plate and were returned to their home cages (soft bedding) when able to walk on their own. Loose ligation of the sciatic nerve in rats would lead to the development of neuropathic pain within two weeks. Compounds were tested in the animals two or three weeks post-surgery.

In tactile stimulation experiments, tactile allodynia was measured using calibrated von Frey filaments (Stoelting, Wood Dale, Ill.) as previously described. Rats were placed into inverted individual plastic containers (20×12.5×20 cm) on top of a suspended wire mesh grid, and acclimated to the test chambers for 20 min. The von Frey filaments with different bending forces (starting with the lowest first and then progressively increasing) were presented perpendicularly to the plantar surface of the selected hind paw, and then hold in this position for approximately 8 sec with enough force to cause a slight bend in the filament. Positive responses included an abrupt withdrawal of the hind paw from the stimulus, or flinching behavior immediately following removal of the stimulus. Compounds tested in the CCI model of neuropathic pain showed a statistically significant change in paw withdrawal latency versus a saline vehicle at less than about 300 micromoles/kg, for example, at less than about 100 micromoles/kg. A compound tested also showed a statistically significant change tactile allodynia versus a saline vehicle at less than about 100 μmoles/kg in the CCI model of neuropathic pain following repeated daily administration for 5 to 12 days, for example, at less than about 30 micromoles/kg in the CCI model of neuropathic pain following repeated daily administration for 5 to 12 days.

D. METHODS OF USING THE COMPOUNDS

One embodiment provides methods for treating pain (for example, osteoarthritic pain, inflammatory pain, post-operative pain, neuropathic pain, nociceptive pain, cancer pain, lower back pain, eye pain) in a mammal (including human) in need of such treatment. The methods comprise administering to the mammal therapeutically effective amount of one or more compounds as described herein, or pharmaceutically acceptable salts or solvates thereof, alone or in combination with one or more pharmaceutically acceptable carrier(s). The method further comprises administration of compounds of the invention as a single dose. The method also comprises repeated or chronic administration of compounds of the invention over a period of days, weeks, months, or longer. In certain embodiments, the methods comprise administering to the mammal therapeutically effective amount(s) of one or more of the compounds as described herein, or pharmaceutically acceptable salts or solvates thereof, in combination with one or more nonsteroidal anti-inflammatory drug (NSAID), or other analgesics (for example, acetaminophen, opioids), or combinations thereof, alone or in combination with one or more pharmaceutically acceptable carrier(s).

Another embodiment provides methods for treating disorders selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount(s) of one or more compound described herein or pharmaceutically acceptable salts or solvates thereof, alone or in combination with one or more pharmaceutically acceptable carrier(s).

Yet another embodiment relates to methods for providing neuroprotection in a mammal in need of such treatment. These methods comprise administering to the mammal therapeutically effective amount(s) of one or more compounds described herein or pharmaceutically acceptable salts or solvates thereof, alone or in combination with one or more pharmaceutically acceptable carrier(s).

Another embodiment provides methods for increasing the therapeutic effectiveness or potency of the present compounds by repeated or chronic administration of the compounds or pharmaceutically acceptable salts or solvates thereof, or pharmaceutical composition(s) thereof, over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. —Neuroinflammation occurs in several neurodegenerative diseases, and induction of microglial $CB_2$ receptors has been observed (Carrier, E. J., et al., Current Drug—Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atherosceloris.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the compounds may be required to achieve the desired therapeutic response. "Repeated or chronic administration" refers to the administration of compounds of the invention daily (i.e., every day) or intermittently (i.e., not every day) over a period of days, weeks, months, or longer. In particular, the treatment of chronic painful conditions may necessitate such repeated or chronic administration of the compounds. Compounds administered may become more effective upon repeated or chronic administration such that the therapeutically effective doses on repeated or chronic administration may be lower than the therapeutically effective dose from a single administration.

Present compounds can also be administered as a pharmaceutical composition comprising the compounds of interest in combination with one or more pharmaceutically acceptable carriers. The phrase "therapeutically effective amount" of the compounds means a sufficient amount of the compound(s) to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds described herein may be administered alone, or in combination with one or more other present compounds, or in combination (i.e. co-administered) with one or more additional pharmaceutical agents. For example, one or more compounds, or pharmaceutically acceptable salts or solvates thereof, may be administered in combination with one or more analgesic (e.g. acetaminophen, opioid such as, but not limited to, morphine), or with one or more nonsteroidal anti-inflammatory drug (NSAID), or combinations thereof. Non limiting examples of NSAID include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds of the invention and one or more additional pharmaceutical agents, as well as administration of the compounds of the invention and each additional pharmaceutical agent, in its own separate pharmaceutical dosage formulation. For example, a compound of the invention and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

The total daily dose of the compounds of this invention administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

E. PHARMACEUTICAL COMPOSITIONS

Further provided herein are pharmaceutical compositions that comprise present compounds or pharmaceutically acceptable salts or solvates thereof, formulated together with one or more non-toxic pharmaceutically acceptable carriers.

Another aspect provides pharmaceutical compositions comprising one or more compounds described herein, or pharmaceutically acceptable salts or solvates thereof, and one or more pharmaceutically acceptable carriers, alone or in combination with one or more analgesics (e.g. acetaminophen, opioids), or in combination with one or more nonsteroidal anti-inflammatory drug (NSAID), or a combination thereof.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated herein are compounds of the invention formed by synthetic means or formed by in vivo biotransformation of a prodrug.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

F. GENERAL SYNTHESIS

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds may be prepared by a variety of processes well known for the preparation of compounds of this class. For example, the compounds of the invention wherein the groups $X^1$, $X^3$, $X^4$, $A^1$, $R^3$, $R^4$, $R^5$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{25}$, $R^x$, and z have the meanings as set forth in the summary section unless otherwise noted, can be synthesized as shown in Schemes 1-7.

Abbreviations which have been used in the descriptions of the Schemes and the Examples that follow are: DMA for N,N-dimethylacetamide, DMF for N,N-dimethylformamide, DMSO for dimethyl sulfoxide, dppf for 1,1'-bis(diphenylphosphino)ferrocene, EDCI or EDC for 1-ethyl-3-[3-(dimethylamino)propyl]-carbodiimide hydrochloride, Et$_2$O for diethyl ether, EtOAc for ethyl acetate, Et$_3$N for triethylamine, HOBT for 1-hydroxybenzotriazole hydrate, MeOH for methanol, n-BuLi for n-butyllithium, OTs for tosylate, OMs for mesylate, and THF for tetrahydrofuran.

Scheme 1

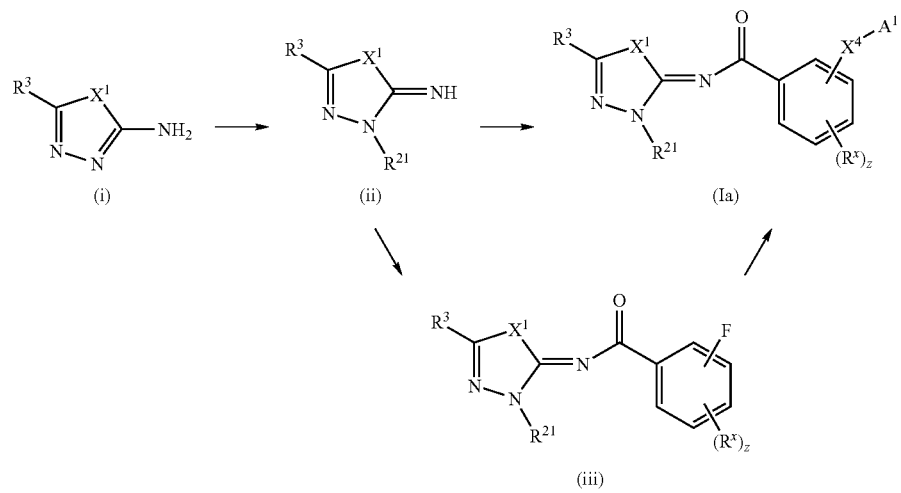

Compounds of formula (Ia) may be prepared according to the methods illustrated in Scheme 1. Amino compounds of formula (i) can be first reacted with compounds of formula $R^{21}$—$X^{101}$, wherein $X^{101}$ is Cl, Br, I, OTs, or OMs, to form the intermediate (ii). This reaction may be performed either neat or in a solvent such as, but not limited to, tetrahydrofuran, dimethylformamide, dimethylsulfoxide or dioxane, at about room temperature or up to 150° C., and optionally in the presence of a catalyst such as but not limited to tetrabutylammonium iodide or sodium iodide. In certain cases, it may be beneficial to conduct this reaction in the presence of a base such as, but not limited to, triethylamine, potassium carbonate, potassium tert-butoxide or sodium hydride. The intermediate (ii) can be converted to the products (Ia) or (iii) by reaction with an appropriate acid chloride or carboxylic acid. For example, intermediate (ii) can be reacted with an acid chloride in a solvent such as, but not limited to, tetrahydrofuran, dimethylformamide or dichloromethane at a temperature from about 25° C. to about 50° C. in the presence of a base such as, but not limited to, triethylamine, diisopropylethylamine or potassium carbonate, and optionally in the presence of a catalyst such as 4-dimethylaminopyridine. Alternatively, intermediate (ii) can be reacted with a carboxylic acid in a solvent such as, but not limited to, tetrahydrofuran or dimethylformamide in the presence of a coupling reagent such as 1,1'-carbonyldiimidazole (CDI), bis(2-oxo-3-oxazolidinyl) phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine. Intermediates of formula (iii) can be converted to compounds of formula (Ia) by reaction with a reagent $HX^4$-$A^1$, in the presence of a base such as, but not limited to, triethylamine, potassium tert-butoxide, sodium tert-butoxide or sodium hydride in a solvent such as, but not limited to, tetrahydrofuran or dimethylformamide at temperatures from 0° C. to 150° C. This reaction may be assisted by microwave irradiation.

Intermediates of formula (iii) can be prepared according to the general procedures as outlined in Scheme 2.

Scheme 2

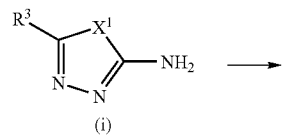

(i)

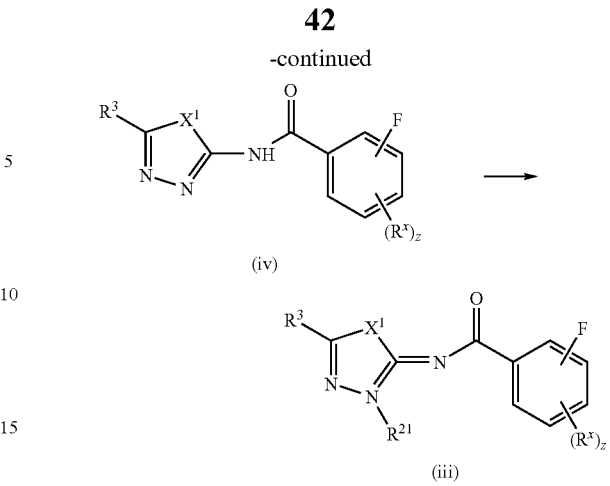

Compounds of formula (i) can be converted to intermediates (iv) by reaction with an acid chloride or carboxylic acid using reaction conditions as described in Scheme 1 for the conversion of (ii) to (iii). The intermediate (iv) can be converted to (iii) by reaction with $R^{21}X^{101}$, wherein $X^{101}$ is Cl, Br, I, OTs, or OMs, using reaction conditions as described in Scheme 1 for the transformation of (i) to (ii).

Similarly, compounds of general formula (I) wherein $A^5$ represents formulae (b)-(e) can be prepared from the appropriate heteroaryl or heterocyclic amines using general procedures as illustrated in Scheme 1 or 2.

Heteroarylamines used to prepare compounds of the invention may be obtained from commercial sources or may be prepared using methods well-known to those skilled in the art. For example, heteroaryl amines of formula (i) wherein $X^1$ is sulfur can be prepared using general procedures as illustrated in Scheme 3.

Scheme 3

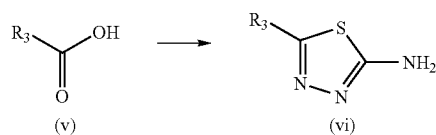

(v)         (vi)

Carboxylic acids of formula (v) can be treated with thiosemicarbazide and phosphorus oxychloride at a temperature of about 90° C., in a solvent such as, but not limited to, dioxane to provide compounds of formula (vi).

Compounds of general formula (I) wherein $A^5$ is formula (b) and $X^2$ is $N(R^{10})$ can be synthesized, for example, using the general procedures as outlined in Scheme 4.

Scheme 4

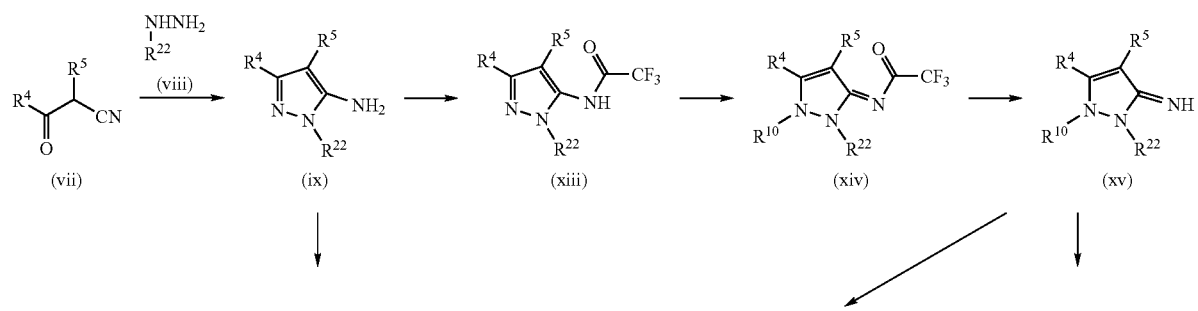

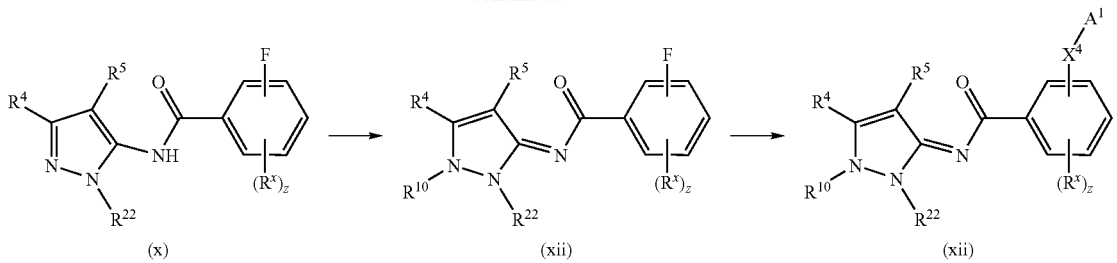

(x) (xii) (xii)

Hydrazines of formula (viii) can be reacted with ketonitriles (vii) in a solvent such as, but not limited to, ethanol, at a temperature of between about 0° C. to about 80° C., to provide intermediates of formula (ix). These intermediate aminopyrazoles (ix) can be treated with appropriate carboxylic acids or acid chlorides according to the methods outlined in Scheme 1 for the conversion of (ii) to (iii) to provide pyrazoles (x). Compounds (x) can be converted to (xi) by reaction with an appropriate alkylating agent such as, but not limited to, a halide, mesylate, tosylate, sulfate, or diphenylmethylsulfonium tetrafluoroborate either neat or in a solvent such as, but not limited, to tetrahydrofuran, toluene, acetonitrile or dioxane. This reaction may be conducted from about 0° C. to about 150° C. In certain cases the addition of a base may be beneficial. Examples of bases that may be used include triethylamine, diisopropylethylamine, potassium carbonate, sodium hydride, sodium hydroxide and lithium diisopropylamide. Compounds of formula (xi) can be converted to compounds of formula (xii) by reaction with a reagent HX⁴-A¹, in the presence of a base such as, but not limited to, triethylamine, potassium tert-butoxide, sodium tert-butoxide or sodium hydride in a solvent such as, but not limited to, tetrahydrofuran or dimethylformamide at temperatures from 0° C. to 150° C. This reaction may be assisted by microwave irradiation.

Alternatively, compounds of formula (ix) can be converted to the trifluoroacetamide (xiii) by reaction with trifluoroacetic anhydride in solvents such as, but not limited to, methylene chloride and in the presence of a base such as, but not limited to, pyridine or triethylamine. Compounds (xiii) can be converted to compounds (xiv) using the conditions described above for the conversion of (x) to (xi). Compounds of formula (xiv) can be converted to (xv) by reaction with aqueous potassium or sodium hydroxide with methanol or ethanol as a co-solvent at temperatures from about room temperature to about 70° C. Compounds (xv) can be converted to either (xi) or (xii) by reaction with the appropriate carboxylic acid or acid chloride according to the conditions of Scheme 1 for the conversion of (ii) to (iii).

Compounds of formula (Id) may be prepared by the general procedure of Scheme 5.

Scheme 5

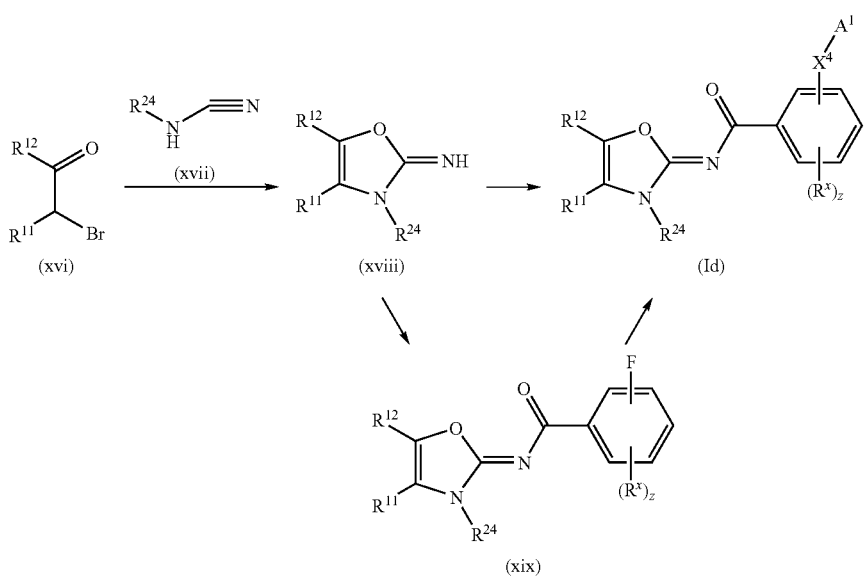

(xvi) (xviii) (Id)

(xix)

Compounds of formula (xvi) when treated with compounds of formula (xvii) in the presence of potassium carbonate, sodium carbonate, or cesium carbonate and in a solvent such as, but not limited to, tetrahydrofuran, dimethoxyethane, dioxane, or methyl ethyl ketone, at a temperature from about 25° C. to about 100° C. are transformed to intermediates of formula (xviii). Intermediates of formula (xviii) can be converted to compounds of formula (Id) or (xix) by reaction with an acid chloride or carboxylic acid using reaction conditions as described in Scheme 1. Intermediates of formula (xix) can be converted to (Id) according to the conditions of Scheme 1 for the conversion of (iii) to (Ia).

Compounds of formula (xvii) can be obtained from the reaction of amines of formula $R^{24}NH_2$ with cyanogen bromide in the presence of sodium carbonate or potassium carbonate in a solvent such as, but not limited to, ether, and at a temperature from about −25° C. to about 0° C.

Scheme 6

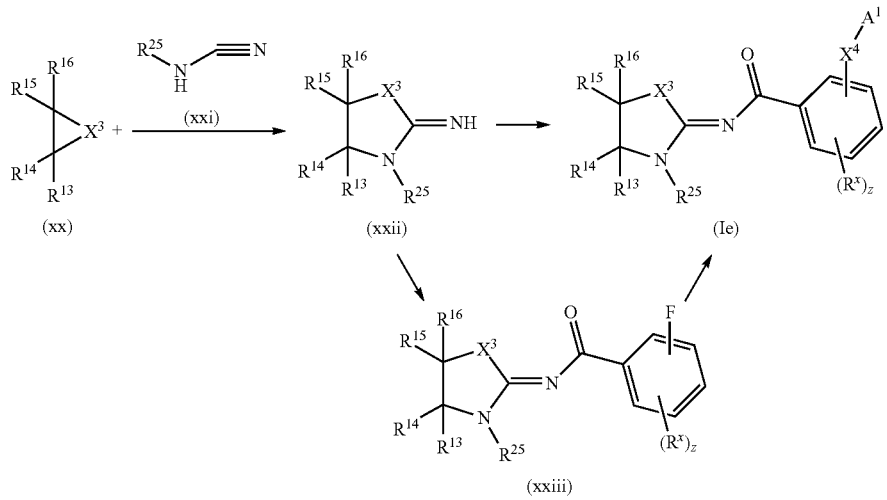

Compounds of formula (Ie) may alternatively be prepared according to the methods of Scheme 6. Intermediates of formula (xx) when treated with compounds of formula (xxi) in the presence of potassium carbonate at a temperature ranging from about 25° C. to about 100° C., in a solvent such as methyl ethyl ketone, are transformed to compounds of formula (xxii). Compounds of formula (xxi) are prepared by the same methods as compounds of formula (xvii). Intermediates of formula (xxii) can be converted to compounds of formula (Ie) or (xxiii) by reaction with an acid chloride or carboxylic acid using reaction conditions as described in Scheme 1. Intermediates of formula (xxiii) can be converted to (Ie) according to the conditions of Scheme 1 for the conversion of (iii) to (Ia).

In the preceding Schemes and methods, the reacting group $HX^4$-$A^1$ may be replaced with a reacting group $HX^4$-$A^{10}$ wherein $A^{10}$ is a derivative of $A^1$ that contains a suitable protecting group attached to a functional group present in $A^1$. For groups $A^{10}$ that contain a protecting group, such groups may be removed using chemical techniques that are well-known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Following removal of any protecting group, molecules can be further transformed to compounds of the invention using standard chemical techniques well-known to those skilled in the art such as alkylation, acylation, reductive amination, sulfonylation, oxidation, reduction and the like.

Compounds of formula (ix) can also be prepared using the methods shown in Scheme 7.

Scheme 7

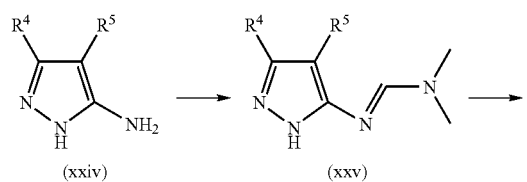

-continued

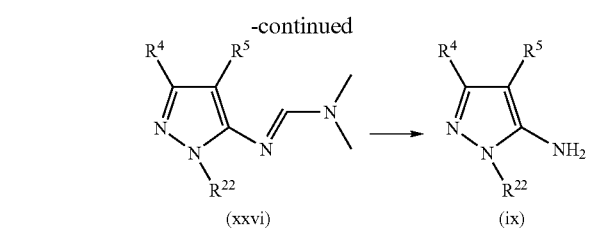

Aminopyrazoles (xxiv) can be converted to the amidine intermediates (xxv) by refluxing in dimethylformamide dimethylacetal or refluxing with a 2- to 3-fold excess of dimethylformamide dimethylacetal in dioxane or other aprotic solvent. Compounds (xxv), in turn, can be alkylated with reagents $R^{22}$-$X^{201}$ wherein $X^{201}$ is Cl, Br, I, OTs, or OMs under phase transfer conditions such as, but not limited to, conducting the reaction in a toluene/water mixture with a phase transfer reagent like tetrabutylammonium hydrogensulfate or tetrabutylammonium iodide at a temperature from 50-110° C., with potassium carbonate as base to provide the intermediates (xxvi). The intermediates (xxvi) can be converted to the intermediates (ix) by reaction with hydrazine hydrate in the presence of acetic acid in a solvent such as, but not limited to, dioxane at temperatures from about 50-100° C. The foregoing sequence to install the $R^{22}$ group can also be accomplished by using a triphenylmethyl (trityl) group on the exocyclic nitrogen of (xxiv) instead of the amidine. Typical conditions for effecting the analogous alkylation in the presence of a trityl group include, but are not limited to, reaction with an alkylating agent $R^{22}$-$X^{201}$ in the presence of a base such as sodium hydride or potassium tert-butoxide in a solvent such as dimethylformamide or tetrahydrofuran. The trityl protecting group can be removed using methods well-known to those skilled in the art such as, for example, treatment of the compound with an acid such as, but not limited to, hydrochloric acid.

Compounds of formula (I) wherein $A^5$ is (b) and $X^2$ is O, and compounds of formula (Ic) may be prepared from isoxazole-3-amines and pyridine-2-amines using synthetic methods that are analogous to those in Schemes 1 and 2. The starting isoxazole-3-amines and pyridine-2-amines are either commercially available or can be prepared by known synthetic methods described in the chemical literature.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

G. EXAMPLES

Example 1

N-{(3E)-5-tert-butyl-1-methyl-2-[(2R)-tetrahydrofuran-2-ylmethyl]-1,2-dihydro-3H-pyrazol-3-ylidene}-2-[(2R)-tetrahydrofuran-2-ylmethoxy]-5-(trifluoromethyl)benzamide

Example 1A (R)-di-tert-butyl 1-((tetrahydrofuran-2-yl)methyl)hydrazine-1,2-dicarboxylate To a mixture of (R)-(tetrahydrofuran-2-yl)methanol (Fluka, 4.0 g, 39.2 mmol) and di-tert-butyl hydrazine-1,2-dicarboxylate (9.1 g, 39.2 mmol) in THF (50 mL) was added triphenylphosphine (14.4 g, 54.8 mmol) followed by (E)-di-tert-butyl diazene-1,2-dicarboxylate (12.6 g, 54.8 mmol), portionwise. This mixture was stirred at ambient temperature for 16 h then was concentrated under reduced pressure and purified by column chromatography (SiO$_2$, 99% hexane/EtOAc to 25% hexane/EtOAc) to give the title compound (11.8 g, 37.3 mmol, 95% yield). MS (DCI/NH$_3$) m/z 317 (M+H)$^+$.

Example 1B (R)-((tetrahydrofuran-2-yl)methyl)hydrazine dihydrochloride

A mixture of the product of Example 1A (11.8 g, 37.3 mmol) and HCl (4 M in dioxane, 46.6 mL, 186 mmol) was stirred at ambient temperature for 16 h. The solids were isolated via filtration and were washed with Et$_2$O. The resulting title compound (6.4 g, 33.8 mmol, 91% yield) was carried on without further purification. MS (DCI/NH$_3$) m/z 117 (M+H)$^+$.

Example 1C (R)-3-tert-butyl-1-((tetrahydrofuran-2-yl)methyl)-1H-pyrazol-5-amine A mixture of the product of Example 1B (6.5 g, 34.4 mmol) and 4,4-dimethyl-3-oxopentanenitrile (4.3 g, 34.4 mmol) in ethanol (40 mL) was warmed to 85° C. and was allowed to stir for 4 h. The mixture was cooled to ambient temperature, concentrated under reduced pressure and the residue was dissolved in CH$_2$Cl$_2$ (10 mL) and saturated, aqueous NaHCO$_3$ (10 mL). The layers were separated and the aqueous layer was extracted with CH$_2$Cl$_2$ (3×10 mL). The combined organics were dried over anhydrous Na$_2$SO$_4$, filtered and concentrated under reduced pressure to provide the crude title compound (7.8 g) which was carried on without purification. MS (DCI/NH$_3$) m/z 224 (M+H)$^+$.

Example 1D

N-{3-tert-butyl-1-[(2R)-tetrahydrofuran-2-ylmethyl]-1H-pyrazol-5-yl}-2-fluoro-5-(trifluoromethyl)benzamide To a solution of the product of Example 1C (7.8 g) and triethylamine (14.6 mL, 105 mmol) in THF (60 mL) at ambient temperature was added 2-fluoro-5-(trifluoromethyl)benzoyl chloride (5.3 mL, 35.0 mmol) dropwise over 10 min. The mixture was stirred at ambient temperature for 3 h. The mixture was quenched with saturated, aqueous NaHCO$_3$ (20 mL) and diluted with EtOAc (20 mL). The layers were separated and the aqueous layer was extracted with EtOAc (3×10 mL). The combined organics were dried over anhydrous Na$_2$SO$_4$, filtered and concentrated under reduced pressure. Purification by column chromatography (SiO$_2$, 40% hexanes/EtOAc) gave the title compound (11.0 g, 26.6 mmol). MS (DCI/NH$_3$) m/z 414 (M+H)$^+$.

Example 1E

N-{(3E)-5-tert-butyl-1-methyl-2-[(2R)-tetrahydrofuran-2-ylmethyl]-1,2-dihydro-3H-pyrazol-3-ylidene}-2-fluoro-5-(trifluoromethyl)benzamide A mixture of the product of Example 1D (14.2 g, 34.3 mmol) and dimethyl sulfate (9.9 mL, 103 mmol) in toluene (40 mL) was warmed to 90° C. and was allowed to stir for 18 h then was cooled to ambient temperature. The mixture concentrated under reduced pressure and was purified by column chromatography (SiO$_2$, 50% hexanes/EtOAc to 100% EtOAc to 9:1:0.1 EtOAc:MeOH:Et$_3$N) to give the title compound (10 g, 23.4 mmol, 68% yield). MS (DCI/NH$_3$) m/z 428 (M+H)$^+$.

Example 1F

N-{(3E)-5-tert-butyl-1-methyl-2-[(2R)-tetrahydrofuran-2-ylmethyl]-1,2-dihydro-3H-pyrazol-3-ylidene}-2-[(2R)-tetrahydrofuran-2-ylmethoxy]-5-(trifluoromethyl)benzamide To the product of Example 1E (0.10 g, 0.23 mmol) in THF (5 mL) was added potassium tert-butoxide (0.053 g, 0.47 mmol). The mixture was stirred at ambient temperature for 20 min then (R)-(tetrahydrofuran-2-yl)methanol (Fluka, 0.023 mL, 0.23 mmol) in THF (5 mL) was added via cannula. The mixture was stirred for 1 h at ambient temperature then was quenched with saturated, aqueous NH$_4$Cl (3 mL) and diluted with EtOAc (3 mL). The layers were separated and the aqueous layer was extracted with EtOAc (3×5 mL). The combined organics were dried over anhydrous Na$_2$SO$_4$, filtered and concentrated under reduced pressure. The crude material was purified by column chromatography (SiO$_2$, 50% hexanes in EtOAc to 100% EtOAc to 10% MeOH in EtOAc) to give the title compound (40 mg, 0.078 mmol, 34% yield). $^1$H NMR (300 MHz, CDCl$_3$) δ ppm 1.43 (s, 9H), 1.68-1.81 (m, 2H), 1.82-1.96 (m, 4H), 1.97-2.11 (m, 2H), 3.66-3.80 (m, 3H), 3.85 (s, 3H), 3.86-3.93 (m, 1H), 3.99-4.06 (m, 1H), 4.10-4.22 (m, 2H), 4.25-4.36 (m, 2H), 4.46-4.54 (m, 1H), 6.99-7.04 (m, 1H), 7.00 (s, 1H), 7.44-7.51 (m, 1H), 7.96 (d, J=2.4 Hz, 1H); MS (DCI/NH$_3$) m/z 510 (M+H)$^+$.

Example 2

2-[(2S)-azetidin-2-ylmethoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide

Example 2A tert-butyl (2S)-2-{[2-({(3E)-5-tert-butyl-1-methyl-2-[(2R)-tetrahydrofuran-2-ylmethyl]-1,2-dihydro-3H-pyrazol-3-ylidene}carbamoyl)-4-(trifluoromethyl)phenoxy]methyl}azetidine-1-carboxylate To a solution of (S)-tert-butyl 2-(hydroxymethyl)azetidine-1-carboxylate (available as described in Abreo et al. *J.* *Med. Chem.* 1996, 39, 817-825; 0.096 g, 0.52 mmol) in THF (5 mL) was added potassium tert-butoxide (0.11 g, 0.94 mmol). This mixture was stirred at ambient temperature for 20 min then the product of Example 1E (0.2 g, 0.47 mmol) in THF (5 mL) was added via cannula. This mixture was stirred at ambient temperature for 4 h then the mixture was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 100% EtOAc to 10% MeOH in EtOAc) to give the title compound (0.12 g, 0.20 mmol, 43% yield). MS (DCI/NH$_3$) m/z 595 (M+H)$^+$.

Example 2B

2-[(2S)-azetidin-2-ylmethoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of the product of Example 2A (40 mg, 0.067 mmol) in CH$_2$Cl$_2$ (1 mL) was added trifluoroacetic acid (0.5 mL, 6.5 mmol). This mixture was stirred at ambient temperature for 2 h then was concentrated under reduced pressure and purified via column chromatography (SiO$_2$, 100% CH$_2$Cl$_2$ to 9:1:0.1 CH$_2$Cl$_2$:CH$_3$OH:NH$_4$OH) to give the free amine which was dissolved in EtOAc (1 mL) and p-toluenesulfonic acid (1 eq) in EtOAc was added. The resulting solids were isolated via filtration to give the title compound as the para-toluenesulfonic acid salt (14 mg, 0.02 mmol, 28% yield). $^1$H NMR (300 MHz, CD$_3$OD) δ ppm 1.47 (s, 9H), 1.66-1.82 (m, 1H), 1.84-1.96 (m, 3H), 2.03-2.17 (m, 2H), 2.36 (s, 3H), 2.61-2.72 (m, 1H), 3.70-3.80 (m, 1H), 3.82-3.91 (m, 1H), 3.99-4.05 (m, 2H), 4.05 (s, 3H), 4.15-4.28 (m, 2H), 4.33-4.48 (m, 2H), 4.45-4.52 (m, 1H), 4.54-4.65 (m, 1H), 6.87 (s, 1H), 7.22 (d, J=7.8 Hz, 2H), 7.29 (d, J=8.5 Hz, 1H), 7.68-7.72 (m, 2H), 7.71-7.74 (m, 1H), 7.99 (d, J=2.4 Hz, 1H); MS (DCI/NH$_3$) m/z 495 (M+H)$^+$. Anal. calculated for C$_{25}$H$_{33}$F$_3$N$_4$O$_3$·1.3C$_7$H$_8$O$_3$S; Calc: C, 57.01; H, 6.09; N, 7.80. Found: C, 57.27; H, 5.81; N, 8.14.

Example 3

N-{(3E)-5-tert-butyl-1-methyl-2-[(2R)-tetrahydrofuran-2-ylmethyl]-1,2-dihydro-3H-pyrazol-3-ylidene}-2-{[(2S)-1-methylazetidin-2-yl]methoxy}-5-(trifluoromethyl)benzamide A solution of the product of Example 2A (90 mg, 0.15 mmol) in formaldehyde (1.0 mL, 36 mmol) and formic acid (2 mL, 52 mmol) was warmed to 100° C. and was allowed to stir for 3 h. The mixture was cooled to ambient temperature concentrated under reduced pressure and was purified via column chromatography (SiO$_2$, 100% CH$_2$Cl$_2$ to 9:1:0.1 CH$_2$Cl$_2$:CH$_3$OH:NH$_4$OH). The resulting free amine was dissolved in EtOAc (1 mL) and p-toluenesulfonic acid (1 eq) in EtOAc was added. The resulting solid was isolated via filtration to give the title compound as the para-toluenesulfonic acid salt (65 mg, 0.095 mmol, 63% yield). $^1$H NMR (300 MHz, CDCl$_3$) δ ppm 1.46 (s, 9H), 1.61-1.72 (m, 2H), 1.82-1.96 (m, 4H), 2.03-2.15 (m, 2H), 2.32 (s, 3H), 2.35-2.43 (m, 1H), 2.62-2.70 (m, 1H), 3.67-3.82 (m, 3H), 4.06 (s, 3H), 4.12-4.23 (m, 1H), 4.25-4.37 (m, 1H), 4.41-4.56 (m, 2H), 4.76-4.90 (m, 1H), 6.87 (s, 1H), 7.08-7.16 (m, 3H), 7.58-7.65 (m, 1H), 7.66-7.72 (m, 2H), 8.14 (d, J=1.4 Hz, 1H); MS (DCI/NH$_3$) m/z 509 (M+H)$^+$; Anal. calculated for C$_{26}$H$_{35}$F$_3$N$_4$O$_3$.C$_7$H$_8$O$_3$S; Calc: C, 58.22; H, 6.37; N, 8.23. Found: C, 57.83; H, 6.00; N, 7.91.

Example 4

2-[(2R)-azetidin-2-ylmethoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide

Example 4A tert-butyl (2R)-2-{[2-({(3E)-5-tert-butyl-1-methyl-2-[(2R)-tetrahydrofuran-2-ylmethyl]-1,2-dihydro-3H-pyrazol-3-ylidene}carbamoyl)-4-(trifluoromethyl)phenoxy]methyl}azetidine-1-carboxylate To a solution of (R)-tert-butyl 2-(hydroxymethyl)azetidine-1-carboxylate (available as described in Abreo et al. *J. Med. Chem.* 1996, 39, 817-825; 0.32 g, 1.7 mmol) in THF (5 mL) was added potassium tert-butoxide (0.25 g, 2.3 mmol). This mixture was stirred at ambient temperature for 20 min then the product of Example 1E (0.24 g, 0.56 mmol) in THF (5 mL) was added via cannula. The mixture was stirred at ambient temperature for 6 h then was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 100% EtOAc to 10% MeOH in EtOAc) to provide the title compound (0.25 g, 0.42 mmol, 75% yield). MS (DCI/NH$_3$) m/z 595 (M+H)$^+$.

Example 4B

2-[(2R)-azetidin-2-ylmethoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of the product of Example 4A (90 mg, 0.15 mmol) in CH$_2$Cl$_2$ (2 mL) was added trifluoroacetic acid (1 mL, 13 mmol). This mixture was stirred at ambient temperature for 2 h then was concentrated under reduced pressure and purified via column chromatography (SiO$_2$, 100% CH$_2$Cl$_2$ to 9:1:0.1 CH$_2$Cl$_2$:CH$_3$OH:NH$_4$OH). The free amine was dissolved in EtOAc (1 mL) and p-toluenesulfonic acid (1 eq) in EtOAc was added. The mixture was stirred at ambient temperature for 6 h then was concentrated under reduced pressure to give the title compound as the para-toluenesulfonic acid salt (25 mg, 0.037 mmol, 25% yield). $^1$H NMR (300 MHz, CD$_3$OD) δ ppm 1.24-1.36 (m, 1H), 1.50 (s, 9H), 1.60-1.73 (m, 1H), 1.89-1.99 (m, 2H), 2.09-2.22 (m, 1H), 2.36 (s, 3H), 2.55-2.77 (m, 2H), 3.72-3.90 (m, 2H), 4.01-4.10 (m, 2H), 4.10-4.14 (m, 3H), 4.17-4.28 (m, 1H), 4.48-4.60 (m, 3H), 4.65-4.78 (m, 1H), 7.00 (s, 1H), 7.22 (d, J=7.9 Hz, 2H), 7.39 (d, J=8.7 Hz, 1H), 7.68 (d, J=7.9 Hz, 2H), 7.86 (s, 1H), 7.97-8.02 (m, 1H); MS (DCI/NH$_3$) m/z 495 (M+H)$^+$.

Example 5

N-{(3E)-5-tert-butyl-1-methyl-2-[(2R)-tetrahydrofuran-2-ylmethyl]-1,2-dihydro-3H-pyrazol-3-ylidene}-2-(2-hydroxy-2-methylpropoxy)-5-(trifluoromethyl)benzamide

Example 5A

2-[2-(benzyloxy)-2-methylpropoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of 2-(benzyloxy)-2-methylpropan-1-ol (Matrix Scientific, 0.20 g, 1.1 mmol) in THF (5 mL) was added potassium tert-butoxide (1M in THF, 2.1 mL, 2.1 mmol). This mixture was stirred at ambient temperature for 20 min then the product of Example 1E (0.3 g, 0.702 mmol) in THF (5 mL) was added via cannula. The mixture was stirred at ambient temperature for 6 h. The mixture was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc then 100% EtOAc then 9:1:0.1 EtOAc:MeOH:Et$_3$N) to give the title compound (0.4 g). MS (DCI/NH$_3$) m/z 588 (M+H)$^+$.

Example 5B

N-{(3E)-5-tert-butyl-1-methyl-2-[(2R)-tetrahydrofuran-2-ylmethyl]-1,2-dihydro-3H-pyrazol-3-ylidene}-2-(2-hydroxy-2-methylpropoxy)-5-(trifluoromethyl)benzamide A solution of the product of Example 5A in ethanol (7 mL) was degassed 3× with a N$_2$ backflush each time. The Pd/C (0.074 g, 0.070 mmol) was added, the mixture was again degassed with a N$_2$ backflush then the mixture was put under an atmosphere of hydrogen (balloon, 1 atm). The mixture was stirred at ambient temperature for 16 h but reaction was incomplete and therefore was allowed to continue to react for an additional 96 h. The mixture was degassed with a N$_2$ backflush then was filtered through Celite and the filtrate was concentrated under reduced pressure. The material was purified by HPLC (Hitachi 7000 series HPLC system in basic conditions (90% gradient of CH$_3$CN in buffer (0.1 M aqueous NH$_4$HCO$_3$, adjusted to pH 10 with NH$_4$OH) over 15 min on a Waters Xterra RP18, 5 m, 250×4.6 mm column (1 mL/min)) to give the title compound (0.21 g, 0.42 mmol, 61% yield). $^1$H NMR (300 MHz, CDCl$_3$) δ ppm 1.28 (s, 6H), 1.42 (s, 9H), 1.62-1.91 (m, 3H), 1.96-2.08 (m, 1H), 3.66-3.81 (m, 2H), 3.87 (s, 3H), 4.03 (s, 2H), 4.17 (dt, J=12.6, 6.8, 2.8 Hz, 1H), 4.24-4.34 (m, 1H), 4.54 (dd, J=15.3, 3.0 Hz, 1H), 6.14-6.30 (m, 1H), 7.00 (d, J=8.3 Hz, 1H), 7.00 (s, 1H), 7.51 (dd, J=8.7, 2.4 Hz, 1H), 8.09 (d, J=2.0 Hz, 1H); MS (DCI/NH$_3$) m/z 498 (M+H)$^+$; Anal. calculated for C$_{25}$H$_{34}$F$_3$N$_3$O$_3$ Calc: C, 60.35; H, 6.89; N, 8.45. Found: C, 60.52; H, 6.98; N, 8.38.

Example 6

N-{(3E)-5-tert-butyl-1-methyl-2-[(2R)-tetrahydrofuran-2-ylmethyl]-1,2-dihydro-3H-pyrazol-3-ylidene}-2-[(1,1-dioxidotetrahydrothien-3-yl)methoxy]-5-(trifluoromethyl)benzamide

Example 6A

Tetrahydrothiophene-3-methanol 1,1-dioxide

To a solution of tetrahydrothiophene-3-carboxylic acid 1,1-dioxide (Enamine, 1 g, 6.1 mmol) in THF (20 mL) at −10° C. was added 4-methylmorpholine (0.67 mL, 6.1 mmol). The mixture was stirred for 1 min then ethyl chloroformate (0.58 mL, 6.1 mmol) was added dropwise. This mixture was stirred at −10° C. for 15 min then was filtered through Celite and the filtrated was added dropwise via syringe to a mixture of NaBH$_4$ (0.52 g, 13.7 mmol) in water (10 mL) at 5° C. The ice-bath was removed after the addition was complete and the mixture was stirred at ambient temperature for 2 h. The mixture was quenched with saturated, aqueous NH$_4$Cl (10 mL) and diluted with EtOAc (10 mL). The layers were separated and the aqueous layer was extracted with EtOAc (3×5 mL). The combined organics were dried over anhydrous Na$_2$SO$_4$, filtered and concentrated under reduced pressure to give the title compound (0.22 g) which was used without further purification. MS (DCI/NH$_3$) m/z 168 (M+NH$_4$)$^+$.

Example 6B

N-{(3E)-5-tert-butyl-1-methyl-2-[(2R)-tetrahydrofuran-2-ylmethyl]-1,2-dihydro-3H-pyrazol-3-ylidene}-2-[(1,1-dioxidotetrahydrothien-3-yl)methoxy]-5 trifluoromethyl)benzamide To a solution of the product of Example 6A (0.22 g, 1.5 mmol) in THF (10 mL) was added potassium tert-butoxide (1 M in THF, 2.9 mL, 2.9 mmol). This mixture was stirred at ambient temperature for 20 min then the product of Example 1E (0.42 g, 0.98 mmol) in THF (5 mL) was added via cannula. The mixture was stirred at ambient temperature for 6 h. The mixture was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc then 100% EtOAc then 9:1:0.1 EtOAc:MeOH:Et$_3$N) to provide the title compound (0.33 g, 0.59 mmol, 61% yield). $^1$H NMR (300 MHz, CDCl$_3$) δ ppm 1.18-1.33 (m, 1H), 1.44 (s, 9H), 1.64-1.92 (m, 4H), 1.94-2.03 (m, 1H), 2.12-2.29 (m, 1H), 2.31-2.47 (m, 1H), 2.90-3.07 (m, 2H), 3.09-3.29 (m, 3H), 3.67-3.81 (m, 2H), 3.88 (s, 2H), 4.06-4.24 (m, 3H), 4.32-4.57 (m, 1H), 6.92 (d, J=8.3 Hz, 1H), 6.98 (d, J=1.2 Hz, 1H), 7.49 (dd, J=8.5, 2.2 Hz, 1H), 7.93 (d, J=2.0 Hz, 1H); MS (DCI/NH$_3$) m/z 558 (M+H)$^+$; Anal. calculated for C$_{26}$H$_{34}$F$_3$N$_3$O$_5$S Calc: C, 56.00; H, 6.15; N, 7.54. Found: C, 56.20; H, 6.25; N, 7.41.

Example 7

N-[(2Z)-3-butyl-5-tert-butyl-1,3,4-thiadiazol-2(3H)-ylidene]-2-[(1-methylpiperidin-2-yl)methoxy]-5-(trifluoromethyl)benzamide

Example 7A

N-(5-tert-butyl-1,3,4-thiadiazol-2-yl)-2-fluoro-5-(trifluoromethyl)benzamide

To a solution of 5-tert-butyl-1,3,4-thiadiazol-2-amine (1.57 g, 10 mmol) and 2-fluoro-5-(trifluoromethyl)benzoyl chloride (2.27 g, 10 mmol) in CH$_2$Cl$_2$ (45 mL) at 0° C. was added dropwise triethylamine (1.7 mL, 12 mmol) and the reaction was allowed to warm to ambient temperature and stirred for 12 hours. The mixture was then washed with water, brine, dried with MgSO$_4$, filtered, and concentrated under reduced pressure to afford 3.2 g of the title compound. MS (DCI/NH$_3$) m/z 348 (M+H)$^+$.

Example 7B

N-[(2Z)-3-butyl-5-tert-butyl-1,3,4-thiadiazol-2(3H)-ylidene]-2-fluoro-5-(trifluoromethyl)benzamide A mixture of the product from Example 7A (348 mg, 1 mmol), 1-iodobutane (551 mg, 3 mmol) and potassium carbonate (276 mg, 2 mmol) in toluene (25 mL) was treated with tetrabutylammonium iodide (11 mg, 0.03 mmol), tetrabutylammonium hydrogen sulfate (10 mg, 0.03 mmol) and tetraethylammonium iodide (11 mg, 0.04 mmol) and the resulting mixture was refluxed for 14 hours. The mixture was washed with water, brine, dried with MgSO$_4$, filtered, and concentrated under reduced pressure. The residue was purified by silica gel chromatography and eluted with hexanes-EtOAc (2:1) to afford 360 mg of the title compound. MS (DCI/NH$_3$) m/z 404 (M+H)$^+$.

Example 7C

N-[(2Z)-3-butyl-5-tert-butyl-1,3,4-thiadiazol-2(3H)-ylidene]-2-[(1-methylpiperidin-2-yl)methoxy]-5-(trifluoromethyl)benzamide A mixture of Example 7B (121 mg, 0.3 mmol) and (1-methylpiperidin-2-yl)methanol (39 mg, 0.3 mmol) in anhydrous THF (10 mL) was treated with 1N potassium tert-butoxide in THF (0.3 mL, 0.3 mmol) and the resulting mixture was stirred at room temperature for 1 hour. Acetic acid was added to adjust the acidity to pH 5 and the mixture was concentrated under reduced pressure. A saturated solution of NaHCO$_3$ was then added and the mixture was extracted with ethyl acetate. The organic layer was washed with water, brine, dried with MgSO$_4$, filtered, and concentrated under reduced pressure. The residue was purified by silica gel chromatography and eluted with EtOAc:MeOH (9:1) to afford 110 mg of the title compound. $^1$H NMR (501 MHz, PYRIDINE-d$_5$) δ ppm 0.88 (t, J=7.3 Hz, 3H), 1.23-1.38 (m, 12H), 1.49 (d, J=12.8 Hz, 1H), 1.59-1.69 (m, 3H), 1.81-1.90 (m, 2H), 1.97-2.05 (m, 1H), 2.18-2.25 (m, 1H), 2.50 (s, 3H), 2.69 (s, 1H), 2.85 (d, J=11.8 Hz, 1H), 4.15 (dd, J=10.0, 5.2 Hz, 1H), 4.41 (t, 2H), 4.50 (dd, J=10.0, 5.0 Hz, 1H), 7.19 (d, J=8.5 Hz, 1H), 7.70 (dd, J=8.6, 2.3 Hz, 1H), 8.53 (d, J=2.4 Hz, 1H); MS (DCI/NH$_3$) m/z 513 (M+H)$^+$. Anal. Calculated for $C_{25}H_{35}F_3N_4O_2S.0.1H_2O$: C, 58.37; H, 6.90; N, 10.89. Found: C, 57.10; H, 7.12; N, 10.54.

Example 8

N-{(3E)-5-tert-butyl-1-methyl-2-[(2R)-tetrahydrofuran-2-ylmethyl]-1,2-dihydro-3H-pyrazol-3-ylidene}-2-[(2)-tetrahydrofuran-2-ylmethoxy]-5-(trifluoromethyl)benzamide Potassium tert-butoxide (0.94 mL, 1M in THF) was added to (S)-(tetrahydrofuran-2-yl)methanol (0.1 g, 0.98 mmol) in 0.5 mL of THF and the mixture stirred for 10 minutes. Example 1E (0.2 g, 0.47 mmol) in 0.5 mL of THF was added and the mixture stirred at ambient temperature for 4 hours. The mixture was diluted with dichloromethane, loaded on silica and chromatographed ($SiO_2$, 0% to 20% methanol in dichloromethane (0.1% $NH_4OH$)) to afford the title compound (0.09 g, 0.18 mmol, 38% yield). $^1$H NMR (300 MHz, $CDCl_3$) δ ppm 1.43 (s, 9H), 1.66-1.81 (m, 2H), 1.80-1.97 (m, 4H), 1.96-2.11 (m, 2H), 3.63-3.82 (m, 3H), 3.83-3.93 (m, 1H), 3.87 (s, 3H), 3.97-4.07 (m, 1H), 4.10-4.24 (m, 2H), 4.25-4.40 (m, 2H), 4.44-4.61 (m, 1H), 7.01 (d, 1H), 7.00 (s, 1H), 7.48 (dd, J=8.1, 2.2 Hz, 1H), 7.96 (d, J=2.4 Hz, 1H). MS (DCI/$NH_3$) m/z 510.3 (M+H)$^+$. Analytical calculated for $C_{26}H_{34}F_3N_3O_4.0.3H_2O$: C, 60.66; H, 6.77; N, 8.16. Found: C, 60.71; H, 6.71; N, 7.76.

Example 9

N-{(3E)-5-tert-butyl-1-methyl-2-[(2R)-tetrahydrofuran-2-ylmethyl]-1,2-dihydro-3H-pyrazol-3-ylidene}-2-(tetrahydro-2H-pyran-4-ylmethoxy)-5-(trifluoromethyl)benzamide The title compound was prepared according to the procedure described in Example 8 by substituting (tetrahydro-2H-pyran-4-yl)methanol for (S)-(tetrahydrofuran-2-yl)methanol (0.08 g, 0.15 mmol, 33% yield). $^1$H NMR (300 MHz, $CDCl_3$) δ ppm 1.37-1.51 (m, 11H), 1.68-1.93 (m, 5H), 1.95-2.07 (m, 1H), 2.08-2.24 (m, 1H), 3.34-3.46 (m, 2H), 3.65-3.82 (m, 2H), 3.85 (s, 3H), 3.92 (d, J=6.8 Hz, 2H), 3.94-4.03 (m, 2H), 4.13-4.23 (m, 1H), 4.24-4.34 (m, 1H), 4.43-4.56 (m, 1H), 6.94 (d, J=8.8 Hz, 1H), 6.98 (s, 1H), 7.48 (dd, J=8.8, 2.0 Hz, 1H), 7.95 (d, J=2.0 Hz, 1H). MS (DCI/$NH_3$) m/z 524.3 (M+H)$^+$. Analytical calculated for $C_{27}H_{36}F_3N_3O_4$: C, 61.94; H, 6.93; N, 8.03. Found: C, 62.22; H, 7.21; N, 7.77.

Example 10

N-{(3E)-5-tert-butyl-1-methyl-2-[(2R)-tetrahydrofuran-2-ylmethyl]-1,2-dihydro-3H-pyrazol-3-ylidene}-2-{[(2S)-1-methylpyrrolidin-2-yl]methoxy}-5-(trifluoromethyl)benzamide The title compound was prepared according to the procedure described in Example 8 by substituting (S)-(1-methylpyrrolidin-2-yl)methanol for (S)-(tetrahydrofuran-2-yl)methanol and chromatographed ($SiO_2$, solvent A—hexane:EtOAc:$Et_3N$ (10:30:1); solvent B—hexane:EtOAc:MeOH:$Et_3N$ (10:30:10:1); 100% solvent A to 100% solvent B over 240 mL then isocratic for 300 mL) to afford the title compound (0.15 g, 0.29 mmol, 49% yield). $^1$H NMR (500 MHz, PYRIDINE-$d_5$) δ ppm 1.18 (s, 9H), 1.47-1.62 (m, 3H), 1.62-1.72 (m, 1H), 1.72-1.82 (m, 2H), 1.92-2.03 (m, 1H), 2.06-2.14 (m, 1H), 2.51 (s, 3H), 2.72-2.82 (m, 1H), 2.91-2.98 (m, 1H), 3.54-3.61 (m, 1H), 3.69-3.75 (m, 1H), 3.79 (s, 3H), 4.06 (dd, J=9.5, 6.1 Hz, 1H), 4.17-4.27 (m, 2H), 4.36 (dd, J=15.0, 6.4 Hz, 1H), 4.59 (dd, J=15.3, 3.1 Hz, 1H), 7.16 (d, J=8.8 Hz, 1H), 7.47 (s, 1H), 7.64 (dd, J=8.5, 2.4 Hz, 1H), 8.45 (d, J=2.4 Hz, 1H). MS (DCI/$NH_3$) m/z 523.3 (M+H)$^+$. Analytical calculated for $C_{27}H_{37}F_3N_4O_3.0.3H_2O$: C, 61.38; H, 7.18; N, 10.60. Found: C, 61.44; H, 7.38; H, 10.34.

Example 11

N-{(3E)-5-tert-butyl-1-methyl-2-[(2R)-tetrahydrofuran-2-ylmethyl]-1,2-dihydro-3H-pyrazol-3-ylidene}-2-[(1-methylazetidin-3-yl)methoxy]-5-trifluoromethyl)benzamide Example 11A tert-butyl 3-{[2-({(3E)-5-tert-butyl-1-methyl-2-[(2R)-tetrahydrofuran-2-ylmethyl]-1,2-dihydro-3H-pyrazol-3-ylidene}carbamoyl)-4-(trifluoromethyl)phenoxy]methyl}azetidine-1-carboxylate The title compound was prepared according to the procedure described in Example 8 by substituting tert-butyl 3-(hydroxymethyl)azetidine-1-carboxylate for (S)-(tetrahydrofuran-2-yl)methanol. (75 mg, 0.13 mmol, 54% yield). $^1$H NMR (300 MHz, $CDCl_3$) δ ppm 1.42 (s, 9H), 1.43 (s, 9H), 1.66-1.82 (m, 2H), 1.82-1.95 (m, 1H), 1.95-2.11 (m, 1H), 2.92-3.13 (m, 1H), 3.65-3.82 (m, 4H), 3.87 (s, 3H), 4.04 (t, J=8.5 Hz, 2H), 4.12-4.21 (m, 1H), 4.23 (d, J=7.1 Hz, 2H), 4.26-4.38 (m, 1H), 4.42-4.57 (m, 1H), 6.97 (d, J=8.7 Hz, 1H), 6.99 (s, 1H), 7.49 (dd, J=8.7, 2.0 Hz, 1H), 7.96 (d, J=2.0 Hz, 1H). MS (DCI/$NH_3$) m/z 595.3 (M+H)$^+$.

Example 11B

N-{(3E)-5-tert-butyl-1-methyl-2-[(2R)-tetrahydrofuran-2-ylmethyl]-1,2-dihydro-3H-pyrazol-3-ylidene}-2-[(1-methylazetidin-3-yl)methoxy]-5-(trifluoromethyl)benzamide To Example 11A (0.12 g, 0.2 mmol) was added 3 mL of 37% aqueous formaldehyde and 6 mL of 88% formic acid. The resulting mixture was heated at 100° C. for 5 hours. The mixture was diluted with EtOAc, washed with 2N NaOH, water, and brine. The aqueous phases were combined and extracted twice with EtOAc. The organic phases were combined, dried with $MgSO_4$ and the residue chromatographed ($SiO_2$, solvent A—hexane:EtOAc:$Et_3N$ (10:30:1); solvent B—hexane:EtOAc:MeOH:$Et_3N$ (10:30:10:1); 100% solvent A to 100% solvent B over 300 mL then isocratic for 300 mL) to afford the title compound (20 mg, 0.04 mmol, 20% yield). $^1$H NMR (500 MHz, PYRIDINE-$d_5$) δ ppm 1.18 (s, 9H), 1.52-1.62 (m, 2H), 1.63-1.73 (m, 1H), 1.73-1.84 (m, 1H), 2.24 (s, 3H), 2.86-2.97 (m, 1H), 3.25 (t, J=6.4 Hz, 2H), 3.34 (t, J=7.5 Hz, 2H), 3.53-3.61 (m, 1H), 3.68-3.75 (m, 1H), 3.79 (s, 3H), 4.20-4.25 (m, 1H), 4.26 (d, J=6.4 Hz, 2H), 4.37 (dd, J=15.3, 6.4 Hz, 1H), 4.59 (dd, J=15.3, 3.1 Hz, 1H), 7.13 (d, J=8.8 Hz, 1H), 7.47 (s, 1H), 7.64 (dd, J=8.5, 2.4 Hz, 1H), 8.47 (d, J=2.4 Hz, 1H). MS (DCI/$NH_3$) m/z 509.3 (M+H)$^+$.

Example 12

N-{(3E)-5-tert-butyl-1-methyl-2-[(2R)-tetrahydrofuran-2-ylmethyl]-1,2-dihydro-3H-pyrazol-3-ylidene}-2-{[(2S)-5-oxopyrrolidin-2-yl]methoxy}-5-(trifluoromethyl)benzamide Sodium hydride (56 mg, 1.4 mmol) was added to (S)-5-(hydroxymethyl)pyrrolidin-2-one (85 mg, 0.74 mmol) dissolved in 0.5 mL dimethylformamide and stirred for 15 minutes. Example 1E (0.15 g, 0.35 mmol) in 0.2 mL of dimethylformamide was added and the resulting mixture was stirred at 45° C. for 20 hours. The mixture was diluted with EtOAc, washed with 2N NaOH, water and brine. The aqueous phases were combined and extracted with EtOAc; the organic layers were combined, dried with MgSO$_4$, and concentrated under reduced pressure. The residue was chromatographed (SiO$_2$, solvent A—hexane:EtOAc:Et$_3$N (5:15:1); solvent B—hexane:EtOAc:MeOH:Et$_3$N (4:12:4:1); 100% solvent A to 100% solvent B over 450 mL) to afford the title compound (0.12 g, 0.23 mmol, 65% yield). $^1$H NMR (300 MHz, CDCl$_3$) δ ppm 1.44 (s, 9H), 1.59-1.79 (m, 3H), 1.80-1.95 (m, 1H), 1.93-2.07 (m, 1H), 2.12-2.28 (m, 1H), 2.31-2.40 (m, 2H), 3.63-3.84 (m, 3H), 3.88 (s, 3H), 4.04-4.21 (m, 2H), 4.25-4.41 (m, 2H), 4.53 (dd, J=15.3, 3.1 Hz, 1H), 6.97 (d, J=8.5 Hz, 1H), 7.03 (s, 1H), 7.50 (dd, J=9.0, 2.2 Hz, 1H), 7.82 (s, 1H), 8.01 (d, J=2.0 Hz, 1H). MS (DCI/NH$_3$) m/z 523.3 (M+H)$^+$. Analytical calculated for C$_{26}$H$_{33}$F$_3$N$_4$O$_4$.0.7H$_2$O: C, 58.43; H, 6.47; N, 10.48. Found: C, 58.49; H, 6.63; N, 10.23.

Example 13

N-{(3E)-5-tert-butyl-1-methyl-2-[(2R)-tetrahydrofuran-2-ylmethyl]-1,2-dihydro-3H-pyrazol-3-ylidene}-2-{[(2R)-5-oxopyrrolidin-2-yl]methoxy}-5-(trifluoromethyl)benzamide The title compound was prepared according to the procedure described in Example 12 by substituting (R)-5-(hydroxymethyl)pyrrolidin-2-one for (S)-5-(hydroxymethyl)pyrrolidin-2-one. (0.07 g, 0.14 mmol, 24% yield). $^1$H NMR (300 MHz, CDCl$_3$) δ ppm 1.44 (s, 9H), 1.67-1.79 (m, 3H), 1.79-1.91 (m, 1H), 1.92-2.07 (m, 1H), 2.13-2.29 (m, 1H), 2.31-2.40 (m, 2H), 3.63-3.84 (m, 3H), 3.88 (s, 3H), 4.03-4.22 (m, 2H), 4.25-4.41 (m, 2H), 4.45-4.59 (m, 1H), 6.97 (d, J=8.3 Hz, 1H), 7.03 (s, 1H), 7.50 (dd, J=8.5, 2.6 Hz, 1H), 7.68-7.85 (m, 1H), 8.01 (d, J=2.4 Hz, 1H). MS (DCI/NH$_3$) m/z 523.3 (M+H)$^+$.

Example 14

N-{(3E)-5-tert-butyl-1-methyl-2-[(2R)-tetrahydrofuran-2-ylmethyl]-1,2-dihydro-3H-pyrazol-3-ylidene}-2-[2-(2,5-dioxopyrrolidin-1-yl)ethoxy]-5-(trifluoromethyl)benzamide Sodium hydride (0.05 g, 1.2 mmol) was added to 1-(2-hydroxyethyl)pyrrolidine-2,5-dione (0.19 g, 1.2 mmol) in 0.3 mL of dimethylformamide and the mixture stirred for 10 minutes. Example 1E (0.25 g, 0.59 mmol) in 1.0 mL of dimethylformamide was added and the reaction stirred at ambient temperature for 20 hours. The mixture was diluted with EtOAc, washed with aqueous NH$_4$Cl, water, brine, dried with MgSO$_4$ and concentrated under reduced pressure. The residue was chromatographed (SiO$_2$, solvent A—hexane:EtOAc:Et$_3$N (10:30:1); solvent B—hexane:EtOAc:MeOH:Et$_3$N (10:30:10:1); 100% solvent A to 100% solvent B over 300 mL then isocratic for 300 mL) to afford the title compound (25 mg, 0.05 mmol, 8% yield). $^1$H NMR (300 MHz, CDCl$_3$) δ ppm 1.44 (s, 9H), 1.71-1.82 (m, 2H), 1.82-1.94 (m, 1H), 1.96-2.08 (m, 1H), 2.74 (s, 4H), 3.68-3.82 (m, 2H), 3.86 (s, 3H), 3.91-3.97 (m, 2H), 4.15-4.23 (m, 1H), 4.23-4.32 (m, 3H), 4.44-4.54 (m, 1H), 6.98 (d, J=8.8 Hz, 1H), 7.01 (s, 1H), 7.47 (dd, J=8.3, 2.2 Hz, 1H), 7.89 (d, J=2.0 Hz, 1H). MS (DCI/NH$_3$) m/z 551.3 (M+H)$^+$.

Example 15

N-{(3E)-5-tert-butyl-1-methyl-2-[(2R)-tetrahydrofuran-2-ylmethyl]-1,2-dihydro-3H-pyrazol-3-ylidene}-2-[2-(2-oxopyrrolidin-1-yl)ethoxy]-5-(trifluoromethyl)benzamide Title compound was prepared according to the procedure described in Example 8 by substituting 1-(2-hydroxyethyl)pyrrolidin-2-one for (S)-(tetrahydrofuran-2-yl)methanol and chromatographed (SiO$_2$, solvent A—hexane:EtOAc:Et$_3$N (10:30:1); solvent B—hexane:EtOAc:MeOH:Et$_3$N (10:30:10:1); 100% solvent A to 100% solvent B over 450 mL then isocratic for 300 mL) to afford the title compound. (0.13 g, 0.24 mmol, 41% yield). $^1$H NMR (300 MHz, CDCl$_3$) δ ppm 1.43 (s, 9H), 1.69-1.83 (m, 2H), 1.84-1.98 (m, 3H), 1.98-2.10 (m, 1H), 2.32 (t, J=8.1 Hz, 2H), 3.62-3.67 (m, 2H), 3.67-3.72 (m, 2H), 3.72-3.82 (m, 2H), 3.87 (s, 3H), 4.12-4.33 (m, 4H), 4.46-4.54 (m, 1H), 6.94 (d, J=8.8 Hz, 1H), 6.98 (s, 1H), 7.49 (dd, J=8.6, 1.9 Hz, 1H), 7.91 (d, J=2.4 Hz, 1H). MS (DCI/NH$_3$) m/z 537.3 (M+H)$^+$. Analytical calculated for C$_{27}$H$_{35}$F$_3$N$_4$O$_4$: C, 60.44; H, 6.57; N, 10.44. Found: C, 60.28; H, 6.49; N, 10.38.

Example 16

N-{(3E)-5-tert-butyl-1-methyl-2-[(2R)-tetrahydrofuran-2-ylmethyl]-1,2-dihydro-3H-pyrazol-3-ylidene}-2-{[(4R)-2,2-dimethyl-1,3-dioxolan-4-yl]methoxy}-5-(trifluoromethyl)benzamide The title compound was prepared according to the procedure described in Example 8 by substituting (R)-(2,2-dimethyl-1,3-dioxolan-4-yl)methanol for (S)-(tetrahydrofuran-2-yl)methanol and chromatographed to afford the title compound. (SiO$_2$, solvent A—hexane:EtOAc:Et$_3$N (10:30:1); solvent B—hexane:EtOAc:MeOH:Et$_3$N (10:30:10:1); 100% solvent A to 100% solvent B over 450 mL then isocratic for 300 mL). (0.13 g, 0.24 mmol, 41% yield). $^1$H NMR (500 MHz, PYRIDINE-d$_5$) δ ppm 1.18 (s, 9H), 1.35 (s, 3H), 1.50 (s, 3H), 1.54-1.62 (m, 2H), 1.64-1.72 (m, 1H), 1.76-1.84 (m, 1H), 3.55-3.61 (m, 1H), 3.70-3.76 (m, 1H), 3.79 (s, 3H), 4.19-4.28 (m, 4H), 4.34-4.40 (m, 2H), 4.58-4.67 (m, 2H), 7.19 (d, J=8.5 Hz, 1H), 7.47 (s, 1H), 7.63 (dd, J=8.8, 2.4 Hz, 1H), 8.49 (d, J=2.1 Hz, 1H). MS (DCI/NH$_3$) m/z 540.3 (M+H)$^+$. Analytical calculated for C$_{27}$H$_{36}$F$_3$N$_3$O$_5$.0.2H$_2$O: C, 59.72; H, 6.75; N, 7.74. Found: C, 59.72; H, 6.82; N, 7.75.

Example 17

N-{(3E)-5-tert-butyl-1-methyl-2-[(2R)-tetrahydrofuran-2-ylmethyl]-1,2-dihydro-3H-pyrazol-3-ylidene}-2-{2-[(4S)-2,2-dimethyl-1,3-dioxolan-4-yl]ethoxy}-5-(trifluoromethyl)benzamide The title compound was prepared according to the procedure described in Example 8 by substituting (S)-2-(2,2-dimethyl-1,3-dioxolan-4-yl)ethanol for (S)-(tetrahydrofuran-2-yl)methanol and chromatographed to afford the title compound. (SiO$_2$, solvent A—hexane:EtOAc:Et$_3$N (10:30:1); solvent B—hexane:EtOAc:MeOH:Et$_3$N (10:30:10:1); 100% solvent A to 100% solvent B over 450 mL then isocratic for 300 mL). (0.13 g, 0.24 mmol, 40% yield). $^1$H NMR (500 MHz, PYRIDINE-d$_5$) δ ppm 1.18 (s, 9H), 1.36 (s, 3H), 1.44 (s, 3H), 1.54-1.62 (m, 2H), 1.65-1.73 (m, 1H), 1.79 (td, J=13.3, 7.0 Hz, 1H), 2.10-2.15 (m, 2H), 3.58 (q, J=7.2 Hz, 1H), 3.70-3.78 (m, 2H), 3.78-3.80 (m, 3H), 4.20-4.29 (m, 4H), 4.36-4.41 (m, 1H), 4.46-4.52 (m, 1H), 4.56-4.61 (m, 1H), 7.12 (d, J=8.5 Hz, 1H), 7.49 (s, 1H), 7.62 (dd, J=8.5, 2.1 Hz, 1H), 8.44 (d, J=2.1 Hz, 1H). MS (DCI/NH$_3$) m/z 554.3 (M+H)$^+$. Analytical calculated for C$_{28}$H$_{38}$F$_3$N$_3$O$_5$.0.4H$_2$O: C, 60.02; H, 6.97; N, 7.50. Found: C, 60.04; H, 7.24; N, 7.53.

Example 18

N-{(3E)-5-tert-butyl-1-methyl-2-[(2R)-tetrahydrofuran-2-ylmethyl]-1,2-dihydro-3H-pyrazol-3-ylidene}-2-{[(4S)-2,2-dimethyl-1,3-dioxolan-4-yl]methoxy}-5-(trifluoromethyl)benzamide The title compound was prepared according to the procedure described in Example 8 by substituting (S)-(2,2-dimethyl-1,3-dioxolan-4-yl)methanol for (S)-(tetrahydrofuran-2-yl)methanol and chromatographed (SiO$_2$, solvent A—hexane:EtOAc:Et$_3$N (10:30:1); solvent B—hexane:EtOAc:MeOH:Et$_3$N (10:30:10:1); 100% solvent A to 100% solvent B over 450 mL then isocratic for 300 mL) to afford the title compound (0.13 g, 0.24 mmol, 41% yield). $^1$H NMR (500 MHz, PYRIDINE-d$_5$) δ ppm 1.18 (s, 9H), 1.35 (s, 3H), 1.50 (s, 3H), 1.54-1.61 (m, 2H), 1.63-1.72 (m, 1H), 1.76-1.83 (m, 1H), 3.55-3.61 (m, 1H), 3.70-3.75 (m, 1H), 3.80 (s, 3H), 4.20-4.28 (m, 4H), 4.34-4.42 (m, 2H), 4.59 (dd, J=15.1, 3.2 Hz, 1H), 4.62-4.67 (m, 1H), 7.19 (d, J=8.5 Hz, 1H), 7.47 (s, 1H), 7.63 (dd, J=8.5, 2.1 Hz, 1H), 8.49 (d, J=2.4 Hz, 1H). MS (DCI/NH$_3$) m/z 554.3 (M+H)$^+$. Analytical calculated for C$_{27}$H$_{36}$F$_3$N$_3$O$_5$.0.4H$_2$O: C, 59.36; H, 6.78; N, 7.69. Found: C, 59.38; H, 6.94; N, 7.60.

Example 19

N-{(3E)-5-tert-butyl-1-methyl-2-[(2R)-tetrahydrofuran-2-ylmethyl]-1,2-dihydro-3H-pyrazol-3-ylidene}-2-[3-methyloxetan-3-yl)methoxy]-5-(trifluoromethyl)benzamide Potassium t-butoxide (1.2 mL, 1M in THF) was added dropwise to a solution of (3-methyloxetan-3-yl)methanol (0.13 g, 1.2 mmol) in 0.5 mL of THF precooled to −40° C. and the mixture stirred for 10 minutes. Example 1E (0.25 g, 0.59 mmol) in 1.0 mL of THF was added, the cooling bath removed and the mixture stirred at ambient temperature for 3 hours. The mixture was diluted with dichloromethane (10 mL), filtered, and chromatographed (SiO$_2$, solvent A—hexane:EtOAc:Et$_3$N (10:30:1); solvent B—hexane:EtOAc:MeOH:Et$_3$N, (10:30:10:1); 100% solvent A to 100% solvent B over 450 mL then isocratic for 300 mL) to afford the title compound (85 mg, 0.17 mmol, 29% yield). $^1$H NMR (500 MHz, PYRIDINE-d$_5$) δ ppm 1.14 (s, 9H), 1.46 (s, 3H), 1.54-1.60 (m, 2H), 1.62-1.70 (m, 1H), 1.75-1.82 (m, 1H), 3.55-3.60 (m, 1H), 3.69-3.74 (m, 1H), 3.78 (s, 3H), 4.20-4.25 (m, 3H), 4.33-4.40 (m, 3H), 4.59 (dd, J=15.1, 3.2 Hz, 1H), 4.79 (d, J=5.8 Hz, 2H), 7.19 (d, J=8.5 Hz, 1H), 7.43 (s, 1H), 7.68 (dd, J=8.5, 2.1 Hz, 1H), 8.51 (d, J=2.4 Hz, 1H). MS (DCI/NH$_3$) m/z 510.3 (M+H)$^+$. Analytical calculated for C$_{26}$H$_{34}$F$_3$N$_3$O$_4$: C, 61.28; H, 6.73; N, 8.25. Found: C, 61.24; H, 6.89; N, 8.21.

Example 20

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutoxy)-5-(trifluoromethyl)benzamide To 3-methylbutane-1,3-diol (0.1 g, 0.98 mmol) was added potassium t-butoxide (0.94 mL, 1M in THF) and stirred for 10 minutes. Example 1E (0.2 g, 0.47 mmol) in 1.2 mL of THF was added and the mixture stirred at ambient temperature for 30 minutes. The mixture was diluted with dichloromethane, 20 μL of glacial acetic acid was added and the resulting mixture was filtered, loaded onto silica and chromatographed. (0-20% MeOH in dichloromethane (0.1% NH$_4$OH) over 900 mL) to afford the title compound (70 mg, 0.14 mmol, 29% yield). $^1$H NMR (300 MHz, CDCl$_3$) δ ppm 1.30 (s, 6H), 1.41 (s, 9H), 1.67-1.92 (m, 3H), 1.94-2.09 (m, 3H), 3.60-3.81 (m, 2H), 3.85 (s, 3H), 4.11-4.23 (m, 1H), 4.23-4.33 (m, 3H), 4.54 (dd, J=15.1, 2.9 Hz, 1H), 6.98 (d, J=8.5 Hz, 1H), 7.01 (s, 1H), 7.53 (dd, J=8.6, 2.2 Hz, 1H), 8.26 (d, J=2.4 Hz, 1H). MS (DCI/NH$_3$) m/z 512.3 (M+H)$^+$. Analytical calculated for C$_{26}$H$_{36}$F$_3$N$_3$O$_4$.0.2H$_2$O: C, 60.56; H, 7.13; N, 8.15. Found: C, 60.57; H, 7.25; N, 8.12.

Example 21

N-{(3E)-5-tert-butyl-1-methyl-2-[(2R)-tetrahydrofuran-2-ylmethyl]-1,2-dihydro-3H-pyrazol-3-ylidene}-2-{[(2S)-tetrahydrofuran-2-ylmethyl]amino}-5-(trifluoromethyl)benzamide A mixture of Example 1E (100 mg, 0.234 mmol), (S)-(tetrahydrofuran-2-yl)methanamine (71 mg, 0.702 mmol) and Et$_3$N (71 mg, 0.702 mmol) in THF (1 mL) was heated at 120° C. in a microwave (Explore, CEM) for 1 hour. The reaction mixture was poured into saturated aqueous NaHCO$_3$ and extracted with EtOAc. The organic extract was dried (Na$_2$SO$_4$), filtered and concentrated. The residue was purified by reverse phase preparative HPLC on a Waters Symmetry C8 column (25 mm×100 mm, 7 μm particle size) using a gradient of 10% to 100% acetonitrile: 0.1% aqueous trifluoroacetic acid over 8 minutes (10 minutes run time) at a flow rate of 40 mL/minutes) to afford 49 mg (41%) of the title compound. $^1$H NMR (400 MHz, CDCl$_3$) δ ppm 1.50 (s, 9H) 1.57-1.76 (m, 2H) 1.91-2.16 (m, 5H) 2.26-2.41 (m, 1H) 3.29 (dd, J=12.58, 9.51 Hz, 1H) 3.40 (dd, J=13.20, 7.06 Hz, 1H) 3.79-4.06 (m, 5H) 4.16 (s, 3H) 4.16-4.22 (m, 1H) 4.23-4.31 (m, 1H) 4.33-4.45 (m, 1H) 5.03-5.14 (m, 1H) 6.85 (d, J=9.21 Hz, 1H) 6.95 (s, 1H) 7.59 (dd, J=8.90, 1.84 Hz, 1H) 7.80 (s, 1H); MS (ESI) m/z 509 (M+H)$^+$.

Example 22

(E)-N-(5-tert-butyl-1-methyl-2(((R)-tetrahydrofuran-2-yl)methyl)-1H-pyrazol-3(2H)-ylidene)-2-(((2R,3S)-3-methoxytetrahydrofuran-2-yl)methoxy)-5-(trifluoromethyl)benzamide Example 22A (2R,3S)-pentane-1,2,3,5-tetraol
Water (50 mL) and R$^a$—Ni, water-wet (5.03 g, 38.6 mmol) were added to (3S,4R)-3,4,5-trihydroxypentanal (25.19 g, 188 mmol) in a 300 mL stainless steel reactor. The mixture was stirred for 1.5 hr at 70° C. under 800 psi (literature 570 psi) of hydrogen. The 270 psi pressure drop was consistent with full conversion, and the DCI-MS showed only ions for the expected product. The mixture was filtered through a nylon membrane, the reactor was rinsed with water, and the filtrate was concentrated and afforded 25.8 g of the title compound. $^1$H NMR (400 MHz, DMSO-d$_6$) δ ppm 1.36-1.48 (m, 1H) 1.66-1.77 (m, 1H) 3.20-3.27 (m, 1H) 3.33 (dd, J=11.66, 6.14 Hz, 1H) 3.38-3.59 (m, 4H) 4.25-4.33 (m, 3H) 4.40 (d, J=5.22 Hz, 1H); MS (ESI) m/z 137 (M+H)$^+$.

Example 22B (2R,3S)-2-(hydroxymethyl)tetrahydrofuran-3-ol

A mixture of the product from Example 22A (25.8 g, 190 mmol) and 4-methylbenzenesulfonic acid monohydrated (710 mg, 3.73 mmol) was refluxed and the water removed as an azeo-tropic mixture with toluene by using a Dean-Stark apparatus. After 4 hrs of refluxing, the reaction mixture was cooled and treated with solid $NaHCO_3$ (3.9 mmol) to neutralize the acid catalyst followed by removal of the solid material by filtration. The filtrate was distilled and collected the fraction at 95-98° C. under a pressure of 0.6 Torr as a colorless oil (15.3 g, 68%). $^1$H NMR (400 MHz, DMSO-$d_6$) δ ppm 1.63-1.74 (m, 1H) 1.84-1.98 (m, 1H) 3.28-3.35 (m, 1H) 3.52-3.59 (m, 1H) 3.69-3.82 (m, 2H) 4.00-4.08 (m, 1H) 4.57 (t, J=5.52 Hz, 1H) 4.82 (d, J=3.99 Hz, 1H).

Example 22C (2R,3S)-2-((bis(4-methoxyphenyl)(phenyl)methoxy)methyl)tetrahydrofuran-3-ol Example 22B (1.6 g, 13.54 mmol) in pyridine (20 mL) was treated with 4,4'-chloro(phenyl)methylenebismethoxybenzene (5.05 g, 14.9 mmol) for 12 hrs at rt. The solvent was removed by vacuum. The residue was diluted with $CH_2Cl_2$, and washed with saturated $NaHCO_3$, and brine. The organics were dried over $MgSO_4$, filtered and concentrated. The residue was purified by column chromatography using an Analogix® Intelliflash280™ ($SiO_2$, 0-100% ethyl acetate in hexanes) to afford 4.25 g (75%) of the title compound. $^1$H NMR (400 MHz, CDCl$_3$) δ ppm 1.73 (d, J=3.99 Hz, 1H) 1.84-1.94 (m, 1H) 2.09-2.22 (m, 1H) 3.08 (dd, J=9.51, 6.14 Hz, 1H) 3.25 (dd, J=9.51, 4.60 Hz, 1H) 3.78 (s, 6H) 3.84-3.90 (m, 1H) 3.97 (dd, J=8.29, 5.52 Hz, 2H) 4.26-4.32 (m, 1H) 6.78-6.86 (m, 4H) 7.17-7.24 (m, 1H) 7.27-7.36 (m, 6H) 7.39-7.46 (m, 2H).

Example 22D (2R,3S)-2-((bis(4-methoxyphenyl)(phenyl)methoxy)methyl)-3-methoxytetrahydrofuran The product from Example 22C (620 mg, 1.47 mmol) in DMF (5 mL) was treated with NaH (60%)(88 mg, 2.2 mmol). The mixture was stirred for 10 min at rt. To the mixture was added dropwise iodomethane (251 mg, 1.57 mmol). The reaction was stirred at rt for 12 hrs. The reaction mixture was quenched with water and extracted with EtOAc. The organic was dried over $MgSO_4$, filtered and concentrated. The residue was purified by column chromatography using an Analogix® Intelliflash280™ ($SiO_2$, 0-100% ethyl acetate in hexanes) to afford 574 mg (90%) of the title compound. $^1$H NMR (400 MHz, CDCl$_3$) δ ppm 1.91-2.02 (m, 2H) 3.09 (dd, J=9.82, 5.52 Hz, 1H) 3.15 (dd, J=9.82, 4.91 Hz, 1H) 3.31 (s, 3H) 3.78 (s, 6H) 3.81-3.93 (m, 2H) 3.94-4.06 (m, 2H) 6.77-6.87 (m, 4H) 7.16-7.23 (m, 1H) 7.26-7.37 (m, 6H) 7.40-7.48 (m, 2H).

Example 22E ((2R,3S)-3-methoxytetrahydrofuran-2-yl)methanol

The product from Example 22D (2.6 g, 6 mmol) in $CH_2Cl_2$ (10 mL) and MeOH (10 mL) was treated with 4-methylbenzenesulfonic acid monohydrate (570 mg, 3 mmol). The mixture was stirred at rt for 1 hr. The mixture was neutralized with excess $Et_3N$. The solvent was removed and the residue was purified by column chromatography using an Analogix® Intelliflash280™ ($SiO_2$, 0-50% MeOH in ethyl acetate) to afford 580 mg (73%) of the title compound. $^1$H NMR (400 MHz, CDCl$_3$) δ ppm 1.85 (t, J=6.14 Hz, 1H) 1.95-2.03 (m, 2H) 3.35 (s, 3H) 3.56-3.65 (m, 1H) 3.71-3.78 (m, 1H) 3.82 (dd, J=8.29, 4.30 Hz, 1H) 3.85-3.93 (m, 2H) 3.95-4.02 (m, 1H).

Example 22F (E)-N-(5-tert-butyl-1-methyl-2-(((R)-tetrahydrofuran-2-yl)methyl)-1H-pyrazol-3(2H)-ylidene)-2-(((2R,3S)-3-methoxytetrahydrofuran-2-yl)methoxy)-5-(trifluoromethyl)benzamide The product from Example 1E and Example 22E were processed using the method described in Example 1F to afford the title compound. $^1$H NMR (400 MHz, CDCl$_3$) δ ppm 1.42 (s, 9H) 1.69-1.79 (m, 2H) 1.92 (m, 4H) 2.07-2.18 (m, 1H) 3.32 (s, 3H) 3.67-3.80 (m, 2H) 3.86 (s, 3H) 3.83-3.92 (m, 1H) 3.93-4.03 (m, 2H) 4.07-4.13 (m, 1H) 4.13-4.25 (m, 3H) 4.30 (dd, J=15.34, 5.52 Hz, 1H) 4.48 (dd, J=15.34, 3.07 Hz, 1H) 6.94-7.04 (m, 2H) 7.47 (dd, J=8.59, 2.45 Hz, 1H) 7.89 (d, J=2.15 Hz, 1H); MS (ESI) m/z 540 (M+H)$^+$.

Example 23

N-{(3E)-5-tert-butyl-1-methyl-2-[(2R)-tetrahydrofuran-2-ylmethyl]-1,2-dihydro-3H-pyrazol-3-ylidene}-2-{[(2R)-tetrahydrofuran-2-ylmethyl]amino}-5-(trifluoromethyl)benzamide The product from Example 1E and (R)-(tetrahydrofuran-2-yl)methanamine were processed using the method described in Example 21 to afford the title compound. $^1$H NMR (400 MHz, CDCl$_3$) δ ppm 1.42 (s, 9H) 1.65-1.80 (m, 4H) 1.79-1.98 (m, 3H) 1.98-2.09 (m, 2H) 3.33 (d, J=5.52 Hz, 2H) 3.67-3.82 (m, 3H) 3.86 (s, 3H) 3.91 (dd, J=13.50, 6.44 Hz, 1H) 4.12-4.27 (m, 2H) 4.36 (dd, J=15.04, 5.22 Hz, 1H) 4.55 (dd, J=15.65, 3.07 Hz, 1H) 6.68 (d, J=8.59 Hz, 1H) 6.96-6.98 (m, 1H) 7.40 (dd, J=8.90, 2.15 Hz, 1H) 8.59 (s, 1H); MS (ESI) m/z 509 (M+H)$^+$.

Example 24

(E)-N-(5-tert-butyl-1-methyl-2(((R)-tetrahydrofuran-2-yl)methyl)-1H-pyrazol-3(2H)-ylidene)-2-(((2R,3R)-3-fluorotetrahydrofuran-2-yl)methoxy)-5-(trifluoromethyl)benzamide

Example 24A (E)-N-(5-tert-butyl-1-methyl-2(((R)-tetrahydrofuran-2-yl)methyl)-1H-pyrazol-3(2H)-ylidene)-2-(((2R,3R)-3-fluorotetrahydrofuran-2-yl)methoxy)-5-(trifluoromethyl)benzamide The product from Example 22C (1.1 g, 2.62 mmol) in $CH_2Cl_2$ (10 mL) was treated dropwise with diethylaminosulfur trifluoride (DAST) (508 mg, 3.14 mmol) at −78° C. The reaction was allowed to warm to room temperature for 12 hrs. The reaction mixture was quenched with saturated aqueous $NaHCO_3$ and extracted with $CH_2Cl_2$. The organic extract was dried ($Na_2SO_4$), filtered and concentrated. The residue was purified by column chromatography using an Analogix® Intelliflash280™ ($SiO_2$, 0-100% ethyl acetate in hexanes) to afford the title compound. $^1$H NMR (400 MHz, CDCl$_3$) δ ppm 2.05-2.27 (m, 2H) 3.32 (dd, J=9.21, 6.14 Hz, 1H) 3.35-3.43 (m, 1H) 3.79 (s, 6H) 3.84-3.95 (m, 2H) 4.03 (dd, J=15.96, 8.59 Hz, 1H) 5.20 (d, J=55.54 Hz, 1H) 6.77-6.86 (m, 4H) 7.17-7.23 (m, 1H) 7.24-7.30 (m, 2H) 7.31-7.38 (m, 4H) 7.44-7.49 (m, 2H).

Example 24B ((2R,3R)-3-fluorotetrahydrofuran-2-yl)methanol

The product from Example 24A was processed using the method described in Example 22E to afford the title compound and (S)-(2,5-dihydrofuran-2-yl)methanol as a by-product that was not separated. $^1$H NMR (400 MHz, CDCl$_3$) δ ppm 2.02-2.42 (m, 2H) 3.51-3.79 (m, 1H) 3.81-3.94 (m, 3H) 4.03-4.15 (m, 1H) 5.24 (d, J=59.84 Hz, 1H).

Example 24C (E)-N-(5-tert-butyl-1-methyl-2-(((R)-tetrahydrofuran-2-yl)methyl)-1H-pyrazol-3(2H)-ylidene)-2-(((2R,3R)-3-fluorotetrahydrofuran-2-yl)methoxy)-5-(trifluoromethyl)benzamide The product from Example 1E and Example 24B were processed using the method described in Example 1F to afford the title compound. $^1$H NMR (400 MHz, CDCl$_3$) δ ppm 1.48 (s, 9H) 1.83-1.96 (m, 2H) 2.08-2.42 (m, 3H) 3.70 (dd, J=14.12, 7.06 Hz, 1H) 3.80 (dd, J=13.50, 6.75 Hz, 1H) 3.97-4.15 (m, 4H) 4.20 (s, 3H) 4.34-4.46 (m, 1H) 4.48-4.60 (m, 1H) 4.59-4.77 (m, 2H) 5.13 (d, J=21.79 Hz, 1H) 5.35 (d, J=54.62 Hz, 1H) 6.89-6.94 (m, 1H) 7.19 (d, J=8.90 Hz, 1H) 7.77 (d, J=7.67 Hz, 1H) 8.26-8.34 (m, 1H); MS (DCI/NH$_3$) m/z 528 (M+1)$^+$.

Example 25

N-{(3E)-5-tert-butyl-1-methyl-2-[(2R)-tetrahydrofuran-2-ylmethyl]-1,2-dihydro-3H-pyrazol-3-ylidene}-2-[(2)-2,5-dihydrofuran-2-ylmethoxy]-5-(trifluoromethyl)benzamide The title compound was obtained as a separate product in the formation of Example 24C. $^1$H NMR (400 MHz, CDCl$_3$) δ ppm 1.49 (s, 9H) 1.53-1.65 (m, 1H) 1.82-1.96 (m, 2H) 2.10-2.29 (m, 1H) 3.64-3.85 (m, 2H) 4.18 (m, 2H) 4.20 (s, 3H) 4.32-4.43 (m, 1H) 4.64-4.71 (m, 2H) 4.66-4.81 (m, 1H) 5.22 (d, J=15.34 Hz, 1H) 5.29-5.37 (m, 1H) 5.86 (d, J=7.36 Hz, 1H) 6.03 (d, J=6.14 Hz, 1H) 7.00 (s, 1H) 7.16 (d, J=8.59 Hz, 1H) 7.72 (d, J=7.36 Hz, 2H) 8.19 (s, 1H); MS (DCI/NH$_3$) m/z 508 (M+1)$^+$.

Example 26

N-{(3E)-5-tert-butyl-1-methyl-2-[(2R)-tetrahydrofuran-2-ylmethyl]-1,2-dihydro-3H-pyrazol-3-ylidene}-2-{methyl[(2S)-tetrahydrofuran-2-ylmethyl]amino}-5-(trifluoromethyl)benzamide The product from Example 21 (100 mg, 0.2 mmol) in DMF (5 mL) was treated with NaH (60%)(15.7 mg, 0.4 mmol) and the mixture stirred for 10 min at rt. To the mixture was added dropwise iodomethane (31 mg, 0.22 mmol) and the reaction was stirred at room temperature for 12 hrs. The reaction mixture was quenched with water and extracted with EtOAc. The organic extract was dried (Na$_2$SO$_4$), filtered, concentrated and purified by HPLC on a Waters Symmetry C8 column (40 mm×100 mm, 7 μm particle size) using a gradient of 10% to 100% acetonitrile: ammonium acetate (10 mM) over 15 min at a flow rate of 70 mL/min to provide the title product. $^1$H NMR (400 MHz, CDCl$_3$) δ ppm 1.43 (s, 9H) 1.67-1.97 (m, 8H) 3.04 (s, 3H) 3.31 (dd, J=13.20, 6.75 Hz, 1H) 3.45 (dd, J=14.42, 4.30 Hz, 1H) 3.64-3.85 (m, 4H) 3.89 (s, 3H) 4.04-4.21 (m, 2H) 4.38 (dd, J=15.34, 5.83 Hz, 1H) 4.58 (dd, J=15.65, 4.30 Hz, 1H) 6.96 (d, J=8.90 Hz, 1H) 6.99 (s, 1H) 7.40 (dd, J=8.90, 2.15 Hz, 1H) 7.83 (d, J=1.84 Hz, 1H); MS (DCI/NH$_3$) m/z 523 (M+1)$^+$.

Example 27

N-[(3E)-5-tert-butyl-2-(cyclopropylmethyl)-1-methyl-1,2-dihydro-3H-pyrazol-3-ylidene]-2-[(2S)-tetrahydrofuran-2-ylmethoxy]-5-(trifluoromethyl)benzamide Example 27A di-tert-butyl 1-(cyclopropylmethyl)hydrazine-1,2-dicarboxylate To a mixture of cyclopropylmethanol (7.15 mL, 90 mmol), di-tert-butyl hydrazine-1,2-dicarboxylate (6.30 g, 27.1 mmol) and triphenylphosphine (28.5 g, 109 mmol) in THF (100 mL) was added (E)-di-tert-butyl diazene-1,2-dicarboxylate (25 g, 109 mmol) in portions at ambient temperature. The reaction mixture was concentrated and allowed to stand overnight. The white solid (PPh$_3$O) precipitated was filtered off and the filtrate was purified by flash chromatography (silica gel, EtOAc in Hexane in 5-25% gradient) to yield 27.5 g (96%) of the title compound.

Example 27B (cyclopropylmethyl)hydrazine dihydrochloride

A mixture of Example 27A (27.5 g, 96 mmol) and 4M HCl in dioxane (80 mL) was stirred at ambient temperature for 4 hours. The white solid precipitate was collected by filtration, washed with ether and dried to yield 15.3 g of the title compound. $^1$H NMR (300 MHz, DMSO-d$_6$) δ ppm 0.22-0.34 (m, 2H), 0.46-0.58 (m, 2H), 0.91-1.06 (m, 1H), 2.79 (d, J=7.12 Hz, 2H), 5.91 (s, 5H); MS (DCI) m/z 87 [M+H]$^+$.

Example 27C 3-tert-butyl-1-(cyclopropylmethyl)-1H-pyrazol-5-amine hydrochloride

A mixture of Example 27B (13.5 g, 85 mmol) and 4,4-dimethyl-3-oxopentanenitrile (11.69 g, 93 mmol) in ethanol (50 mL) was refluxed at 90° C. for 6 hours. The mixture was concentrated under reduced pressure and ethyl acetate (20 mL) added to the residue. The white solid precipitate was filtered, washed with ether and dried to yield 17.5 g (90%) of title compound as a white solid. $^1$H NMR (300 MHz, DMSO-d$_6$) δ ppm 0.42-0.54 (m, 4H), 1.16-1.27 (m, 1H), 1.28 (s, 9H), 4.02 (d, J=7.12 Hz, 2H), 5.53 (s, 1H), 6.91 (s, 2H), 14.05 (s, 1H); MS (DCI) m/z 294 [M+H]$^+$.

Example 27D

N-(3-tert-butyl-1-(cyclopropylmethyl)-1H-pyrazol-5-yl)-2,2,2-trifluoroacetamide

To a mixture of Example 27C (13 g, 56.6 mmol) and pyridine (18.31 mL, 226 mmol) in CH$_2$Cl$_2$ (150 mL) was added 2,2,2-trifluoroacetic anhydride (15.73 mL, 113 mmol) dropwise at ambient temperature. The mixture was stirred at ambient temperature for 2 hours, and then water (20 mL) and CH$_2$Cl$_2$ (20 mL) were added. The organic layer was washed with saturated NaHCO$_3$ aqueous, brine and concentrated. Purification by chromatography (silica gel, EtOAc/Hexane in 10-60% gradient) afforded 4.35 g (88%) of the title compound. $^1$H NMR (300 MHz, DMSO-d$_6$) δ ppm 0.21-0.33 (m, 2H), 0.38-0.49 (m, 2H), 1.04-1.16 (m, 1H), 1.23 (s, 9H), 3.82 (d, J=6.78 Hz, 2H), 6.17 (s, 1H), 11.31 (s, 1H); MS (ESI) m/z 289 [M+H]$^+$, 287 [M−H].

Example 27E (E)-N-(5-tert-butyl-2-(cyclopropylmethyl)-1-methyl-1H-pyrazol-3(2H)-ylidene)-2,2,2-trifluoroacetamide A mixture of Example 27D (11.6 g, 40 mmol) and dimethyl sulfate (20.2 g, 160 mmol) in toluene (10 mL) was heated in a microwave at 150° C. for 30 min. The mixture was concentrated and purified by flash chromatography (silica gel, MeOH/Et$_3$N (10:1)/EtOAc in 10-60% gradient) to yield 6.6 g (54.4%) of the title compound. $^1$H NMR (300 MHz, DMSO-d$_6$) ppm 0.41-0.53 (m, 4H), 1.15-1.27 (m, 1H), 1.38 (s, 9H), 3.98 (s, 3H), 4.20 (d, J=7.12 Hz, 2H), 6.70 (s, 1H); MS (ESI) m/z 304 [M+H]$^+$, 302 [M−H].

Example 27F 5-tert-butyl-2-(cyclopropylmethyl)-1-methyl-1H-pyrazol-3(2H)-imine

A mixture of Example 27E (6.37 g, 21 mmol) and 6N NaOH aqueous (20 mL) in MeOH (100 mL) was stirred at 50° C. overnight, and then concentrated under reduced pressure. The residue was extracted by CH$_2$Cl$_2$ (30 mL×3) and the combined organic layers were washed with brine and concentrated to yield 3.8 g (87%) of the title compound as a white solid. $^1$H NMR (300 MHz, DMSO-d$_6$) δ ppm 0.37-0.44 (m, 2H), 0.47-0.54 (m, 2H), 1.07-1.20 (m, 1H), 1.29-1.36 (m, 9H), 3.78 (s, 3H), 4.10 (d, J=6.74 Hz, 2H), 5.60 (s, 1H), 7.19 (s, 1H); MS (+DCI) m/z 208 [M+H]$^+$.

Example 27G

N-[(3E)-5-tert-butyl-2-(cyclopropylmethyl)-1-methyl-1,2-dihydro-3H-pyrazol-3-ylidene]-2-fluoro-5-(trifluoromethyl)benzamide To Example 27F (3.52 g, 17 mmol) in CH$_2$Cl$_2$ (50 mL) was added triethylamine (7.1 mL, 51 mmol), then 2-fluoro-5-(trifluoromethyl)benzoyl chloride (3.85 g, 17 mmol) dropwise and the mixture was stirred at ambient temperature for 2 hours. Water (20 mL) and CH$_2$Cl$_2$ (20 mL) were added, and the organic layer was washed with brine and concentrated. Purification by flash chromatography (silica gel, MeOH/Et$_3$N (10:1) in EtOAc in 5-40% gradient) afforded 6.3 g (93% yield) of the title compound. $^1$H NMR (300 MHz, DMSO-d$_6$) δ ppm 0.42-0.56 (m, 4H), 1.15-1.29 (m, 1H), 1.36-1.45 (m, 9H), 3.95 (s, 3H), 4.24 (d, J=7.14 Hz, 2H), 6.84 (s, 1H), 7.33-7.43 (m, 1H), 7.70-7.78 (m, 1H), 8.12 (dd, J=6.74, 2.38 Hz, 1H); MS (+DCI) m/z 398 [M+H]$^+$.

Example 27H

N-[(3E)-5-tert-butyl-2-(cyclopropylmethyl)-1-methyl-1,2-dihydro-3H-pyrazol-3-ylidene]-2-[(2S)-tetrahydrofuran-2-ylmethoxy]-5-(trifluoromethyl)benzamide To (S)-(tetrahydrofuran-2-yl)methanol (102 mg, 1.0 mmol) in THF (8 mL) was added potassium tert-butoxide (112 mg, 1.0 mmol), then Example 27G (199 mg, 0.501 mmol) in portions. The mixture was stirred at ambient temperature for 2 hours, quenched with saturated aqueous NH$_4$Cl and extracted by EtOAc (3×10 mL). The combined organic layer was concentrated under reduced pressure. Purification by flash chromatography (silica gel, MeOH/Et$_3$N (10:1)/EtOAc in 10-60% gradient) yielded 156 mg (65%) of the title compound. $^1$H NMR (300 MHz, DMSO-d$_6$) δ ppm 0.41-0.51 (m, 4H), 1.11-1.25 (m, 1H), 1.37-1.44 (m, 9H), 1.65-1.99 (m, 4H), 3.58-3.67 (m, 1H), 3.70-3.82 (m, 1H), 3.90 (s, 3H), 3.98-4.03 (m, 2H), 4.09-4.20 (m, 3H), 6.79 (s, 1H), 7.15 (d, J=8.33 Hz, 1H), 7.55 (dd, J=8.53, 2.58 Hz, 1H), 7.63 (d, J=2.38 Hz, 1H); MS (ESI) m/z 480 [M+H]$^+$, 478 [M−H].

Example 28

N-{(3E)-5-tert-butyl-1-methyl-2-[(2R)-tetrahydrofuran-2-ylmethyl]-1,2-dihydro-3H-pyrazol-3-ylidene}-3-chloro-2-[(2)-tetrahydrofuran-2-ylmethoxy]-5-trifluoromethyl)benzamide Example 28A N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide The title compound was prepared according to the procedure described in Example 1E, substituting 2-fluoro-5-(trifluoromethyl)benzoyl chloride with 3-chloro-2-fluoro-5-(trifluoromethyl)benzoyl chloride to provide the title compound as a white solid. $^1$H NMR (300 MHz, DMSO-d$_6$) δ ppm 1.38 (s, 9H), 1.65-1.98 (m, 4H), 3.56-3.68 (m, 1H), 3.69-3.81 (m, 1H), 3.93 (s, 3H), 4.14-4.25 (m, 1H), 4.30-4.47 (m, 2H), 6.83 (s, 1H), 7.99-8.16 (m, 2H); MS (ESI) m/z 462 [M+H]$^+$, 460 [M−H].

Example 28B

N-{(3E)-5-tert-butyl-1-methyl-2-[(2R)-tetrahydrofuran-2-ylmethyl]-1,2-dihydro-3H-pyrazol-3-ylidene}-3-chloro-2-[(2S)-tetrahydrofuran-2-ylmethoxy]-5-trifluoromethyl)benzamide The title compound was made from (S)-(tetrahydrofuran-2-yl)methanol and Example 28A in 58.8% yield according to the procedure described in Example 27H. $^1$H NMR (300 MHz, DMSO-d$_6$) δ ppm 1.39 (s, 9H), 1.61-1.98 (m, 8H), 3.56-3.67 (m, 2H), 3.68-3.78 (m, 2H), 3.91 (s, 3H), 3.95-4.05 (m, 1H), 4.04-4.20 (m, 3H), 4.31-4.39 (m, 2H), 6.81 (s, 1H), 7.73 (d, J=2.38 Hz, 1H), 7.78 (d, J=2.38 Hz, 1H); MS (ESI) m/z 544 [M+H]$^+$, 542[M−H].

Example 29

N-[(2Z)-3-butyl-5-tert-butyl-1,3,4-thiadiazol-2(3H)-ylidene]-2-{[(2S)-1-methylpyrrolidin-2-yl]methoxy}-5-(trifluoromethyl)benzamide To a solution of (S)-(1-methylpyrrolidin-2-yl)methanol (0.177 mL, 1.5 mmol) in THF (5 mL) was added NaH 60% (62 mg, 1.5 mmol) and the mixture stirred for 10 minutes. The product from Example 7B was added and the reaction mixture was stirred at ambient temperature for 8 hours. The mixture was quenched with aqueous NH$_4$Cl, extracted with EtOAc, the organic layer was washed with brine, dried with MgSO$_4$ and the solvent removed. The residue was purified by using an Analogix® Intelliflash280™ (0-10% MeOH/CH$_2$Cl$_2$) to afford the title compound (190 mg). $^1$H NMR (300 MHz, DMSO-d$_6$) δ ppm 0.91 (t, J=7.3 Hz, 3H), 1.22-1.38 (m, 2H), 1.39 (s, 9H), 1.49-1.71 (m, 3H), 1.73-1.87 (m, 2H), 1.87-2.00 (m, 1H), 2.17 (q, J=8.6 Hz, 1H), 2.33 (s, 3H), 2.55-2.68 (m, 1H), 2.82-3.02 (m, 1H), 3.89-4.17 (m, 2H), 4.34 (t, J=7.1 Hz, 2H), 7.32 (d, J=8.7 Hz, 1H), 7.78 (dd, J=8.7, 2.4 Hz, 1H), 8.02 (d, J=2.4 Hz, 1H). MS (ESI/NH$_3$) m/z 499 (M+H)$^+$. Anal. calcd for C$_{24}$H$_{33}$F$_3$N$_4$O$_2$S: C, 57.81; H, 6.67; N, 11.24. Found: C, 57.70; H, 6.71; N, 11.19.

Example 30

N-[(3E)-5-tert-butyl-2-(4-fluorobenzyl)-1-methyl-1,2-dihydro-3H-pyrazol-3-ylidene]-2-[(2S)-tetrahydrofuran-2-ylmethoxy]-5-(trifluoromethyl)benzamide

Example 30A 3-tert-butyl-1-(4-fluorobenzyl)-1H-pyrazol-5-amine

To a solution of (4-fluorobenzyl)hydrazine dihydrochloride (1.0 g, 4.7 mmol, Matrix) in ethyl alcohol (2 mL) was added 4,4-dimethyl-3-oxopentanenitrile (0.6 g, 4.7 mmol, Aldrich). After stirring at 85° C. for 2 h, the reaction mixture was cooled, concentrated, diluted with ethyl acetate (10 mL) and washed with saturated NaHCO$_3$ (10 mL). The aqueous layer was extracted with ethyl acetate (2×10 mL). The combined organic extracts were dried over anhydrous Na$_2$SO$_4$, filtered and concentrated under reduced pressure to obtain 1.3 g (99%) of the title compound. MS (ESI$^+$) m/z 248 (M+H)$^+$.

Example 30B

N-(3-tert-butyl-1-(4-fluorobenzyl)-1H-pyrazol-5-yl)-2-fluoro-5-(trifluoromethyl)benzamide To a solution of Example 30A (0.7 g, 2.6 mmol) in tetrahydrofuran (20 mL) were added 2-fluoro-5-(trifluoromethyl)benzoyl chloride (0.46 mL, 3.1 mmol, Aldrich) and pyridine (0.62 mL, 7.6 mmol). After stirring at 60° C. for 16 h, the reaction mixture was cooled and quenched with saturated NaHCO$_3$ (20 mL). The aqueous layer was extracted with ethyl acetate (3×30 mL). The combined organic extracts were dried over anhydrous Na$_2$SO$_4$, filtered and concentrated under reduced pressure. The residue was purified by column chromatography using an Analogix® Intelliflash280™ (SiO$_2$, O-25% ethyl acetate in methylene chloride) to afford 0.75 g (67%) of the title compound. MS (ESI$^+$) m/z 438 (M+H)$^+$.

Example 30C

N-[(3E)-5-tert-butyl-2-(4-fluorobenzyl)-1-methyl-1,2-dihydro-3H-pyrazol-3-ylidene]-2-fluoro-5-(trifluoromethyl)benzamide Example 30B and dimethyl sulfate were processed as described for Example 1E to obtain the title compound. MS (ESI$^+$) m/z 452 (M+H)$^+$.

Example 30D

N-[(3E)-5-tert-butyl-2-(4-fluorobenzyl)-1-methyl-1,2-dihydro-3H-pyrazol-3-ylidene]-2-[(2S)-tetrahydrofuran-2-ylmethoxy]-5-(trifluoromethyl)benzamide Example 30C, (S)-(tetrahydrofuran-2-yl)methanol (Julich chiral solutions) and sodium t-butoxide were processed as described for Example 1F to obtain the title compound. $^1$H NMR (300 MHz, DMSO-d$_6$) δ ppm 1.35 (s, 9H), 1.57-1.76 (m, 2H), 1.75-1.96 (m, 2H), 3.55-3.63 (m, 1H), 3.67-3.75 (m, 1H), 3.70 (s, 3H), 3.97 (d, J=2.1 Hz, 1H), 3.98 (s, 1H), 3.99-4.09 (m, 1H), 5.56 (s, 2H), 6.87 (s, 1H), 7.07-7.39 (m, 5H), 7.55 (dd, J=8.7, 2.6 Hz, 1H), 7.66 (d, J=2.5 Hz, 1H); MS (ESI$^+$) m/z 534 (M+H)$^+$.

Example 31

N-{(3E)-5-tert-butyl-1-methyl-2-[1-methyl-4,5-dihydroisoxazol-5-yl)methyl]-1,2-dihydro-3H-pyrazol-3-ylidene}-2-[(2S)-tetrahydrofuran-2-ylmethoxy]-5-(trifluoromethyl)benzamide

Example 31A 1-allyl-3-tert-butyl-1H-pyrazol-5-amine

Allylhydrazine (70% in water, Wako) and 4,4-dimethyl-3-oxopentanenitrile (Aldrich) were processed as described for Example 30A to obtain the title compound. MS (ESI$^+$) m/z 180 (M+H)$^+$.

Example 31B

N-(1-allyl-3-tert-butyl-1H-pyrazol-5-yl)-2-fluoro-5-(trifluoromethyl)benzamide

Example 31A and 2-fluoro-5-(trifluoromethyl)benzoyl chloride were processed as described for Example 30B to obtain the title compound. MS (ESI$^+$) m/z 370 (M+H)$^+$.

Example 31C

N-[(3E)-2-allyl-5-tert-butyl-1-methyl-1,2-dihydro-3H-pyrazol-3-ylidene]-2-fluoro-5-(trifluoromethyl)benzamide Example 31B and dimethyl sulfate were processed as described for Example 1E to obtain the title compound. MS (ESI$^+$) m/z 384 (M+H)$^+$.

Example 31D

N-[(3E)-5-tert-butyl-1-methyl-2-prop-2-en-1-yl-1,2-dihydro-3H-pyrazol-3-ylidene]-2-[(2S)-tetrahydrofuran-2-ylmethoxy]-5-(trifluoromethyl)benzamide Example 31C, (S)-(tetrahydrofuran-2-yl)methanol (Julich chiral solutions) and sodium t-butoxide were processed as described for Example 1F to obtain the title compound. MS (ESI$^+$) m/z 466 (M+H)$^+$.

Example 31E

N-{(3E)-5-tert-butyl-1-methyl-2-[3-methyl-4,5-dihydroisoxazol-5-yl]methyl]-1,2-dihydro-3H-pyrazol-3-ylidene}-2-[(2S)-tetrahydrofuran-2-ylmethoxy]-5-(trifluoromethyl)benzamide To a solution of (E)-acetaldehyde oxime (28 mg, 0.47 mmol, Aldrich) in chloroform (6 mL) were added N-chlorosuccinimide (101 mg, 0.76 mmol, Aldrich) and pyridine (5 µL). After stirring at room temperature for 5 h, Example 31D (44 mg, 0.1 mmol) and triethylamine (48 mg, 0.47 mmol) were added to the reaction mixture. After stirring at room temperature for 16 h, the reaction mixture was quenched with water (5 mL). The aqueous layer was extracted with methylene chloride (3×10 mL). The combined organic extracts were dried over anhydrous Na$_2$SO$_4$, filtered and concentrated under reduced pressure. The residue was then purified by column chromatography using an Analogix® Intelliflash280™ (SiO$_2$, 5-100% of solvent A in solvent B wherein solvent A is triethylamine/MeOH/EtOAc (0.1/1/10) and solvent B is hexane). $^1$H NMR (300 MHz, DMSO-d$_6$) δ ppm 1.37 (s, 9H), 1.67-1.78 (m, 2H), 1.80 (s, 3H), 1.82-2.01 (m, 2H), 2.82-3.10 (m, 2H), 3.58-3.66 (m, 1H), 3.73 (q, J=7.0 Hz, 1H), 3.85 (s, 3H), 3.93-4.04 (m, 2H), 4.05-4.16 (m, 1H), 4.34 (d, J=4.9 Hz, 2H), 4.74-4.88 (m, 1H), 6.77 (s, 1H), 7.15 (d, J=8.9 Hz, 1H), 7.55 (dd, J=9.5, 1.5 Hz, 1H), 7.64 (d, J=2.1 Hz, 1H); MS (ESI$^+$) m/z 523 (M+H)$^+$.

Example 32

N-[(2Z)-5-tert-butyl-3-[(2R)-tetrahydrofuran-2-ylmethyl]-1,3-oxazol-2(3H)-ylidene]-2-{[(2S)-1-methylpyrrolidin-2-yl]methoxy}-5-(trifluoromethyl)benzamide

Example 32A (R)—N-((tetrahydrofuran-2-yl)methyl)cyanamide

To a stirred mixture of cyanogen bromide (2.2 g, 20.8 mmol) and anhydrous Na$_2$CO$_3$ (4.2 g, 39.6 mmol) in dry ether (30 mL) cooled between −20 and −10° C. was added (R)-(tetrahydro-furan-2-yl)-methylamine (Aldrich) (2.0 g, 19.8 mmol) over 10 minutes. Stirring was continued for an additional 1.5 hours at −20 to −10° C. Then the mixture was filtered and concentrated to provide 2.21 g of the title product. MS (ESI) m/z 127 (M+H)$^+$.

Example 32B (R)-5-tert-butyl-3-((tetrahydrofuran-2-yl)methyl)oxazol-2(3H)-imine A mixture of Example 32A (2.35 g, 18.63 mmol), 1-bromo-3,3-dimethylbutan-2-one (2.52 mL, 18.63 mmol) and potassium carbonate (2.57 g, 18.63 mmol) in 2-butanone (75 mL) was heated to 80° C. overnight. The mixture was poured into water, and extracted with ethyl acetate (2×). The combined organic extracts were dried over Na$_2$SO$_4$, filtered, concentrated under reduced pressure to afford the title compound. MS (ESI) m/z 225 (M+H)$^+$.

Example 32C

N-[(2Z)-5-tert-butyl-3-[(2R)-tetrahydrofuran-2-ylmethyl]-1,3-oxazol-2(3H)-ylidene]-2-fluoro-5-(trifluoromethyl)benzamide A mixture of Example 32B (2 g, 8.92 mmol), 1H-benzo[d][1,2,3]triazol-1-ol hydrate (1.37 g, 8.92 mmol), N1-((ethylimino)methylene)-N3,N3-dimethylpropane-1,3-diamine hydrochloride (1.71 g, 8.92 mmol), 2-fluoro-5-(trifluoromethyl)benzoic acid (1.86 g, 8.92 mmol), and triethylamine (1.86 mL, 13.37 mmol) in 30 mL of THF was heated at 80° C. for 12 hr. The mixture was cooled to room temperature, diluted with EtOAc, washed with NaHCO$_3$, dried over MgSO$_4$ and concentrated. The residue was purified by flash chromatography on SiO$_2$ (Hexanes:EtOAc, 0 to 50%) to give the title compound. MS (ESI) m/z 415 (M+H)$^+$.

Example 32D

N-[(2Z)-5-tert-butyl-3-[(2R)-tetrahydrofuran-2-ylmethyl]-1,3-oxazol-2(3H)-ylidene]-2-{[(2S)-1-methylpyrrolidin-2-yl]methoxy}-5-(trifluoromethyl)benzamide To a solution of (S)-(1-methylpyrrolidin-2-yl)methanol (Aldrich) (0.860 mL, 7.24 mmol) in 15 mL of THF was added sodium tert-butoxide (0.696 g, 7.24 mmol). The reaction was stirred at 22° C. for 20 min. The reaction was cooled to 5° C. and a solution of Example 32C (1.5 g, 3.62 mmol) in 5 mL of THF was added. The reaction was stirred at 5° C. for 2 h, then at 22° C. for 1 h. The solvent was evaporated under reduced pressure. The residue was dissolved with methylene chloride, washed with NaHCO$_3$, dried over Na$_2$SO$_4$ and concentrated. The residue was purified by flash chromatography on SiO$_2$ using an Analogix® Intelliflash280™ (solvent A=CH$_2$Cl$_2$; solvent B=3 N NH$_3$/MeOH:CH$_2$Cl$_2$ (1:9); eluting with A:B (100:0) changing to A:B (0:100) over the run time of approximately 30 minutes) to afford the title compound. $^1$H NMR (300 MHz, CDCl$_3$) δ ppm 1.17 (s, 9H), 1.53-1.98 (m, 8H), 1.97-2.15 (m, 2H), 2.19-2.35 (m, 1H), 2.46 (s, 3H), 2.62-2.81 (m, 1H), 3.07 (t, J=8.1 Hz, 1H), 3.62 (dd, J=14.1, 7.6 Hz, 1H), 3.72-3.94 (m, 2H), 4.01-4.21 (m, 2H), 6.53 (s, 1H), 6.96 (d, J=8.8 Hz, 1H), 7.55 (dd, J=9.0, 2.9 Hz, 1H), 7.93 (d, J=2.0 Hz, 1H); MS (ESI) m/z 511 (M+H)$^+$.

Example 33

N-{(2Z)-5,5-dimethyl-3-[(2R)-tetrahydrofuran-2-ylmethyl]-1,3-thiazolidin-2-ylidene}-2-{[(2S)-1-methylpyrrolidin-2-yl]methoxy}-5-(trifluoromethyl)benzamide

Example 33A (S)-2-((1-methylpyrrolidin-2-yl)methoxy)-5-(trifluoromethyl)benzonitrile To a solution of (S)-(1-methylpyrrolidin-2-yl)methanol (5.2 g, 45.1 mmol) in 25 mL of THF was added sodium hydride (1.970 g, 49.3 mmol). The reaction was stirred at 22° C. for 20 min. and 2-fluoro-5-(trifluoromethyl)benzonitrile (Aldrich) (8.54 g, 45.1 mmol) was added in 5 mL of THF. The reaction was stirred at 22° C. for 3 h. The solvent was evaporated under reduced pressure. The residue was dissolved in ether, washed with brine, water, dried with magnesium sulfate and concentrated to afford the title compound. MS (ESI) m/z 285 (M+H)$^+$.

Example 33B (S)-2-((1-methylpyrrolidin-2-yl)methoxy)-5-(trifluoromethyl)benzoic acid Example 33A (11.66 g, 41 mmol) was dissolved in ethanol and 15 mL of water was added. The reaction was heated at 40° C., then sodium hydroxide (7.58 mL, 144 mmol) was added followed by hydrogen peroxide (7.09 mL, 123 mmol), which was added in 4 portions, each portion one hour apart. The reaction was heated at 40° C. for 4 more hours. The reaction was monitored by LC/MS and after almost all the nitrile was converted to the amide, sodium hydroxide (6.49 mL, 123 mmol) was added followed by 10 mL of water. The reaction was heated at 80° C. for 12 h. The ethanol was evaporated and 100 mL of water was added. The solution was washed (25 mL×2) with ether. The aqueous solution was neutralized to pH 7 with 6 N HCl and the water was evaporated. The precipitate was suspended in ethanol (150 mL), the solution was heated to 60° C. and filtered. The solution was concentrated; toluene was added and evaporated under reduced pressure to afford the title product; MS (ESI) m/z 304 (M+H)$^+$.

Example 33C (R)-5,5-dimethyl-3-((tetrahydrofuran-2-yl)methyl)thiazolidin-2-imine A mixture of 2,2-dimethylthiirane (689 mg, 7.82 mmol), Example 32A (986 mg, 7.82 mmol) and potassium carbonate (1.08 g, 7.82 mmol) in 2-butanone (15 mL) was heated to 80° C. overnight. The mixture was poured into water, and extracted with ethyl acetate (2×). The combined organic extracts were dried over Na$_2$SO$_4$, filtered, concentrated under reduced pressure to afford the title compound. MS (ESI) m/z 215 (M+H)$^+$.

Example 33D

N-{(2Z)-5,5-dimethyl-3-[(2R)-tetrahydrofuran-2-ylmethyl]-1,3-thiazolidin-2-ylidene}-2-{[(2S)-1-methylpyrrolidin-2-yl]methoxy}-5-(trifluoromethyl)benzamide A mixture of Example 33C (700 mg, 3.27 mmol), 1H-benzo[d][1,2,3]triazol-1-ol hydrate (500 mg, 3.27 mmol), N1-((ethylimino)methylene)-N3,N3-dimethylpropane-1,3-diamine hydrochloride (626 mg, 3.27 mmol), Example 33B (991 mg, 3.27 mmol) and triethylamine (683 μL, 4.90 mmol) in 16 mL of THF was heated at 80° C. for 12 hr. The mixture was cooled to room temperature, diluted with EtOAc, washed with NaHCO$_3$, dried over MgSO$_4$ and concentrated. The residue was purified by flash chromatography on SiO$_2$ using an Analogix® Intelliflash280™ (solvent A=CH$_2$Cl$_2$; solvent B=3 N NH$_3$/MeOH:CH$_2$Cl$_2$ (1:9); eluting with A:B (100:0) changing to A:B (0:100) over the run time of approximately 25 minutes) to give the title compound; $^1$H NMR (300 MHz, CDCl$_3$) δ ppm 1.51 (s, 3H), 1.54 (s, 3H), 1.56-2.16 (m, 8H), 2.23-2.37 (m, 1H), 2.50 (s, 3H), 2.71-2.89 (m, 1H), 3.02-3.16 (m, 1H), 3.47-3.61 (m, 2H), 3.67 (d, J=10.7 Hz, 1H), 3.70-3.82 (m, 1H), 3.82-4.30 (m, 5H), 6.99 (d, J=8.3 Hz, 1H), 7.58 (dd, J=8.7, 2.4 Hz, 1H), 8.13 (d, J=2.4 Hz, 1H); MS (ESI) m/z 500 (M+H)$^+$.

Example 34

2-[(tert-butylamino)oxy]-N-[(2Z)-3-butyl-5-tert-butyl-1,3,4-thiadiazol-2(3H)-ylidene]-5-(trifluoromethyl)benzamide To a solution of N-tert-butylhydroxylamine (prepared from commercially available N-tert-butylhydroxylamine acetate (Aldrich) by neutralizing with saturated sodium bicarbonate solution and extracting the free base with diethyl ether) (1.79 g, 20 mmol) and Example 7B (4.1 g, 10 mmol) in anhydrous THF (50 mL) was added potassium tert-butoxide (1N solution in THF) (15 mL, 15 mmol) and the reaction mixture was stirred at 40° C. for 20 hours. The solvent was removed under reduced pressure and the residue was partitioned between water and ethyl acetate. The organic layer was washed with brine, dried with MgSO$_4$, filtered, and concentrated under reduced pressure. The residue was purified by silica gel chromatography and eluted with hexane:diethyl ether (17:3) to provide 3.5 g of the title compound. $^1$H NMR (300 MHz, DMSO-d$_6$) δ ppm 0.92 (t, J=7.3 Hz, 3H), 1.12 (s, 9H), 1.25-1.42 (m, 11H), 1.72-1.94 (m, 2H), 4.36 (t, J=7.1 Hz, 2H), 7.34 (s, 1H), 7.69-7.87 (m, 2H), 8.12 (d, J=2.4 Hz, 1H); MS (DCI/NH$_3$) m/z 473 (M+H)$^+$. Anal. calculated for C$_{22}$H$_{31}$F$_3$N$_4$O$_2$S: C, 55.92; H, 6.61; N, 11.86. Found: C, 55.91; H, 6.54; N, 11.84.

Example 35

N-[(2Z)-3-butyl-5-tert-butyl-1,3,4-thiadiazol-2(3H)-ylidene]-2-{(2Z)-2-[(6-methylpyridin-2-yl)methylene]hydrazino}-5-(trifluoromethyl)benzamide To a mixture of (Z)-isomer from Example 205A (238 mg, 1.01 mmol) and Example 7B (240 mg, 0.6 mmol) in anhydrous DMSO (15 mL) was added solid potassium tert-butoxide (100 mg, 0.89 mmol) and the resulting mixture was stirred at 90° C. for 16 hours. Water was added and the mixture was extracted with EtOAc. The ethyl acetate layer was washed with water, brine, dried with anhydrous MgSO$_4$, filtered, and concentrated under reduced pressure. The residue was purified by silica gel chromatography and eluted with 2:1 hexanes-Et$_2$O to afford 25 mg of the title compound. $^1$H NMR (300 MHz, DMSO-d$_6$) δ ppm 0.79 (t, J=7.3 Hz, 3H), 1.09-1.27 (m, 2H), 1.30-1.40 (m, 9H), 1.54-1.76 (m, 5H), 4.18 (t, J=7.1 Hz, 2H), 6.93 (d, J=8.8 Hz, 2H), 7.10-7.28 (m, 3H), 7.84 (dd, J=9.0, 2.2 Hz, 1H), 8.20 (d, J=2.0 Hz, 1H); MS (ESI$^+$) m/z 519 (M+H)$^+$.

Example 36

N-{(3E)-5-tert-butyl-1-methyl-2-[(2R)-tetrahydrofuran-2-ylmethyl]-1,2-dihydro-3H-pyrazol-3-ylidene}-2-{[(5R)-5-methyltetrahydrofuran-2-yl]methoxy}-5-(trifluoromethyl)benzamide Example 36A ((5R)-5-methyltetrahydrofuran-2-yl)methanol To a solution of (R)-hex-5-en-2-ol (5.0 g, 50 mmol, Aldrich) in chloroform (100 mL) were adde methyltrioxorhenium(VII) (0.37 g, 1.5 mmol, Aldrich) and hydrogen peroxide (5.7 g, 50 mmol, 30% in water, Aldrich). After stirring at room temperature for 16 hours, the reaction mixture was quenched with potassium carbonate, and extracted with diethyl ether (2×50 mL). The combined organic extracts were dried over anhydrous MgSO$_4$, filtered and concentrated under reduced pressure to provide 7.7 g (75%) of the title compound. MS (DCI$^+$) m/z 134 (M+NH$_4$)$^+$.

Example 36B

N-{(3E)-5-tert-butyl-1-methyl-2-[(2R)-tetrahydrofuran-2-ylmethyl]-1,2-dihydro-3H-pyrazol-3-ylidene}-2-{[(5R)-5-methyltetrahydrofuran-2-yl]methoxy}-5-(trifluoromethyl)benzamide Example 1E, Example 36A and sodium tert-butoxide were processed as described in Example 1F to obtain the title compound. $^1$H NMR (300 MHz, DMSO-d$_6$) δ ppm 1.05-1.15 (m, 3H), 1.38 (s, 9H), 1.64-2.09 (m, 8H), 3.56-3.66 (m, 1H), 3.68-3.80 (m, 1H), 3.87 (s, 3H), 3.90-4.06 (m, 3H), 4.08-4.20 (m, 1H), 4.21-4.28 (m, 1H), 4.30-4.36 (m, 2H), 6.77-6.82 (m, 1H), 7.15 (dd, J=8.5, 5.1 Hz, 1H), 7.55 (dd, J=8.8, 2.4 Hz, 1H), 7.66 (t, J=2.5 Hz, 1H); MS (ESI) m/z 524 (M+H)$^+$.

Example 37

N-{(3E)-5-tert-butyl-1-methyl-2-[(2R)-tetrahydrofuran-2-ylmethyl]-1,2-dihydro-3H-pyrazol-3-ylidene}-2-{[(5S)-5-methyltetrahydrofuran-2-yl]methoxy}-5-(trifluoromethyl)benzamide

Example 37A ((5S)-5-methyltetrahydrofuran-2-yl)methanol

Commercially available (S)-hex-5-en-2-ol (Aldrich), methyltrioxorhenium(VII) (Aldrich) and hydrogen peroxide (Aldrich) were processed as described in Example 36A to provide the title compound MS (DCI m/z 134 (M+NH$_4$)$^+$.

Example 37B

N-{(3E)-5-tert-butyl-1-methyl-2-[(2R)-tetrahydrofuran-2-ylmethyl]-1,2-dihydro-3H-pyrazol-3-ylidene}-2-{[(5S)-5-methyltetrahydrofuran-2-yl]methoxy}-5-(trifluoromethyl)benzamide Example 1E, Example 37A and sodium tert-butoxide were processed as described in Example 1F to obtain the title compound. $^1$H NMR (300 MHz, DMSO-d$_6$) δ ppm 1.03-1.16 (m, 3H), 1.38 (s, 9H), 1.64-2.10 (m, 8H), 3.57-3.66 (m, 1H), 3.68-3.80 (m, 1H), 3.87 (s, 3H), 3.95-4.05 (m, 2H), 4.06-4.29 (m, 3H), 4.28-4.37 (m, 2H), 6.76-6.82 (m, 1H), 7.15 (dd, J=8.6, 4.2 Hz, 1H), 7.55 (dd, J=9.0, 2.2 Hz, 1H), 7.63-7.69 (m, 1H); MS (ESI$^+$) m/z 524 (M+H)$^+$. Anal. calculated for C$_{27}$H$_{36}$F$_3$N$_3$O$_4$: C, 61.94; H, 6.93; N, 8.03. Found: C, 61.56; H, 6.88; N, 7.91.

Example 38

N-{(3E)-5-tert-butyl-1-methyl-2-[(2R)-tetrahydrofuran-2-ylmethyl]-1,2-dihydro-3H-pyrazol-3-ylidene}-2-(pyridin-2-ylmethoxy)-5-(trifluoromethyl)benzamide A solution of potassium t-butoxide (0.94 mL, 1 M in THF) was added to a solution of pyridin-2-ylmethanol (0.11 g, 0.98 mmol) in THF (0.5 mL) and the mixture stirred for 10 minutes. A solution of Example 1E (0.2 g, 0.47 mmol) in THF (0.8 mL) was added and the mixture stirred at ambient temperature for 1 hour. The mixture was diluted with dichloromethane (10 mL) and glacial acetic acid (50 µL) was added. The resulting solution was concentrated and the residue purified by chromatography (SiO$_2$, solvent A=hexane:EtOAc:Et$_3$N (1:3:0.1), solvent B=hexane:EtOAc:MeOH:Et$_3$N (1:3:1:0.1), 100% solvent A to 75% solvent B/solvent A gradient over 450 mL then isocratic for 180 mL) to afford the title compound (0.15 g, 0.29 mmol, 62% yield). $^1$H NMR (300 MHz, DMSO-d$_6$) δ ppm 1.38 (s, 9H), 1.60-1.75 (m, 3H), 1.75-1.84 (m, 1H), 3.54-3.63 (m, 1H), 3.67-3.76 (m, 1H), 3.87 (s, 3H), 4.08-4.17 (m, 1H), 4.24-4.38 (m, 2H), 5.29 (s, 2H), 6.83 (s, 1H), 7.18 (d, J=8.8 Hz, 1H), 7.32 (ddd, J=7.5, 4.9, 1.2 Hz, 1H), 7.56 (dd, J=8.6, 1.9 Hz, 1H), 7.62 (d, J=7.8 Hz, 1H), 7.76 (d, J=2.4 Hz, 1H), 7.80 (td, J=7.8, 1.7 Hz, 1H), 8.55-8.58 (m, 1H); MS (DCI/NH$_3$) m/z 517.2 (M+H)$^+$.

Example 39

N-[(3E)-5-tert-butyl-2-[(2R)-tetrahydrofuran-2-ylmethyl]isoxazol-3(2H)-ylidene]-2-{[(2S)-1-methylpyrrolidin-2-yl]methoxy}-5-(trifluoromethyl)benzamide

Example 39A (R)-(tetrahydrofuran-2-yl)methyl 4-methylbenzenesulfonate

To a solution of (R)-(tetrahydrofuran-2-yl)methanol (1.0 g, 9.8 mmol) in CH$_2$Cl$_2$ (3 mL) and pyridine (3 mL) at ambient temperature was added 4-methylbenzene-1-sulfonyl chloride (2.0 g, 10.3 mmol) portionwise over 5 min. The mixture was stirred for 16 hours at ambient temperature then quenched by the addition of 5% aqueous HCl (10 mL). The layers were separated and the aqueous phase was extracted with CH$_2$Cl$_2$ (3×5 mL). The combined organic extracts were dried over anhydrous Na$_2$SO$_4$, filtered, and concentrated under reduced pressure. The residue was purified by column chromatography (SiO$_2$, 75% hexanes in EtOAc) to afford the title compound (1.7 g, 6.8 mmol, 69% yield). MS (DCI/NH$_3$) m/z 257 (M+H)$^+$ and 274 (M+NH$_4$)$^+$.

Example 39B (R)-5-tert-butyl-2-((tetrahydrofuran-2-yl)methyl)isoxazol-3(2H)-imine A mixture of 5-tert-butylisoxazol-3-amine (1 g, 7.1 mmol) and a solution of Example 39A (1.7 g, 6.8 mmol) in 1.5 mL DMF was warmed to 85° C. and was allowed to stir for 70 hours at 85° C. The mixture was cooled to ambient temperature, concentrated under reduced pressure. The residue was purified by column chromatography (SiO$_2$, 50% hexanes in EtOAc then 10% CH$_3$OH in EtOAc) to afford the title compound (0.48 g, 1.2 mmol, 17% yield). MS (DCI/NH$_3$) m/z 225 (M+H)$^+$.

Example 39C (S)-2-((1-methylpyrrolidin-2-yl)methoxy)-5-(trifluoromethyl)benzoic acid To a solution of (S)-(1-methylpyrrolidin-2-yl)methanol (3.49 mL, 29.4 mmol) in THF (50 mL) was added potassium tert-butoxide (39.2 mL, 39.2 mmol). The mixture was stirred at ambient temperature for 30 min then a solution of methyl 2-fluoro-5-(trifluoromethyl)benzoate (4.35 g, 19.6 mmol, Widdowson, D. A.; Wilhelm, R. *Chem. Commun.*, 2003, 578-579) in THF (10 mL) was added via cannula. The mixture was stirred at ambient temperature for 4 hours then quenched with saturated aqueous NaHCO$_3$ (10 mL) and was diluted with EtOAc (10 mL). The layers were separated and the aqueous phase was extracted with EtOAc (3×5 mL). The combined organic extracts were dried over anhydrous Na$_2$SO$_4$, filtered and concentrated under reduced pressure. Purification by column chromatography (SiO$_2$, 50% hex/EtOAc then 100% EtOAc then 9:1:0.1 EtOAc/MeOH/Et$_3$N) afforded an approximate 1:1:1 mixture of (S)-methyl 2-((1-methylpyrrolidin-2-yl)methoxy)-5-(trifluoromethyl)benzoate:(1-methylpyrrolidin-2-yl)methyl 2-(((S)-1-methylpyrrolidin-2-yl)methoxy)-5-(trifluoromethyl)benzoate:(S)-tert-butyl 2-((1-methylpyrrolidin-2-yl)methoxy)-5-(trifluoromethyl)benzoate.

This mixture was dissolved in EtOH (50 mL) and a solution of 30% aqueous KOH (10 mL) was added. The mixture was warmed to 45° C. and stirred for 2 h then cooled to ambient temperature and partially concentrated under reduced pressure. The mixture was diluted with Et$_2$O and the layers were separated. The aqueous phase was acidified to pH 5, extracted with a 4:1 mixture of CH$_2$Cl$_2$ and isopropanol, and the organic extract was concentrated to obtain the title compound (2.8 g, 47% yield from methyl 2-fluoro-5-(trifluoromethyl)benzoate). MS (DCI/NH$_3$) m/z 304 (M+H)$^+$.

Example 39D

N-[(3E)-5-tert-butyl-2-[(2R)-tetrahydrofuran-2-ylmethyl]isoxazol-3(2H)-ylidene]-2-{[(2S)-1-methylpyrrolidin-2-yl]methoxy}-5-(trifluoromethyl)benzamide A mixture of Example 39C (0.33 g, 1.1 mmol) and thionyl chloride (10 mL) was warmed to reflux (90° C.) and stirred for 2 hours. The mixture was cooled to ambient temperature and then concentrated under reduced pressure. The residue was diluted with toluene (10 mL) and then concentrated under reduced pressure (3×) to afford the desired acid chloride. To a solution of Example 39B (0.25 g, 1.1 mmol) in THF (20 mL) was added Et$_3$N (0.47 mL, 3.3 mmol) followed by the acid chloride. The mixture was warmed to 50° C. and was allowed to stir for 2 hours then was stirred at ambient temperature for 14 hours. The mixture was quenched with saturated aqueous NH$_4$Cl (10 mL) and diluted with EtOAc (10 mL). The layers were separated and the aqueous phase was extracted with EtOAc (3×7 mL). The combined organic extracts were dried over Na$_2$SO$_4$, filtered, and concentrated under reduced pressure. Purification by column chromatography (SiO$_2$, 60% hexanes in EtOAc) afforded the title compound (0.17 g, 0.33 mmol, 30% yield). $^1$H NMR (300 MHz, CDCl$_3$) δ ppm 1.35 (s, 9H) 1.70-1.84 (m, 4H) 1.85-1.96 (m, 2H) 1.97-2.10 (m, 2H) 2.23-2.35 (m, 1H) 2.47 (s, 3H) 2.72-2.83 (m, 1H) 3.03-3.14 (m, 1H) 3.74-3.97 (m, 3H) 4.08-4.25 (m, 2H) 4.27-4.38 (m, 2H) 6.99 (d, J=8.8 Hz, 1H) 7.08 (s, 1H) 7.54 (dd, J=9.0, 2.2 Hz, 1H) 8.02 (d, J=2.4 Hz, 1H); MS (DCI/NH$_3$) m/z 510 (M+H)$^+$; Anal. calculated for C$_{26}$H$_{34}$F$_3$N$_3$O$_4$: Calc: C, 61.28; H, 6.73; N, 8.25. Found: C, 60.97; H, 6.94; N, 7.99.

Example 40

N-{(3E)-5-tert-butyl-1-methyl-2-[(2R)-tetrahydrofuran-2-ylmethyl]-1,2-dihydro-3H-pyrazol-3-ylidene}-2-(pyrazin-2-ylmethoxy)-5-(trifluoromethyl)benzamide The title compound was prepared as described in Example 38, substituting pyrazin-2-ylmethanol for pyridin-2-ylmethanol (0.07 g, 0.13 mmol, 27% yield). $^1$H NMR (300 MHz, DMSO-d$_6$) δ ppm 1.38 (s, 9H), 1.63-1.74 (m, 3H), 1.74-1.84 (m, 1H), 3.54-3.63 (m, 1H), 3.67-3.76 (m, 1H), 3.87 (s, 3H), 4.08-4.18 (m, 1H), 4.24-4.39 (m, 2H), 5.39 (s, 2H), 6.82 (s, 1H), 7.28 (d, J=8.8 Hz, 1H), 7.60 (dd, J=8.6, 1.9 Hz, 1H), 7.80 (d, J=2.0 Hz, 1H), 8.60-8.62 (m, 1H), 8.65 (dd, J=2.5, 1.5 Hz, 1H), 8.94 (d, J=1.4 Hz, 1H); MS (DCI/NH$_3$) m/z 518.3 (M+H)$^+$. Anal. calculated for C$_{26}$H$_{30}$F$_3$N$_5$O$_3$: C, 60.34; H, 5.84; N, 13.53. Found: C, 60.35; H, 5.90; N, 13.34.

Example 41 tert-butyl 2-[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenoxy]ethylcarbamate To a solution of tert-butyl 2-hydroxyethylcarbamate (0.63 mL, 4.1 mmol) in THF (15 mL) was added potassium tert-butoxide (0.76 g, 6.8 mmol). The mixture was stirred at ambient temperature for 20 min then a solution of Example 1E (0.58 g, 1.4 mmol) in THF (5 mL) was added via cannula. The mixture was stirred at ambient temperature for 1 hour then diluted with saturated aqueous NaHCO$_3$ (5 mL) and extracted with EtOAc (4×5 mL). The combined organic extracts were dried over anhydrous Na$_2$SO$_4$, filtered, and concentrated under reduced pressure. Purification by column chromatography (SiO$_2$, 100% EtOAc to 10% MeOH in EtOAc) provided the title compound (0.64 g, 1.1 mmol, 83% yield). $^1$H NMR (300 MHz, CDCl$_3$) δ ppm 1.41 (s, 9H) 1.43 (s, 9H) 1.69-1.92 (m, 4H) 1.99-2.07 (m, 1H) 3.46-3.55 (m, 2H) 3.68-3.82 (m, 2H) 3.88 (s, 3H) 4.15-4.30 (m, 2H) 4.33 (d, J=5.9 Hz, 1H) 4.52 (dd, J=15.1, 2.8 Hz, 1H) 6.90-6.96 (m, 1H) 7.01 (d, J=8.3 Hz, 1H) 7.07 (s, 1H) 7.50 (dd, J=8.5, 2.2 Hz, 1H) 8.05 (d, J=1.6 Hz, 1H); MS (DCI/NH$_3$) m/z 569 (M+H)$^+$.

Example 42

N-{(3E)-5-tert-butyl-1-methyl-2-[(2R)-tetrahydrofuran-2-ylmethyl]-1,2-dihydro-3H-pyrazol-3-ylidene}-2-(2,3-dihydroxypropoxy)-5-(trifluoromethyl)benzamide A 60% dispersion of sodium hydride in mineral oil (0.19 g, 4.7 mmol) was added to a −40° C. solution of 4-(hydroxymethyl)-1,3-dioxolan-2-one (0.56 g, 4.7 mmol) in dimethylformamide (1.0 mL) and the mixture stirred for 20 minutes. A solution of Example 1E (0.2 g, 0.47 mmol) in dimethylformamide (1.0 mL) was added and the mixture was allowed to warm to ambient temperature and stirred for 3 hours. The mixture was partitioned between saturated aqueous NH$_4$Cl (5 mL) and diethyl ether (50 mL) and the phases separated. The organic extract was washed with water and brine, dried with MgSO$_4$, filtered, and concentrated. The residue was purified by chromatography (SiO$_2$, solvent A—hexanes:EtOAc:Et$_3$N (1:3:0.1), solvent B—hexane:EtOAc:MeOH:Et$_3$N (1:3:1:0.1) 100% solvent A to 75% solvent B/25% solvent A over 450 mL then isocratic for 180 mL) to afford the title compound (0.03 g, 0.06 mmol, 13% yield). $^1$H NMR (500 MHz, Pyridine-d$_5$) δ ppm 1.15 (s, 9H), 1.54-1.60 (m, 2H), 1.60-1.69 (m, 1H), 1.76-1.84 (m, 1H), 3.52-3.59 (m, 1H), 3.67-3.74 (m, 1H), 3.83 (s, 3H), 4.17-4.25 (m, 3H), 4.38 (dd, J=15.0, 6.4 Hz, 1H), 4.52-4.58 (m, 1H), 4.58-4.65 (m, 2H), 4.78 (dd, J=9.6, 3.5 Hz, 1H), 7.30 (d, J=8.5 Hz, 1H), 7.36 (s, 1H), 7.65 (dd, J=8.5, 2.4 Hz, 1H), 8.57 (d, J=2.1 Hz, 1H); MS (DCI/NH$_3$) m/z 500.3 (M+H)$^+$.

Example 43

N-{(3E)-5-tert-butyl-1-methyl-2-[(2R)-tetrahydrofuran-2-ylmethyl]-1,2-dihydro-3H-pyrazol-3-ylidene}-2-(pyridin-3-ylmethoxy)-5-(trifluoromethyl)benzamide The title compound was prepared as described in Example 38, substituting pyridin-3-ylmethanol for pyridin-2-ylmethanol (0.17 g, 0.33 mmol, 70% yield). $^1$H NMR (300 MHz, DMSO-d$_6$) δ ppm 1.38 (s, 9H), 1.59-1.72 (m, 3H), 1.72-1.84 (m, 1H), 3.54-3.63 (m, 1H), 3.67-3.75 (m, 1H), 3.87 (s, 3H), 4.06-4.14 (m, 1H), 4.22-4.36 (m, 2H), 5.29 (s, 2H), 6.81 (s, 1H), 7.23 (d, J=8.8 Hz, 1H), 7.34-7.45 (m, 1H), 7.55-7.63 (m, 1H), 7.75 (d, J=2.0 Hz, 1H), 7.84-7.97 (m, 1H), 8.52 (dd, J=4.7, 1.7 Hz, 1H), 8.70 (d, J=1.4 Hz, 1H); MS (DCI/NH$_3$) m/z 517.3 (M+H)$^+$. Anal. calculated for C$_{27}$H$_{31}$F$_3$N$_4$O$_3$: C, 62.78; H, 6.05; N, 10.85. Found: C, 62.66; H, 6.16; N, 10.75.

Example 44

N-{(3E)-5-tert-butyl-1-methyl-2-[(2R)-tetrahydrofuran-2-ylmethyl]-1,2-dihydro-3H-pyrazol-3-ylidene}-2-({(5S)-2-oxo-3-[(1R)-1-phenylethyl]-1,3-oxazolidin-5-yl}methoxy)-5-(trifluoromethyl)benzamide The title compound was prepared as described in Example 38, substituting (S)-5-(hydroxymethyl)-3-((R)-1-phenylethyl)oxazolidin-2-one for pyridin-2-ylmethanol (0.3 g, 0.48 mmol, 82% yield). $^1$H NMR (500 MHz, Pyridine-d$_5$) δ ppm 1.18 (s, 9H), 1.47 (d, J=7.0 Hz, 3H), 1.53-1.61 (m, 2H), 1.68-1.76 (m, 1H), 1.77-1.84 (m, 1H), 3.46 (dd, J=8.7, 6.6 Hz, 1H), 3.57 (q, J=7.2 Hz, 1H), 3.67-3.75 (m, 2H), 3.82 (s, 3H), 4.24 (m, 1H), 4.29-4.38 (m, 2H), 4.46 (dd, J=15.1, 6.6 Hz, 1H), 4.64 (dd, J=15.3, 3.1 Hz, 1H), 5.02-5.08 (m, 1H), 5.29 (q, J=7.1 Hz, 1H), 7.05 (d, J=8.5 Hz, 1H), 7.26 (t, J=7.3 Hz, 1H), 7.37 (t, J=7.8 Hz, 2H), 7.46 (s, 1H), 7.47 (d, J=7.6 Hz, 2H), 7.55-7.60 (m, 1H), 8.52 (d, J=2.4 Hz, 1H); MS (DCI/NH$_3$) m/z 629.4 (M+H)$^+$.

Example 45

N-{(3E)-5-tert-butyl-1-methyl-2-[(2R)-tetrahydrofuran-2-ylmethyl]-1,2-dihydro-3H-pyrazol-3-ylidene}-2-{2-[(methylsulfonyl)amino]ethoxy}-5-(trifluoromethyl)benzamide

Example 45A 2-(2-aminoethoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of Example 41 (0.63 g, 1.1 mmol) in CH$_2$Cl$_2$ (5 mL) at ambient temperature was added trifluoroacetic acid (2.0 mL, 26.0 mmol). The mixture was stirred at ambient temperature for 3 hours then concentrated under reduced pressure. Purification by column chromatography (SiO$_2$, 50% EtOAc/Hex to 100% EtOAc to 9:1:0.1 EtOAc:MeOH:Et$_3$N then 9:1:0.1 CH$_2$Cl$_2$:MeOH:NH$_4$OH) afforded the title compound (0.50 g, 1.0 mmol, 96% yield). MS (DCI/NH$_3$) m/z 469 (M+H)$^+$.

Example 45B

N-{(3E)-5-tert-butyl-1-methyl-2-[(2R)-tetrahydrofuran-2-ylmethyl]-1,2-dihydro-3H-pyrazol-3-ylidene}-2-{2-[(methylsulfonyl)amino]ethoxy}-5-(trifluoromethyl)benzamide To a solution of Example 45A (0.20 g, 0.43 mmol) in THF (7 mL) was added Et$_3$N (0.13 mL, 0.94 mmol) followed by methanesulfonyl chloride (50 μL, 0.65 mmol). The mixture was stirred at ambient temperature for 16 hours, then diluted with saturated aqueous NaHCO$_3$ (5 mL) and extracted with EtOAc (4×5 mL). The combined organic extracts were dried over anhydrous Na$_2$SO$_4$, filtered, and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (60 mg, 0.11 mmol, 26% yield). $^1$H NMR (300 MHz, CDCl$_3$) δ ppm 1.44 (s, 9H) 1.67-1.91 (m, 3H) 1.97-2.09 (m, 1H) 2.89 (s, 3H) 3.46 (dd, J=4.8 Hz, 2H) 3.68-3.79 (m, 2H) 3.90 (s, 3H) 4.12-4.23 (m, 1H) 4.31-4.36 (m, 3H) 4.54 (dd, J=15.3, 3.0 Hz, 1H) 7.04 (d, J=8.7 Hz, 1H) 7.07 (s, 1H) 7.54 (dd, J=8.1, 2.2 Hz, 1H) 8.07 (d, J=2.4 Hz, 1H); MS (DCI/NH$_3$) m/z 547 (M+H)$^+$. Anal. calculated for C$_{24}$H$_{33}$F$_3$N$_4$O$_5$S: Calc: C, 52.74; H, 6.09; N, 10.25. Found: C, 52.49; H, 6.23; N, 10.18.

Example 46

N-[(3E)-5-tert-butyl-2-(cyclopropylmethyl)-1-methyl-1,2-dihydro-3H-pyrazol-3-ylidene]-2-(pyrazin-2-ylmethoxy)-5-(trifluoromethyl)benzamide To a solution of pyrazin-2-ylmethanol (55 mg, 0.5 mmol) in THF (4 mL) was added potassium tert-butoxide (110 mg, 1.0 mmol). After stirring for 10 min, Example 27G (100 mg, 0.25 mmol) was added to the reaction mixture in portions. The mixture was stirred at ambient temperature for 2 hours, quenched with saturated aqueous NH$_4$Cl and extracted by EtOAc (3×10 mL). The combined organic extracts were concentrated under reduced pressure. Purification by flash chromatography (silica gel, MeOH/Et$_3$N (10:1) in CH$_2$Cl$_2$ in 0-30% gradient) provided 61 mg (47%) of the title compound. $^1$H NMR (300 MHz, DMSO-d$_6$) δ ppm 0.34-0.49 (m, 4H), 1.08-1.24 (m, 1H), 1.33-1.44 (m, 9H), 3.90 (s, 3H), 4.15 (d, J=7.1 Hz, 2H), 5.39 (s, 2H), 6.83 (s, 1H), 7.27 (d, J=8.8 Hz, 1H), 7.60 (dd, J=8.7, 1.9 Hz, 1H), 7.77 (d, J=2.4 Hz, 1H), 8.56-8.70 (m, 2H), 8.93 (d, J=1.4 Hz, 1H); MS (DCI/NH$_3$) m/z 488 (M+H)$^+$.

Example 47

N-{(3E)-5-tert-butyl-1-methyl-2-[(2R)-tetrahydrofuran-2-ylmethyl]-1,2-dihydro-3H-pyrazol-3-ylidene}-2-[2-(2-ethoxyethoxy)ethoxy]-5-(trifluoromethyl)benzamide The title compound was prepared as described in Example 38, substituting 2-(2-ethoxyethoxy)ethanol for pyridin-2-ylmethanol (0.13 g, 0.24 mmol, 51% yield). $^1$H NMR (500 MHz, Pyridine-d$_5$) δ ppm 1.12 (t, J=7.0 Hz, 3H), 1.19 (s, 9H), 1.54-1.62 (m, 2H), 1.65-1.73 (m, 1H), 1.75-1.84 (m, 1H), 3.42 (q, J=6.8 Hz, 2H), 3.54-3.56 (m, 2H), 3.57-3.61 (m, 1H), 3.70-3.75 (m, 3H), 3.80 (s, 3H), 3.91-3.94 (m, 2H), 4.25 (m, 1H), 4.34-4.37 (m, 2H), 4.37-4.41 (m, 1H), 4.60 (dd, J=15.1, 3.2 Hz, 1H), 7.17 (d, J=8.5 Hz, 1H), 7.47 (s, 1H), 7.59-7.62 (m, 1H), 8.47 (d, J=2.4 Hz, 1H); MS (DCI/NH$_3$) m/z 542.3 (M+H)$^+$. Anal calculated for C$_{27}$H$_{38}$F$_3$N$_3$O$_5$: C, 59.88; H, 7.07; N, 7.76. Found: C, 59.78; H, 7.12; N, 7.66.

Example 48

N-{(3E)-5-tert-butyl-1-methyl-2-[(2R)-tetrahydrofuran-2-ylmethyl]-1,2-dihydro-3H-pyrazol-3-ylidene}-2-[2-(2-oxoimidazolidin-1-yl)ethoxy]-5-(trifluoromethyl)benzamide Dichloromethane was added to 1-(2-hydroxyethyl)imidazolidin-2-one (75% in water), the phases separated and the organic extract was dried with MgSO₄, filtered, and concentrated under reduced pressure. The residue was diluted with toluene (10 mL) and concentrated under reduced pressure (3×) and then used as described. To a suspension of 1-(2-hydroxyethyl)imidazolidin-2-one (0.15 g, 1.2 mmol) in THF (1.5 mL) at −20° C. was added sodium hydride (0.09 g, 2.3 mmol, of a 60% dispersion in mineral oil). After 20 minutes a solution of Example 1E (0.2 g, 0.47 mmol) in THF (0.8 mL) was added the mixture was stirred at ambient temperature for 20 hours. The mixture was partitioned between saturated aqueous NH₄Cl (3 mL) and ethylacetate (50 mL) and the phases separated. The organic extract was washed with water and brine, dried with MgSO₄, filtered and concentrated. The residue was purified by chromatography (SiO₂, solvent A—hexane:EtOAc:Et₃N (1:3:0.1), solvent B—hexane: EtOAc:MeOH:Et₃N (1:3:1:0.1) 100% solvent A to 100% solvent B over 450 mL then isocratic for 180 mL.) to afford the title compound (0.12 g, 0.22 mol, 48% yield). ¹H NMR (300 MHz, DMSO-d₆) δ ppm 1.37 (s, 9H), 1.66-1.78 (m, 3H), 1.79-1.92 (m, 1H), 3.12 (t, J=7.8 Hz, 2H), 3.36 (t, J=5.6 Hz, 2H), 3.42-3.50 (m, 2H), 3.57-3.66 (m, 1H), 3.69-3.78 (m, 1H), 3.87 (s, 3H), 4.09-4.19 (m, 3H), 4.28-4.34 (m, 2H), 6.30 (s, 1H), 6.77 (s, 1H), 7.17 (d, J=8.5 Hz, 1H), 7.57 (dd, J=8.6, 1.9 Hz, 1H), 7.66 (d, J=2.4 Hz, 1H); MS (DCI/NH₃) m/z 538.3 (M+H)⁺.

Example 49

N-{(3E)-5-tert-butyl-1-methyl-2-[(2R)-tetrahydrofuran-2-ylmethyl]-1,2-dihydro-3H-pyrazol-3-ylidene}-2-{2-[(cyclopropylsulfonyl)amino]ethoxy}-5-(trifluoromethyl)benzamide Cyclopropanesulfonyl chloride (Matrix Scientific, 0.045 g, 0.32 mmol) was added to a solution of Example 45A (0.15 g, 0.32 mmol) in of THF (5 mL) followed by Et₃N (0.13 mL, 0.96 mmol). The mixture was stirred at ambient temperature for 1 hour then diluted with dichloromethane (15 mL) and washed with water and brine. The organic extract was dried with MgSO₄, filtered, and concentrated. The residue was purified by chromatography (SiO₂, solvent A=hexane: EtOAc:Et₃N (1:3:0.1), solvent B=hexane:EtOAc:MeOH: Et₃N (1:3:1:0.1); 100% solvent A to 100% solvent B over 300 mL then isocratic for 180 mL) to afford the title compound (0.07 g, 0.12 mmol, 38% yield). ¹H NMR (500 MHz, pyridine-d₅) δ ppm 0.84-0.91 (m, 2H), 1.22 (s, 9H), 1.33-1.39 (m, 2H), 1.55-1.62 (m, 2H), 1.62-1.71 (m, 1H), 1.76-1.86 (m, 1H), 2.79-2.90 (m, 1H), 3.54-3.62 (m, 1H), 3.69-3.75 (m, 1H), 3.76 (s, 2H), 3.85 (s, 3H), 4.18-4.26 (m, 1H), 4.39 (dd, J=15.3, 6.7 Hz, 1H), 4.46 (t, J=4.9 Hz, 1H), 4.62 (dd, J=15.3, 3.1 Hz, 1H), 7.24 (d, J=8.5 Hz, 1H), 7.47 (s, 1H), 7.66 (dd, J=8.5, 2.1 Hz, 1H), 8.54 (d, J=2.1 Hz, 1H), 9.33 (s, 1H); MS (DCI/NH₃) m/z 573.3 (M+H)⁺.

Example 50

N-{(3E)-5-tert-butyl-1-methyl-2-[(2R)-tetrahydrofuran-2-ylmethyl]-1,2-dihydro-3H-pyrazol-3-ylidene}-2-{2-[(ethylsulfonyl)amino]ethoxy}-5-(trifluoromethyl)benzamide The title compound was prepared as described in Example 49, substituting ethanesulfonyl chloride for cyclopropanesulfonyl chloride (0.07 g, 0.13 mmol, 39% yield). ¹H NMR (500 MHz, pyridine-d₅) δ ppm 1.22 (s, 9H), 1.46 (t, J=7.3 Hz, 3H), 1.55-1.62 (m, 2H), 1.63-1.71 (m, 1H), 1.77-1.86 (m, 1H), 3.30 (q, J=7.4 Hz, 2H), 3.54-3.62 (m, 1H), 3.69 (s, 2H), 3.70-3.75 (m, 1H), 3.86 (s, 3H), 4.18-4.25 (m, 1H), 4.38 (d, J=6.7 Hz, 1H), 4.39-4.44 (m, 2H), 4.62 (dd, J=15.1, 3.2 Hz, 1H), 7.20-7.24 (m, 1H), 7.45 (s, 1H), 7.65 (dd, J=8.5, 1.8 Hz, 1H), 8.53 (d, J=2.1 Hz, 1H), 9.28 (s, 1H); MS (DCI/NH₃) m/z 561.3 (M+H)⁺.

Example 51

N-[(3E)-5-tert-butyl-2-(cyclopropylmethyl)-1-methyl-1,2-dihydro-3H-pyrazol-3-ylidene]-2-(3-hydroxy-3-methylbutoxy)-5-(trifluoromethyl)benzamide The title compound was prepared according to the procedure described for Example 46, substituting 3-methylbutane-1,3-diol for pyrazin-2-ylmethanol (72% yield). ¹H NMR (300 MHz, DMSO-d₆) δ ppm 0.34-0.55 (m, 4H), 1.14 (s, 6H), 1.17-1.22 (m, 1H), 1.39 (s, 9H), 1.83 (t, J=7.0 Hz, 2H), 3.91 (s, 3H), 4.11-4.24 (m, 4H), 4.61 (s, 1H), 6.78 (s, 1H), 7.17 (d, J=8.5 Hz, 1H), 7.59 (dd, J=8.7, 1.9 Hz, 1H), 7.75 (d, J=2.0 Hz, 1H); MS (DCI/NH₃) m/z 482 (M+H)⁺.

Example 52

N-{(3E)-5-tert-butyl-1-methyl-2-[(2R)-tetrahydrofuran-2-ylmethyl]-1,2-dihydro-3H-pyrazol-3-ylidene}-2-{[(2S)-5,5-dimethyltetrahydrofuran-2-yl]methoxy}-5-(trifluoromethyl)benzamide Example 52A (5S)-5-((tetrahydro-2H-pyran-2-yloxy)methyl)dihydrofuran-2(3H)-one To a solution of (S)-5-(hydroxymethyl)dihydrofuran-2 (3H)-one (1.0 g, 8.6 mmol, Acros) in dichloromethane (10 mL) were added 3,4-dihydro-2H-pyran (0.94 mL, 10.3 mmol, Aldrich) and pyridinium p-toluenesulfonate (0.22 g, 0.86 mmol, Aldrich). After stirring at room temperature overnight, the reaction mixture was washed with water (5 mL) and brine (5 mL). The organic extract was dried (Na₂SO₄), filtered, and concentrated. The residue was purified by column chromatography using an Analogix® Intelliflash280™ (SiO₂, 0-100% ethyl acetate in hexanes) to obtain 1.6 g (93%) of the title compound. MS (DCI/NH₃) m/z 218 (M+NH₄)⁺.

Example 52B (2S)-5-methyl-1-(tetrahydro-2H-pyran-2-yloxy)hexane-2,5-diol

To a solution of Example 52A (1.6 g, 8.0 mmol) in tetrahydrofuran (20 mL) at 0° C. was added a solution of methyl magnesium bromide in diethyl ether (5.3 mL, 16.0 mmol, Aldrich), dropwise. The reaction mixture was stirred at 0° C. for 4 hours and then allowed to warm to room temperature and stirred overnight. The reaction mixture was quenched with saturated aqueous NH₄Cl (50 mL) and extracted with ethyl acetate (3×50 mL). The combined organic extracts were dried (Na₂SO₄), filtered, and concentrated to obtain 1.8 g (97%) of the title compound. MS (DCI/NH₃) m/z 233 (M+H)⁺.

Example 52C (S)-(5,5-dimethyltetrahydrofuran-2-yl)methanol

To a solution of Example 52B (1.8 g, 7.8 mmol) in tetrahydrofuran (3 mL) was added pyridinium p-toluenesulfonate (1.95 g, 7.8 mmol, Aldrich). After stirring at room temperature overnight, the reaction mixture was washed with water (5 mL) and brine (5 mL). The organic layer was dried (Na$_2$SO$_4$), filtered, and concentrated. The residue was purified by column chromatography using an Analogix® Intelliflash280™ (SiO$_2$, 0-100% ethyl acetate in hexanes) to obtain 0.3 g (30%) of the title compound. MS (DCI/NH$_3$) m/z 149 (M+NH$_4$)$^+$.

Example 52D

N-{(3E)-5-tert-butyl-1-methyl-2-[(2R)-tetrahydrofuran-2-ylmethyl]-1,2-dihydro-3H-pyrazol-3-ylidene}-2-{[(2S)-5,5-dimethyltetrahydrofuran-2-yl]methoxy}-5-(trifluoromethyl)benzamide The title compound was prepared as described in Example 1F, substituting Example 52C for (R)-(tetrahydrofuran-2-yl)methanol. $^1$H NMR (500 MHz, DMSO-d$_6$) δ ppm 1.13 (s, 6H), 1.36 (s, 9H), 1.59-1.78 (m, 5H), 1.80-1.91 (m, 2H), 1.96-2.08 (m, 1H), 3.56-3.65 (m, 1H), 3.69-3.78 (m, 1H), 3.86 (s, 3H), 3.92-4.04 (m, 2H), 4.09-4.23 (m, 2H), 4.25-4.36 (m, 2H), 6.78 (s, 1H), 7.14 (d, J=8.5 Hz, 1H), 7.54 (d, J=8.8 Hz, 1H), 7.65 (s, 1H); MS (ESI$^+$) m/z 538 (M+H)$^+$.

Example 53

N-{(3E)-5-tert-butyl-1-methyl-2-[(2R)-tetrahydrofuran-2-ylmethyl]-1,2-dihydro-3H-pyrazol-3-ylidene}-2-(2-cyclopent-1-en-1-ylethoxy)-5-(trifluoromethyl)benzamide Example 53A 1-(2-hydroxyethyl)cyclopentanol A solution of 1,4-dibromobutane (10 g, 46 mmol) in THF (100 mL) was treated with magnesium (2.81 g, 116 mmol) and I$_2$ (100 mg). The mixture was stirred at room temperature for 3 hours a solution of oxetan-2-one (3.34 g, 46.3 mmol) in THF (25 mL) was added dropwise. The reaction mixture was stirred at room temperature for 12 hours then quenched with saturated aqueous NH$_4$Cl and extracted with isopropanol/CH$_2$Cl$_2$ (1:3) (2×100 mL). The combined organic extracts were dried over MgSO$_4$, filtered and concentrated. The residue was purified by distillation (95-100° C. at 0.6 Torr) to provide 1.1 g (18%) of the title compound. MS (DCI/NH$_3$) m/z 148 (M+NH$_4$)$^+$.

Example 53B

N-{(3E)-5-tert-butyl-1-methyl-2-[(2R)-tetrahydrofuran-2-ylmethyl]-1,2-dihydro-3H-pyrazol-3-ylidene}-2-(2-cyclopent-1-en-1-ylethoxy)-5-(trifluoromethyl)benzamide The title compound was prepared as described in Example 1F, substituting Example 53A for (R)-(tetrahydrofuran-2-yl)methanol. $^1$H NMR (400 MHz, CDCl$_3$) δ ppm 1.41 (s, 9H) 1.68-1.91 (m, 5H) 1.93-2.06 (m, 1H) 2.21-2.33 (m, 4H) 2.61 (t, J=8.0, 7.1 Hz, 2H) 3.64-3.80 (m, 2H) 3.84 (s, 3H) 4.18 (t, J=7.7 Hz, 3H) 4.31 (dd, J=15.3, 5.8 Hz, 1H) 4.49 (dd, J=15.3, 3.4 Hz, 1H) 5.42 (brs, 1H) 6.96 (d, J=8.6 Hz, 1H) 7.04 (s, 1H) 7.48 (d, J=8.6 Hz, 1H) 7.95 (s, 1H); MS (ESI$^+$) m/z 520 (M+H)$^+$.

Example 54

N-{(3E)-5-tert-butyl-1-methyl-2-[(2R)-tetrahydrofuran-2-ylmethyl]-1,2-dihydro-3H-pyrazol-3-ylidene}-2-{[1-(methylsulfonyl)azetidin-3-yl]methoxy}-5-(trifluoromethyl)benzamide Example 54A tert-butyl 3-{[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenoxy]methyl}azetidine-1-carboxylate A solution of potassium tert-butoxide (0.94 mL, 1 M in THF) was added to tert-butyl 3-(hydroxymethyl)azetidine-1-carboxylate (0.18 g, 0.98 mmol) in THF (0.5 mL) and the mixture stirred for 10 minutes at ambient temperature. A solution of Example 1E (0.2 g, 0.5 mmol) in THF (0.8 mL) was added and the mixture stirred for 1 hour. The reaction mixture was partitioned between EtOAc (15 mL) and saturated NaHCO$_3$ (1 mL). The organic extract was washed with water and brine, dried with MgSO$_4$, filtered and concentrated. The residue was purified by chromatography (SiO$_2$, solvent A—hexane:EtOAc:Et$_3$N (1:3:0.2), solvent B—hexane:EtOAc:MeOH:Et$_3$N (1:3:1:0.2) 100% Solvent A to 75% solvent B/25% solvent A over 300 mL then isocratic for 180 mL) to afford the title compound (0.25 g, 0.42 mmol, 90% yield). $^1$H NMR (500 MHz, pyridine-d$_5$) δ ppm 1.19 (s, 9H), 1.48-1.51 (m, 9H), 1.55-1.63 (m, 2H), 1.64-1.71 (m, 1H), 1.75-1.83 (m, 1H), 3.00 (m, 1H), 3.59 (q, J=7.1 Hz, 1H), 3.70-3.75 (m, 1H), 3.80 (s, 3H), 3.97 (dd, J=8.4, 5.3 Hz, 2H), 4.04-4.10 (m, 2H), 4.20-4.25 (m, 1H), 4.26 (d, J=7.0 Hz, 2H), 4.37 (dd, J=15.3, 6.4 Hz, 1H), 4.59 (dd, J=15.1, 3.2 Hz, 1H), 7.16 (d, J=8.5 Hz, 1H), 7.45 (s, 1H), 7.65 (dd, J=8.7, 2.3 Hz, 1H), 8.48 (d, J=2.4 Hz, 1H); MS (DCI/NH$_3$) m/z 595.3 (M+H)$^+$.

Example 54B 2-(azetidin-3-ylmethoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide Trifluoroacetic acid (0.65 mL, 8.4 mmol) was added to a solution of Example 54A (0.25 g, 0.42 mmol) in dichloromethane (2.0 mL) and the solution was stirred for 2 hours at ambient temperature. The solvent was removed under reduced pressure. The residue was diluted with EtOAc and concentrated under reduced pressure twice. The residue was diluted with EtOAc, dried over anhydrous K$_2$CO$_3$, filtered. The solvent was removed under reduced pressure to afford the title compound (0.21 g, 0.42 mmol, 100% yield). $^1$H NMR (500 MHz, pyridine-d$_5$) δ ppm 1.23 (s, 9H), 1.62-1.70 (m, 2H), 1.71-1.79 (m, 1H), 1.90-1.98 (m, 1H), 2.84-2.92 (m, 1H), 3.59-3.66 (m, 1H), 3.74-3.81 (m, 1H), 3.87-3.91 (m, 1H), 3.92 (s, 3H), 4.25 (d, J=1.5 Hz, 2H), 4.31 (qd, J=6.9, 3.2 Hz, 1H), 4.47 (dd, J=15.3, 7.0 Hz, 1H), 4.63-4.75 (m, 3H), 7.13 (d, J=8.5 Hz, 1H), 7.34 (s, 1H), 7.75 (dd, J=8.5, 2.4 Hz, 1H), 8.96 (d, J=2.4 Hz, 1H); MS (ESI$^+$) m/z 495.2 [M+H]$^+$.

Example 54C

N-{(3E)-5-tert-butyl-1-methyl-2-[(2R)-tetrahydrofuran-2-ylmethyl]-1,2-dihydro-3H-pyrazol-3-ylidene}-2-{[1-(methylsulfonyl)azetidin-3-yl]methoxy}-5-(trifluoromethyl)benzamide Methanesulfonyl chloride (0.05 g, 0.4 mmol) was added to a solution of Example 54B (0.21 g, 0.4 mmol) in THF (5.0 mL) followed by triethylamine (0.17 mL, 1.2 mmol). The mixture was stirred for 1 hour at ambient temperature, then partitioned between EtOAc (15 mL) and saturated NaHCO$_3$ (1 mL). The organic extract was washed with water and brine, dried with MgSO$_4$, filtered and concentrated. The residue was purified by chromatography (SiO$_2$, solvent A—hexane: EtOAc:Et$_3$N (1:3:0.2), solvent B—hexane:EtOAc:MeOH: Et$_3$N (1:3:1:0.2) 100% solvent A to 100% solvent B over 450 mL then isocratic for 180 mL) to afford the title compound (0.12 g, 0.21 mmol, 49% yield). $^1$H NMR (500 MHz, pyridine-d$_5$) δ ppm 1.21 (s, 9H), 1.54-1.62 (m, 2H), 1.64-1.71 (m, 1H), 1.75-1.85 (m, 1H), 3.01-3.09 (m, 1H), 3.31 (s, 3H), 3.54-3.63 (m, 1H), 3.69-3.76 (m, 1H), 3.85 (s, 3H), 4.05 (t, J=8.1 Hz, 2H), 4.09 (d, J=4.3 Hz, 2H), 4.22-4.28 (m, 1H), 4.36-4.46 (m, 3H), 4.62 (dd, J=15.1, 3.2 Hz, 1H), 7.12 (d, J=8.8 Hz, 1H), 7.46 (s, 1H), 7.65 (dd, J=8.7, 2.3 Hz, 1H), 8.48 (d, J=2.4 Hz, 1H); MS (ESI$^+$) m/z 573.2 [M+H]$^+$.

Example 55

2-[2-(benzyloxy)-2-methylpropoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of 2-(benzyloxy)-2-methylpropan-1-ol (1.0 g, 5.3 mmol) in THF (10 mL) was added potassium tert-butoxide (0.98 g, 8.8 mmol). The mixture was stirred at ambient temperature for 20 min then a solution of Example 1E (0.75 g, 1.8 mmol) in THF (5 ml) was added via cannula. The mixture was stirred at ambient temperature for 6 hours then diluted with saturated aqueous NaHCO$_3$ (5 mL) and extracted with EtOAc (4×5 mL). The combined organic extracts were dried over anhydrous Na$_2$SO$_4$, filtered and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (0.92 g, 1.6 mmol, 89% yield). $^1$H NMR (300 MHz, CDCl$_3$) δ ppm 1.40 (s, 9H) 1.41 (s, 6H) 1.57-1.87 (m, 3H) 1.91-2.00 (m, 1H) 3.61-3.75 (m, 2H) 3.79 (s, 3H) 4.03 (s, 2H) 4.07-4.15 (m, 1H) 4.18-4.28 (m, 1H) 4.35-4.48 (m, 1H) 4.60 (s, 2H) 6.93 (s, 1H) 6.96 (d, J=8.5 Hz, 1H) 7.16-7.31 (m, 5H) 7.47 (dd, J=8.6, 1.5 Hz, 1H) 7.89 (d, J=2.4 Hz, 1H); MS (DCI/NH$_3$) m/z 588 (M+H)$^+$. Anal. calculated for C$_{32}$H$_{40}$F$_3$N$_3$O$_4$: Calc: C, 65.40; H, 6.86; N, 7.15. Found: C, 65.38; H, 7.23; N, 7.25.

Example 56

N-{(3E)-5-tert-butyl-1-methyl-2-[(2R)-tetrahydrofuran-2-ylmethyl]-1,2-dihydro-3H-pyrazol-3-ylidene}-2-[2-(methylsulfonyl)ethoxy]-5-(trifluoromethyl)benzamide To a solution of Example 57 (0.16 g, 0.32 mmol) in CH$_2$Cl$_2$ (5 mL) was added m-chloroperbenzoic acid (0.22 g, 0.96 mmol) portionwise over 5 min. The mixture was stirred at ambient temperature for 90 min then diluted with saturated aqueous NaHCO$_3$ (5 mL) and extracted with EtOAc (4×5 mL). The combined organic extracts were dried over anhydrous Na$_2$SO$_4$, filtered and concentrated under reduced pressure. Purification by column chromatography (SiO$_2$, 50% hex/EtOAc to 100% EtOAc to 9:1:0.1 EtOAc:MeOH:Et$_3$N) afforded the title compound (0.10 g, 0.19 mmol, 59% yield). $^1$H NMR (300 MHz, CDCl$_3$) δ ppm 1.43 (s, 9H) 1.63-1.94 (m, 3H) 1.98-2.09 (m, 1H) 3.16 (s, 3H) 3.49 (t, J=5.4 Hz, 2H) 3.69-3.81 (m, 2H) 3.88 (s, 3H) 4.14-4.30 (m, 2H) 4.47-4.55 (m, 3H) 6.94 (s, 1H) 6.98 (d, J=8.7 Hz, 1H) 7.54 (dd, J=8.1, 2.2 Hz, 1H) 7.99 (d, J=2.4 Hz, 1H); MS (DCI/NH$_3$) m/z 532 (M+H)$^+$. Anal. calculated for C$_{24}$H$_{32}$F$_3$N$_3$O$_5$S-0.1H$_2$O: Calc: C, 54.04; H, 6.08; N, 7.88. Found: C, 53.75; H, 6.11; N, 8.10.

Example 57

N-{(3E)-5-tert-butyl-1-methyl-2-[(2R)-tetrahydrofuran-2-ylmethyl]-1,2-dihydro-3H-pyrazol-3-ylidene}-2-[2-(methylthio)ethoxy]-5-(trifluoromethyl)benzamide To a solution of 2-(methylthio)ethanol (0.24 mL, 2.8 mmol) in THF (10 mL) was added potassium tert-butoxide (0.42 g, 3.7 mmol). The mixture was stirred at ambient temperature for 20 min then Example 1E (0.40 g, 0.94 mmol) was added. The mixture was stirred at ambient temperature for 2 hours then diluted with saturated aqueous NaHCO$_3$ (5 mL) and extracted with EtOAc (4×5 mL). The combined organic extracts were dried over anhydrous NaSO$_4$, filtered and concentrated under reduced pressure. Purification by column chromatography (SiO$_2$, 50% hexanes/EtOAc to 100% EtOAc to 9:1:0.1 EtOAc:MeOH:Et$_3$N) afforded the title compound (0.45 g, 0.90 mmol, 96% yield). $^1$H NMR (300 MHz, CDCl$_3$) δ ppm 1.43 (s, 9H) 1.68-1.91 (m, 3H) 1.97-2.05 (m, 1H) 2.18 (s, 3H) 2.92 (t, J=7.3 Hz, 2H) 3.70-3.80 (m, 2H) 3.86 (s, 3H) 4.15-4.22 (m, 1H) 4.24-4.35 (m, 3H) 4.50 (dd, J=15.6, 2.7 Hz, 1H) 6.97 (d, J=8.5 Hz, 1H) 7.03 (s, 1H) 7.49 (dd, J=8.5, 1.7 Hz, 1H) 7.97 (d, J=2.0 Hz, 1H); MS (DCI/NH$_3$) m/z 500 (M+H)$^+$; Anal. calculated for C$_{24}$H$_{32}$F$_3$N$_3$O$_3$S-0.2H$_2$O: Calc: C, 57.29; H, 6.49; N, 8.35. Found: C, 57.06; H, 6.53; N, 8.22.

Example 58

N-{(3E)-5-tert-butyl-1-methyl-2-[(2R)-tetrahydrofuran-2-ylmethyl]-1,2-dihydro-3H-pyrazol-3-ylidene}-2-[3-(methylthio)propoxy]-5-(trifluoromethyl)benzamide To a solution of 3-(methylthio)propan-1-ol (0.25 mL, 2.5 mmol) in THF (5 mL) was added potassium tert-butoxide (0.37 g, 3.3 mmol). The mixture was stirred at ambient temperature for 20 min then a solution of Example 1E (0.35 g, 0.82 mmol) in THF (5 mL) was added. The mixture was stirred at ambient temperature for 2 hours then diluted with saturated aqueous NaHCO$_3$ (5 mL) and extracted with EtOAc (4×5 mL). The combined organic extracts were dried over anhydrous NaSO$_4$, filtered and concentrated under reduced pressure. Purification by column chromatography (SiO$_2$, 50% hexanes/EtOAc to 100% EtOAc to 9:1:0.1 EtOAc: MeOH:Et$_3$N) afforded the title compound (0.28 g, 0.55 mmol, 67% yield). $^1$H NMR (300 MHz, CDCl$_3$) δ ppm 1.43 (s, 9H) 1.68-1.91 (m, 3H) 1.98-2.06 (m, 1H) 2.08 (s, 3H) 2.09-2.15 (m, 2H) 2.68 (t, J=7.1 Hz, 2H) 3.69-3.79 (m, 2H) 3.86 (s, 3H) 4.18 (t, J=6.3 Hz, 3H) 4.26-4.35 (m, 1H) 4.49 (dd, J=15.1, 2.8 Hz, 1H) 6.97 (d, J=8.7 Hz, 1H) 7.02 (s, 1H) 7.48 (dd, J=8.3, 2.0 Hz, 1H) 7.95 (d, J=2.4 Hz, 1H); MS (DCI/NH$_3$) m/z 514 (M+H)$^+$; Anal. calculated for C$_{25}$H$_{34}$F$_3$N$_3$O$_3$S) Calc: C, 58.46; H, 6.67; N, 8.18. Found: C, 58.26; H, 6.74; N, 8.04.

Example 59

N-[(2E)-5-tert-butyl-1-[(2R)-tetrahydrofuran-2-ylmethyl]pyridin-2(1H)-ylidene]-2-{[(2S)-1-methylpyrrolidin-2-yl]methoxy}-5-(trifluoromethyl)benzamide

Example 59A tert-butyl 5-tert-butylpyridin-2-ylcarbamate

To a mixture of anhydrous CuCN (2.7 g, 30.4 mmol) in 100 mL of THF was added a solution of tert-butylmagnesium chloride (30.4 mL, 60.2 mmol, 2M solution in THF) under $N_2$ at −78° C. After 20 minutes, tert-butyl 5-bromopyridin-2-ylcarbamate (2.1 g, 7.6 mmol, Aldrich) was added. The reaction mixture was stirred for 2 hours at −78° C. and then at room temperature for 12 hours. The mixture was quenched with saturated aqueous $NH_4OH$ and basified to pH 7 with 20% aqueous NaOH. The solid was filtered through a pad of Celite. The filtrate was extracted with ether and washed with water. The organic extract was dried over $MgSO_4$ and concentrated. Purification by column chromatography ($SiO_2$: 0-15% hexanes/ethyl acetate gradient) afforded 0.4 g of the title compound. MS (ESI$^+$) m/z 251 (M+H)$^+$.

Example 59B 5-tert-butylpyridin-2-amine

To a 0° C. solution of Example 59A (1.0 g, 40 mmol) in dichloromethane (3 mL) was added trifluoroacetic acid (3. mL, 40 mmol). The reaction mixture was stirred at ambient temperature for 3 hours then concentrated under reduced pressure. The residue was diluted with ethyl acetate (100 mL) and washed with saturated aqueous $NaHCO_3$. The layers were separated and the aqueous phase was extracted with ethyl acetate (5×100 mL). The combined organic extracts were dried over anhydrous $Na_2SO_4$, filtered and concentrated under reduced pressure to provide the title compound. MS (ESI$^+$) m/z 151 (M+H)$^+$.

Example 59C (R)-5-tert-butyl-1-((tetrahydrofuran-2-yl)methyl)pyridin-2(1H)-imine A mixture of Example 59B (0.5 g, 3.3 mmol), (R)-(tetrahydrofuran-2-yl)methyl 4-methylbenzenesulfonate (0.9 g, 3.6 mmol), and tetraethylammonium iodide (0.4 g, 1.6 mmol) in N,N-dimethylformamide (1.0 mL) was heated at 95° C. for 16 hours. After cooling to ambient temperature, the mixture was quenched with saturated $NaHCO_3$ (10 mL) and extracted with dichloromethane (3×30 mL). The combined organic extracts were dried over anhydrous $Na_2SO_4$, filtered and concentrated under reduced pressure to provide the title compound. LCMS (APCI$^+$) m/z 235 (M+H)$^+$.

Example 59D

N-[(2E)-5-tert-butyl-1-[(2R)-tetrahydrofuran-2-ylmethyl]pyridin-2(1H)-ylidene]-2-{[(2S)-1-methylpyrrolidin-2-yl]methoxy}-5-(trifluoromethyl)benzamide The title compound was prepared as described in Example 33D, substituting Example 59C for Example 33C. $^1$H NMR (400 MHz, DMSO-d$_6$) δ ppm 1.26 (s, 9H), 1.55-1.69 (m, 4H), 1.75-1.95 (m, 4H), 2.08-2.20 (m, 1H), 2.32 (s, 3H), 2.52-2.60 (m, 1H), 2.86-2.97 (m, 1H), 3.61-3.68 (m, 1H), 3.74-3.82 (m, 1H), 3.90-4.05 (m, 2H), 4.18-4.26 (m, 1H), 4.26-4.34 (m, 1H), 4.51 (dd, J=12.4, 3.2 Hz, 1H), 7.20 (d, J=8.9 Hz, 1H), 7.63 (dd, J=8.6, 2.1 Hz, 1H), 7.77 (d, J=2.5 Hz, 1H), 7.86 (d, J=2.1 Hz, 1H), 7.92 (dd, J=9.5, 2.5 Hz, 1H), 8.13 (d, J=9.5 Hz, 1H); MS (ESI$^+$) m/z 520 (M+H)$^+$.

Example 60

N-{(3E)-5-tert-butyl-1-methyl-2-[(2R)-tetrahydrofuran-2-ylmethyl]-1,2-dihydro-3H-pyrazol-3-ylidene}-2-[3-(methylsulfonyl)propoxy]-5-(trifluoromethyl)benzamide To a solution of Example 58 (0.25 g, 0.49 mmol) in $CH_2Cl_2$ (7 mL) was added m-chloroperbenzoic acid (0.33 g, 1.5 mmol) portionwise over 5 min. The mixture was stirred at ambient temperature for 90 min then quenched with saturated aqueous $NaHCO_3$ (5 mL) and diluted with $CH_2Cl_2$ (10 mL). The layers were separated and the aqueous phase was extracted with $CH_2Cl_2$ (3×5 mL). The combined organic extracts were dried over anhydrous $Na_2SO_4$, filtered and concentrated under reduced pressure. Purification by column chromatography ($SiO_2$, 50% hex/EtOAc to 100% EtOAc to 9:1:0.1 EtOAc:MeOH:Et$_3$N) afforded the title compound (0.14 g, 0.26 mmol, 53% yield). $^1$H NMR (300 MHz, CDCl$_3$) δ ppm 1.44 (s, 9H) 1.64-1.94 (m, 3H) 1.95-2.08 (m, 1H) 2.27-2.38 (m, 2H) 2.89 (s, 3H) 3.36-3.43 (m, 2H) 3.66-3.79 (m, 2H) 3.88 (s, 3H) 4.09-4.24 (m, 3H) 4.25-4.35 (m, 1H) 4.50 (dd, J=15.1, 2.8 Hz, 1H) 6.95 (d, J=8.7 Hz, 1H) 6.99 (s, 1H) 7.50 (dd, J=8.7, 2.4 Hz, 1H) 7.95 (d, J=2.4 Hz, 1H); MS (DCI/NH$_3$) m/z 546 (M+H)$^+$. Anal. calculated for $C_{25}H_{34}F_3N_3O_5S$: Calc: C, 55.03; H, 6.28; N, 7.70. Found: C, 54.65; H, 6.43; N, 7.53.

Example 61

N-{(3E)-5-tert-butyl-1-methyl-2-[(2R)-tetrahydrofuran-2-ylmethyl]-1,2-dihydro-3H-pyrazol-3-ylidene}-2-{[(2S)-1-(methylsulfonyl)pyrrolidin-2-yl]methoxy}-5-(trifluoromethyl)benzamide The title compound was prepared as described in Example 54C, substituting Example 62B for Example 54B (0.08 g, 0.14 mmol, 39% yield). $^1$H NMR (300 MHz, DMSO-d$_6$) δ ppm 1.38 (s, 9H), 1.63-1.90 (m, 5H), 1.92-2.03 (m, 3H), 2.93 (s, 3H), 3.23-3.29 (m, 2H), 3.58-3.66 (m, 1H), 3.70-3.79 (m, 1H), 3.88 (s, 3H), 3.94-4.01 (m, 2H), 4.06-4.19 (m, 2H), 4.29-4.35 (m, 2H), 6.78 (s, 1H), 7.17 (d, J=8.7 Hz, 1H), 7.58 (d, J=8.7 Hz, 1H), 7.67 (d, J=2.0 Hz, 1H); MS (ESI$^+$) m/z 587.3 [M+H]$^+$.

Example 62

N-{(3E)-5-tert-butyl-1-methyl-2-[(2R)-tetrahydrofuran-2-ylmethyl]-1,2-dihydro-3H-pyrazol-3-ylidene}-2-[(2S)-pyrrolidin-2-ylmethoxy]-5-(trifluoromethyl)benzamide

Example 62A tert-butyl (2S)-2-{[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenoxy]methyl}pyrrolidine-1-carboxylate The title compound was prepared as described in Example 54A, substituting (5)-tert-butyl 2-(hydroxymethyl)pyrrolidine-1-carboxylate for tert-butyl 3-(hydroxymethyl)azetidine-1-carboxylate (0.2 g, 0.33 mmol, 56% yield); MS (ESI$^+$) m/z 609.4 [M+H]

Example 62B

N-{(3E)-5-tert-butyl-1-methyl-2-[(2R)-tetrahydrofuran-2-ylmethyl]-1,2-dihydro-3H-pyrazol-3-ylidene}-2-[(2S)-pyrrolidin-2-ylmethoxy]-5-(trifluoromethyl)benzamide The title compound was prepared by the procedure described in Example 54B, substituting Example 62A for Example 54A (0.18 g, 0.35 mmol, 108% yield). $^1$H NMR (500 MHz, pyridine-d$_5$) δ ppm 1.28 (s, 9H), 1.58-1.71 (m, 4H), 1.79-1.88 (m, 1H), 1.89-2.00 (m, 3H), 2.02-2.12 (m, 1H), 3.47-3.56 (m, 1H), 3.57-3.64 (m, 2H), 3.73-3.81 (m, 1H), 4.06 (s, 3H), 4.25-4.33 (m, 1H), 4.33-4.41 (m, 1H), 4.43-4.50 (m, 2H), 4.50-4.61 (m, 1H), 4.83-4.93 (m, 1H), 7.25-7.32 (m, 2H), 7.73 (d, J=8.5 Hz, 1H), 8.46 (s, 1H); MS (ESI$^+$) m/z 509.2 [M+H]$^+$.

Example 63

N-[(3E)-5-tert-butyl-2-(cyclopropylmethyl)-1-methyl-1,2-dihydro-3H-pyrazol-3-ylidene]-2-{[(2S)-1-(methylsulfonyl)azetidin-2-yl]methoxy}-5-(trifluoromethyl)benzamide

Example 63A tert-butyl (2S)-2-{[2-({[(3E)-5-tert-butyl-2-(cyclopropylmethyl)-1-methyl-1,2-dihydro-3H-pyrazol-3-ylidene]amino}carbonyl)-4-(trifluoromethyl)phenoxy]methyl}azetidine-1-carboxylate The title compound was prepared as described in Example 46, substituting (S)-tert-butyl 2-(hydroxymethyl)azetidine-1-carboxylate for pyrazin-2-ylmethanol (89% yield). $^1$H NMR (300 MHz, CDCl$_3$) δ ppm 0.47-0.63 (m, 4H), 1.01-1.16 (m, J=7.93 Hz, 1H), 1.41 (s, 9H), 1.44 (s, 9H), 2.21-2.34 (m, 1H), 2.34-2.48 (m, 1H), 3.74-3.87 (m, 5H), 4.08-4.30 (m, 3H), 4.30-4.44 (m, 1H), 4.50 (d, J=5.55 Hz, 1H), 7.00 (s, 1H), 7.04 (d, J=8.33 Hz, 1H), 7.47 (dd, J=8.53, 2.18 Hz, 1H), 7.92 (d, J=2.38 Hz, 1H); MS (DCI/NH$_3$) m/z 565 (M+H)$^+$.

Example 63B

2-[(2S)-azetidin-2-ylmethoxy]-N-[(3E)-5-tert-butyl-2-(cyclopropylmethyl)-1-methyl-1,2-dihydro-3H-pyrazol-3-ylidene]-5-(trifluoromethyl)benzamide A solution of Example 63A (500 mg, 0.886 mmol) and 2,2,2-trifluoroacetic acid (0.682 ml, 8.86 mmol) in CH$_2$Cl$_2$ (5 ml) was stirred at ambient temperature overnight, and then concentrated under reduced pressure. The residue was portioned between CH$_2$Cl$_2$ (30 mL) and saturated aqueous NaHCO$_3$ (30 mL). The aqueous phase was extracted with CH$_2$Cl$_2$ (2×20 mL). The combined organic extracts were washed with brine, dried over MgSO$_4$, filtered, and concentrated. Purification by flash chromatography (silica gel, MeOH/Et$_3$N (9:1) in CH$_2$Cl$_2$ in 0-30% gradient) provided 300 mg (73%) of the title compound. $^1$H NMR (300 MHz, DMSO-d$_6$) δ ppm 0.34-0.58 (m, 4H), 1.05-1.26 (m, 1H), 1.37-1.42 (m, 9H), 2.00-2.16 (m, 1H), 2.16-2.33 (m, 1H), 3.23-3.39 (m, 1H), 3.39-3.54 (m, 1H), 3.63-3.78 (m, 1H), 3.88-3.91 (m, 3H), 4.00-4.22 (m, 5H), 6.78-6.80 (m, 1H), 7.21 (d, J=8.82 Hz, 1H), 7.57 (dd, J=8.65, 1.86 Hz, 1H), 7.69 (d, J=2.03 Hz, 1H); MS (ESI$^+$) m/z 465 (M+H)$^+$, 463 [M−H].

Example 63C

N-[(3E)-5-tert-butyl-2-(cyclopropylmethyl)-1-methyl-1,2-dihydro-3H-pyrazol-3-ylidene]-2-{[(2S)-1-(methylsulfonyl)azetidin-2-yl]methoxy}-5-(trifluoromethyl)benzamide To a solution of Example 63B (220 mg, 0.474 mmol) and triethylamine (0.132 ml, 0.947 mmol) in CH$_2$Cl$_2$ (6 ml) was added methanesulfonyl chloride (0.055 ml, 0.710 mmol) dropwise. The mixture was stirred at ambient temperature for 2 hours then portioned between CH$_2$Cl$_2$ and water. The organic extract was washed with brine and concentrated. Purification by chromatography (silica gel, MeOH/Et$_3$N (9:1) in CH$_2$Cl$_2$ in 0-30% gradient) provided 160 mg (62% yield) of the title compound. $^1$H NMR (300 MHz, CDCl$_3$) δ ppm 0.41-0.68 (m, 4H), 1.01-1.18 (m, 1H), 1.41-1.49 (m, 9H), 2.25-2.45 (m, 2H), 2.91 (s, 3H), 3.71-3.80 (m, 1H), 3.83 (s, 3H), 3.93-4.07 (m, 1H), 4.14-4.33 (m, 4H), 4.59-4.80 (m, 1H), 6.95-7.06 (m, 2H), 7.50 (dd, J=8.82, 1.70 Hz, 1H), 7.92 (d, J=2.37 Hz, 1H); MS (DCI/NH$_3$) m/z 543 (M+H)$^+$.

Example 64

N-{(3E)-5-tert-butyl-1-methyl-2-[(2R)-tetrahydrofuran-2-ylmethyl]-1,2-dihydro-3H-pyrazol-3-ylidene}-2-[2-methyl-2-(methylthio)propoxy]-5-(trifluoromethyl)benzamide To a solution of 2-methyl-2-(methylthio)propan-1-ol (0.20 g, 1.7 mmol) in THF (5 mL) was added potassium tert-butoxide (0.38 g, 3.4 mmol). The mixture was stirred at ambient temperature for 20 min then a solution of Example 1E (0.36 g, 0.84 mmol) in THF (5 mL) was added via cannula. The mixture was stirred at ambient temperature for 1 h then diluted with saturated aqueous NaHCO$_3$ (10 mL) and extracted with EtOAc (4×5 mL). The combined organic extracts were dried over anhydrous NaSO$_4$, filtered and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (0.28 g, 0.53 mmol, 63% yield). $^1$H NMR (300 MHz, CDCl$_3$) δ ppm 1.42 (s, 6H) 1.43 (s, 9H) 1.66-1.90 (m, 3H) 1.95-2.06 (m, 1H) 2.11 (s, 3H) 3.66-3.82 (m, 2H) 3.85 (s, 3H) 4.00 (s, 2H) 4.12-4.22 (m, 1H) 4.27 (dd, J=15.1, 5.6 Hz, 1H) 4.49 (dd, J=15.1, 2.8 Hz, 1H) 6.93 (s, 1H) 6.94 (d, J=9.9 Hz, 1H) 7.47 (dd, J=8.5, 2.2 Hz, 1H) 7.88 (d, J=2.4 Hz, 1H); MS (DCI/NH$_3$) m/z 528 (M+H)$^+$; Anal. calculated for C$_{26}$H$_{36}$F$_3$N$_3$O$_3$S: Calc: C, 59.18; H, 6.88; N, 7.96. Found: C, 59.18; H, 6.79; N, 7.82.

Example 65

N-{(3E)-5-tert-butyl-1-methyl-2-[(2R)-tetrahydrofuran-2-ylmethyl]-1,2-dihydro-3H-pyrazol-3-ylidene}-2-[2-methyl-2-(methylsulfonyl)propoxy]-5-(trifluoromethyl)benzamide To a solution of Example 64 (0.17 g, 0.32 mmol) in CH$_2$Cl$_2$ (5 mL) was added m-chloroperbenzoic acid (0.22 g, 0.97 mmol) portionwise over 5 min. The mixture was stirred at ambient temperature for 90 min then diluted with saturated aqueous NaHCO$_3$ (5 mL) and extracted with EtOAc (4×5 mL). The combined organic extracts were dried over anhydrous NaSO₄, filtered and concentrated under reduced pressure. Purification by column chromatography (SiO₂, 50% hex/EtOAc to 100% EtOAc to 9:1:0.1 EtOAc:MeOH:Et₃N) afforded the title compound (0.145 g, 0.26 mmol, 80% yield). ¹H NMR (300 MHz, CDCl₃) δ ppm 1.43 (s, 9H) 1.56 (s, 6H) 1.63-1.94 (m, 3H) 1.96-2.06 (m, 1H) 3.10 (s, 3H) 3.68-3.83 (m, 2H) 3.88 (s, 3H) 4.07-4.19 (m, 1H) 4.21-4.29 (m, 1H) 4.22 (s, 2H) 4.49 (dd, J=14.7, 2.8 Hz, 1H) 6.89 (s, 1H) 6.94 (d, J=8.7 Hz, 1H) 7.52 (dd, J=8.5, 2.2 Hz, 1H) 7.94 (d, J=2.4 Hz, 1H); MS (DCI/NH₃) m/z 560 (M+H)⁺. Anal. calculated for C₂₆H₃₆F₃N₃O₅S: Calc: C, 55.80; H, 6.48; N, 7.51. Found: C, 55.69; H, 6.42; N, 7.40.

Example 66

2-[(2S)-azetidin-2-ylmethoxy]-N-[(2Z)-5-tert-butyl-3-[(2R)-tetrahydrofuran-2-ylmethyl]-1,3-oxazol-2(3H)-ylidene]-5-(trifluoromethyl)benzamide Example 66A tert-butyl (2S)-2-{[2-({[(2Z)-5-tert-butyl-3-[(2R)-tetrahydrofuran-2-ylmethyl]-1,3-oxazol-2(3H)-ylidene]amino}carbonyl)-4-(trifluoromethyl)phenoxy]methyl}azetidine-1-carboxylate The title compound was prepared as described in Example 32D, substituting tert-butyl 2-(hydroxymethyl)azetidine-1-carboxylate for (S)-(1-methylpyrrolidin-2-yl)methanol to afford the title compound. MS (ESI⁺) m/z 582 (M+H)⁺.

Example 66B

2-[(2S)-azetidin-2-ylmethoxy]-N-[(2Z)-5-tert-butyl-3-[(2R)-tetrahydrofuran-2-ylmethyl]-1,3-oxazol-2(3H)-ylidene]-5-(trifluoromethyl)benzamide The title compound was prepared as described in Example 4B, substituting Example 66A for Example 4A. ¹H NMR (400 MHz, chloroform-d) δ ppm 1.33 (s, 9H) 1.51-1.65 (m, 1H) 1.86-1.99 (m, 2H) 2.02-2.15 (m, 1H) 2.55-2.75 (m, 2H) 3.71-3.85 (m, 2H) 3.86-3.93 (m, 1H) 4.05 (s, 1H) 4.11-4.31 (m, 3H) 4.34 (dd, J=14.27, 2.30 Hz, 1H) 4.64 (dd, J=10.59, 6.29 Hz, 1H) 5.05 (s, 1H) 6.84 (s, 1H) 7.07 (d, J=8.59 Hz, 1H) 7.73 (dd, J=8.59, 2.15 Hz, 1H) 8.12 (d, J=2.15 Hz, 1H); MS (ESI⁺) m/z 482 (M+H)⁺.

Example 67

N-{(3E)-5-tert-butyl-1-methyl-2-[(2R)-tetrahydrofuran-2-ylmethyl]-1,2-dihydro-3H-pyrazol-3-ylidene}-2-{[(2S)-1-(methylsulfonyl)azetidin-2-yl]methoxy}-5-(trifluoromethyl)benzamide Example 67A tert-butyl (2S)-2-{[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenoxy]methyl}azetidine-1-carboxylate The title compound was prepared as described in Example 54A, substituting (S)-tert-butyl 2-(hydroxymethyl)azetidine-1-carboxylate for tert-butyl 3-(hydroxymethyl)azetidine-1-carboxylate (0.21 g, 0.35 mmol, 43% yield). ¹H NMR (300 MHz, DMSO-d₆) δ ppm 1.32 (s, 9H), 1.37 (s, 9H), 1.63-1.79 (m, 3H), 1.79-1.94 (m, 1H), 2.23 (q, J=7.5 Hz, 2H), 3.54-3.80 (m, 4H), 3.87 (s, 3H), 4.05-4.23 (m, 2H), 4.32 (d, J=5.1 Hz, 2H), 4.34-4.46 (m, 2H), 6.79 (s, 1H), 7.18 (d, J=8.8 Hz, 1H), 7.56 (dd, J=8.6, 1.9 Hz, 1H), 7.73 (d, J=2.0 Hz, 1H); MS (DCI/NH₃) m/z 595.2 (M+H)⁺.

Example 67B

2-[(2S)-azetidin-2-ylmethoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was prepared as described in Example 54B, substituting Example 67A for Example 54A (0.2 g, 0.4 mmol, 100% yield). ¹H NMR (300 MHz, DMSO-d₆) δ ppm 1.44 (s, 9H), 1.49-1.67 (m, 1H), 1.73-1.95 (m, 2H), 1.97-2.12 (m, 1H), 2.32-2.47 (m, 1H), 2.52-2.62 (m, 1H), 3.62-3.71 (m, 1H), 3.72-3.82 (m, 1H), 3.82-3.98 (m, 3H), 4.11 (s, 3H), 4.13-4.23 (m, 1H), 4.42-4.58 (m, 2H), 4.60-4.76 (m, 2H), 6.93 (s, 1H), 7.45 (d, J=8.7 Hz, 1H), 7.92 (s, 1H), 7.98 (d, J=8.7 Hz, 1H), 11.22 (s, 1H); MS (DCI/NH₃) m/z 495.2 (M+H)⁺.

Example 67C

N-{(3E)-5-tert-butyl-1-methyl-2-[(2R)-tetrahydrofuran-2-ylmethyl]-1,2-dihydro-3H-pyrazol-3-ylidene}-2-{[(2S)-1-(methylsulfonyl)azetidin-2-yl]methoxy}-5-(trifluoromethyl)benzamide The title compound was prepared as described in Example 54C, substituting the product of Example 67B for the product of Example 54B (0.11 g, 0.19 mmol, 63% yield). ¹H NMR (500 MHz, pyridine-d₅) δ ppm 1.19 (s, 9H), 1.53-1.62 (m, 2H), 1.63-1.72 (m, 1H), 1.76-1.84 (m, 1H), 2.13-2.21 (m, 1H), 2.47-2.55 (m, 1H), 3.24 (s, 3H), 3.58 (q, J=7.3 Hz, 1H), 3.68-3.75 (m, 1H), 3.82 (s, 3H), 3.83-3.89 (m, 1H), 3.98-4.04 (m, 1H), 4.24 (qd, J=6.7, 3.4 Hz, 1H), 4.36 (dd, J=10.7, 4.6 Hz, 1H), 4.42 (dd, J=15.1, 6.6 Hz, 1H), 4.49 (dd, J=10.4, 4.3 Hz, 1H), 4.58 (dd, J=15.1, 3.2 Hz, 1H), 4.79-4.85 (m, 1H), 7.18 (d, J=8.5 Hz, 1H), 7.46 (s, 1H), 7.62 (dd, J=8.5, 2.1 Hz, 1H), 8.49 (d, J=2.1 Hz, 1H); MS (DCI/NH₃) m/z 573.1 (M+H)⁺.

Example 68

2-(3-hydroxy-3-methylbutoxy)-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide Example 68A 3-(1-methylcyclopropyl)-3-oxopropanenitrile To a solution of diisopropylamine (7.43 ml, 52.6 mmol) in 60 mL of THF at −78° C. was added a solution of n-BuLi in hexanes (2.5M, 21.0 mL, 52.6 mmol). The mixture was stirred at −78° C. for 30 min then acetonitrile (2.76 ml, 52.6 mmol) was added. After 30 min, methyl 1-methylcyclopropanecarboxylate (3.0 g, 52.6 mmol) was added and the reaction mixture was stirred at −78° C. for 1 hour then allowed to warm to room temperature and stirred overnight. The mixture was concentrated and the residue was diluted with water and extracted with ether. The aqueous phase was acidified with 6N aqueous HCl to pH 2-3 and extracted with ether. The combined organic extracts were dried over MgSO₄, filtered, and concentrated to afford the title compound 2.89 g (89%). MS (DCI/NH$_3$) m/z 124 (M+H)$^+$.

Example 68B (R)-3-(1-methylcyclopropyl)-1-(tetrahydrofuran-2-yl)methyl)-1H-pyrazol-5-amine The title compound was prepared as described in Example 1C, substituting Example 68A for 4,4-dimethyl-3-oxopentanenitrile. MS (DCI/NH$_3$) m/z 222 (M+H)$^+$.

Example 68C (R)-2-fluoro-N-(3-(1-methylcyclopropyl)-1-(tetrahydrofuran-2-yl)methyl)-1H-pyrazol-5-yl)-5-(trifluoromethyl)benzamide The title compound was prepared as described in Example 1D substituting Example 68B for Example 1C. MS (DCI/NH$_3$) m/z 412 (M+H)$^+$.

Example 68D (R,E)-2-fluoro-N-(1-methyl-5-(1-methylcyclopropyl)-2-((tetrahydrofuran-2-yl)methyl)-1H-pyrazol-3 (2H)-ylidene)-5-(trifluoromethyl)benzamide The title compound was prepared as described in Example 1E substituting Example 68C for Example 1D. MS (DCI/NH$_3$) m/z 426 (M+H)$^+$.

Example 68E 2-(3-hydroxy-3-methylbutoxy)-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide A mixture of Example 68D (600 mg, 1.41 mmol), 3-methylbutane-1,3-diol (294 mg, 2.82 mmol) and sodium 2-methylpropan-2-olate (271 mg, 2.82 mmol) in THF (30 mL) was heated at 40° C. for 12 hours. The reaction mixture was diluted with H$_2$O and extracted with EtOAc (2×). The combined organic extracts were dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 391 mg (54%) of the title compound. $^1$H NMR (500 MHz, chloroform-d) δ ppm 0.76-0.83 (m, 2H) 0.89-0.98 (m, 2H) 1.31 (s, 6H) 1.34 (s, 3H) 1.69-1.82 (m, 2H) 1.81-1.90 (m, 1H) 1.96-2.11 (m, 3H) 3.66-3.80 (m, 2H) 3.83 (s, 3H) 4.15-4.32 (m, 4H) 4.52 (dd, J=14.49, 2.59 Hz, 1H) 5.62 (s, 1H) 6.98 (d, J=8.54 Hz, 1H) 7.03 (s, 1H) 7.53 (dd, J=8.54, 2.14 Hz, 1H) 8.30 (d, J=2.14 Hz, 1H); MS (DCI/NH$_3$) m/z 510 (M+H)$^+$.

Example 69

N-[(2Z)-5-tert-butyl-3-[(2R)-tetrahydrofuran-2-ylmethyl]-1,3,4-thiadiazol-2(3H)-ylidene]-2-{[(2S)-1-methylpyrrolidin-2-yl]methoxy}-5-(trifluoromethyl)benzamide

Example 69A tert-butyl 5-tert-butyl-1,3,4-thiadiazol-2-ylcarbamate

To mixture of 5-tert-butyl-1,3,4-thiadiazol-2-amine (20.0 g, 127 mmol, Aldrich) and N$_1$,N$_1$,N$_2$,N$_2$-tetramethylethane-1,2-diamine (0.19 mL, 1.27 mmol) in dichloromethane was added di-tert-butyl dicarbonate (30.5 g, 140 mmol) at room temperature. The mixture was stirred at room temperature for 12 hours then washed with aqueous sodium bicarbonate. The organic layer was dried over Na$_2$SO$_4$, filtered and concentrated under reduced pressure. Purification by chromatography using an Analogix® Intelliflash280™ (SiO$_2$, 0 to 15% Hex:EtOAc gradient) afforded the title compound. MS (ESI$^+$) m/z 258 (M+H)$^+$.

Example 69B tert-butyl (2Z)-5-tert-butyl-3-[(2R)-tetrahydrofuran-2-ylmethyl]-1,3,4-thiadiazol-2(3H)-ylidenecarbamate To a mixture of Example 69A (20.0 g, 78.0 mmol) and Example 39A (21.9 g, 85.0 mmol) in THF/DMF (4/1) was added potassium 2-methylpropan-2-olate (13.1 g, 117 mmol). The mixture was heated at 75° C. for 16 hours then cooled to room temperature, diluted with ether and washed with aqueous NaHCO$_3$. The organic extract was dried over Na$_2$SO$_4$ and concentrated under reduced pressure. The residue was purified by flash chromatography on SiO$_2$ using an Analogix® Intelliflash280™ (Hexanes:EtOAc, 0 to 50% gradient) to afford the title compound. MS (ESI$^+$) m/z 342 (M+H)$^+$.

Example 69C (R)-5-tert-butyl-3-((tetrahydrofuran-2-yl)methyl)-1,3,4-thiadiazol-2(3H)-imine A mixture of Example 69B (7.50 g, 22.0 mmol) and 2,2,2-trifluoroacetic acid (13.5 mL, 176 mmol) was stirred at 22° C. for 8 hours. The volatiles were removed under reduced pressure and the residue was diluted with dichloromethane and washed with saturated aqueous NaHCO$_3$. The organic extract was dried over Na$_2$SO$_4$ and concentrated to give the title compound. MS (ESI$^+$) m/z 242 (M+H)$^+$.

Example 69D

N-[(2Z)-5-tert-butyl-3-[(2R)-tetrahydrofuran-2-ylmethyl]-1,3,4-thiadiazol-2(3H)-ylidene]-2-{[(2S)-1-methylpyrrolidin-2-yl]methoxy}-5-(trifluoromethyl)benzamide A mixture of Example 69C (200 mg, 0.83 mmol), 1H-benzo[d][1,2,3]triazol-1-ol hydrate (127 mg, 0.83 mmol), N$_1$-((ethylimino)methylene)-N$_3$,N$_3$-dimethylpropane-1,3-diamine hydrochloride (159 mg, 0.83 mmol), Example 33B (251 mg, 0.83 mmol), and triethylamine (173 μL, 1.24 mmol) in THF (8 mL) was stirred at 60° C. for 4 hours then cooled to ambient temperature. The mixture was diluted with ethyl acetate, washed with aqueous NaHCO$_3$ and the organic extract was concentrated. The residue was purified by flash chromatography on SiO$_2$ using an Analogix® Intelliflash280™ (Hexanes-EtOAc, 0 to 65% gradient) to give the title compound. $^1$H NMR (300 MHz, CDCl$_3$) δ ppm 1.42 (s, 9H), 1.65-1.89 (m, 4H), 1.88-2.13 (m, 4H), 2.24-2.35 (m, 1H), 2.48 (s, 3H), 3.75-3.84 (m, 1H), 3.89-4.00 (m, 2H), 4.10-4.17 (m, 1H), 4.24-4.31 (m, 1H), 4.44-4.60 (m, 1H), 7.04 (d, J=8.8 Hz, 1H), 7.62 (dd, J=8.1, 2.4 Hz, 1H), 8.23 (d, J=2.0 Hz, 1H); MS (ESI$^+$) m/z 527 (M+H)$^+$.

Example 70

2-(2-hydroxy-2-methylpropoxy)-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide The title compound was prepared as described in Example 68E substituting Example 81D for 3-methylbutane-1,3-diol. $^1$H NMR (500 MHz, chloroform-d) δ ppm 0.75-0.87 (m, 2H) 0.89-1.01 (m, 2H) 1.21-1.33 (m, 6H) 1.37 (s, 3H) 1.62-1.81 (m, 1H) 1.81-1.92 (m, 1H) 1.97-2.13 (m, 1H) 3.67-3.80 (m, 2H) 3.85 (s, 3H) 4.02 (s, 2H) 4.13-4.31 (m, 2H) 4.52 (dd, J=14.95, 2.75 Hz, 1H) 6.26 (s, 1H) 6.96 (s, 1H) 7.00 (d, J=8.54 Hz, 1H) 7.51 (dd, J=8.54, 2.14 Hz, 1H) 8.07 (d, J=2.14 Hz, 1H); MS (DCI/NH$_3$) m/z 496 (M+H)$^+$.

Example 71

N-[(3E)-5-tert-butyl-2-(cyclopropylmethyl)-1-methyl-1,2-dihydro-3H-pyrazol-3-ylidene]-2-(2-hydroxy-2-methylpropoxy)-5-(trifluoromethyl)benzamide

Example 71A (E)-2-(2-(benzyloxy)-2-methylpropoxy)-N-(5-tert-butyl-2-(cyclopropylmethyl)-1-methyl-1H-pyrazol-3(2H)-ylidene)-5-(trifluoromethyl)benzamide The title compound was prepared as described in Example 46, substituting 2-(benzyloxy)-2-methylpropan-1-ol for pyrazin-2-ylmethanol (90% yield). $^1$H NMR (300 MHz, DMSO-d$_6$) δ ppm 0.32-0.50 (m, 4H), 1.06-1.20 (m, 1H), 1.26-1.30 (m, 6H), 1.36 (s, 9H), 3.87 (s, 3H), 4.02 (s, 2H), 4.13 (d, J=6.78 Hz, 2H), 4.52 (s, 2H), 6.79 (s, 1H), 7.12-7.26 (m, 6H), 7.53-7.60 (m, 1H), 7.65 (s, 1H); MS (ESI$^+$) m/z 558 (M+H)$^+$, 556 (M−H)$^−$.

Example 71B

N-[(3E)-5-tert-butyl-2-(cyclopropylmethyl)-1-methyl-1,2-dihydro-3H-pyrazol-3-ylidene]-2-(2-hydroxy-2-methylpropoxy)-5-(trifluoromethyl)benzamide A mixture of Example 71A (1.0 g, 1.8 mmol), palladium hydroxide on carbon (Pearlman's catalyst, 20 wt. %) in MeOH (20 mL) in a 50 mL pressure bottle was stirred under 30 psi hydrogen at ambiant temperature for 17 hours. The mixture was then filtered and concentrated. Purification by flash chromatography (SiO$_2$, solvent A=90:10:1 CH$_2$Cl$_2$/MeOH/Et$_3$N, eluted with CH$_2$Cl$_2$ to 30% Solvent A/CH$_2$Cl$_2$ gradient) afforded title compound (210 mg, 25%). $^1$H NMR (300 MHz, DMSO-d$_6$) δ ppm 0.34-0.58 (m, 4H), 1.15 (s, 6H), 1.17-1.25 (m, 1H), 1.39 (s, 9H), 3.88 (s, 2H), 3.93 (s, 3H), 4.19 (d, J=7.14 Hz, 2H), 5.43 (s, 1H), 6.76 (s, 1H), 7.19 (d, J=8.33 Hz, 1H), 7.60 (dd, J=8.72, 1.98 Hz, 1H), 7.79 (d, J=2.38 Hz, 1H); MS (ESI$^+$) m/z 468 (M+H)$^+$, 466 (M−H)$^−$.

Example 72

N-{(2Z)-5,5-dimethyl-3-[(2R)-tetrahydrofuran-2-ylmethyl]-1,3-oxazolidin-2-ylidene}-2-{[(2S)-1-methylpyrrolidin-2-yl]methoxy}-5-(trifluoromethyl)benzamide

Example 72A (R)-5,5-dimethyl-3-((tetrahydrofuran-2-yl)methyl)oxazolidin-2-imine A mixture of Example 32A (0.6 g, 4.9 mmol), cesium carbonate (1.6 g, 4.9 mmol) and 2,2-dimethyloxirane (0.35 g, 4.9 mmol, Alfa-aesar) in 1,2-dimethoxyethane (20 mL) was heated to 80° C. overnight. The mixture was poured into water, and extracted with ethyl acetate (2×20 mL). The combined organic extracts were dried over Na$_2$SO$_4$, filtered, concentrated under reduced pressure to afford the title compound. LCMS (APCI$^+$) m/z 198 (M+H)$^+$.

Example 72B

N-{(2Z)-5,5-dimethyl-3-[(2R)-tetrahydrofuran-2-ylmethyl]-1,3-oxazolidin-2-ylidene}-2-{[(2S)-1-methylpyrrolidin-2-yl]methoxy}-5-(trifluoromethyl)benzamide The title compound was prepared as described in Example 33D, substituting Example 72A for Example 33C. $^1$H NMR (300 MHz, DMSO-d$_6$) δ ppm 1.31 (s, 3H), 1.32 (s, 3H), 1.48-1.75 (m, 4H), 1.76-2.03 (m, 4H), 2.18 (q, J=8.6 Hz, 1H), 2.34 (s, 3H), 2.52-2.62 (m, 1H), 2.93 (d, 1H), 3.25-3.37 (m, 1H), 3.41-3.46 (m, 1H), 3.47-3.57 (m, 2H), 3.66 (d, 1H), 3.77 (d, 1H), 3.91 (d, 1H), 4.05 (d, 2H), 7.21 (d, J=8.3 Hz, 1H), 7.59-7.76 (m, 2H); MS (ESI$^+$) m/z 484 (M+H)$^+$.

Example 73

N-{(2Z)-5-tert-butyl-3-[(2R)-tetrahydrofuran-2-ylmethyl]-1,3-oxazolidin-2-ylidene}-2-{[(2S)-1-methylpyrrolidin-2-yl]methoxy}-5-(trifluoromethyl)benzamide

Example 73A 5-tert-butyl-3-(((R)-tetrahydrofuran-2-yl)methyl)oxazolidin-2-imine The title compound was prepared as described in Example 72A, substituting 2-tert-butyloxirane (Aldrich) for 2,2-dimethyloxirane. LCMS (APCI$^+$) m/z 226 (M+H)$^+$.

Example 73B

N-{(2Z)-5-tert-butyl-3-[(2R)-tetrahydrofuran-2-ylmethyl]-1,3-oxazolidin-2-ylidene}-2-{[(2S)-1-methylpyrrolidin-2-yl]methoxy}-5-(trifluoromethyl)benzamide The title compound was prepared as described in Example 33D, substituting Example 73A for Example 33C. $^1$H NMR (300 MHz, DMSO-d$_6$) δ ppm 0.70 (s, 9H), 1.48-1.75 (m, 4H), 1.76-2.06 (m, 4H), 2.11-2.23 (m, 1H), 2.34 (s, 3H), 2.52-2.60 (m, 1H), 2.88-3.00 (m, 1H), 3.40-3.60 (m, 2H), 3.59-3.94 (m, 4H), 3.95-4.15 (m, 3H), 4.30-4.40 (m, 1H), 7.21 (d, J=8.8 Hz, 1H), 7.57 (d, J=2.4 Hz, 1H), 7.62-7.71 (m, J=8.6, 2.2 Hz, 1H); MS (ESI$^+$) m/z 512 (M+H)$^+$.

Example 74

N-[(2Z)-5-tert-butyl-3-[(2R)-tetrahydrofuran-2-ylmethyl]-1,3-oxazol-2(3H)-ylidene]-2-{[(2S)-1-methylazetidin-2-yl]methoxy}-5-(trifluoromethyl)benzamide A mixture of Example 2B (80 mg, 0.17 mmol), formaldehyde (54 mg, 0.67 mmol) and sodium triacetoxyhydroborate (141 mg, 0.665 mmol) in MeOH (10 mL) was stirred at room temperature for 12 hours. The reaction mixture was quenched with saturated aqueous NaHCO$_3$, and extracted with EtOAc (2×). The combined organic extracts were dried (MgSO$_4$), filtered, and concentrated. Purification by flash chromatography afforded 65 mg (79%) of the title compound. $^1$H NMR (400 MHz, chloroform-d) δ ppm 1.18 (s, 9H) 1.59-1.70 (m, J=7.67 Hz, 1H) 1.82-1.94 (m, J=9.21 Hz, 2H) 1.97-2.10 (m, 3H) 2.28-2.41 (m, 3H) 2.80 (s, 1H) 3.41 (s, 2H) 3.63 (dd, J=14.12, 7.36 Hz, 1H) 3.76-3.83 (m, 1H) 3.81-3.93 (m, 1H) 3.97-4.11 (m, 3H) 4.10-4.21 (m, 1H) 6.52 (s, 1H) 6.97 (d, J=8.59 Hz, 1H) 7.53 (d, J=2.46 Hz, 1H) 7.95 (d, J=2.15 Hz, 1H); MS (DCI/NH$_3$) m/z 496 (M+H)$^+$.

Example 75

N-[(2Z)-5-tert-butyl-3-(cyclobutylmethyl)-1,3-oxazol-2(3H)-ylidene]-2-{[(2S)-1-methylpyrrolidin-2-yl]methoxy}-5-(trifluoromethyl)benzamide

Example 75A 5-tert-butyl-3-(cyclobutylmethyl)oxazol-2(3H)-imine

To a mixture of cyanic bromide (2.7 g, 25.8 mmol) and anhydrous sodium carbonate (7.5 g, 70.5 mmol) in dichloromethane (20 mL) cooled between −20 to −10° C. was added a solution of cyclobutylmethanamine in dichloromethane (30 mL) dropwise. Stirring was continued for an additional 1.5 hours at −20 to −10° C. The mixture was filtered and concentrated to provide 0.4 g of N-(cyclobutylmethyl)cyanamide.

A mixture of N-(cyclobutylmethyl)cyanamide (0.40 g, 3.6 mmol), cesium carbonate (2.4 g, 7.3 mmol) and 1-bromo-3,3-dimethylbutan-2-one (0.50 mL, 3.6 mmol, Aldrich) in 1,2-dimethoxyethane (20 mL) was heated to 80° C. overnight. The mixture was poured into water, and extracted with ethyl acetate (2×20 mL). The combined organic extracts were dried over Na$_2$SO$_4$, filtered, concentrated under reduced pressure to provide the title compound (0.6 g). LCMS (APCI$^+$) m/z 209 (M+H)$^+$.

Example 75B

N-[(2Z)-5-tert-butyl-3-(cyclobutylmethyl)-1,3-oxazol-2(3H)-ylidene]-2-{[(2S)-1-methylpyrrolidin-2-yl]methoxy}-5-(trifluoromethyl)benzamide The title compound was prepared as described in Example 33D, substituting Example 75A for Example 33C. $^1$H NMR (300 MHz, DMSO-d$_6$) δ ppm 1.10 (s, 9H), 1.10 (s, 2H), 1.53-1.89 (m, 4H), 1.91 (s, 3H), 1.93-2.08 (m, 2H), 2.23-2.47 (m, 2H), 2.65-2.82 (m, 1H), 2.89-3.11 (m, 1H), 3.74 (d, J=7.5 Hz, 2H), 3.88-4.20 (m, 4H), 7.10 (s, 1H), 7.24 (d, J=8.3 Hz, 1H), 7.64-7.77 (m, 2H); MS (ESL) m/z 494 (M+H)$^+$.

Example 76

N-[(2Z)-3-butyl-5-tert-butyl-1,3-oxazol-2(3H)-ylidene]-2-{[(2S)-1-methylpyrrolidin-2-yl]methoxy}-5-(trifluoromethyl)benzamide

Example 76A 5-tert-butyl-3-butyloxazol-2(3H)-imine

The titled compound was prepared as described in example 75A, substituting butan-1-amine for cyclobutylmethanamine. LCMS (APCI$^+$) m/z 197 (M+H)$^+$.

Example 76B

N-[(2Z)-3-butyl-5-tert-butyl-1,3-oxazol-2(3H)-ylidene]-2-{[(2S)-1-methylpyrrolidin-2-yl]methoxy}-5-(trifluoromethyl)benzamide The title compound was prepared as described in Example 33D, substituting Example 76A for Example 33C. $^1$H NMR (300 MHz, DMSO-d$_6$) δ ppm 0.90 (t, J=7.3 Hz, 3H), 1.09 (s, 9H), 1.19-1.37 (m, 2H), 1.43-1.76 (m, 5H), 1.78-1.94 (m, 1H), 2.10-2.22 (m, 1H), 2.30 (s, 3H), 2.85-3.00 (m, 1H), 3.33-3.44 (m, 1H), 3.69 (t, J=7.3 Hz, 2H), 3.84-3.94 (m, 1H), 3.95-4.04 (m, 1H), 7.13 (s, 1H), 7.22 (d, J=9.1 Hz, 1H), 7.59-7.71 (m, 2H); MS (ESI$^+$) m/z 482 (M+H)$^+$.

Example 77

N-[(2Z)-5-tert-butyl-3-[(2R)-tetrahydrofuran-2-ylmethyl]-oxazol-2(3H)-ylidene]-2-(2-pyrrolidin-1-ylethoxy)-5-(trifluoromethyl)benzamide The title compound was prepared as described in Example 32D, substituting tert-butyl 2-(pyrrolidin-1-yl)ethanol for (S)-(1-methylpyrrolidin-2-yl)methanol. $^1$H NMR (400 MHz, chloroform-d) δ ppm 1.18 (s, 9H) 1.58-1.71 (m, 1H) 1.72-1.81 (m, 4H) 1.82-1.96 (m, 2H) 1.96-2.19 (m, 1H) 2.53-2.70 (m, 4H) 2.90 (t, J=6.44 Hz, 2H) 3.64 (dd, J=14.27, 7.52 Hz, 1H) 3.73-3.92 (m, 2H) 4.06 (dd, J=14.12, 2.76 Hz, 1H) 4.11-4.25 (m, 3H) 6.52 (s, 1H) 6.97 (d, J=8.59 Hz, 1H) 7.55 (dd, J=8.59, 2.45 Hz, 1H) 7.96 (d, J=2.15 Hz, 1H); MS (ESI$^+$) m/z 510 (M+H)$^+$.

Example 78

2-[2-(acetylamino)ethoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was prepared as described in Example 1F substituting N-(2-hydroxyethyl)acetamide for then (R)-(tetrahydrofuran-2-yl)methanol. $^1$H NMR (500 MHz, chloroform-d) δ ppm 1.44 (s, 9H) 1.72-1.83 (m, 1H) 1.84-1.93 (m, 1H) 2.07 (s, 3H) 3.43 (d, J=4.88 Hz, 1H) 3.63 (q, J=4.88 Hz, 2H) 3.74 (d, J=5.80 Hz, 2H) 3.79 (t, J=6.87 Hz, 1H) 3.91 (s, 3H) 4.14-4.41 (m, 4H) 4.56 (dd, J=15.26, 2.75 Hz, 1H) 6.96-7.12 (m, 2H) 7.54 (dd, J=8.85, 2.14 Hz, 1H) 8.09 (d, J=2.14 Hz, 1H) 8.96-9.12 (m, 1H); MS (DCI/NH$_3$) m/z 511 (M+H)$^+$.

Example 79

N-{(3E)-5-tert-butyl-1-methyl-2-[(2R)-tetrahydrofuran-2-ylmethyl]-1,2-dihydro-3H-pyrazol-3-ylidene}-2-({(2E)-2-[(tetrahydro-2H-pyran-2-yloxy)imino]propyl}oxy)-5-(trifluoromethyl)benzamide

Example 79A (2E)-1-hydroxyacetone O-tetrahydro-2H-pyran-2-yloxime

To a solution of 1-hydroxypropan-2-one (1 g, 13.5 mmol) and O-(tetrahydro-2H-pyran-2-yl)hydroxylamine (1.9 g, 16.2 mmol) in pyridine (7 mL) and methanol (20 mL) was added acetic acid (0.23 mL, 4 mmol) and the resulting mixture was stirred at room temperature for 12 hours. The mixture was then concentrated under reduced pressure and the residue was treated with a saturated solution of $NaHCO_3$ and extracted with ethyl acetate. The organic layer was washed with brine, dried with $MgSO_4$ and concentrated under reduced pressure. The residue was purified by chromatography (EtOAc-Hexanes 2:1) to afford 1.8 g of the title compound. MS (DCI/$NH_3$) m/z 174 (M+H)$^+$.

Example 79B

N-{(3E)-5-tert-butyl-1-methyl-2-[(2R)-tetrahydrofuran-2-ylmethyl]-1,2-dihydro-3H-pyrazol-3-ylidene}-2-({(2E)-2-[(tetrahydro-2H-pyran-2-yloxy)imino]propyl}oxy)-5-(trifluoromethyl)benzamide Example 79A (186 mg, 2 mmol), N-{(3E)-5-tert-butyl-1-methyl-2-[(2R)-tetrahydrofuran-2-ylmethyl]-1,2-dihydro-3H-pyrazol-3-ylidene}-2-fluoro-5-(trifluoromethyl)benzamide (Example 1E, 230 mg, 1 mmol) and a 1N solution of potassium tert-butoxide in THF (1.5 mL, 1.5 mmol) were combined in THF (15 mL) and the mixture was stirred at 50° C. for 16 hours. The mixture was then concentrated under reduced pressure and the residue partitioned between EtOAc and water. The organic layer was washed with brine, dried with $MgSO_4$ and concentrated under reduced pressure. The residue was purified by chromatography ($CH_2Cl_2$-MeOH 9:1) to afford 300 mg of the title compound. $^1$H NMR (300 MHz, DMSO-$d_6$) δ ppm 1.40 (s, 9H), 1.47-1.90 (m, 10H), 1.99 (s, 3H), 3.55-3.80 (m, 4H), 3.85-3.95 (m, J=6.3 Hz, 3H), 4.27-4.41 (m, 1H), 4.68 (s, 2H), 4.68 (s, 2H), 5.12-5.23 (m, 1H), 6.82 (s, 1H), 7.24 (d, J=11.9 Hz, 1H), 7.60 (s, 1H), 7.74 (s, 1H); MS (DCI/$NH_3$) m/z 581 (M+H)$^+$.

Example 80

N-{(3E)-5-tert-butyl-1-methyl-2-[(2R)-tetrahydrofuran-2-ylmethyl]-1,2-dihydro-3H-pyrazol-3-ylidene}-2-(tetrahydro-2H-thiopyran-4-ylmethoxy)-5-(trifluoromethyl)benzamide A solution of potassium tert-butoxide (2.3 mL, 1 M in THF) was added to a solution (tetrahydro-2H-thiopyran-4-yl)methanol (0.33 g, 2.5 mmol) in THF (0.5 mL) and stirred for 10 minutes. A solution of Example 1E (0.5 g, 1.2 mmol) in THF (2.0 mL) was added and the mixture stirred at ambient temperature for 2 hours. The reaction mixture was partitioned between EtOAc (15 mL) and saturated $NaHCO_3$ (1 mL). The organic extract was washed with water and brine, dried with $MgSO_4$, filtered and concentrated. The residue was purified by chromatography ($SiO_2$, solvent A=hexanes, solvent B=hexane:EtOAc:$Et_3$N (1:3:0.2), gradient of 100% solvent A to 100% solvent B over 600 mL then isocratic for 180 mL) to afford the title compound (0.45 g, 0.83 mmol, 71% yield). $^1$H NMR (300 MHz, DMSO-$d_6$) δ ppm 1.24-1.45 (m, 1H), 1.38 (s, 9H), 1.64-1.74 (m, 2H), 1.74-1.90 (m, 3H), 2.04-2.14 (m, 2H), 2.53-2.69 (m, 2H), 2.59 (s, 3H), 3.57-3.67 (m, 1H), 3.69-3.79 (m, 1H), 3.84-3.91 (m, 2H), 3.87 (s, 3H), 4.08-4.20 (m, 1H), 4.32 (dd, J=5.2, 2.0 Hz, 2H), 6.76 (s, 1H), 7.13 (d, J=8.7 Hz, 1H), 7.56 (dd, J=8.7, 2.4 Hz, 1H), 7.67 (d, J=2.4 Hz, 1H); MS (DCI/$NH_3$) m/z 540.3 (M+H)$^+$.

Example 81

N-[(3E)-2-butyl-5-tert-butyl-1-methyl-1,2-dihydro-3H-pyrazol-3-ylidene]-2-(2-hydroxy-2-methylpropoxy)-5-(trifluoromethyl)benzamide

Example 81A 3-tert-butyl-1-butyl-1H-pyrazol-5-amine

A mixture of butylhydrazine oxalate (10 g, 56.1 mmol) and 4,4-dimethyl-3-oxopentanenitrile (7.0 g, 56.1 mmol) in ethanol (100 mL) was warmed to 85° C. and stirred for 3 hours. The mixture was cooled to ambient temperature, concentrated under reduced pressure and the residue was partitioned between $CH_2Cl_2$ (100 mL) and saturated aqueous $NaHCO_3$ (100 mL). The layers were separated and the aqueous phase was extracted with $CH_2Cl_2$ (3×15 mL). The combined organic extracts were dried over $Na_2SO_4$, filtered, and concentrated under reduced pressure to provide the title compound (10 g, 51.2 mmol, 91% yield). MS (DCI/$NH_3$) m/z 196 (M+H)$^+$.

Example 81B

N-(1-butyl-3-tert-butyl-1H-pyrazol-5-yl)-2-fluoro-5-(trifluoromethyl)benzamide

To a solution of Example 81A (30.3 g, 155 mmol) and $Et_3$N (64.9 mL, 465 mmol) in THF (500 mL) at ambient temperature was added 2-fluoro-5-(trifluoromethyl)benzoyl chloride (23.5 mL, 155 mmol) dropwise over 30 minutes via syringe pump. The mixture was stirred at ambient temperature for 1 hour then diluted with saturated aqueous $NaHCO_3$ (100 mL) and extracted with EtOAc (200 mL). The layers were separated and the aqueous phase was extracted with EtOAc (3×20 mL). The combined organic extracts were dried over anhydrous $Na_2SO_4$, filtered, and concentrated under reduced pressure. Purification of the residue by column chromatography ($SiO_2$, 50% hexanes/EtOAc) provided the title compound (50.3 g, 130 mmol, 84% yield). MS (ESI$^+$) m/z 386 (M+H)$^+$.

Example 81C

N-[(3E)-2-butyl-5-tert-butyl-1-methyl-1,2-dihydro-3H-pyrazol-3-ylidene]-2-fluoro-5-(trifluoromethyl)benzamide To a solution of Example 81B (50.2 g, 130 mmol) in toluene (500 mL) was added methyl trifluoromethanesulfonate (21.4 mL, 195 mmol). The mixture was warmed to 100° C. and stirred for 20 hours. The mixture was cooled to ambient temperature then diluted with water (200 mL) and acetone (500 mL). This solution was stirred for 30 minutes then concentrated $NH_4$OH (100 mL) was added. The mixture was stirred for 30 minutes then partially concentrated under reduced pressure. The residue was diluted with EtOAc (300 mL) and brine (100 mL), the layers were separated and the aqueous phase was extracted with EtOAc (3×30 mL). The combined organic extracts were dried over anhydrous Na$_2$SO$_4$, filtered, and concentrated under reduced pressure. The residue was purified by column chromatography (SiO$_2$, 80% hexanes/EtOAc to 100% EtOAc to 10% MeOH in EtOAc) and the fractions collected and concentrated. The material was then dissolved in EtOAc (150 mL) and was washed with 10% NaOH (100 mL). The layers were separated, the aqueous phase was extracted with EtOAc (3×50 mL) and the combined organic extracts were dried over anhydrous Na$_2$SO$_4$, filtered and concentrated under reduced pressure to give (46.3 g, 116 mmol, 89% yield) the title compound. MS (ESI$^+$) m/z 400 (M+H)$^+$.

Example 81D 2-methylpropane-1,2-diol

To a mixture of 2-benzyloxy-2-methyl-1-propanol (Manchester Organics, 15 g, 83 mmol) in MeOH (200 mL) was added 20% Pd(OH)$_2$—C, wet (3.0 g, 21.4 mmol) in a 500 mL stainless steel pressure bottle. The mixture was stirred for 70 minutes at ambient temperature under 30 psi of H$_2$. The mixture was filtered through a nylon membrane, concentrated under reduced pressure and the residue was diluted with Et$_2$O. This material was dried over anhydrous Na$_2$SO$_4$, filtered, and concentrated under reduced pressure to give the title compound (7.4 g, 82 mmol, 99% yield). MS (DCI/NH$_3$) m/z 108 (M+NH$_4$)$^+$.

Example 81E

N-[(3E)-2-butyl-5-tert-butyl-1-methyl-1,2-dihydro-3H-pyrazol-3-ylidene]-2-(2-hydroxy-2-methylpropoxy)-5-(trifluoromethyl)benzamide To a solution of Example 81D (7.6 g, 84 mmol) in THF (300 mL) at 0° C. was added potassium tert-butoxide (18.9 g, 168 mmol). The ice bath was removed and the mixture was stirred for 45 min then a solution of Example 81C (22.4 g, 56.1 mmol) in THF (100 mL) was added. The mixture was stirred for 2 hours at ambient temperature then partitioned between saturated aqueous NaHCO$_3$ (100 mL) and EtOAc (100 mL). The layers were separated and the aqueous phase was extracted with EtOAc (3×20 mL). The combined organic extracts were dried over anhydrous Na$_2$SO$_4$, filtered, and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (15 g, 31.9 mmol, 57% yield). $^1$H NMR (300 MHz, CDCl$_3$) δ ppm 0.95 (t, J=7.3 Hz, 3H) 1.28 (s, 6H) 1.32-1.42 (m, 2H) 1.42 (s, 9H) 1.61-1.72 (m, 2H) 3.75 (s, 3H) 4.03 (s, 2H) 4.27 (dd, J=7.8 Hz, 2H) 6.16 (s, 1H) 7.00 (d, J=8.5 Hz, 1H) 6.99 (s, 1H) 7.51 (dd, J=8.6, 1.9 Hz, 1H) 8.13 (d, J=2.4 Hz, 1H); MS (DCI/NH$_3$) m/z 470 (M+H)$^+$; Anal. calculated for C$_{24}$H$_{34}$F$_3$N$_3$O$_3$: Calc: C, 61.39; H, 7.30; N, 8.95. Found: C, 61.33; H, 7.38; N, 8.91.

Example 82

N-{(3E)-5-tert-butyl-1-methyl-2-[(2R)-tetrahydrofuran-2-ylmethyl]-1,2-dihydro-3H-pyrazol-3-ylidene}-2-[4-(methylthio butoxy]-5-(trifluoromethyl)benzamide The title compound was prepared as described in Example 80, substituting 4-(methylthio)butan-1-ol for (tetrahydro-2H-thiopyran-4-yl)methanol (0.18 g, 0.34 mmol, 73% yield). $^1$H NMR (500 MHz, Pyridine-d$_5$) δ ppm 1.18 (s, 9H), 1.54-1.62 (m, 2H), 1.64-1.72 (m, 1H), 1.75-1.83 (m, 1H), 1.83-1.92 (m, 4H), 2.01 (s, 3H), 2.49 (t, J=7.0 Hz, 2H), 3.55-3.61 (m, 1H), 3.69-3.75 (m, 1H), 3.80 (s, 3H), 4.10 (t, J=6.0 Hz, 2H), 4.24 (qd, J=6.7, 3.4 Hz, 1H), 4.38 (dd, J=15.1, 6.6 Hz, 1H), 4.61 (dd, J=15.1, 3.2 Hz, 1H), 7.12 (d, J=8.5 Hz, 1H), 7.48 (s, 1H), 7.64 (dd, J=8.5, 2.1 Hz, 1H), 8.45 (d, J=2.1 Hz, 1H); MS (DCI/NH$_3$) m/z 528.3 (M+H)$^+$.

Example 83

N-{(3E)-5-tert-butyl-1-methyl-2-[(2R)-tetrahydrofuran-2-ylmethyl]-1,2-dihydro-3H-pyrazol-3-ylidene}-2-[4-(methylsulfonyl)butoxy]-5-(trifluoromethyl)benzamide To a solution of Example 82 (0.15 g, 0.28 mmol) in dichloromethane (5 mL) was added 3-chlorobenzoperoxoic acid (0.16 g, 77% hydrate, 0.7 mmol) in portions. The mixture was stirred at ambient temperature for 90 minutes then partitioned between EtOAc (50 mL) and 1% Na$_2$S$_2$O$_3$ (10 mL). The organic extract was washed with 10% aqueous NaHCO$_3$ and brine, dried with MgSO$_4$, filtered and concentrated. The residue was purified by chromatography (SiO$_2$, solvent A=hexanes:EtOAc:Et$_3$N (1:3:0.2), solvent B=hexanes: EtOAc:MeOH:Et$_3$N (1:3:1:0.2), gradient from 100% solvent A to 100% solvent B over 600 mL then isocratic for 180 mL) to afford the title compound (0.1 g, 0.18 mmol, 63% yield). $^1$H NMR (500 MHz, Pyridine-d$_5$) δ ppm 1.23 (s, 9H), 1.53-1.60 (m, 2H), 1.63-1.70 (m, 1H), 1.73-1.81 (m, 1H), 1.85-1.91 (m, 2H), 2.22-2.29 (m, 2H), 3.23 (s, 3H), 3.55-3.61 (m, 3H), 3.68-3.74 (m, 1H), 3.83 (s, 3H), 4.06 (t, J=5.8 Hz, 2H), 4.23 (qd, J=6.8, 3.2 Hz, 1H), 4.39 (dd, J=15.1, 6.6 Hz, 1H), 4.62 (dd, J=15.1, 3.2 Hz, 1H), 7.06 (d, J=8.5 Hz, 1H), 7.48 (s, 1H), 7.63 (dd, J=8.7, 2.3 Hz, 1H), 8.47 (d, J=2.4 Hz, 1H); MS (DCI/NH$_3$) m/z 560.3 (M+H)$^+$; Anal. calculated for C$_{26}$H$_{36}$F$_3$N$_3$O$_5$S: C, 55.80; H, 6.48; N, 7.51. Found: C, 55.74; H, 6.46; N, 7.39.

Example 84

N-[(2Z)-3-butyl-5-tert-butyl-1,3,4-thiadiazol-2(3H)-ylidene]-2-(2-hydroxy-2-methylpropoxy)-5-(trifluoromethyl)benzamide To a solution of Example 81D (114 mg, 1.26 mmol) in 3 mL of THF was added sodium hydride (44.6 mg, 1.12 mmol). The mixture was stirred for 10 min at room temperature and then cooled to 5° C. Example 7B (300 mg, 0.74 mmol) was added and the mixture was stirred for 2 hours. The reaction mixture was diluted with ether and washed with brine. The aqueous phase was extracted with ether (2×20 mL) and the combined organic extracts were dried over MgSO$_4$, filtered and concentrated under educed pressure. Purification by chromatography on SiO$_2$ using an Analogix® Intelliflash280™ (Hexanes-EtOAc, 0-30% gradient) afforded the title compound. $^1$H NMR (300 MHz, CDCl$_3$) δ ppm 0.99 (t, J=7.3 Hz, 3H), 1.35 (s, 6H), 1.38-1.45 (m, 2H), 1.41 (s, 9H), 1.82-1.96 (m, 2H), 4.02 (s, 2H), 4.40 (t, J=7.3 Hz, 2H), 5.00 (s, 1H), 7.05 (d, J=8.7 Hz, 1H), 7.65 (dd, J=8.3, 2.0 Hz, 1H), 8.37 (d, J=2.4 Hz, 1H); MS (ESI$^+$) m/z 474 (M+H)$^+$.

Example 85

N-[(2Z)-5-tert-butyl-3-(3-cyanopropyl)-1,3,4-thiadiazol-2(3H)-ylidene]-2-(3-cyanopropoxy)-5-(trifluoromethyl)benzamide A mixture of Example 7A (400 mg, 1.15 mmol), potassium carbonate (318 mg, 2.30 mmol) and 4-bromobutanenitrile (170 mg, 1.15 mmol) in toluene (8 mL) and dioxane 2 mL was treated with tetrabutylammonium hydrogensulfate (2.74 mg, 8.06 µmol), tetrabutylammonium iodide (2.98 mg, 8.06 µmol) and tetraethylammonium iodide (296 mg, 1.15 mmol) and the resulting mixture was warmed to reflux for 24 hours. After cooling to ambient temperature the mixture was washed with water and brine. The organic extract was dried with $MgSO_4$, filtered, and concentrated under reduced pressure. The residue was purified by chromatography on $SiO_2$ using an Analogix® Intelliflash280™ (Hexanes-EtOAc, 0-30% gradient) to give the title compound. $^1H$ NMR (300 MHz, $CDCl_3$) δ ppm 1.44 (s, 9H), 2.15-2.27 (m, 2H), 2.32 (q, J=6.6 Hz, 2H), 2.48 (t, J=6.6 Hz, 2H), 2.75 (t, J=7.1 Hz, 2H), 4.23 (t, J=5.8 Hz, 2H), 4.54 (t, J=6.4 Hz, 2H), 7.04 (d, J=8.5 Hz, 1H), 7.67 (dd, J=8.3, 2.2 Hz, 1H), 8.29 (d, J=2.4 Hz, 1H); MS ($ESI^+$) m/z 480 $(M+H)^+$.

Example 86

N-[(3E)-5-tert-butyl-2-(cyclobutylmethyl)-1-methyl-1,2-dihydro-3H-pyrazol-3-ylidene]-2-(2-hydroxy-2-methylpropoxy)-5-(trifluoromethyl)benzamide

Example 86A cyclobutylmethyl 4-methylbenzenesulfonate

To a solution of cyclobutylmethanol (25 g, 290 mmol) in $CH_2Cl_2$ (200 mL) and pyridine (100 mL) was added 4-(dimethylamino)pyridine (1.8 g, 14.5 mmol) followed by p-toluenesulfonyl chloride (55.3 g, 290 mmol). The mixture was allowed to stir at ambient temperature for 20 hours then quenched with 5% aqueous HCl (30 mL). The layers were separated and the aqueous phase was extracted with $CH_2Cl_2$ (3×15 mL). The combined organic extracts were dried over $Na_2SO_4$, filtered and concentrated under reduced pressure. Purification by column chromatography ($SiO_2$, 75% hexanes in EtOAc) afforded the title compound (50.8 g, 211 mmol, 73% yield). MS ($DCI/NH_3$) m/z 258 $(M+NH_4)^+$.

Example 86B 3-tert-butyl-1-(cyclobutylmethyl)-1H-pyrazol-5-amine

To a solution of Example 86A (50.8 g, 211 mmol) in EtOH (300 mL) was added hydrazine hydrate (15.4 mL, 317 mmol). The mixture was warmed to reflux (85° C.) and was allowed to stir for 20 hours. The mixture was cooled to ambient temperature then 4,4-dimethyl-3-oxopentanenitrile (39.6 g, 317 mmol) was added and the mixture was again warmed to reflux (85° C.) and was allowed to stir for 5 hours. After cooling to ambient temperature, the mixture was concentrated under reduced pressure, and the residue was portioned between $CH_2Cl_2$ (100 mL) and saturated aqueous $NaHCO_3$ (100 mL). The layers were separated and the aqueous phase was extracted with $CH_2Cl_2$ (3×15 mL). The combined organic extracts were dried over $Na_2SO_4$, filtered and concentrated under reduced pressure. Purification by column chromatography ($SiO_2$, 20% hexanes/EtOAc) provided the title compound (21.2 g, 102 mmol, 49% yield). MS (DCI/$NH_3$) m/z 208 $(M+H)^+$.

Example 86C

N-[3-tert-butyl-1-(cyclobutylmethyl)-1H-pyrazol-5-yl]-2-fluoro-5-(trifluoromethyl)benzamide To a solution of Example 86B (0.82 g, 3.9 mmol) and $Et_3N$ (1.6 mL, 11.8 mmol) in THF (10 mL) at ambient temperature was added 2-fluoro-5-(trifluoromethyl)benzoyl chloride (0.60 mL, 3.9 mmol) dropwise over 1 min. The mixture was stirred at ambient temperature for 2 h then was quenched with saturated aqueous $NaHCO_3$ (10 mL) and diluted with EtOAc (10 mL). The layers were separated and the aqueous phase was extracted with EtOAc (3×5 mL). The combined organic extracts were dried over anhydrous $Na_2SO_4$, filtered, and concentrated under reduced pressure. Purification by column chromatography ($SiO_2$, 60% hexanes/EtOAc) provided the title compound (1.15 g, 2.9 mmol, 74% yield). MS (DCI/$NH_3$) m/z 398 $(M+H)^+$.

Example 86D

N-[(3E)-5-tert-butyl-2-(cyclobutylmethyl)-1-methyl-1,2-dihydro-3H-pyrazol-3-ylidene]-2-fluoro-5-(trifluoromethyl)benzamide A mixture of Example 86C (1.1 g, 2.9 mmol) and dimethyl sulfate (0.82 mL, 8.6 mmol) in toluene (4 mL) was warmed to 90° C. and stirred for 48 hours. After cooling to ambient temperature, the mixture was concentrated under reduced pressure and the residue was purified by column chromatography ($SiO_2$, 50% hexanes/EtOAc to 100% EtOAc to 9:1:0.1 EtOAc:MeOH:$Et_3N$) to afford the title compound (0.80 g, 1.9 mmol, 68% yield). MS (DCI/$NH_3$) m/z 412 $(M+H)^+$.

Example 86E

N-[(3E)-5-tert-butyl-2-(cyclobutylmethyl)-1-methyl-1,2-dihydro-3H-pyrazol-3-ylidene]-2-(2-hydroxy-2-methylpropoxy)-5-(trifluoromethyl)benzamide To a solution of Example 81D (0.10 g, 1.1 mmol) in THF (5 mL) at ambient temperature was added potassium tert-butoxide (0.25 g, 2.2 mmol). The mixture was stirred for 15 min at ambient temperature then a solution of Example 86D (0.30 g, 0.73 mmol) in THF (5 mL) was added via cannula. The mixture was stirred at ambient temperature for 16 hours then partitioned between saturated aqueous $NaHCO_3$ (10 mL) and EtOAc (20 mL). The layers were separated and the aqueous phase was extracted with EtOAc (3×10 mL). The combined organic extracts were dried over anhydrous $Na_2SO_4$, filtered and concentrated under reduced pressure. Purification by column chromatography ($SiO_2$, 50% hexanes/EtOAc then 100% EtOAc then 9:1:0.1 EtOAc:MeOH:$Et_3N$) afforded the title compound (0.19 g, 0.40 mmol, 54% yield). $^1H$ NMR (300 MHz, $CDCl_3$) δ ppm 1.29 (s, 6H) 1.41 (s, 9H) 1.81-1.96 (m, 4H) 1.98-2.09 (m, 2H) 2.58-2.72 (m, 1H) 3.72 (s, 3H) 4.03 (s, 2H) 4.34 (d, J=7.1 Hz, 2H) 7.00 (d, J=8.5 Hz, 1H) 7.00 (s, 1H) 7.52 (dd, J=8.3, 2.2 Hz, 1H) 8.15 (d, J=2.4 Hz, 1H); MS (DCI/$NH_3$) m/z 482 $(M+H)^+$; Anal. calculated for $C_{25}H_{34}F_3N_3O_3$: Calc: C, 62.35; H, 7.12; N, 8.73. Found: C, 62.39; H, 7.12; N, 8.59.

Example 87

N-[(3E)-5-tert-butyl-1-methyl-2-(3,3,3-trifluoropropyl)-1,2-dihydro-3H-pyrazol-3-ylidene]-2-(2-hydroxy-2-methylpropoxy)-5-(trifluoromethyl)benzamide

Example 87A 3,3,3-trifluoropropyl 4-methylbenzenesulfonate

To a solution of 3,3,3-trifluoropropan-1-ol (5.0 g, 43.8 mmol) in $CH_2Cl_2$ (25 mL) and pyridine (25 mL) was added 4-(dimethylamino)pyridine (0.27 g, 2.2 mmol) followed by p-toluenesulfonyl chloride (8.4 g, 43.8 mmol). The mixture was allowed to stir at ambient temperature for 72 h then was quenched with 5% aqueous HCl (20 mL). The layers were separated and the aqueous phase was extracted with $CH_2Cl_2$ (3×7 mL). The combined organic extracts were dried over $Na_2SO_4$, filtered, and concentrated under reduced pressure. Purification by column chromatography ($SiO_2$, 75% hexanes in EtOAc) afforded the title compound (8.0 g, 29.8 mmol, 68% yield). MS (DCI/$NH_3$) m/z 286 (M+$NH_4$)$^+$.

Example 87B 3-tert-butyl-1-(3,3,3-trifluoropropyl)-1H-pyrazol-5-amine

To a solution of Example 87A (8.0 g, 29.8 mmol) in EtOH (75 mL) was added hydrazine hydrate (3.92 mL, 81 mmol). The mixture was warmed to reflux (85° C.) and stirred for 20 hours. The mixture was cooled to ambient temperature then 4,4-dimethyl-3-oxopentanenitrile (10.1 g, 81 mmol) was added and the mixture was again warmed to reflux (85° C.) and stirred for an additional 4 hours. The mixture was concentrated under reduced pressure and the residue was dissolved in $CH_2Cl_2$ (30 mL) and saturated aqueous $NaHCO_3$ (20 mL) was added slowly. The layers were separated and the aqueous phase was extracted with $CH_2Cl_2$ (3×10 mL). The combined organic extracts were dried over $Na_2SO_4$, filtered and concentrated under reduced pressure to provide title compound (7.01 g, 29.8 mmol, 100% yield). MS (DCI/$NH_3$) m/z 236 (M+H)$^+$.

Example 87C

N-[3-tert-butyl-1-(3,3,3-trifluoropropyl)-1H-pyrazol-5-yl]-2-fluoro-5-(trifluoromethyl)benzamide To a solution of Example 87B (7.01 g, 29.8 mmol) and $Et_3N$ (12.5 mL, 89 mmol) in THF (30 mL) at ambient temperature was added 2-fluoro-5-(trifluoromethyl)benzoyl chloride (4.5 mL, 29.8 mmol) dropwise over 1 min. The mixture was stirred at ambient temperature for 2 hours then was partitioned between saturated aqueous $NaHCO_3$ (10 mL) and EtOAc (10 mL). The layers were separated and the aqueous phase was extracted with EtOAc (3×5 mL). The combined organic extracts were dried over anhydrous $Na_2SO_4$, filtered, and concentrated under reduced pressure. Purification by column chromatography ($SiO_2$, 70% hexanes/EtOAc) provided the title compound (6.2 g, 14.5 mmol, 49% yield). MS (DCI/$NH_3$) m/z 426 (M+H)$^+$.

Example 87D

N-[(3E)-5-tert-butyl-1-methyl-2-(3,3,3-trifluoropropyl)-1,2-dihydro-3H-pyrazol-3-ylidene]-2-fluoro-5-(trifluoromethyl)benzamide A mixture of Example 87C (6.2 g, 14.5 mmol) and dimethyl sulfate (4.14 mL, 43.4 mmol) in toluene (20 mL) was warmed to 90° C. for 48 hours. After cooling to ambient temperature, the mixture was concentrated under reduced pressure and the residue purified by column chromatography ($SiO_2$, 50% hexanes/EtOAc to 100% EtOAc to 9:1:0.1 EtOAc:MeOH:$Et_3N$) to afford the title compound (3.5 g, 7.9 mmol, 54% yield). MS (DCI/$NH_3$) m/z 440 (M+H)$^+$.

Example 87E

N-[(3E)-5-tert-butyl-1-methyl-2-(3,3,3-trifluoropropyl)-1,2-dihydro-3H-pyrazol-3-ylidene]-2-(2-hydroxy-2-methylpropoxy)-5-(trifluoromethyl)benzamide To a solution of Example 81D (0.21 g, 2.3 mmol) and Example 87D (0.51 g, 1.2 mmol) in THF (10 mL) at ambient temperature was added potassium tert-butoxide (0.39 g, 3.5 mmol). The mixture was stirred at ambient temperature for 2 hours then partitioned between saturated aqueous $NaHCO_3$ (5 mL) and EtOAc (5 mL). The layers were separated and the aqueous phase was extracted with EtOAc (3×5 mL). The combined organic extracts were dried over $Na_2SO_4$, filtered, and concentrated under reduced pressure. Purification by column chromatography ($SiO_2$, 50% hexanes/EtOAc to 100% EtOAc to 9:1:0.1 EtOAc:MeOH:$Et_3N$) afforded the title compound (0.080 g, 0.16 mmol, 14% yield). $^1$H NMR (300 MHz, $CDCl_3$) δ ppm 1.29 (s, 6H) 1.42 (s, 9H) 2.53-2.71 (m, 2H) 3.75 (s, 3H) 4.03 (s, 2H) 4.48 (t, J=7.0 Hz, 2H) 7.01 (d, J=8.8 Hz, 1H) 7.01 (s, 1H) 7.54 (dd, J=8.5, 2.0 Hz, 1H) 8.12 (d, J=2.4 Hz, 1H); MS (DCI/$NH_3$) m/z 510 (M+H)$^+$; Anal. calculated for $C_{23}H_{29}F_6N_3O_3$: Calc: C, 54.22; H, 5.74; N, 8.25. Found: C, 54.02; H, 5.52; N, 8.33.

Example 88

N-{(3E)-5-tert-butyl-1-methyl-2-[(2R)-tetrahydrofuran-2-ylmethyl]-1,2-dihydro-3H-pyrazol-3-ylidene}-2-[(2S)-piperidin-2-ylmethoxy]-5-(trifluoromethyl)benzamide A solution of potassium tert-butoxide (0.94 mL, 1 M in THF) was added to a solution of (S)-tert-butyl 2-(hydroxymethyl)piperidine-1-carboxylate (0.2 g, 0.98 mmol) in THF (0.5 mL). The mixture was stirred at ambient temperature for 10 minutes then a solution of Example 1E (0.2 g, 0.47 mmol) in THF (1.0 mL). After stirring for 2 hours, the mixture was concentrated and the residue purified by chromatography ($SiO_2$, solvent A=hexane:EtOAc:$Et_3N$ (1:3:0.2), solvent B=hexane:EtOAc:MeOH:$Et_3N$ (1:3:2:0.2), gradient from 100% solvent A to 100% solvent B over 300 mL then isocratic for 300 mL). Fractions with m/z=523 were pooled and concentrated and the residue purified by reverse phase chromatography (water/trifluoroacetic acid (0.1%) and acetonitrile) to afford the title compound as the bis-trifluoracetate salt (35 mg, 0.067 mmol, 14% yield). $^1$H NMR (500 MHz, Pyridine-d$_5$) δ ppm 1.19 (s, 9H), 1.21-1.29 (m, 1H), 1.29-1.39 (m, 1H), 1.41-1.55 (m, 2H), 1.54-1.62 (m, 3H), 1.63-1.71 (m, 2H), 1.75-1.83 (m, 1H), 2.57-2.66 (m, 1H), 3.08-3.17 (m, 2H), 3.54-3.61 (m, 1H), 3.69-3.76 (m, 1H), 3.82 (s, 3H), 4.09 (t, J=9.0 Hz, 1H), 4.19-4.25 (m, 2H), 4.37 (dd, J=15.3, 6.7 Hz, 1H), 4.61 (dd, J=15.3, 3.1 Hz, 1H), 7.15 (d, J=8.5 Hz, 1H), 7.40 (s, 1H), 7.64 (dd, J=8.5, 2.1 Hz, 1H), 8.51 (d, J=2.4 Hz, 1H); MS (DCI/$NH_3$) m/z 523.3 (M+H)$^+$.

Example 89

N-{(3E)-5-tert-butyl-1-methyl-2-[(2R)-tetrahydrofuran-2-ylmethyl]-1,2-dihydro-3H-pyrazol-3-ylidene}-5-chloro-2-(2-hydroxy-2-methylpropoxy)benzamide Example 89A (R)-di-tert-butyl 1-((tetrahydrofuran-2-yl)methyl)hydrazine-1,2-dicarboxylate To a mixture of (R)-(tetrahydrofuran-2-yl)methanol (Fluka, 4.0 g, 39.2 mmol) and di-tert-butyl hydrazine-1,2- dicarboxylate (9.1 g, 39.2 mmol) in THF (50 mL) was added triphenylphosphine (14.4 g, 54.8 mmol) followed by (E)-di-tert-butyl diazene-1,2-dicarboxylate (12.6 g, 54.8 mmol) portionwise. This mixture was stirred at ambient temperature for 16 hours then concentrated under reduced pressure and purified by column chromatography ($SiO_2$, 1-25% EtOAc/hexanes gradient) to give the title compound (11.8 g, 37.3 mmol, 95% yield). MS ($DCI/NH_3$) m/z 317 (M+H)+.

Example 89B (R)-((tetrahydrofuran-2-yl)methyl)hydrazine

A mixture of Example 89A (11.8 g, 37.3 mmol) and HCl (4 M solution in dioxane, 46.6 mL, 186 mmol) was stirred at ambient temperature for 16 hours. The solids were collected by filtration ($Et_2O$ wash) and dried to afford the dihydrochloride salt of the title compound (6.4 g, 33.8 mmol, 91% yield). MS ($DCI/NH_3$) m/z 117 (M+H)+.

Example 89C (R)-3-tert-butyl-1-((tetrahydrofuran-2-yl)methyl)-1H-pyrazol-5-amine A mixture of Example 89B (6.5 g, 34.4 mmol) and 4,4-dimethyl-3-oxopentanenitrile (4.3 g, 34.4 mmol) in ethanol (40 mL) was warmed to 85° C. and stirred for 4 hours. After cooling to ambient temperature, the mixture was concentrated under reduced pressure and the residue was partitioned between $CH_2Cl_2$ (10 mL) and saturated aqueous $NaHCO_3$ (10 mL). The layers were separated and the aqueous phase was extracted with $CH_2Cl_2$ (3×10 mL). The combined organic extracts were dried over anhydrous $Na_2SO_4$, filtered and concentrated under reduced pressure to provide title compound (7.8 g, 35.0 mmol, 100% yield). MS ($DCI/NH_3$) m/z 224 (M+H)+.

Example 89D

N-{3-tert-butyl-1-[(2R)-tetrahydrofuran-2-ylmethyl]-1H-pyrazol-5-yl}-2,2,2-trifluoroacetamide To a solution of Example 89C (4.15 g, 18.6 mmol) and triethylamine (7.8 mL, 55.8 mmol) in $CH_2Cl_2$ (30 mL) at 0° C. was added 2,2,2-trifluoroacetic anhydride (2.6 mL, 18.6 mmol) dropwise via syringe pump over 20 minutes. The ice-bath was removed and the mixture was stirred at ambient temperature for 1 hour. The mixture was concentrated under reduced pressure and purified by column chromatography ($SiO_2$, 40% hexanes/EtOAc) to provide the title compound (5.3 g, 16.6 mmol, 89% yield). MS ($DCI/NH_3$) m/z 320 (M+H)+.

Example 89E

N-{(3E)-5-tert-butyl-1-methyl-2-[(2R)-tetrahydrofuran-2-ylmethyl]-1,2-dihydro-3H-pyrazol-3-ylidene}-2,2,2-trifluoroacetamide A mixture of Example 89D (5.3 g, 16.6 mmol) and dimethyl sulfate (4.8 mL, 49.8 mmol) in toluene (7 mL) was warmed to 90° C. for 72 hours. After cooling to ambient temperature the mixture was concentrated under reduced pressure. And the residue purified by column chromatography ($SiO_2$, 50% hexanes/EtOAc to 100% EtOAc to 9:1:0.1 EtOAc:MeOH:$Et_3N$) to give the title compound (2.8 g, 8.4 mmol, 51% yield). MS ($DCI/NH_3$) m/z 334 (M+H)+.

Example 89F 5-tert-butyl-1-methyl-2-[(2R)-tetrahydrofuran-2-ylmethyl]-1,2-dihydro-3H-pyrazol-3-imine To a solution of Example 89E (2.3 g, 6.8 mmol) in MeOH (12 mL) was added sodium hydroxide (1.4 g, 34.0 mmol) in water (2.5 mL). This mixture was warmed to 50° C. and stirred for 16 hours then cooled to ambient temperature and concentrated under reduced pressure. The residue was diluted with 10 mL $CH_2Cl_2$ and 5 mL $H_2O$. The layers were separated and the aqueous phase was extracted with $CH_2Cl_2$ (3×5 mL). The combined organic extracts were dried over anhydrous $Na_2SO_4$, filtered and concentrated under reduced pressure. Recrystallization from methanol and ethyl acetate afforded the title compound (1.6 g, 6.7 mmol, 99% yield). MS ($DCI/NH_3$) m/z 238 (M+H)+.

Example 89G

N-{(3E)-5-tert-butyl-1-methyl-2-[(2R)-tetrahydrofuran-2-ylmethyl]-1,2-dihydro-3H-pyrazol-3-ylidene}-5-chloro-2-fluorobenzamide Triethylamine (1.2 mL, 8.8 mmol) was added to a solution of 5-chloro-2-fluorobenzoyl chloride (0.57 g, 2.95 mmol) and Example 89F (0.7 g, 2.95 mmol) in THF (6 mL) at room temperature. The reaction mixture was stirred for 3 hours then partitioned between EtOAc (15 mL) and saturated $NaHCO_3$ (1 mL). The organic extract was washed with water and brine, dried with $MgSO_4$, filtered and concentrated. The residue was purified by chromatography ($SiO_2$, solvent A=hexane:EtOAc:$Et_3N$ (1:3:0.2), solvent B=hexane:EtOAc:MeOH:$Et_3N$ (1:3:1:0.2), 0 to 20% solvent B/solvent A gradient over 300 mL then isocratic for 180 mL) to afford the title compound (0.6 g, 1.5 mmol, 52% yield). $^1$H NMR (300 MHz, DMSO-$d_6$) δ ppm 1.38 (s, 9H), 1.67-1.82 (m, 3H), 1.84-1.96 (m, 1H), 3.59-3.67 (m, 1H), 3.71-3.79 (m, 1H), 3.91 (s, 3H), 4.14-4.23 (m, 1H), 4.32-4.46 (m, 2H), 6.82 (s, 1H), 7.14-7.23 (m, 1H), 7.42 (ddd, J=8.5, 3.6, 3.4 Hz, 1H), 7.78 (dd, J=6.3, 3.2 Hz, 1H); MS ($DCI/NH_3$) m/z 394.2 (M+H)+.

Example 89H

N-{(3E)-5-tert-butyl-1-methyl-2-[(2R)-tetrahydrofuran-2-ylmethyl]-1,2-dihydro-3H-pyrazol-3-ylidene}-5-chloro-2-(2-hydroxy-2-methylpropoxy)benzamide A solution of potassium tert-butoxide (1.5 mL, 1 M in THF) was added to Example 81D (0.14 g, 1.6 mmol). After 10 minutes, a solution of Example 89G (0.3 g, 0.76 mmol) in THF (1.5 mL) was added and the mixture stirred for 20 hours. The reaction mixture was partitioned between EtOAc (15 mL) and saturated $NaHCO_3$ (1 mL). The organic extract was washed with water and brine, dried with $MgSO_4$, filtered and concentrated. The residue was purified by chromatography ($SiO_2$, solvent A=hexane:EtOAc:$Et_3N$ (1:3:0.2), solvent B=hexane:EtOAc:MeOH:$Et_3N$ (1:3:1:0.2), solvent A for 450 mL then 5% solvent B/solvent A for 300 mL) to afford the title compound (0.09 g, 0.19 mmol, 26% yield). $^1$H NMR (500 MHz, Pyridine-$d_5$) δ ppm 1.12 (s, 9H), 1.46 (s, 3H), 1.47 (s, 3H), 1.51-1.57 (m, 2H), 1.57-1.64 (m, 1H), 1.71-1.79 (m, 1H), 3.52-3.57 (m, 1H), 3.66-3.71 (m, 1H), 3.80 (s, 3H), 4.15 (s, 2H), 4.15-4.19 (m, 1H), 4.36 (dd, J=15.3, 6.7 Hz, 1H), 4.59

(dd, J=15.3, 3.1 Hz, 1H), 7.10 (s, 1H), 7.11 (s, 1H), 7.33 (s, 1H), 7.38 (dd, J=8.8, 2.7 Hz, 1H), 8.26 (d, J=2.7 Hz, 1H); MS (DCI/NH$_3$) m/z 464.3 (M+H)$^+$. Anal. calculated for: C$_{24}$H$_{34}$ClN$_3$O$_4$ C, 62.12; H, 7.39; N, 9.06. Found: C, 62.23; H, 7.54; N, 9.02.

Example 90

N-{(3E)-5-tert-butyl-1-methyl-2-[(2R)-tetrahydrofuran-2-ylmethyl]-1,2-dihydro-3H-pyrazol-3-ylidene}-5-cyano-2-(2-hydroxy-2-methylpropoxy)benzamide Example 90A N-{(3E)-5-tert-butyl-1-methyl-2-[(2R)-tetrahydrofuran-2-ylmethyl]-1,2-dihydro-3H-pyrazol-3-ylidene}-5-cyano-2-fluorobenzamide A solution of oxalyl chloride (5.1 mL, 2 M in CH$_2$Cl$_2$) was added to a solution of Example 102B (0.56 g, 3.4 mmol) in CH$_2$Cl$_2$ (2 mL), followed by catalytic dimethylformamide (10 µL). The solution was stirred for 1 hour then concentrated under reduced pressure. The residue was diluted with toluene (5 mL) and the volatiles were removed under reduced pressure. To a solution of the resultant residue in THF (5 mL) was added Example 89F (0.8 g, 3.4 mmol) followed by triethylamine (2.8 mL, 20.2 mmol) and the mixture was stirred at ambient temperature for 3 hours. The reaction mixture was partitioned between EtOAc (15 mL) and saturated NaHCO$_3$ (1 mL). The organic extract was washed with water and brine, dried with MgSO$_4$, filtered and concentrated. The residue was purified by chromatography (hexanes:EtOAc:Et$_3$N (1:3:0.2)) to afford the title compound (0.6 g, 1.6 mmol, 46% yield). $^1$H NMR (300 MHz, DMSO-d$_6$) δ ppm 1.38 (s, 9H), 1.67-1.83 (m, 3H), 1.84-1.99 (m, 1H), 3.59-3.67 (m, 1H), 3.70-3.79 (m, 1H), 3.91 (s, 3H), 4.13-4.25 (m, 1H), 4.32-4.47 (m, 2H), 6.82 (s, 1H), 7.38 (dd, J=10.3, 8.7 Hz, 1H), 7.87 (ddd, J=8.4, 4.5, 2.2 Hz, 1H), 8.20 (dd, J=6.7, 2.4 Hz, 1H); MS (DCI/NH$_3$) m/z 385.3 (M+H)$^+$.

Example 90B

N-{(3E)-5-tert-butyl-1-methyl-2-[(2R)-tetrahydrofuran-2-ylmethyl]-1,2-dihydro-3H-pyrazol-3-ylidene}-5-cyano-2-(2-hydroxy-2-methylpropoxy)benzamide To a solution of Example 81D (0.18 g, 2.0 mmol) in THF (2.0 mL) was added to sodium t-butoxide (0.38 g, 3.9 mmol). After 10 minutes, a solution of Example 90A (0.25 g, 0.65 mmol) in THF (0.8 mL) was added and the mixture stirred at ambient temperature for 1 hour. The mixture was partitioned between EtOAc (15 mL) and saturated NaHCO$_3$ (1 mL). The organic extract was washed with water and brine, dried with MgSO$_4$, filtered and concentrated. The residue was purified by chromatography (SiO$_2$, solvent A=hexane:EtOAc:Et$_3$N (1:3:0.2), solvent B=hexane:EtOAc:MeOH:Et$_3$N (1:3:1:0.2), 0 to 20% solvent B/solvent A gradient over 600 mL) to afford the title compound (0.15 g, 0.33 mmol, 51% yield). $^1$H NMR (500 MHz, Pyridine-d$_5$) δ ppm 1.13 (s, 9H), 1.47 (s, 3H), 1.48 (s, 3H), 1.51-1.57 (m, 2H), 1.57-1.64 (m, 1H), 1.72-1.79 (m, 1H), 3.52-3.58 (m, 1H), 3.66-3.72 (m, 1H), 3.82 (s, 3H), 4.17 (s, 2H), 4.18-4.21 (m, 1H), 4.37 (dd, J=15.1, 6.6 Hz, 1H), 4.61 (dd, J=15.3, 3.1 Hz, 1H), 7.16 (d, J=8.5 Hz, 1H), 7.34 (s, 1H), 7.66 (dd, J=8.5, 2.1 Hz, 1H), 8.55 (d, J=2.4 Hz, 1H); MS (DCI/NH$_3$) m/z 455.4 (M+H)$^+$. Anal. calculated for: C$_{25}$H$_{34}$N$_4$O$_4$: C, 66.06; H, 7.54; N, 12.33. Found: C, 66.13; H, 7.64; N, 12.14.

Example 91

N-{(3E)-5-tert-butyl-1-methyl-2-[(2R)-tetrahydrofuran-2-ylmethyl]-1,2-dihydro-3H-pyrazol-3-ylidene}-2-{[(2R)-2-hydroxypropyl]oxy}-5-(trifluoromethyl)benzamide The title compound was prepared as described in Example 1F, substituting (R)-propane-1,2-diol for (R)-(tetrahydrofuran-2-yl)methanol. $^1$H NMR (500 MHz, chloroform-d) δ ppm 1.17 (d, J=6.10 Hz, 3H) 1.37-1.49 (m, 9H) 1.66-1.81 (m, J=6.71 Hz, 2H) 1.83-1.90 (m, 1H) 1.98-2.07 (m, 1H) 3.64-3.87 (m, 3H) 3.89 (s, 3H) 4.09-4.22 (m, 2H) 4.25-4.42 (m, 2H) 4.53 (s, 1H) 6.70 (s, 1H) 6.97-7.12 (m, 1H) 7.52 (s, 1H) 8.09 (s, 1H); MS (DCI/NH$_3$) m/z 484 (M+H)$^+$.

Example 92

N-[(2E)-1-butyl-4-tert-butylpyridin-2(1H)-ylidene]-2-(2-hydroxy-2-methylpropoxy)-5-(trifluoromethyl)benzamide Example 92A 4-tert-butyl-1-butylpyridin-2(1H)-imine A mixture of 4-tert-butylpyridin-2-amine (500 mg, 3.33 mmol) and 1-iodobutane (500 µL) was heated at 85° C. for 1 hour. After cooling to room temperature, the precipitate was isolated by filtration (hexane wash) and dried to afford 515 mg (64%) of the hydrochloride salt of the title compound. MS (DCI/NH$_3$) m/z 207 (M+H)$^+$.

Example 92B

N-[(2E)-1-butyl-4-tert-butylpyridin-2(1H)-ylidene]-2-fluoro-5-(trifluoromethyl)benzamide A mixture of Example 92A (315 mg, 1.3 mmol), 2-fluoro-5-(trifluoromethyl)benzoic acid (324 mg, 1.56 mmol), Et$_3$N (543 µL, 3.89 mmol) and propylphosphonic anhydride (927 µL, 1.56 mmol) in THF (15 mL) was stirred at room temperature for 12 hours. The reaction mixture was quenched with NaHCO$_3$ and extracted twice with EtOAc. The combined organic extracts were dried over MgSO$_4$, filtered and concentrated. The residue was purified by column chromatography using an Analogix® Intelliflash280™ (SiO$_2$, 10-100% EtOAc/hexanes gradient) to afford 228 mg (44%) of the title compound. MS (DCI/NH$_3$) m/z 397 (M+H)$^+$.

Example 92C

N-[(2E)-1-butyl-4-tert-butylpyridin-2(1H)-ylidene]-2-(2-hydroxy-2-methylpropoxy)-5-(trifluoromethyl)benzamide To a solution of Example 81D (154 mg, 1.71 mmol) in 5 mL of THF was added sodium hydride (68.4 mg, 1.71 mmol of 60% dispersion in mineral oil). The reaction mixture was stirred at 22° C. for 20 minutes then a solution of Example 92B (226 mg, 0.57 mmol) in THF (3 mL) was added. After 2 h, the volatiles were removed under reduced pressure and the residue was dissolved in ether, washed with brine and water, dried with magnesium sulfate and concentrated. The residue was purified by column chromatography using an Analogix® Intelliflash280™ (SiO$_2$, 10 to 100% EtOAc/hexanes gradient) to afford 157 mg (59%) of the title compound. $^1$H NMR (500 MHz, chloroform-d) δ ppm 0.96 (t, J=7.48 Hz, 3H) 1.30 (s, 9H) 1.32 (s, 6H) 1.35-1.46 (m, 2H) 1.77-1.97 (m, 2H) 4.03 (s, 2H) 4.16-4.30 (m, 2H) 5.56 (s, 1H) 6.65 (dd, J=7.02, 2.14 Hz, 1H) 7.01 (d, J=8.85 Hz, 1H) 7.49 (d, J=7.02 Hz, 1H) 7.56 (dd, J=8.54, 2.14 Hz, 1H) 8.16 (d, J=2.14 Hz, 1H) 8.32 (d, J=2.14 Hz, 1H); MS (DCI/NH$_3$) m/z 467 (M+H)$^+$.

Example 93

N-[(2Z)-3-butyl-5-tert-butyl-1,3-oxazol-2(3H)-ylidene]-2-(2-hydroxy-2-methylpropoxy)-5-(trifluoromethyl)benzamide Example 93A N-butylcyanamide The title compound was prepared as described in Example 32A substituting butan-1-amine for ((R)-(tetrahydro-furan-2-yl)-methylamine. MS (DCI/NH$_3$) m/z 99 (M+H)$^+$.

Example 93B 5-tert-butyl-3-butyloxazol-2(3H)-imine

The title compound was prepared as described in Example 32B substituting Example 93A for Example 32A. MS (DCI/NH$_3$) m/z 197 (M+H)$^+$.

Example 93C 1-(2-bromo-4-(trifluoromethyl)phenoxy)-2-methylpropan-2-ol

The title compound was prepared as described in Example 68E substituting 2-bromo-1-fluoro-4-(trifluoromethyl)benzene for Example 68D and Example 81D for 3-methylbutane-1,3-diol. MS (DCI/NH$_3$) m/z 312 (M)$^+$.

Example 93D methyl 2-(2-hydroxy-2-methylpropoxy)-5-(trifluoromethyl)benzoate

To a solution of Example 93C (2.77 g, 8.85 mmol) and triethyl amine (3.70 ml, 26.5 mmol) in methanol (30 mL) in a 50 mL pressure bottle under Argon were added to Pd(dppf) (0.324 g, 0.442 mmol, Heraeus). The mixture was pressurized with carbon monoxide (50 psi), and stirred at 100° C. for 6 hours. Another 2.5 mol % of Pd(dppf) was added, and the mixture was carbonylated for another 12 hours at 100° C. Filtration of the mixture and concentration of the filtrate under reduced pressure provided the title compound. MS (DCI/NH$_3$) m/z 293 (M+1)$^+$ Example 93E 2-(2-hydroxy-2-methylpropoxy)-5-(trifluoromethyl)benzoic acid A solution of Example 93D (1.12 g, 3.83 mmol) and lithium hydroxide hydrate (482 mg, 11.5 mmol) in THF (20 mL) and water (10 mL) was stirred at room temperature for 12 hours. The pH was adjusted to 3-4 by the addition of 10% aqueous HCl and the mixture was extracted twice with isopropanol/CH$_2$Cl$_2$ (1:3). The combined organic extracts were dried and concentrated under reduced pressure to afford the title compound. $^1$H NMR (500 MHz, DMSO-d$_6$) δ ppm 1.23 (s, 6H) 3.87 (s, 2H) 7.31 (d, J=8.85 Hz, 1H) 7.84 (dd, J=8.70, 2.29 Hz, 1H) 7.92 (d, J=2.14 Hz, 1H).

Example 93F

N-[(2Z)-3-butyl-5-tert-butyl-1,3-oxazol-2(3H)-ylidene]-2-(2-hydroxy-2-methylpropoxy)-5-(trifluoromethyl)benzamide A mixture of Example 93B (400 mg, 2.03 mmol), Example 93E (300 mg, 1.08 mmol), EDCI (782 mg, 4.08 mmol), HOBt (624 mg, 4.08 mmol) and 4-(dimethylamino)pyridine (50 mg) in pyridine (20 mL) was stirred at room temperature for 12 hours. The reaction mixture mixture was concentrated, and diluted with water and extracted with ethyl acetate. The organic extract was dried (Na$_2$SO$_4$), filtered and concentrated. Purification by flash chromatography (silica gel, 20% to 100% EtOAc/hexanes gradient) afforded 213 mg (23%) of the title compound. $^1$H NMR (500 MHz, chloroform-d) δ ppm 0.96 (t, J=7.48 Hz, 3H) 1.26 (s, 9H) 1.31 (s, 6H) 1.33-1.45 (m, 2H) 1.72 (t, J=7.63 Hz, 2H) 3.78 (t, J=7.32 Hz, 2H) 3.99 (s, 2H) 4.82-5.02 (m, 1H) 6.29 (s, 1H) 7.00 (d, J=8.54 Hz, 1H) 7.58 (dd, J=8.54, 1.83 Hz, 1H) 8.14 (d, J=2.14 Hz, 1H); MS (ESI$^+$) m/z 457 (M+H)$^+$.

Example 94

N-[(2Z)-3-butyl-5,5-dimethyl-1,3-thiazolidin-2-ylidene]-2-(2-hydroxy-2-methylpropoxy)-5-(trifluoromethyl)benzamide Example 94A 3-butyl-5,5-dimethylthiazolidin-2-imine A mixture of 2,2-dimethyl-thiirane (TCI, 1.5 g, 17 mmol), N-butyl-cyanamide (1.7 g, 17 mmol) (prepared as described in Ross J. Med. Chem. 1979, 22; 412) and potassium carbonate (2.4 g, 17 mmol) in 2-butanone (15 mL) was heated to 80° C. overnight. The mixture was poured into water, and extracted twice with ethyl acetate. The combined organic extracts were dried over Na$_2$SO$_4$, filtered, concentrated under reduced pressure to afford 2.11 g of the title compound.

Example 94B (Z)—N-(3-butyl-5,5-dimethylthiazolidin-2-ylidene)-2-fluoro-5-(trifluoromethyl)benzamide The title compound was prepared as described in Example 30B substituting Example 94A for Example 30A. MS (ESI$^+$) m/z 377 (M+H)$^+$.

Example 94C

N-[(2Z)-3-butyl-5,5-dimethyl-1,3-thiazolidin-2-ylidene]-2-(2-hydroxy-2-methylpropoxy)-5-(trifluoromethyl)benzamide The title compound was prepared as described in Example 92C substituting Example 94B for Example 92B. $^1$H NMR (500 MHz, chloroform-d) δ ppm 0.97 (t, J=7.48 Hz, 3H) 1.33 (s, 6H) 1.37-1.42 (m, 2H) 1.52 (s, 6H) 1.58-1.70 (m, 2H) 3.43 (s, 2H) 3.71 (t, J=7.32 Hz, 2H) 3.97 (s, 2H) 7.00 (d, J=8.54 Hz, 1H) 7.61 (dd, J=8.70, 2.29 Hz, 1H) 8.29 (d, J=2.44 Hz, 1H); MS (ESI$^+$) m/z 447 (M+H)$^+$.

Example 95

N-[(3E)-5-tert-butyl-1-methyl-2-(tetrahydro-2H-pyran-4-ylmethyl)-1,2-dihydro-3H-pyrazol-3-ylidene]-2-(2-hydroxy-2-methylpropoxy)-5-(trifluoromethyl)benzamide

Example 95A (tetrahydro-2H-pyran-4-yl)methyl 4-methylbenzenesulfonate

To a solution of (tetrahydro-2H-pyran-4-yl)methanol (5.0 g, 43.0 mmol) in $CH_2Cl_2$ (40 mL) and pyridine (30 mL) was added 4-(dimethylamino)pyridine (0.26 g, 2.2 mmol) followed by p-toluenesulfonyl chloride (8.2 g, 43.0 mmol). The mixture was allowed to stir at ambient temperature for 16 hours then was quenched with 5% aqueous HCl (15 mL) and the layers were separated. The aqueous phase was extracted with $CH_2Cl_2$ (3×10 mL). The combined organic extracts were dried over $Na_2SO_4$, filtered and concentrated under reduced pressure. Purification by column chromatography ($SiO_2$, 75% hexanes in EtOAc) afforded the title compound (9.1 g, 33.7 mmol, 78% yield). MS ($DCI/NH_3$) m/z 288 $(M+NH_4)^+$.

Example 95B 3-tert-butyl-1-((tetrahydro-2H-pyran-4-yl)methyl)-1H-pyrazol-5-amine To a solution of Example 95A (9.1 g, 33.7 mmol) in EtOH (50 mL) was added hydrazine hydrate (3.3 mL, 67.3 mmol). The mixture was warmed to reflux (85° C.) and was allowed to stir for 20 hours. The mixture was cooled to ambient temperature then 4,4-dimethyl-3-oxopentanenitrile (8.4 g, 67.3 mmol) was added and the mixture was again warmed to reflux (85° C.) and was allowed to stir for 6 hours. The mixture was concentrated under reduced pressure and the residue was dissolved in $CH_2Cl_2$ (30 mL) and saturated aqueous $NaHCO_3$ (20 mL) was added slowly. The layers were separated and the aqueous phase was extracted with $CH_2Cl_2$ (3×10 mL). The combined organic extracts were dried over $Na_2SO_4$, filtered and concentrated under reduced pressure. Purification via column chromatography ($SiO_2$, 50% hexanes/EtOAc to 100% EtOAc to 9:1:0.1 EtOAc:MeOH:$Et_3N$) provided the title compound (5.2 g, 21.9 mmol, 65% yield). MS ($DCI/NH_3$) m/z 238 $(M+H)^+$.

Example 95C

N-[3-tert-butyl-1-(tetrahydro-2H-pyran-4-ylmethyl)-1H-pyrazol-5-yl]-2,2,2-trifluoroacetamide To a solution of Example 95B (5.2 g, 22.1 mmol) and $Et_3N$ (9.2 mL, 66.2 mmol) in $CH_2Cl_2$ (60 mL) at 0° C. was added 2,2,2-trifluoroacetic anhydride (3.1 mL, 22.1 mmol) dropwise via syringe pump over 20 min. The ice-bath was removed after the addition was complete and the mixture was stirred at ambient temperature for 1 hour. The mixture was concentrated under reduced pressure and was purified by column chromatography ($SiO_2$, 50% hexanes/EtOAc) to provide the title compound (7.2 g, 21.6 mmol, 98% yield). MS ($DCI/NH_3$) m/z 334 $(M+H)^+$.

Example 95D

N-[(3E)-5-tert-butyl-1-methyl-2-(tetrahydro-2H-pyran-4-ylmethyl)-1,2-dihydro-3H-pyrazol-3-ylidene]-2,2,2-trifluoroacetamide A mixture of Example 95C (7.2 g, 21.6 mmol) and dimethyl sulfate (6.2 mL, 64.8 mmol) in Toluene (20 mL) was warmed to 90° C. for 72 hours then cooled to ambient temperature. The mixture was concentrated under reduced pressure and the residue purified by column chromatography ($SiO_2$, 50% hexanes/EtOAc to 100% EtOAc to 9:1:0.1 EtOAc:MeOH:$Et_3N$) to afford the title compound (4.2 g, 12.1 mmol, 56% yield). MS ($DCI/NH_3$) m/z 348 $(M+H)^+$.

Example 95E 5-tert-butyl-1-methyl-2-(tetrahydro-2H-pyran-4-ylmethyl)-1,2-dihydro-3H-pyrazol-3-imine To a solution of Example 95D (4.2 g, 12.1 mmol) in MeOH (25 mL) was added sodium hydroxide (2.4 g, 61 mmol) in water (5 mL). The mixture was warmed to 50° C. for 4 hours then cooled to ambient temperature and concentrated under reduced pressure. The residue was partitioned between $CH_2Cl_2$ (20 mL) and $H_2O$ (10 mL). The layers were separated and the aqueous phase was extracted with $CH_2Cl_2$ (3×5 mL). The combined organic extracts were dried over anhydrous $Na_2SO_4$, filtered and concentrated under reduced pressure to give the crude title compound (3.2 g, 12.7 mmol, 105% yield), which was carried on without purification. MS ($DCI/NH_3$) m/z 252 $(M+H)^+$.

Example 95F

N-[(3E)-5-tert-butyl-1-methyl-2-(tetrahydro-2H-pyran-4-ylmethyl)-1,2-dihydro-3H-pyrazol-3-ylidene]-2-fluoro-5-(trifluoromethyl)benzamide To a solution of Example 95E (0.53 g, 2.1 mmol) and $Et_3N$ (0.88 mL, 6.3 mmol) in THF (10 mL) was added 2-fluoro-5-(trifluoromethyl)benzoyl chloride (0.320 mL, 2.108 mmol). The mixture was stirred at ambient temperature for 4 h then was quenched with saturated aqueous $NaHCO_3$ (10 mL) and diluted with EtOAc (10 mL). The layers were separated and the aqueous phase was extracted EtOAc (3×10 mL). The combined organic extracts were dried over $Na_2SO_4$, filtered and concentrated under reduced pressure. Purification by column chromatography ($SiO_2$, 50% hexanes in EtOAc) afforded the title compound (0.48 g, 1.1 mmol, 52% yield). MS ($DCI/NH_3$) m/z 442 $(M+H)^+$.

Example 95G

N-[(3E)-5-tert-butyl-1-methyl-2-(tetrahydro-2H-pyran-4-ylmethyl)-1,2-dihydro-3H-pyrazol-3-ylidene]-2-(2-hydroxy-2-methylpropoxy)-5-(trifluoromethyl)benzamide To a solution of Example 81D (0.17 g, 1.9 mmol) in THF (5 mL) at ambient temperature was added potassium tert-butoxide (0.37 g, 3.3 mmol). The mixture was allowed to stir for 15 min at ambient temperature then a solution of Example 95F (0.48 g, 1.1 mmol) in THF (5 mL) was added via cannula. The mixture was stirred at ambient temperature for 16 h then partitioned between saturated aqueous $NaHCO_3$ (10 mL) and EtOAc (20 mL). The layers were separated and the aqueous phase was extracted with EtOAc (3×10 mL). The combined organic extracts were dried over anhydrous Na$_2$SO$_4$, filtered, concentrated and purified via column chromatography (SiO$_2$, 50% hexanes/EtOAc then 100% EtOAc then 9:1:0.1 EtOAc: MeOH:Et$_3$N) to afford the title compound (0.40 g, 0.78 mmol, 72% yield). $^1$H NMR (300 MHz, CDCl$_3$) δ ppm 1.29 (s, 6H) 1.41-1.53 (m, 4H) 1.42 (s, 9H) 2.03-2.21 (m, 1H) 3.33 (dt, J=11.3, 2.8 Hz, 2H) 3.73 (s, 3H) 3.92-3.99 (m, 2H) 4.03 (s, 2H) 4.15 (d, J=7.1 Hz, 2H) 6.15 (s, 1H) 7.01 (d, J=8.3 Hz, 1H) 7.01 (s, 1H) 7.52 (dd, J=8.3, 2.4 Hz, 1H) 8.14 (d, J=2.0 Hz, 1H); MS (DCI/NH$_3$) m/z 512 (M+H)$^+$; Anal. calculated for C$_{26}$H$_{36}$F$_3$N$_3$O$_4$: Calc: C, 61.04; H, 7.09; N, 8.21. Found: C, 60.97; H, 7.17; N, 8.16.

Example 96

N-[(2Z)-5-tert-butyl-3-(oxetan-2-ylmethyl)-1,3,4-thiadiazol-2(3H)-ylidene]-2-(2-hydroxy-2-methylpropoxy)-5-(trifluoromethyl)benzamide Example 96A N-[(2Z)-5-tert-butyl-3-(oxetan-2-ylmethyl)-1,3,4-thiadiazol-2(3H)-ylidene]-2-fluoro-5-(trifluoromethyl)benzamide The title compound was prepared as described in Example 7B, substituting 1-oxetan-2-ylmethyl 4-methylbenzenesulfonate for 1-iodobutane. MS (DCI/NH$_3$) m/z 418 (M+H)$^+$ Example 96B N-[(2Z)-5-tert-butyl-3-(oxetan-2-ylmethyl)-1,3,4-thiadiazol-2(3H)-ylidene]-2-(2-hydroxy-2-methylpropoxy)-5-(trifluoromethyl)benzamide Example 96A and Example 81D were processed as described in Example 92C to afford the title compound. $^1$H NMR (500 MHz, chloroform-d) δ ppm 1.34 (d, J=2.14 Hz, 6H) 1.41 (s, 9H) 2.59-2.71 (m, 1H) 2.75-2.89 (m, 1H) 4.01 (s, 2H) 4.53-4.65 (m, 2H) 4.65-4.72 (m, 1H) 4.81 (dd, J=13.88, 6.26 Hz, 1H) 4.85-4.97 (m, 1H) 5.22-5.39 (m, 1H) 7.05 (d, J=8.54 Hz, 1H) 7.65 (dd, J=8.70, 2.29 Hz, 1H) 8.35 (d, J=2.14 Hz, 1H) MS (DCI/NH$_3$) m/z 488 (M+H)$^+$.

Example 97

N-[(2Z)-5-tert-butyl-3-[(3-methyloxetan-3-yl)methyl]-1,3,4-thiadiazol-2(3H)-ylidene]-2-(2-hydroxy-2-methylpropoxy)-5-(trifluoromethyl)benzamide Example 97A N-[(2Z)-5-tert-butyl-3-[(3-methyloxetan-3-yl)methyl]-1,3,4-thiadiazol-2(3H)-ylidene]-2-fluoro-5-(trifluoromethyl)benzamide The title compound was prepared according as described in Example 7B, substituting 3-(chloromethyl)-3-methyloxetane (Aldrich) for 1-iodobutane. MS (DCI/NH$_3$) m/z 432 (M+H)$^+$ Example 97B N-[(2Z)-5-tert-butyl-3-[3-methyloxetan-3-yl)methyl]-1,3,4-thiadiazol-2(3H)-ylidene]-2-(2-hydroxy-2-methylpropoxy)-5-(trifluoromethyl)benzamide Example 97A and Example 81D were processed as described in Example 92C to afford the title compound. $^1$H NMR (500 MHz, chloroform-d) δ ppm 1.32 (s, 3H) 1.35 (s, 6H) 1.40 (s, 9H) 4.02 (s, 2H) 4.42 (d, J=6.10 Hz, 2H) 4.63 (s, 2H) 4.84 (d, J=6.10 Hz, 2H) 4.88 (s, 1H) 7.05 (d, J=8.54 Hz, 1H) 7.66 (dd, J=8.54, 2.44 Hz, 1H) 8.29 (d, J=2.44 Hz, 1H); MS (DCI/NH$_3$) m/z 502 (M+H)$^+$.

Example 98

N-{(3E)-5-tert-butyl-1-methyl-2-[(2R)-tetrahydrofuran-2-ylmethyl]-1,2-dihydro-3H-pyrazol-3-ylidene}-2-{[(2S)-2-hydroxypropyl]oxy}-5-(trifluoromethyl)benzamide The title compound was prepared as described in Example 1F, substituting (S)-propane-1,2-diol for (R)-(tetrahydrofuran-2-yl)methanol. $^1$H NMR (500 MHz, chloroform-d) δ ppm 1.17 (d, J=6.10 Hz, 3H) 1.37-1.48 (m, 9H) 1.67-1.78 (m, 2H) 1.80-1.91 (m, 1H) 1.95-2.08 (m, 1H) 3.67-3.79 (m, 2H) 3.85 (t, J=9.76 Hz, 1H) 3.86-3.94 (m, 3H) 4.08-4.20 (m, 2H) 4.24-4.43 (m, 2H) 4.54 (d, J=14.65 Hz, 1H) 6.70 (s, 1H) 7.00-7.13 (m, 2H) 7.52 (d, J=7.32 Hz, 1H) 8.09 (s, 1H) 8.04-8.14 (m, 1H); MS (DCI/NH$_3$) m/z 484 (M+H)$^+$.

Example 99

N-[(3E)-5-tert-butyl-1-methyl-2-pentyl-1,2-dihydro-3H-pyrazol-3-ylidene]-2-(2-hydroxy-2-methylpropoxy)-5-(trifluoromethyl)benzamide Example 99A pentyl 4-methylbenzenesulfonate To a solution of pentan-1-ol (9.2 mL, 85 mmol) in CH$_2$Cl$_2$ (70 mL) and pyridine (50 mL) was added 4-(dimethylamino) pyridine (0.52 g, 4.3 mmol) followed by p-toluenesulfonyl chloride (16.2 g, 85 mmol). The mixture was allowed to stir at ambient temperature for 18 h then was quenched with 5% aqueous HCl (10 mL) and the layers were separated. The aqueous phase was extracted with CH$_2$Cl$_2$ (3×5 mL). The combined organic extracts were dried over Na$_2$SO$_4$, filtered and concentrated under reduced pressure. Purification by column chromatography (SiO$_2$, 75% hexanes in EtOAc) afforded the title compound (13.1 g, 53.9 mmol, 63% yield). MS (DCI/NH$_3$) m/z 260 (M+NH$_4$)$^+$.

Example 99B 3-tert-butyl-1-pentyl-1H-pyrazol-5-amine

To a solution of Example 99A (10.0 g, 41.3 mmol) in EtOH (85 mL) was added hydrazine hydrate (3.02 mL, 61.9 mmol). The mixture was warmed to reflux (85° C.) and was allowed to stir for 20 hours. The mixture was cooled to ambient temperature then 4,4-dimethyl-3-oxopentanenitrile (7.78 g, 61.9 mmol) was added and the mixture was again warmed to reflux (85° C.) and was allowed to stir for 4 hours then the mixture was concentrated under reduced pressure and the residue was dissolved in CH$_2$Cl$_2$ (100 mL) and saturated aqueous NaHCO$_3$ (50 mL) was added slowly. The layers were separated and the aqueous phase was extracted with CH$_2$Cl$_2$ (3×10 mL). The combined organic extracts were dried over Na$_2$SO$_4$, filtered and concentrated under reduced pressure. Purification by column chromatography (SiO$_2$, 50% hexanes/ EtOAc) provided the title compound (7.6 g, 36.3 mmol, 88% yield). MS (DCI/NH$_3$) m/z 210 (M+H)$^+$.

Example 99C

N-(3-tert-butyl-1-pentyl-1H-pyrazol-5-yl)-2,2,2-trifluoroacetamide

To a solution of Example 99B (7.6 g, 36.3 mmol) and $Et_3N$ (15.2 mL, 109 mmol) in $CH_2Cl_2$ (100 mL) at 0° C. was added 2,2,2-trifluoroacetic anhydride (5.1 mL, 36.3 mmol) dropwise via syringe pump over 20 min. The ice-bath was removed and the mixture was stirred at ambient temperature for 1 h then concentrated under reduced pressure. The residue was purified by column chromatography ($SiO_2$, 40% hexanes/EtOAc) to provide the title compound (7.8 g, 25.6 mmol, 71% yield). MS (DCI/$NH_3$) m/z 306 (M+H)$^+$.

Example 99D

N-[(3E)-5-tert-butyl-1-methyl-2-pentyl-1,2-dihydro-3H-pyrazol-3-ylidene]-2,2,2-trifluoroacetamide A mixture of Example 99C (7.8 g, 25.6 mmol) and dimethyl sulfate (7.4 mL, 77 mmol) in toluene (10 mL) was warmed to 90° C. for 48 h then cooled to ambient temperature. The mixture was concentrated under reduced pressure and the residue was purified by column chromatography ($SiO_2$, 50% hexanes/EtOAc to 100% EtOAc to 9:1:0.1 EtOAc:MeOH:$Et_3N$) to afford the title compound (4.5 g, 14.1 mmol, 55% yield). MS (DCI/$NH_3$) m/z 320 (M+H)$^+$.

Example 99E 5-tert-butyl-1-methyl-2-pentyl-1H-pyrazol-3(2H)-imine

To a solution of Example 99D (4.5 g, 14.1 mmol) in MeOH (25 mL) was added sodium hydroxide (2.8 g, 70.5 mmol) in water (5 mL). The mixture was warmed to 50° C. for 4 hours then cooled to ambient temperature. The mixture was concentrated under reduced pressure and then diluted with $CH_2Cl_2$ (20 mL) and $H_2O$ (10 mL). The layers were separated and the aqueous phase was extracted with $CH_2Cl_2$ (3×5 mL). The combined organic extracts were dried over anhydrous $Na_2SO_4$, filtered and concentrated under reduced pressure to give the crude title compound (3.5 g, 15.5 mmol, 110% yield). MS (DCI/$NH_3$) m/z 224 (M+H)$^+$.

Example 99F

N-[(3E)-5-tert-butyl-1-methyl-2-pentyl-1,2-dihydro-3H-pyrazol-3-ylidene]-2-fluoro-5-(trifluoromethyl)benzamide To a solution of Example 99E (0.53 g, 2.4 mmol) and $Et_3N$ (1.0 mL, 7.1 mmol) in THF (10 mL) was added 2-fluoro-5-(trifluoromethyl)benzoyl chloride (0.36 mL, 2.4 mmol). The mixture was stirred at ambient temperature for 4 hours then was partitioned between saturated aqueous $NaHCO_3$ (10 mL) and EtOAc (10 mL). The layers were separated and the aqueous phase was extracted EtOAc (3×7 mL). The combined organic extracts were dried over $Na_2SO_4$, filtered and concentrated under reduced pressure. Purification by column chromatography ($SiO_2$, 50% hexanes in EtOAc) afforded the title compound (0.68 g, 1.6 mmol, 69% yield). MS (DCI/$NH_3$) m/z 414 (M+H)$^+$.

Example 99G

N-[(3E)-5-tert-butyl-1-methyl-2-pentyl-1,2-dihydro-3H-pyrazol-3-ylidene]-2-(2-hydroxy-2-methylpropoxy)-5-(trifluoromethyl)benzamide To a solution of Example 81D (0.26 g, 2.9 mmol) in THF (10 mL) at ambient temperature was added potassium tert-butoxide (0.55 g, 4.9 mmol). After 15 min, a solution of Example 99F (0.68 g, 1.6 mmol) in THF (5 mL) was added via cannula. The mixture was stirred at ambient temperature for 16 h then partitioned between saturated aqueous $NaHCO_3$ (10 mL) and EtOAc (10 mL). The layers were separated and the aqueous phase was extracted with EtOAc (3×7 mL). The combined organic extracts were dried over anhydrous $Na_2SO_4$, filtered, and concentrated. Purification by column chromatography ($SiO_2$, 50% hexanes/EtOAc then 100% EtOAc then 9:1:0.1 EtOAc:MeOH:$Et_3N$) afforded the title compound (0.60 g, 1.2 mmol, 75% yield). $^1H$ NMR (300 MHz, $CDCl_3$) δ ppm 0.84-0.92 (m, 3H) 1.28 (s, 6H) 1.30-1.49 (m, 4H) 1.42 (s, 9H) 1.62-1.76 (m, 2H) 3.75 (s, 3H) 4.03 (s, 2H) 4.26 (dd, J=7.5 Hz, 2H) 6.18 (s, 1H) 7.00 (d, J=8.5 Hz, 1H) 7.00 (s, 1H) 7.51 (dd, J=8.6, 1.9 Hz, 1H) 8.12 (d, J=2.0 Hz, 1H); MS (DCI/$NH_3$) m/z 484 (M+H)$^+$; Anal. calculated for $C_{25}H_{36}F_3N_3O_3$: Calc: C, 62.09; H, 7.50; N, 8.69. Found: C, 62.34; H, 7.53; N, 8.72.

Example 100

N-[(3E)-2-butyl-5-tert-butylisoxazol-3(2H)-ylidene]-2-(2-hydroxy-2-methylpropoxy)-5-(trifluoromethyl)benzamide

Example 100A 5-tert-butyl-2-butylisoxazol-3(2H)-imine

The title compound was prepared using the procedure as described in Example 92A substituting 5-tert-butylisoxazol-3-amine for tert-butylpyridin-2-amine. MS (DCI/$NH_3$) m/z 197 (M+H)$^+$.

Example 100B

N-[(3E)-2-butyl-5-tert-butylisoxazol-3(2H)-ylidene]-2-(2-hydroxy-2-methylpropoxy)-5-(trifluoromethyl)benzamide The title compound was prepared using the procedure as described in Example 93F substituting Example 100A for Example 93B. $^1H$ NMR (500 MHz, chloroform-d) δ ppm 0.95 (t, J=7.32 Hz, 3H) 1.33-1.36 (m, 6H) 1.35-1.41 (m, 2H) 1.46 (s, 9H) 1.83-1.95 (m, 2H) 4.11 (s, 2H) 4.75 (t, J=7.17 Hz, 2H) 7.10 (d, J=8.85 Hz, 1H) 7.31 (s, 1H) 7.80 (dd, J=8.85, 2.14 Hz, 1H) 8.13 (d, J=2.14 Hz, 1H); MS (DCI/$NH_3$) m/z 457 (M+H)$^+$.

Example 101

N-{(3E)-5-tert-butyl-1-methyl-2-[(2R)-tetrahydrofuran-2-ylmethyl]-1,2-dihydro-3H-pyrazol-3-ylidene}-2-[(2-hydroxybut-3-enyl)oxy]-5-(trifluoromethyl)benzamide The title compound was prepared using the procedure as described in Example 1F substituting but-3-ene-1,2-diol for (R)-(tetrahydrofuran-2-yl)methanol. $^1H$ NMR (500 MHz, chloroform-d) δ ppm 1.38-1.47 (m, 9H) 1.63-1.79 (m, 2H) 1.79-1.92 (m, 1H) 2.04 (d, J=7.02 Hz, 1H) 3.64-3.81 (m, 2H) 3.90 (s, 3H) 3.89-4.00 (m, 1H) 4.16 (s, 1H) 4.31 (dd, 1H) 4.42 (dd, J=10.22, 2.59 Hz, 1H) 4.54 (s, 2H) 5.20 (d, J=10.37 Hz, 1H) 5.42 (d, J=18.00 Hz, 1H) 5.84 (dd, J=10.83, 5.64 Hz, 1H) 7.01-7.11 (m, 2H) 7.17 (s, 1H) 7.53 (s, 1H) 8.10 (s, 1H); MS (DCI/NH$_3$) m/z 488 (M+H)$^+$.

Example 102

N-[(3E)-5-tert-butyl-1-methyl-2-(tetrahydro-2H-pyran-4-ylmethyl)-1,2-dihydro-3H-pyrazol-3-ylidene]-5-cyano-2-(2-hydroxy-2-methylpropoxy)benzamide Example 102A methyl 5-cyano-2-fluorobenzoate A solution of 3-bromo-4-fluorobenzonitrile (25 g, 125 mmol) in MeOH (200 mL) was added to Pd(dppf) (Heraeus, 1.83 g, 2.5 mmol) and Li$_2$CO$_3$ (18.7 g, 250 mmol) in a 500 mL stainless steel pressure bottle. The mixture was pressurized with CO (60 psi), and stirred at 80° C. for 7 hours. The mixture was filtered through Celite (EtOAc wash) and the filtrate was concentrated under reduced pressure. Purification by column chromatography (SiO$_2$, 60% hexanes/EtOAc) afforded the title compound (17.8 g, 99 mmol, 79% yield). MS (DCI/NH$_3$) m/z 197 (M+NH$_4$)$^+$.

Example 102B 5-cyano-2-fluorobenzoic acid

To a solution of Example 102A (3.0 g, 16.8 mmol) in ethanol (50 mL) was added a solution of KOH (40% aqueous, 15 mL). The mixture was warmed to 45° C. and was allowed to stir for 2 hours until all solids had dissolved. The mixture was cooled to ambient temperature and partially concentrated under reduced pressure. The material was diluted with EtOAc and acidified with 10% aqueous HCl. Layers were separated and the aqueous phase was extracted EtOAc (3×20 mL). The combined organic extracts were dried over Na$_2$SO$_4$, filtered and concentrated under reduced pressure to give the title compound (3.0 g, 16.4 mmol, 98% yield). MS (DCI/NH$_3$) m/z 183 (M+NH$_4$)$^+$.

Example 102C

N-[(3E)-5-tert-butyl-1-methyl-2-(tetrahydro-2H-pyran-4-ylmethyl)-1,2-dihydro-3H-pyrazol-3-ylidene]-5-cyano-2-fluorobenzamide A mixture of Example 102B (0.37 g, 2.0 mmol) and thionyl chloride (5 mL) was warmed to reflux (90° C.) for 2 hours then cooled to ambient temperature and concentrated under reduced pressure. The residue was diluted with toluene (10 mL) and was concentrated under reduced pressure (3×) to afford the acid chloride. To a solution of Example 95E (0.50 g, 2.0 mmol) and Et$_3$N (0.83 mL, 6.0 mmol) in THF (10 mL) was added the freshly prepared acid chloride. After 4 h the mixture was partitioned between saturated aqueous NaHCO$_3$ (10 mL) and EtOAc (10 mL). The layers were separated and the aqueous phase was extracted EtOAc (3×10 mL). The combined organic extracts were dried over Na$_2$SO$_4$, filtered and concentrated under reduced pressure. Purification by column chromatography (SiO$_2$, 50% hexanes in EtOAc) afforded the title compound (0.22 g, 0.55 mmol, 28% yield). MS (DCI/NH$_3$) m/z 399 (M+H)$^+$.

Example 102D

N-[(3E)-5-tert-butyl-1-methyl-2-(tetrahydro-2H-pyran-4-ylmethyl)-1,2-dihydro-3H-pyrazol-3-ylidene]-5-cyano-2-(2-hydroxy-2-methylpropoxy)benzamide To a solution of Example 81D (87 mg, 0.97 mmol) in THF (5 mL) at ambient temperature was added potassium tert-butoxide (0.19 g, 1.7 mmol). After 20 min, a solution of Example 102C (0.22 g, 0.55 mmol) in THF (3 mL) was added via cannula. The mixture was stirred at ambient temperature for 3 h then partitioned between saturated aqueous NaHCO$_3$ (7 mL) and EtOAc (10 mL). The layers were separated and the aqueous phase was extracted with EtOAc (3×5 mL). The combined organic extracts were dried over anhydrous Na$_2$SO$_4$, filtered and concentrated. Purification by column chromatography (SiO$_2$, 50% hexanes/EtOAc then 100% EtOAc then 9:1:0.1 EtOAc:MeOH:Et$_3$N) afforded the title compound (0.19 g, 0.40 mmol, 72% yield). $^1$H NMR (300 MHz, CDCl$_3$) δ ppm 1.28 (s, 6H) 1.38-1.51 (m, 4H) 1.42 (s, 9H) 1.97-2.11 (m, 1H) 3.32 (dt, J=10.9, 3.6 Hz, 2H) 3.75 (s, 3H) 3.92-3.99 (m, 2H) 4.03 (s, 2H) 4.16 (d, J=7.1 Hz, 2H) 5.94 (s, 1H) 6.96-7.01 (m, 2H) 7.57 (dd, J=8.5, 2.2 Hz, 1H) 8.12 (d, J=2.0 Hz, 1H); MS (DCI/NH$_3$) m/z 469 (M+H)$^+$; Anal. calculated for C$_{26}$H$_{36}$N$_4$O$_4$: Calc: C, 66.64; H, 7.74; N, 11.96. Found: C, 66.96; H, 7.81; N, 11.95.

Example 103

N-{(3E)-5-tert-butyl-1-methyl-2-[(2R)-tetrahydrofuran-2-ylmethyl]-1,2-dihydro-3H-pyrazol-3-ylidene}-2-{[(1S,2S)-2-hydroxy-1-methylpropyl]oxy}-5-(trifluoromethyl)benzamide The title compound was prepared using the procedure as described in Example 1F substituting (2S,3S)-butane-2,3-diol for (R)-(tetrahydrofuran-2-yl)methanol. $^1$H NMR (500 MHz, chloroform-d) δ ppm 1.17 (d, J=6.10 Hz, 3H) 1.34-1.52 (m, 9H) 1.61 (s, 3H) 1.71-1.79 (m, 2H) 1.80-1.89 (m, 1H) 1.97-2.10 (m, 1H) 3.60-3.79 (m, 2H) 3.82-3.94 (m, 1H) 3.88 (s, 3H) 3.99-4.08 (m, 1H) 4.09-4.21 (m, 1H) 4.35 (dd, J=15.41, 5.65 Hz, 1H) 4.44-4.55 (m, 1H) 6.95-7.14 (m, 2H) 7.30 (s, 1H) 7.50 (d, J=7.93 Hz, 1H) 8.04 (s, 1H); MS (DCI/NH$_3$) m/z 498 (M+H)$^+$.

Example 104

N-{(3E)-5-tert-butyl-1-methyl-2-[(2R)-tetrahydrofuran-2-ylmethyl]-1,2-dihydro-3H-pyrazol-3-ylidene}-2-{[(1R,2R)-2-hydroxy-1-methylpropyl]oxy}-5-(trifluoromethyl)benzamide The title compound was prepared using the procedure as described in Example 1F substituting (2R,3R)-butane-2,3-diol for (R)-(tetrahydrofuran-2-yl)methanol. $^1$H NMR (500 MHz, chloroform-d) δ ppm 1.17 (d, J=6.10 Hz, 3H) 1.44 (s, 9H) 1.45 (s, 3H) 1.64-1.72 (m, 1H) 1.74-1.91 (m, 2H) 1.97-2.07 (m, 1H) 3.67-3.82 (m, 2H) 3.83-3.93 (m, 1H) 3.83-3.95 (m, 3H) 4.00-4.08 (m, 1H) 4.16-4.26 (m, 2H) 4.59 (d, J=12.21 Hz, 1H) 6.93-7.11 (m, 2H) 7.30 (s, 1H) 7.50 (d, J=7.93 Hz, 1H) 8.04 (s, 1H); MS (DCI/NH$_3$) m/z 498 (M+H)$^+$.

Example 105

2-{[(2S)-3-(tert-butylamino)-2-hydroxypropyl]oxy}-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was prepared using the procedure as described in Example 1F substituting (S)-3-(tert-butylamino) propane-1,2-diol for (R)-(tetrahydrofuran-2-yl)methanol. $^1$H NMR (500 MHz, chloroform-d) δ ppm 1.37-1.46 (m, 9H) 1.50 (s, 9H) 1.54-1.65 (m, 1H) 1.75-1.96 (m, 2H) 1.96-2.17 (m, 1H) 1.96-2.17 (m, 1H) 3.09 (s, 1H) 3.24 (s, 1H) 3.63-3.79 (m, 2H) 3.99 (s, 1H) 4.07-4.17 (m, 1H) 4.08-4.19 (m, 3H) 4.35-4.54 (m, 2H) 4.66 (s, 1H) 4.89 (s, 1H) 6.94 (s, 1H) 7.15 (d, J=8.54 Hz, 1H) 7.82 (dd, J=8.54, 2.14 Hz, 1H) 8.41 (d, J=2.14 Hz, 1H) 8.94 (s, 1H) 9.21 (s, 1H) 10.56 (s, 1H); MS (DCI/NH$_3$) m/z 555 (M+H)$^+$.

Example 106

N-[(3E)-5-tert-butyl-2-(cyclopentylmethyl)-1-methyl-1,2-dihydro-3H-pyrazol-3-ylidene]-2-(2-hydroxy-2-methylpropoxy)-5-(trifluoromethyl)benzamide

Example 106A

N-[(3-tert-butyl-1-(cyclopentylmethyl)-1H-pyrazol-5-yl]-2-fluoro-5-(trifluoromethyl)benzamide To a solution of Example 127B (8.5 g, 38.4 mmol) and triethylamine (16.1 mL, 115 mmol) in THF (75 mL) at ambient temperature was added 2-fluoro-5-(trifluoromethyl)benzoyl chloride (5.82 mL, 38.4 mmol) dropwise over 1 minute. After 2 hours, the mixture was partitioned between saturated aqueous NaHCO$_3$ (10 mL) and EtOAc (10 mL). The layers were separated and the aqueous phase was extracted with EtOAc (3×5 mL). The combined organics were dried over anhydrous Na$_2$SO$_4$, filtered, concentrated under reduced pressure. The residue was purified by chromatography (SiO$_2$, 70% hexanes/EtOAc) to afford the title compound (12 g, 29.2 mmol, 76% yield). MS (DCI/NH$_3$) m/z 412.3 (M+H)$^+$.

Example 106B

N-[(3E)-5-tert-butyl-2-(cyclopentylmethyl)-1-methyl-1,2-dihydro-3H-pyrazol-3-ylidene]-2-fluoro-5-(trifluoromethyl)benzamide A mixture of Example 106A (12 g, 29.2 mmol) and dimethyl sulfate (8.36 mL, 87 mmol) in Toluene (20 mL) was warmed to 90° C. 48 hours then cooled to ambient temperature. The mixture concentrated under reduced pressure and the residue purified by chromatography (SiO$_2$, 50% hexanes/EtOAc to 100% EtOAc to 9:1:0.1 EtOAc:MeOH:Et$_3$N) to give the title compound (7.83 g, 18.40 mmol, 63.1% yield). MS (DCI/NH$_3$) m/z 426.3 (M+H)$^+$.

Example 106C

N-[(3E)-5-tert-butyl-2-(cyclopentylmethyl)-1-methyl-1,2-dihydro-3H-pyrazol-3-ylidene]-2-(2-hydroxy-2-methylpropoxy)-5-(trifluoromethyl)benzamide A solution of potassium tert-butoxide (2.8 mL, 1 M in THF) was added to Example 81D (0.13 g, 1.5 mmol). After 10 minutes, a solution of Example 106B (0.3 g, 0.7 mmol) in THF (0.5 mL) was added. The mixture was stirred for 2 hours then partitioned between EtOAc and saturated aqueous NaHCO$_3$. The organic extract was washed with water and brine, dried with MgSO$_4$, filtered, and concentrated under reduced pressure. The residue was purified by chromatography (Solvent A=hexane:EtOAc:Et$_3$N (2:2:0.2), Solvent B=hexane:EtOAc:MeOH:Et$_3$N (2:2:1:0.2), 0-50% solvent B/solvent A gradient over 500 mL) to afford the title compound (0.2 g, 0.4 mmol, 57% yield). $^1$H NMR (500 MHz, Pyridine-d$_5$) δ ppm 1.17 (s, 9H), 1.34-1.43 (m, 4H), 1.47-1.54 (m, 9H), 1.57-1.65 (m, 2H), 2.24-2.37 (m, 1H), 3.77 (s, 3H), 4.20 (s, 2H), 4.33 (d, J=7.3 Hz, 2H), 7.24 (d, J=8.5 Hz, 1H), 7.37 (s, 1H), 7.69 (dd, J=8.5, 2.4 Hz, 1H), 8.62 (d, J=2.1 Hz, 1H); MS (DCI/NH$_3$) m/z 496.4 (M+H)$^+$. Anal. calculated for C$_{26}$H$_{36}$F$_3$N$_3$O$_3$: C, 63.01; H, 7.32; N, 8.48. Found: C, 63.09; H, 7.49; N, 8.30.

Example 107

N-{(3E)-5-tert-butyl-1-methyl-2-[(2R)-tetrahydrofuran-2-ylmethyl]-1,2-dihydro-3H-pyrazol-3-ylidene}-2-{[(2S)-2-hydroxybut-3-enyl]oxy}-5-(trifluoromethyl)benzamide The title compound was prepared using the procedure as described in Example 1F substituting (S)-but-3-ene-1,2-diol for (R)-(tetrahydrofuran-2-yl)methanol. $^1$H NMR (500 MHz, chloroform-d) δ ppm 1.43 (s, 9H) 1.62-1.81 (m, 2H) 1.80-1.93 (m, 1H) 2.04 (dd, J=12.36, 5.03 Hz, 1H) 3.63-3.81 (m, 2H) 3.85-3.95 (m, 3H) 3.89-3.99 (m, 1H) 4.17 (s, 1H) 4.26-4.36 (m, 1H) 4.42 (dd, J=10.22, 2.59 Hz, 1H) 4.47-4.65 (m, 2H) 5.20 (d, J=10.37 Hz, 1H) 5.42 (d, J=17.39 Hz, 1H) 5.77-5.95 (m, 1H) 6.98-7.15 (m, 2H) 7.17 (s, 1H) 7.53 (s, 1H) 8.10 (s, 1H); MS (DCI/NH$_3$) m/z 496 (M+H)$^+$.

Example 108

N-[(3E)-2-butyl-5-tert-butyl-1-methyl-1,2-dihydro-3H-pyrazol-3-ylidene]-5-cyano-2-(2-hydroxy-2-methylpropoxy)benzamide

Example 108A

N-(1-butyl-3-tert-butyl-1H-pyrazol-5-yl)-2,2,2-trifluoroacetamide

To a solution of Example 81A (10 g, 51.2 mmol) and Et$_3$N (21.4 mL, 154 mmol) in CH$_2$Cl$_2$ (100 mL) at 0° C. was added 2,2,2-trifluoroacetic anhydride (7.1 mL, 51.2 mmol) dropwise via syringe pump over 20 minutes. The ice-bath was removed after the addition was complete and the mixture was stirred at ambient temperature for 1 hour. The mixture was concentrated under reduced pressure and was purified by chromatography (SiO$_2$, 40% hexanes/EtOAc) to provide the title compound (13.5 g, 46.3 mmol, 91% yield). MS (DCI/NH$_3$) m/z 292 (M+H)$^+$.

Example 108B

N-[(3E)-2-butyl-5-tert-butyl-1-methyl-1,2-dihydro-3H-pyrazol-3-ylidene]-2,2,2-trifluoroacetamide A mixture of Example 108A (13.5 g, 46.3 mmol) and dimethyl sulfate (13.3 mL, 139 mmol) in toluene (40 mL) was warmed to 90° C. and stirred for 72 hour then cooled to ambient temperature. The mixture concentrated under reduced pressure and purified by column chromatography (SiO$_2$, 50% hexanes/EtOAc to 100% EtOAc to 9:1:0.1 EtOAc:MeOH:Et$_3$N) to afford the title compound (7.3 g, 23.7 mmol, 51% yield). MS (DCI/NH$_3$) m/z 306 (M+H)$^+$.

Example 108C 2-butyl-5-tert-butyl-1-methyl-1,2-dihydro-3H-pyrazol-3-imine

To a solution of Example 108B (7.3 g, 23.7 mmol) in MeOH (35 mL) was added sodium hydroxide (4.8 g, 119 mmol) in water (7 mL). The mixture was warmed to 50° C. for 6 hours then cooled to ambient temperature. The mixture was concentrated under reduced pressure and then diluted with CH$_2$Cl$_2$ (20 mL) and H$_2$O (10 mL). The layers were separated and the aqueous phase was extracted with CH$_2$Cl$_2$ (3×10 mL). The combined organic extracts were dried over anhydrous Na$_2$SO$_4$, filtered and concentrated under reduced pressure to give the title compound (4.9 g, 23.4 mmol, 99% yield). MS (DCI/NH$_3$) m/z 210 (M+H)$^+$.

Example 108D

A mixture of Example 102B (0.53 g, 2.9 mmol) and thionyl chloride (8.4 mL, 115 mmol) was warmed to reflux (90° C.) for 2 hours. The mixture was cooled to ambient temperature and concentrated under reduced pressure. The residue was diluted with toluene (10 mL) and was concentrated under reduced pressure (3×) to provide the acid chloride. To a solution of Example 108C (0.60 g, 2.9 mmol) and Et$_3$N (1.2 mL, 8.6 mmol) in THF (10 mL) was added the freshly prepared acid chloride. The mixture was allowed to stir at ambient temperature for 4 hours then partitioned between saturated aqueous NaHCO$_3$ (10 mL) and EtOAc (10 mL). The layers were separated and the aqueous phase was extracted EtOAc (3×10 mL). The combined organic extracts were dried over Na$_2$SO$_4$, filtered and concentrated under reduced pressure. Purification by column chromatography (SiO$_2$, 50% hexanes in EtOAc to 100% EtOAc to 9:1:0.1 EtOAc:MeOH:Et$_3$N) afforded the title compound (0.70 g, 2.0 mmol, 69% yield). MS (DCI/NH$_3$) m/z 357 (M+H)$^+$.

Example 108E

N-[(3E)-2-butyl-5-tert-butyl-1-methyl-1,2-dihydro-3H-pyrazol-3-ylidene]-5-cyano-2-(2-hydroxy-2-methylpropoxy)benzamide To a solution of Example 81D (0.21 g, 2.4 mmol) in THF (5 mL) at ambient temperature was added potassium tert-butoxide (0.45 g, 4.0 mmol). The mixture was allowed to stir for 20 min at ambient temperature then a solution of Example 108D (0.48 g, 1.3 mmol) in THF (5 mL) was added via cannula. The mixture was stirred at ambient temperature for 3 h then the mixture was quenched with saturated aqueous NaHCO$_3$ (5 mL) and was diluted with EtOAc (10 mL). The layers were separated and the aqueous phase was extracted with EtOAc (3×5 mL). The combined organic extracts were dried over anhydrous Na$_2$SO$_4$, filtered and concentrated under educed pressure. Purification by column chromatography (SiO$_2$, 50% hexanes/EtOAc then 100% EtOAc then 9:1:0.1 EtOAc:MeOH:Et$_3$N) afforded the title compound (0.50 g, 1.2 mmol, 87% yield). $^1$H NMR (300 MHz, CDCl$_3$) δ ppm 0.96 (t, J=7.3 Hz, 3H) 1.28 (s, 6H) 1.31-1.40 (m, 2H) 1.42 (s, 9H) 1.61-1.73 (m, 2H) 3.77 (s, 3H) 4.02 (s, 2H) 4.27 (t, J=7.3 Hz, 2H) 6.01 (s, 1H) 6.98 (d, J=8.7 Hz, 1H) 6.98 (s, 1H) 7.55 (dd, J=8.3, 2.0 Hz, 1H) 8.13 (d, J=2.0 Hz, 1H); MS (DCI/NH$_3$) m/z 427 (M+H)$^+$; Anal. calculated for C$_{24}$H$_{34}$N$_4$O$_3$: Calc: C, 67.58; H, 8.03; N, 13.13. Found: C, 67.41; H, 7.80; N, 13.07.

Example 109

N-{(3E)-5-tert-butyl-1-methyl-2-[(2R)-tetrahydrofuran-2-ylmethyl]-1,2-dihydro-3H-pyrazol-3-ylidene}-2-{[(2S)-2-hydroxybutyl]oxy}-5-(trifluoromethyl)benzamide A suspension of Example 107 (40 mg, 0.081 mmol) and 10% Pd/C (20 mg) was stirred under an atmosphere of hydrogen (balloon) at room temperature for 2 hours. The mixture was filtered through Celite, and the filtrate was concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 27 mg (67%) of the title compound. $^1$H NMR (500 MHz, chloroform-d) δ ppm 1.00 (t, J=7.32 Hz, 3H) 1.42 (s, 9H) 1.60 (s, 3H) 1.65-1.80 (m, 2H) 1.81-1.91 (m, 1H) 1.97-2.08 (m, 1H) 3.66-3.81 (m, 2H) 3.85-3.92 (m, 3H) 3.87-3.97 (m, 1H) 4.17 (s, 1H) 4.31 (d, J=5.49 Hz, 1H) 4.39 (d, J=7.93 Hz, 1H) 4.55 (d, J=14.34 Hz, 1H) 6.62 (s, 1H) 6.95-7.16 (m, 2H) 7.51 (s, 1H) 8.09 (s, 1H); MS (DCI/NH$_3$) m/z 498 (M+H)$^+$.

Example 110

N-{(3E)-5-tert-butyl-1-methyl-2-[(2R)-tetrahydrofuran-2-ylmethyl]-1,2-dihydro-3H-pyrazol-3-ylidene}-2-(2-hydroxy-2-methylbutoxy)-5-(trifluoromethyl)benzamide The title compound was prepared using the procedure as described in Example 1F substituting 2-methylbutane-1,2-diol for (R)-(tetrahydrofuran-2-yl)methanol. $^1$H NMR (500 MHz, chloroform-d) δ ppm 0.90-0.96 (m, 3H) 1.21 (s, 3H) 1.42 (s, 9H) 1.58-1.66 (m, 2H) 1.69-1.72 (m, 1H) 1.72-1.79 (m, 1H) 1.79-1.90 (m, 1H) 1.96-2.08 (m, 1H) 3.65-3.80 (m, 2H) 3.87 (s, 3H) 3.93-4.04 (m, 1H) 4.04-4.15 (m, 1H) 4.17 (dd, J=6.10, 2.44 Hz, 1H) 4.22-4.34 (m, 1H) 4.45-4.63 (m, 1H) 6.04 (s, 1H) 6.87-7.10 (m, 2H) 7.40-7.63 (m, 1H) 8.07 (s, 1H); MS (DCI/NH$_3$) m/z 512 (M+H)$^+$.

Example 111

N-{(3E)-5-tert-butyl-1-methyl-2-[(2R)-tetrahydrofuran-2-ylmethyl]-1,2-dihydro-3H-pyrazol-3-ylidene}-2-{[(2S)-2-hydroxy-3-methylbutyl]oxy}-5-(trifluoromethyl)benzamide The title compound was prepared using the procedure as described in Example 1F substituting (S)-3-methylbutane-1,2-diol for (R)-(tetrahydrofuran-2-yl)methanol. $^1$H NMR (500 MHz, chloroform-d) δ ppm 0.98 (dd, J=23.50, 6.71 Hz, 6H) 1.41 (s, 9H) 1.66-1.79 (m, 3H) 1.78-1.92 (m, 1H) 1.98-2.08 (m, 1H) 3.66-3.73 (m, 2H) 3.74-3.80 (m, 1H) 3.88 (s, 3H) 3.97 (t, J=9.92 Hz, 1H) 4.11-4.24 (m, 1H) 4.29 (dd, J=15.26, 5.80 Hz, 1H) 4.39-4.50 (m, 1H) 4.56 (dd, J=15.10, 2.29 Hz, 1H) 6.56 (s, 1H) 7.00-7.12 (m, 2H) 7.52 (d, J=7.93 Hz, 1H) 8.10 (s, 1H); MS (DCI/NH$_3$) m/z 512 (M+H)$^+$.

Example 112

N-{(3E)-5-tert-butyl-1-methyl-2-[(2R)-tetrahydrofuran-2-ylmethyl]-1,2-dihydro-3H-pyrazol-3-ylidene}-2-{[(2S)-2-hydroxy-3,3-dimethylbutyl]oxy}-5-(trifluoromethyl)benzamide The title compound was prepared using the procedure as described in Example 1F substituting (S)-3,3-dimethylbutane-1,2-diol for (R)-(tetrahydrofuran-2-yl)methanol. $^1$H NMR (500 MHz, chloroform-d) δ ppm 0.96 (s, 9H) 1.24-1.31 (m, 1H) 1.42 (s, 9H) 1.66-1.77 (m, 2H) 1.85 (dd, J=12.82, 6.41 Hz, 1H) 1.98-2.07 (m, 1H) 3.61-3.69 (m, 1H) 3.67-3.73 (m, 1H) 3.72-3.80 (m, 1H) 3.88 (s, 3H) 3.91-3.99 (m, 1H) 4.17 (d, J=6.41 Hz, 1H) 4.28 (dd, J=15.26, 5.80 Hz, 1H) 4.52-4.62 (m, 1H) 6.54 (s, 1H) 6.97-7.12 (m, 2H) 7.52 (d, J=8.24 Hz, 1H) 8.11 (s, 1H); MS (DCI/NH$_3$) m/z 526 (M+H)$^+$.

Example 113

N-[(3E)-5-tert-butyl-2-(cyclobutylmethyl)-1-methyl-1,2-dihydro-3H-pyrazol-3-ylidene]-5-cyano-2-(2-hydroxy-2-methylpropoxy)benzamide Example 113A N-(3-tert-butyl-1-(cyclobutylmethyl)-1H-pyrazol-5-yl)-2,2,2-trifluoroacetamide To a solution of Example 86B (12.3 g, 59.5 mmol) and Et$_3$N (24.9 mL, 179 mmol) in CH$_2$Cl$_2$ (150 mL) at 0° C. was added 2,2,2-trifluoroacetic anhydride (8.3 mL, 59.5 mmol) dropwise via syringe pump over 20 minutes. The ice-bath was removed after the addition was complete and the mixture was stirred at ambient temperature for 1 hour. The mixture was concentrated under reduced pressure and was purified by column chromatography (SiO$_2$, 40% hexanes/EtOAc) to provide the title compound (16.2 g, 53.4 mmol, 90% yield). MS (DCI/NH$_3$) m/z 427 (M+H)$^+$.

Example 113B

N-[(3E)-5-tert-butyl-2-(cyclobutylmethyl)-1-methyl-1,2-dihydro-3H-pyrazol-3-ylidene]-2,2,2-trifluoroacetamide To a solution of Example 113A (16.2 g, 53.4 mmol) in toluene (100 mL) was added methyl trifluoromethanesulfonate (10.1 g, 61.4 mmol). The mixture was warmed to 100° C. for 16 hours. The mixture was cooled to ambient temperature then was diluted with water (20 mL) and acetone (~200 mL) was added until solution became homogeneous. This solution was allowed to stir for 1 hour then concentrated NH$_4$OH (30 mL) was added. The mixture was stirred for 30 min then the mixture was partially concentrated under reduced pressure. The mixture was diluted with EtOAc (30 mL) and brine (15 mL) and the layers were separated. The aqueous phase was extracted with EtOAc (3×10 mL). The combined organic extracts were dried over anhydrous Na$_2$SO$_4$, filtered and concentrated under reduced pressure. Purification by column chromatography (SiO$_2$, 50% hex/EtOAc to 100% EtOAc to 10% MeOH in EtOAc) afforded the title compound (9.8 g, 31 mmol, 58% yield). MS (DCI/NH$_3$) m/z 318 (M+H)$^+$.

Example 113C 5-tert-butyl-2-(cyclobutylmethyl)-1-methyl-1H-pyrazol-3(2H)-imine

To a solution of Example 113B (9.8 g, 31 mmol) in MeOH (50 mL) was added sodium hydroxide (6.1 g, 154 mmol) in water (10 mL). The mixture was warmed to 50° C. and stirred for 4 hours then cooled to ambient temperature. The mixture was concentrated under reduced pressure and then diluted with CH$_2$Cl$_2$ (20 mL) and H$_2$O (10 mL). The layers were separated and the aqueous phase was extracted with CH$_2$Cl$_2$ (3×5 mL). The combined organic extracts were dried over anhydrous Na$_2$SO$_4$, filtered and concentrated under reduced pressure to give the crude title compound (7.8 g, 35.2 mmol, 115% yield), which was carried on without purification. MS (DCI/NH$_3$) m/z 222 (M+H)$^+$.

Example 113D

N-[(3E)-5-tert-butyl-2-(cyclobutylmethyl)-1-methyl-1,2-dihydro-3H-pyrazol-3-ylidene]-5-cyano-2-fluorobenzamide A mixture of Example 102B (0.65 g, 3.5 mmol) and thionyl chloride (10.3 mL, 141 mmol) was warmed to reflux (90° C.) and stirred for 2 hours. The mixture was cooled to ambient temperature and concentrated under reduced pressure. This crude material was diluted with toluene (10 mL) and was concentrated under reduced pressure (3×) to provide the acid chloride. To a solution of Example 113C (0.78 g, 3.52 mmol) and Et$_3$N (1.5 mL, 10.6 mmol) in THF (10 mL) was added acid chloride. The mixture was allowed to stir at ambient temperature for 4 hours then was quenched with saturated aqueous NaHCO$_3$ (10 mL) and diluted with EtOAc (10 mL). The layers were separated and the aqueous phase was extracted EtOAc (3×10 mL). The combined organic extracts were dried over Na$_2$SO$_4$, filtered, and concentrated under reduced pressure. Purification by column chromatography (SiO$_2$, 50% hexanes in EtOAc to 100% EtOAc to 9:1:0.1 EtOAc:MeOH:Et$_3$N) afforded the title compound (1.1 g, 3.0 mmol, 84% yield). MS (ESI$^+$) m/z 369 (M+H)$^+$.

Example 113E

N-[(3E)-5-tert-butyl-2-(cyclobutylmethyl)-1-methyl-1,2-dihydro-3H-pyrazol-3-ylidene]-5-cyano-2-(2-hydroxy-2-methylpropoxy)benzamide To a solution of Example 81D (0.26 g, 2.9 mmol) in THF (10 mL) at ambient temperature was added potassium tert-butoxide (0.55 g, 4.9 mmol). The mixture was allowed to stir for 20 minutes at ambient temperature then a solution of Example 113D (0.60 g, 1.6 mmol) in THF (5 mL) was added via cannula. The mixture was stirred at ambient temperature for 3 hours then the mixture was quenched with saturated aqueous NaHCO$_3$ (5 mL) and was diluted with EtOAc (10 mL). The layers were separated and the aqueous phase was extracted with EtOAc (3×5 mL). The combined organic extracts were dried over anhydrous Na$_2$SO$_4$, filtered, concentrated and purified via column chromatography (SiO$_2$, 50% hexanes/EtOAc then 100% EtOAc then 9:1:0.1 EtOAc:MeOH:Et$_3$N) to afford the title compound (0.43 g, 0.98 mmol, 60% yield). $^1$H NMR (300 MHz, CDCl$_3$) δ ppm 1.29 (s, 6H) 1.41 (s, 9H) 1.80-1.92 (m, 4H) 1.98-2.07 (m, 2H) 2.53-2.73 (m, 1H) 3.73 (s, 3H) 4.03 (s, 2H) 4.33 (d, J=7.1 Hz, 2H) 6.04 (s, 1H) 6.99 (d, J=8.3 Hz, 1H) 6.99 (s, 1H) 7.56 (dd, J=8.5, 2.2 Hz, 1H) 8.15 (d, J=2.0 Hz, 1H); MS (ESI$^+$) m/z 439 (M+H)$^+$; Anal. calculated for C$_{25}$H$_{34}$N$_4$O$_3$: Calc: C, 68.47; H, 7.81; N, 12.78. Found: C, 68.27; H, 7.47; N, 12.68.

Example 114

N-[(3E)-2-(cyclopentylmethyl)-5-isopropyl-1-methyl-1,2-dihydro-3H-pyrazol-3-ylidene]-2-(2-hydroxy-2-methylpropoxy)-5-(trifluoromethyl)benzamide

Example 114A cyclopentylmethyl 4-methylbenzenesulfonate

A mixture of cyclopentylmethanol (2.5 g, 25 mmol), 4-methylbenzene-1-sulfonyl chloride (5.23 g, 27.5 mmol) in $CH_2Cl_2$ (50 mL) at 0° C. was treated with triethylamine (4.17 mL, 30 mmol) and the mixture was allowed to warm to room temperature for 8 hours. The mixture was then washed with water, brine, dried with anhydrous $MgSO_4$ and concentrated under reduced pressure to afford 6.5 g the title compound. MS ($DCI/NH_3$) m/z 272 $(M+NH_4)^+$.

Example 114B (E)-N'-(3-isopropyl-1H-pyrazol-5-yl)-N,N-dimethylformimidamide

A mixture of 3-isopropyl-1H-pyrazol-5-amine (1.25 g, 10 mmol) and 1,1-dimethoxy-N,N-dimethylmethanamine (12 g, 100 mmol) in dioxane (30 mL) was heated at reflux for 10 hours. The mixture was concentrated under reduced pressure and the residue was purified by chromatography ($CH_2Cl_2$-MeOH 9:1) to afford 1.75 g of title compound. MS ($DCI/NH_3$) m/z 181 $(M+H)^+$.

Example 114C (E)-N'-(1-(cyclopentylmethyl)-3-isopropyl-1H-pyrazol-5-yl)-N,N-dimethylformimidamide A mixture of Example 114A (6.3 g, 25 mmol), Example 114B (3.61 g, 20 mmol), potassium carbonate (5.53 g, 40 mmol), tetrabutylammonium iodide (30 mg, 0.08 mmol), tetrabutylammonium hydrogen sulfate (30 mg, 0.09 mmol) in toluene (75 mL) was heated at reflux for 16 hours. The mixture was then diluted with ethyl acetate and washed with water, brine, dried with $MgSO_4$ and concentrated under reduced pressure. The residue was purified by chromatography ($CH_2Cl_2$-MeOH 9:1) to afford 2 g of the title compound. MS ($DCI/NH_3$) m/z 263 $(M+H)^+$.

Example 114D 1-(cyclopentylmethyl)-3-isopropyl-1H-pyrazol-5-amine

A mixture of Example 114C (1.88 g, 7.16 mmol), hydrazine hydrate (0.28 g, 8.6 mmol) and acetic acid (0.41 mL, 7.16 mmol) in dioxane (20 mL) was heated at reflux for 5 hours. The mixture was then concentrated under reduced pressure, the residue was treated with saturated $NaHCO_3$ solution and extracted with EtOAc to afford 1.3 g of the title compound. MS ($DCI/NH_3$) m/z 208 $(M+H)^+$.

Example 114E

N-[(3E)-2-(cyclopentylmethyl)-5-isopropyl-1,2-dihydro-3H-pyrazol-3-ylidene]-2-fluoro-5-(trifluoromethyl)benzamide To a solution of Example 114D (1.5 g, 7.24 mmol) and $NaHCO_3$ (0.91 g, 10.9 mmol) in ethyl acetate (20 mL) and water (15 mL) was added dropwise a solution of 2-fluoro-(5-trifluoromethyl)benzoyl chloride (1.8 g, 8 mmol) in EtOAc (5 mL) and the mixture was left at room temperature with vigorous stirring. The acetate layer was washed with brine, dried with $MgSO_4$ and concentrated under reduced pressure. The residue was purified by chromatography (Hexane-EtOAc 2:1) to afford 2.5 g of the title compound. $^1H$ NMR (300 MHz, DMSO-$d_6$) δ ppm 1.08-1.30 (m, 7H), 1.37-1.71 (m, 7H), 2.25-2.38 (m, 1H), 2.71-2.95 (m, 1H), 3.90 (d, J=7.5 Hz, 2H), 6.18 (s, 1H), 7.65 (t, J=8.9 Hz, 1H), 7.93-8.09 (m, 2H), 10.49 (s, 1H). MS ($DCI/NH_3$) m/z 398 $(M+H)^+$.

Example 114F

N-[(3E)-2-(cyclopentylmethyl)-5-isopropyl-1-methyl-1,2-dihydro-3H-pyrazol-3-ylidene]-2-fluoro-5-(trifluoromethyl)benzamide A neat mixture Example 114E (2 g, 5.03 mmol) and diphenyl-methylsulfonium tetrafluoroborate (2.9 g, 10.07 mmol) was heated at 80° C. for 33 hours. The residue was dissolved in $CH_2Cl_2$ and washed with saturated $NaHCO_3$ solution, brine, dried with $MgSO_4$ and concentrated under reduced pressure. Purification by chromatography (EtOAc-MeOH 9:1) gave 1.4 g of the title compound. MS ($DCI/NH_3$) m/z 412 $(M+H)^+$.

Example 114G

N-[(3E)-2-(cyclopentylmethyl)-5-isopropyl-1-methyl-1,2-dihydro-3H-pyrazol-3-ylidene]-2-(2-hydroxy-2-methylpropoxy)-5-(trifluoromethyl)benzamide To a mixture of Example 114F (206 mg, 0.50 mmol) and Example 81D (90 mg, 1.0 mmol) in THF (15 mL) was added a 1N THF solution of potassium tert-butoxide (1.3 mL, 0.65 mmol) and the mixture was heated at 45° C. for 3 hours. The mixture was concentrated under reduced pressure and the residue was partitioned between EtOAc and water. The acetate layer was washed with brine, dried with $MgSO_4$ and concentrated under reduced pressure. The residue was purified by chromatography ($CH_2Cl_2$-MeOH 9:1) to afford 70 mg of the title compound. $^1H$ NMR (300 MHz, $CDCl_3$) δ ppm 1.22-1.42 (m, 14H), 1.49-1.81 (m, 6H), 2.21-2.37 (m, 1H), 2.78-2.97 (m, 1H), 3.63 (s, 3H), 4.04 (s, 2H), 4.21 (d, J=7.5 Hz, 2H), 6.31 (s, 1H), 6.92-7.06 (m, 2H), 7.51 (d, J=8.5 Hz, 1H), 8.14 (d, J=1.7 Hz, 1H); MS ($ESI^+$) m/z 482 $(M+H)^+$.

Example 115

N-[(3E)-5-tert-butyl-1-methyl-2-pentyl-1,2-dihydro-3H-pyrazol-3-ylidene]-5-cyano-2-(2-hydroxy-2-methylpropoxy)benzamide

Example 115A

N-[(3E)-5-tert-butyl-1-methyl-2-pentyl-1,2-dihydro-3H-pyrazol-3-ylidene]-5-cyano-2-fluorobenzamide A mixture of Example 102B (0.66 g, 3.6 mmol) and thionyl chloride (10.5 mL, 143 mmol) was warmed to reflux (90° C.) and stirred for 2 hours. The mixture was cooled to ambient temperature and was concentrated under reduced pressure. This crude material was diluted with toluene (10 mL) and was concentrated under reduced pressure (3×) to provide the crude acid chloride. To a solution of Example 99E (0.80 g, 3.6 mmol) and Et₃N (1.5 mL, 10.8 mmol) in THF (10 mL) was added the acid chloride. The mixture was allowed to stir at ambient temperature for 4 hours then partitioned between saturated aqueous NaHCO₃ (10 mL) and EtOAc (10 mL). The layers were separated and the aqueous phase was extracted EtOAc (3×10 mL). The combined organic extracts were dried over Na₂SO₄, filtered, and concentrated under reduced pressure. Purification by column chromatography (SiO₂, 50% hexanes in EtOAc to 100% EtOAc to 9:1:0.1 EtOAc:MeOH:Et₃N) afforded the title compound (0.72 g, 1.9 mmol, 54% yield). MS (DCI/NH₃) m/z 371 (M+H)⁺.

Example 115B

N-[(3E)-5-tert-butyl-1-methyl-2-pentyl-1,2-dihydro-3H-pyrazol-3-ylidene]-5-cyano-2-(2-hydroxy-2-methylpropoxy)benzamide To a solution of Example 81D (0.19 g, 2.1 mmol) in THF (10 mL) at ambient temperature was added potassium tert-butoxide (0.41 g, 3.6 mmol). The mixture was allowed to stir for 20 minutes at ambient temperature then a solution of Example 115A (0.45 g, 1.2 mmol) in THF (5 mL) was added via cannula. The mixture was stirred at ambient temperature for 3 hours then the mixture was quenched with saturated aqueous NaHCO₃ (5 mL) and was diluted with EtOAc (10 mL). The layers were separated and the aqueous phase was extracted with EtOAc (3×5 mL). The combined organic extracts were dried over anhydrous Na₂SO₄, filtered, concentrated and purified via column chromatography (SiO₂, 50% hexanes/EtOAc then 100% EtOAc then 9:1:0.1 EtOAc:MeOH:Et₃N) to provide the title compound (0.45 g, 1.0 mmol, 84% yield). ¹H NMR (300 MHz, CDCl₃) δ ppm 0.90 (t, J=7.0 Hz, 3H) 1.26-1.44 (m, 4H) 1.28 (s, 6H) 1.42 (s, 9H) 1.61-1.77 (m, 2H) 3.77 (s, 3H) 4.03 (s, 2H) 4.20-4.32 (m, 2H) 6.04 (s, 1H) 6.98 (d, J=8.8 Hz, 1H) 6.98 (s, 1H) 7.55 (dd, J=8.6, 2.2 Hz, 1H) 8.13 (d, J=2.4 Hz, 1H); MS (ESI⁺) m/z 441 (M+H)⁺; Anal. calculated for C₂₅H₃₆N₄O₃: Calc: C, 68.15; H, 8.24; N, 12.72. Found: C, 68.33; H, 8.41; N, 12.64.

Example 116

N-{(3E)-5-tert-butyl-1-methyl-2-[(2R)-tetrahydrofuran-2-ylmethyl]-1,2-dihydro-3H-pyrazol-3-ylidene}-2-(3-hydroxy-2,2-dimethylpropoxy)-5-(trifluoromethyl)benzamide The title compound was prepared using the procedure as described in Example 1F, substituting 2,2-dimethylpropane-1,3-diol for (R)-(tetrahydrofuran-2-yl)methanol. ¹H NMR (500 MHz, chloroform-d) δ ppm 1.03 (d, J=2.44 Hz, 6H) 1.36-1.46 (m, 9H) 1.67-1.80 (m, 2H) 1.78-1.90 (m, 1H) 1.96-2.07 (m, 1H) 3.49-3.63 (m, 2H) 3.67-3.83 (m, 2H) 3.85 (s, 1H) 3.84-3.91 (m, 3H) 4.12-4.23 (m, 1H) 4.29 (dd, J=15.26, 5.80 Hz, 1H) 4.54 (dd, J=15.41, 2.90 Hz, 1H) 5.29 (t, J=7.02 Hz, 1H) 6.86-7.11 (m, 2H) 7.52 (dd, J=8.54, 2.14 Hz, 1H) 8.21 (d, J=2.14 Hz, 1H); MS (DCI/NH₃) m/z 512 (M+H)⁺.

Example 117

N-{(3E)-5-tert-butyl-1-methyl-2-[(2R)-tetrahydrofuran-2-ylmethyl]-1,2-dihydro-3H-pyrazol-3-ylidene}-2-(2-ethyl-2-hydroxybutoxy)-5-(trifluoromethyl)benzamide Example 117A 2-ethylbutane-1,2-diol A solution of 2-ethyl-2-hydroxybutanoic acid (1 g, 7.57 mmol) in THF (30 mL) was treated with lithium aluminum hydride (431 mg, 11.4 mmol). The reaction mixture was stirred at room temperature for 12 hours then quenched with 15% aqueous NaOH, followed by water. The mixture was filtered through Celite. The aqueous phase was extracted with isopropanol/CH₂Cl₂ (1:3) (2×100 mL). The organic extracts were combined, dried with MgSO₄, filtered, and concentrated under reduced pressure. The residue was purified by chromatography to afford 297 mg, (34%) of the title compound. ¹H NMR (500 MHz, DMSO-d₆) δ ppm 0.80 (t, J=7.48 Hz, 3H) 0.97 (s, 3H) 1.35 (q, J=7.53 Hz, 2H) 3.08-3.21 (m, 2H) 3.91 (s, 1H) 4.41 (t, J=5.65 Hz, 1H).

Example 117B

N-{(3E)-5-tert-butyl-1-methyl-2-[(2R)-tetrahydrofuran-2-ylmethyl]-1,2-dihydro-3H-pyrazol-3-ylidene}-2-(2-ethyl-2-hydroxybutoxy)-5-(trifluoromethyl)benzamide The title compound was prepared as described in Example 1F, substituting Example 117A for (R)-(tetrahydrofuran-2-yl)methanol. ¹H NMR (500 MHz, chloroform-d) δ ppm 0.89 (t, J=7.32 Hz, 6H) 1.42 (s, 9H) 1.55-1.65 (m, 4H) 1.64-1.79 (m, 2H) 1.78-1.92 (m, 1H) 1.92-2.09 (m, 1H) 3.64-3.83 (m, 2H) 3.87 (s, 3H) 4.05 (s, 2H) 4.17 (dd, J=6.26, 2.59 Hz, 1H) 4.28 (dd, J=15.26, 5.80 Hz, 1H) 4.53 (dd, J=15.26, 2.75 Hz, 1H) 5.84 (s, 1H) 6.87-7.09 (m, 2H) 7.51 (dd, J=8.39, 1.68 Hz, 1H) 8.07 (d, J=1.83 Hz, 1H); MS (DCI/NH₃) m/z 526 (M+H)⁺.

Example 118 methyl 3-[2-[({(3E)-5-tert-butyl-1-methyl]-2-[(2R)-tetrahydrofuran-2-ylmethyl-1,2-dihydro-3H-pyrazol-3-ylidene}amino)carbonyl]-4-(trifluoromethyl)phenoxy]-2,2-dimethylpropanoate To a solution of methyl 3-hydroxy-2,2-dimethylpropanoate (0.291 g, 2.199 mmol) in THF (5 mL) at ambient temperature was added sodium hydride (0.064 g, 2.53 mmol). The mixture was allowed to stir for 5 min before Example 1D (0.47 g, 1.1 mmol) was added in one portion. The mixture was quenched with saturated NH₄Cl solution and extracted with EtOAc (3×10 mL). The combined organic extracts were dried over anhydrous Na₂SO₄, filtered, concentrated. The residue was purified by preparative HPLC on a Waters Symmetry C8 column (25 mm×100 mm, 7 µm particle size) using a gradient of 10% to 100% acetonitrile: 10 mM ammonium acetate over 8 min (10 min run time) at a flow rate of 40 mL/min to obtain the title compound (210 mg, 0.39 mmol, 34% yield). ¹H NMR (300 MHz, CDCl₃) δ ppm 1.31 (s, 6H) 1.44 (s, 9H) 1.67-1.86 (m, 3H) 1.97-2.05 (m, 1H) 3.65 (s, 3H) 3.67-3.81 (m, 2H) 3.89 (s, 3H) 4.09 (s, 2H) 4.14-4.17 (m, 1H) 4.27-4.34 (m, 1H) 4.56-4.62 (m, 1H) 6.92 (s, 1H) 6.96 (d, J=8.48 Hz, 1H) 7.47-7.51 (m, 1H) 7.86 (d, J=2.03 Hz, 1H); MS (DCI/NH₃) m/z 540 (M+H)⁺.

Example 119

N-{(3E)-5-tert-butyl-1-methyl-2-[(2R)-tetrahydrofuran-2-ylmethyl]-1,2-dihydro-3H-pyrazol-3-ylidene}-2-(3-hydroxy-2,2,3-trimethylbutoxy)-5-(trifluoromethyl)benzamide To a solution of Example 118 (320 mg, 0.593 mmol) in THF (5 mL) at 0° C. was added methylmagnesium bromide (2.118 mL, 2.97 mmol). The mixture was allowed to warm to room temperature then quenched with saturated NH$_4$Cl solution and extracted with EtOAc. The organics were combined, dried, concentrated, and purified by column chromatography using an Analogix® Intelliflash280™ (SiO$_2$, 15-100% gradient of hexane in solvent B, solvent B=5% triethyl amine, 10% MeOH in ethyl acetate) to afford the title compound (129 mg, 40%). $^1$H NMR (300 MHz, CDCl$_3$) δ ppm 1.07 (s, 6H) 1.22 (s, 6H) 1.41 (s, 9H) 1.69-1.85 (m, 3H) 1.95-2.03 (m, 1H) 3.67-3.80 (m, 2H) 3.84 (s, 3H) 3.88 (s, 2H) 4.15-4.18 (m, 1H) 4.23-4.31 (m, 1H) 4.56 (dd, J=15.27, 2.97 Hz, 1H) 6.91-7.00 (m, 2H) 7.52 (dd, J=8.53, 2.18 Hz, 1H) 8.29 (d, J=1.98 Hz, 1H); MS (DCI/NH$_3$) m/z 540 (M+H)$^+$.

Example 120

N-[(3E)-5-tert-butyl-2-(cyclobutylmethyl)-1-methyl-1,2-dihydro-3H-pyrazol-3-ylidene]-2-{[(2S)-5-oxopyrrolidin-2-yl]methoxy}-5-(trifluoromethyl)benzamide To a solution of (S)-5-(hydroxymethyl)-2-pyrrolidinone (0.25 g, 2.2 mmol) in THF (10 mL) at ambient temperature was added NaH (0.23 g, 5.8 mmol). The mixture was allowed to stir for 20 minutes at ambient temperature then a solution of Example 86D (0.60 g, 1.5 mmol) in THF (5 mL) was added via cannula. The mixture was stirred at 50° C. for 3 hours then was allowed to stir for 16 hours at ambient temperature. An additional equivalent of the (S)-5-(hydroxymethyl)-2-pyrrolidinone and two equivalents of NaH were added. The mixture was allowed to stir at 50° C. for 2 hours. The mixture was cooled to ambient temperature and was quenched with saturated aqueous NaHCO$_3$ (5 mL) and was diluted with EtOAc (10 mL). The layers were separated and the aqueous phase was extracted with EtOAc (3×5 mL). The combined organic extracts were dried over anhydrous Na$_2$SO$_4$, filtered, concentrated and purified via column chromatography (SiO$_2$, 50% hexanes/EtOAc then 100% EtOAc then 9:1:0.1 EtOAc:MeOH:Et$_3$N) to afford the title compound (0.62 g, 1.2 mmol, 84% yield). $^1$H NMR (300 MHz, CDCl$_3$) δ ppm 1.43 (s, 9H) 1.64-1.79 (m, 1H) 1.83-1.95 (m, 4H) 1.96-2.07 (m, 2H) 2.12-2.30 (m, 1H) 2.32-2.40 (m, 2H) 2.57-2.72 (m, 1H) 3.73 (s, 3H) 3.80 (t, J=9.7 Hz, 1H) 4.06-4.20 (m, 1H) 4.31-4.40 (m, 3H) 6.98 (d, J=8.3 Hz, 1H) 7.04 (s, 1H) 7.51 (dd, J=8.7, 2.0 Hz, 1H) 7.82 (s, 1H) 8.06 (d, J=2.4 Hz, 1H); MS (DCI/NH$_3$) m/z 507 (M+H)$^+$; Anal. calculated for C$_{26}$H$_{33}$F$_3$N$_4$O$_3$: Calc: C, 61.65; H, 6.57; N, 11.06. Found: C, 61.26; H, 6.68; N, 11.01.

Example 121

N-{(3E)-5-tert-butyl-1-methyl-2-[(2R)-tetrahydrofuran-2-ylmethyl]-1,2-dihydro-3H-pyrazol-3-ylidene}-2-(2-hydroxy-2-methylpropoxy)-5-nitrobenzamide Example 121A N-{(3E)-5-tert-butyl-1-methyl-2-[(2R)-tetrahydrofuran-2-ylmethyl]-1,2-dihydro-3H-pyrazol-3-ylidene}-2-fluoro-5-nitrobenzamide A solution of Example 89F (0.3 g, 1.096 mmol) in THF (5 mL) was added 2-fluoro-5-nitrobenzoic acid (0.426 g, 2.301 mmol), triethylamine (0.765 ml, 5.48 mmol), and propylphosphonic anhydride solution (1.631 ml, 2.74 mmol) was stirred overnight. The reaction solution was washed with saturated NaHCO$_3$, dried, concentrated and the residue was purified by column chromatography using an Analogix® Intelliflash280™ (SiO$_2$, 15-100% solvent B in hexane, solvent B=5% triethyl amine, 10% MeOH in ethyl acetate)) to afford the title compound (0.41 g, 1.014 mmol, 93% yield). $^1$H NMR (300 MHz, CDCl$_3$) δ ppm 1.44 (s, 9H) 1.76-1.90 (m, 3H) 2.04-2.17 (m, 1H) 3.70-3.82 (m, 2H) 3.92 (s, 3H) 4.22-4.26 (m, 1H) 4.30-4.38 (m, 1H) 4.55-4.62 (m, 1H) 7.09 (s, 1H) 7.17 (t, J=9.32 Hz, 1H) 8.19 (ddd, J=8.72, 3.97, 3.57 Hz, 1H) 8.95 (dd, J=6.35, 3.17 Hz, 1H); MS (DCI/NH$_3$) m/z 405 (M+H)$^+$.

Example 121B meth 3-[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenoxy]-2,2-dimethylpropanoate The title compound was prepared and isolated in 60% yield as described in Example 1F, substituting Example 121A for Example 1E, and substituting Example 81D for (R)-(tetrahydrofuran-2-yl)methanol. $^1$H NMR (300 MHz, CDCl$_3$) δ ppm 1.30 (s, 6H) 1.43 (s, 9H) 1.71-1.87 (m, 3H) 2.06-2.17 (m, 1H) 3.69-3.79 (m, 2H) 3.90 (s, 3H) 4.07 (s, 2H) 4.15-4.24 (m, 1H) 4.26-4.35 (m, 1H) 4.53-4.59 (m, 1H) 6.97-7.02 (m, 2H) 8.17 (dd, J=8.92, 2.97 Hz, 1H) 8.74 (d, J=2.78 Hz, 1H); MS (DCI/NH$_3$) m/z 475 (M+H)$^+$.

Example 122

N-[(3E)-5-tert-butyl-2-(3-methoxypropyl)-1-methyl-1,2-dihydro-3H-pyrazol-3-ylidene]-2-(2-hydroxy-2-methylpropoxy)-5-(trifluoromethyl)benzamide Example 122A 3-methoxypropyl 4-methylbenzenesulfonate To a solution of 3-methoxypropan-1-ol (15.9 mL, 166 mmol) in CH$_2$Cl$_2$ (75 mL) and pyridine (50 mL) was added 4-(dimethylamino)pyridine (1.0 g, 8.3 mmol) followed by p-toluenesulfonyl chloride (31.7 g, 166 mmol). The mixture was allowed to stir at ambient temperature for 72 hours then was quenched with 5% aqueous HCl (20 mL), extracted with CH$_2$Cl$_2$ (3×10 mL). The combined organic extracts were dried over Na$_2$SO$_4$, filtered and concentrated under reduced pressure. Purification by column chromatography (SiO$_2$, 75% hexanes in EtOAc) afforded the title compound (31 g, 127 mmol, 76% yield). MS (DCI/NH$_3$) m/z 262 (M+NH$_4$)$^+$.

Example 122B 3-tert-butyl-1-(3-methoxypropyl)-1H-pyrazol-5-amine

To a solution of Example 122A (31 g, 127 mmol) in EtOH (150 mL) was added hydrazine hydrate (8.0 mL, 165 mmol). The mixture was warmed to reflux (85° C.) and was allowed to stir for 20 hours. The mixture was cooled to ambient temperature then 4,4-dimethyl-3-oxopentanenitrile (20.7 g, 165 mmol) was added and the mixture was again warmed to reflux (85° C.) and was allowed to stir for 6 hours. The mixture was concentrated under reduced pressure and the residue was dissolved in CH$_2$Cl$_2$ (100 mL) and saturated aqueous NaHCO$_3$ (50 mL) was added slowly. The layers were separated and the aqueous phase was extracted with CH$_2$Cl$_2$ (3×10 mL). The combined organic extracts were dried over Na$_2$SO$_4$, filtered and concentrated under reduced pressure.

Purification by column chromatography (SiO$_2$, 50% hexanes in EtOAc to 100% EtOAc to 9:1:0.1 EtOAc:MeOH:Et$_3$N) afforded the title compound (11.4 g, 54.0 mmol, 42.5% yield). MS (DCI/NH$_3$) m/z 212 (M+H)$^+$.

Example 122C

N-(3-tert-butyl-1-(3-methoxypropyl)-1H-pyrazol-5-yl)-2,2,2-trifluoroacetamide

To a solution of Example 122B (11.4 g, 54.0 mmol) and Et$_3$N (22.6 mL, 162 mmol) in CH$_2$Cl$_2$ (130 mL) at 0° C. was added 2,2,2-trifluoroacetic anhydride (8.3 mL, 59.3 mmol) dropwise via syringe pump over 20 min. The ice-bath was removed after the addition was complete and the mixture was stirred at ambient temperature for 1 hour. The mixture was concentrated under reduced pressure and was purified by column chromatography (SiO$_2$, 40% hexanes/EtOAc) to provide the title compound (16.2 g, 52.7 mmol, 98% yield). MS (DCI/NH$_3$) m/z 308 (M+H)$^+$.

Example 122D

N-[(3E)-5-tert-butyl-2-(3-methoxypropyl)-1-methyl-1,2-dihydro-3H-pyrazol-3-ylidene]-2,2,2-trifluoroacetamide To a solution of Example 122C (16.2 g, 52.7 mmol) in toluene (100 mL) was added methyl trifluoromethanesulfonate (8.7 mL, 79 mmol). The mixture was warmed to 100° C. and was allowed to stir for 16 hours. The mixture was cooled to ambient temperature then was diluted with water (30 mL) and acetone (~150 mL) was added until solution became homogeneous. This solution was allowed to stir for 30 minutes then concentrated NH$_4$OH (30 mL) was added. The mixture was stirred for 30 minutes then partially concentrated under reduced pressure, diluted with EtOAc (30 mL) and brine (15 mL) and the layers were separated. The aqueous phase was extracted with EtOAc (3×10 mL). The combined organic extracts were dried over anhydrous Na$_2$SO$_4$, filtered and concentrated under reduced pressure. Purification by column chromatography (SiO$_2$, 50% hex/EtOAc to 100% EtOAc to 10% MeOH in EtOAc) afforded the title compound (13.1 g, 40.7 mmol, 77% yield). MS (DCI/NH$_3$) m/z 322 (M+H)$^+$.

Example 122E 5-tert-butyl-2-(3-methoxypropyl)-1-methyl-1,2-dihydro-3H-pyrazol-3-imine To a solution of Example 122D (13.1 g, 40.7 mmol) in MeOH (60 mL) was added a solution of sodium hydroxide (8.1 g, 204 mmol) in water (15 mL). The mixture was warmed to 50° C. and was allowed to stir for 4 hours then was cooled to ambient temperature. The mixture was concentrated under reduced pressure and then diluted with CH$_2$Cl$_2$ (20 mL) and H$_2$O (10 mL). The layers were separated and the aqueous phase was extracted with CH$_2$Cl$_2$ (3×10 mL). The combined organic extracts were dried over anhydrous Na$_2$SO$_4$, filtered and concentrated under reduced pressure to give the title compound (8.6 g, 38.0 mmol, 93% yield). MS (DCI/NH$_3$) m/z 226 (M+H)$^+$.

Example 122F

N-[(3E)-5-tert-butyl-2-(3-methoxypropyl)-1-methyl-1,2-dihydro-3H-pyrazol-3-ylidene]-2-fluoro-5-(trifluoromethyl)benzamide To a solution of Example 122E (1.3 g, 5.9 mmol) and Et$_3$N (2.5 mL, 17.7 mmol) in THF (15 mL) was added 2-fluoro-5-(trifluoromethyl)benzoyl chloride (0.89 mL, 5.9 mmol). The mixture was allowed to stir at ambient temperature for 4 hours then partitioned between saturated aqueous NaHCO$_3$ (15 mL) and EtOAc (15 mL). The layers were separated and the aqueous phase was extracted EtOAc (3×10 mL). The combined organic extracts were dried over anhydrous Na$_2$SO$_4$, filtered, and concentrated under reduced pressure. Purification by column chromatography (SiO$_2$, 50% hexanes in EtOAc to 100% EtOAc to 9:1:0.1 EtOAc:MeOH:Et$_3$N) afforded the title compound (1.3 g, 3.2 mmol, 54% yield). MS (DCI/NH$_3$) m/z 416 (M+H)$^+$.

Example 122G

N-[(3E)-5-tert-butyl-2-(3-methoxypropyl)-1-methyl-1,2-dihydro-3H-pyrazol-3-ylidene]-2-(2-hydroxy-2-methylpropoxy)-5-(trifluoromethyl)benzamide To a solution of Example 81D (0.20 g, 2.166 mmol) in THF (10 mL) at ambient temperature was added potassium tert-butoxide (0.49 g, 4.3 mmol). The mixture was allowed to stir for 20 minutes at ambient temperature then a solution of Example 122F (0.60 g, 1.4 mmol) in THF (5 mL) was added via cannula. The mixture was stirred at ambient temperature for 3 hours then the mixture was quenched with saturated aqueous NaHCO$_3$ (5 mL) and was diluted with EtOAc (10 mL). The layers were separated and the aqueous phase was extracted with EtOAc (3×5 mL). The combined organic extracts were dried over anhydrous Na$_2$SO$_4$, filtered, concentrated and purified via column chromatography (SiO$_2$, 50% hexanes/EtOAc then 100% EtOAc then 9:1:0.1 EtOAc:MeOH:Et$_3$N) to afford the title compound (0.42 g, 0.87 mmol, 60% yield). $^1$H NMR (300 MHz, CDCl$_3$) δ ppm 1.28 (s, 6H) 1.42 (s, 9H) 1.93-2.05 (m, 2H) 3.30 (s, 3H) 3.35 (t, J=5.8 Hz, 2H) 3.78 (s, 3H) 4.03 (s, 2H) 4.36 (t, J=6.9 Hz, 2H) 6.17 (s, 1H) 7.00 (d, J=7.5 Hz, 1H) 6.99 (s, 1H) 7.51 (dd, J=8.5, 1.8 Hz, 1H) 8.11 (d, J=2.4 Hz, 1H); MS (DCI/NH$_3$) m/z 486 (M+H)$^+$; Anal. calculated for C$_{24}$H$_{34}$F$_3$N$_3$O$_4$: Calc: C, 59.37; H, 7.06; N, 8.65. Found: C, 59.47; H, 7.09; N, 8.60.

Example 123

N-[(3E)-5-tert-butyl-1-methyl-2-propyl-1,2-dihydro-3H-pyrazol-3-ylidene]-5-cyano-2-(2-hydroxy-2-methylpropoxy)benzamide Example 123A 3-tert-butyl-1-propyl-1H-pyrazol-5-amine A mixture of propylhydrazine oxalate (5.0 g, 30.5 mmol) and 4,4-dimethyl-3-oxopentanenitrile (3.8 g, 30.5 mmol) in 60 mL of absolute ethanol was warmed to 85° C. and stirred for 4 hours. The solvent was removed under reduced pressure and the residue was partitioned between CH$_2$Cl$_2$ and 2 N aqueous NaOH. The aqueous phase was extracted with CH$_2$Cl$_2$ (3×10 mL). The combined organic extracts were dried with Na₂SO₄ and concentrated under reduced pressure to afford the title compound (5.4 g, 30 mmol, 98% yield). MS (ESI⁺) m/z 182 [M+H]⁺.

Example 123B

N-(3-tert-butyl-1-propyl-1H-pyrazol-5-yl)-2,2,2-trifluoroacetamide

Trifluoroacetic anhydride (1.9 mL, 13.2 mmol) was added to a solution of Et₃N (5.5 mL, 39.7 mmol) and Example 123A (2.4 g, 13.2 mmol) in CH₂Cl₂ (25 mL) at 0° C. The cooling bath was removed and the mixture stirred for 2 hours. The mixture was concentrated and the residue was purified by chromatography (solvent A=hexane:EtOAc:Et₃N (3:1:0.2), solvent B=hexane:EtOAc:MeOH:Et₃N (2:2:1:0.2) gradient of 100% solvent A to 100% solvent B over 300 mL then isocratic for 1000 mL) to afford the title compound (2.9 g, 10.5 mmol, 79% yield). MS (DCI/NH₃) m/z 278.2 (M+H)⁺.

Example 123C

N-[(3E)-5-tert-butyl-1-methyl-2-propyl-1,2-dihydro-3H-pyrazol-3-ylidene]-2,2,2-trifluoroacetamide A mixture of Example 123B (2.9 g, 10.5 mmol) and dimethyl sulfate (3.0 mL, 31.4 mmol) in toluene (10 mL) was heated to 90° C. and stirred for 72 hours. The mixture was cooled to ambient temperature, concentrated under reduced pressure and the residue was purified by chromatography (solvent A=hexane:EtOAc:Et₃N (1:1:0.2), solvent B=hexane:EtOAc:MeOH:Et₃N (2:2:1:0.2), gradient of 100% solvent A to 100% solvent B over 600 mL, isocratic for 600 mL) to afford the title compound (1.5 g, 5.2 mmol, 42% yield). MS (DCI/NH₃) m/z 292.3 (M+H)⁺.

Example 123D 5-tert-butyl-1-methyl-2-propyl-1H-pyrazol-3(2H)-imine

To a solution of Example 123C (1.0 g, 3.4 mmol) in MeOH (5 mL) was added a solution of sodium hydroxide (0.7 g, 17.2 mmol) in water (1 mL) and the solution was warmed to 50° C. and stirred for 3 hours. The mixture was concentrated and the residue partitioned between CH₂Cl₂ and water. The aqueous phase was extracted with CH₂Cl₂ (3×10 mL). The combined organic extracts were dried with MgSO₄, filtered and concentrated. The residue was recrystallized from MeOH and EtOAc to afford the title compound. (0.5 g, 2.6 mmol, 75% yield). MS (DCI/NH₃) m/z 196.1 (M+H)⁺.

Example 123E

N-[(3E)-5-tert-butyl-1-methyl-2-propyl-1,2-dihydro-3H-pyrazol-3-ylidene]-5-cyano-2-fluorobenzamide A solution of oxalyl chloride (3.8 mL, 2 M in CH₂Cl₂) was added to a solution of Example 102B (0.42 g, 2.6 mmol) in CH₂Cl₂ (2 mL) followed by dimethylformamide (10 μL) and the mixture was stirred for 1 hour. The mixture was concentrated under reduced pressure. The residue was diluted with toluene and concentrated under reduced pressure (2×) to afford the acid chloride. A solution of Example 123D (0.5 g, 2.6 mmol) in THF (5.0 mL) was added to the acid chloride followed by Et₃N (2.1 mL, 15.4 mmol). The mixture was stirred for 4 hours, diluted with EtOAc, washed with NaHCO₃, water, brine, dried with MgSO₄ and the solvent removed. The residue was purified by chromatography (Solvent A=hexane:EtOAc:Et₃N (2:2:0.2), Solvent B=hexane: EtOAc:MeOH:Et₃N (2:2:1:0.2), 100% solvent A for 300 mL then 10% solvent B/solvent A for 600 mL) to afford the title compound. (0.6 g, 1.6 mmol, 46% yield). MS (DCI/NH₃) m/z 385.3 (M+H)⁺.

Example 123F

N-[(3E)-5-tert-butyl-1-methyl-2-propyl-1,2-dihydro-3H-pyrazol-3-ylidene]-5-cyano-2-(2-hydroxy-2-methylpropoxy)benzamide Potassium t-butoxide (1.2 mL, 1 M in THF) was added to a solution of Example 81D (55 mg, 0.6 mmol) in THF (0.1 mL). After 10 minutes, a solution of Example 123E (0.1 g, 0.29 mmol) in THF (0.1 mL) was added and the mixture was stirred at ambient temperature for 1 hour. The reaction mixture was partitioned between EtOAc (15 mL) and saturated NaHCO₃ (1 mL). The organic extract was washed with water and brine, dried with MgSO₄, filtered and concentrated. The residue was purified by chromatography (100% CH₂Cl₂ to 20% MeOH/CH₂Cl₂ over 900 mL) to afford the title compound (30 mg, 0.07 mmol, 25% yield). ¹H NMR (300 MHz, Methanol-d₄) δ ppm 0.94 (t, J=7.5 Hz, 3H), 1.28 (s, 6H), 1.47 (s, 9H), 1.70-1.87 (m, 2H), 4.00 (s, 2H), 4.01 (s, 3H), 4.34 (t, J=7.5 Hz, 2H), 6.82 (s, 1H), 7.24 (d, J=8.8 Hz, 1H), 7.74 (d, J=7.8 Hz, 1H), 7.90 (s, 1H); MS (DCI/NH₃) m/z 413.2 (M+H)⁺.

Example 124

3-[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenoxy]-2,2-dimethylpropanoic acid To a solution of Example 118 (230 mg, 0.426 mmol) in MeOH (2 mL) at ambient temperature was added sodium hydroxide (68.2 mg, 1.705 mmol) in H₂O (0.5 mL). The mixture was stirred at ambient temperature overnight and extracted with EtOAc. The aqueous phase was acidified with 2N aqueous HCl. The resulting mixture was concentrated and the residue was purified by preparative HPLC on a Waters Symmetry C8 column (25 mm×100 mm, 7 μm particle size) using a gradient of 10% to 100% acetonitrile: 0.1% aqueous trifluoroacetic acid over 8 min (10 min run time) at a flow rate of 40 mL/min to yield the title compound as TFA salt (61 mg, 22%). ¹H NMR (300 MHz, DMSO-$d_6$) δ ppm 1.19 (d, J=1.59 Hz, 6H) 1.44 (s, 9H) 1.50-1.65 (m, 1H) 1.77-1.91 (m, 2H) 1.99-2.09 (m, 1H) 3.62-3.71 (m, 2H) 3.71-3.83 (m, 2H) 4.11 (s, 3H) 4.16 (s, 2H) 4.53-4.65 (m, 2H) 6.87 (s, 1H) 7.42-7.48 (m, 1H) 7.83-7.97 (m, 2H) 11.13 (b, 1H); MS (DCI/NH₃) m/z 526 (M+H)⁺.

Example 125

N-[(3E)-5-tert-butyl-1-methyl-2-propyl-1,2-dihydro-3H-pyrazol-3-ylidene]-2-(2-hydroxy-2-methylpropoxy)-5-(trifluoromethyl)benzamide

Example 125A

N-[(3E)-5-tert-butyl-1-methyl-2-propyl-1,2-dihydro-3H-pyrazol-3-ylidene]-2-fluoro-5-(trifluoromethyl)benzamide Triethylamine (0.32 mL, 2.3 mmol) was added to a solution of Example 123D (0.15 g, 0.77 mmol) and 2-fluoro-5-(trifluoromethyl)benzoyl chloride (0.12 mL, 0.77 mmol) in THF (2.0 mL). After 4 hours the reaction mixture was partitioned between EtOAc (15 mL) and saturated NaHCO$_3$ (1 mL). The organic extract was washed with water and brine, dried with MgSO$_4$, filtered and concentrated. The residue was purified by chromatography (hexanes:EtOAc:MeOH:Et$_3$N (4:4:1:0.2) to afford the title compound (0.27 g, 0.70 mmol, 91% yield). LCMS (APCI) m/z 396.3 [M+H]$^+$.

Example 125B

N-[(3E)-5-tert-butyl-1-methyl-2-propyl-1,2-dihydro-3H-pyrazol-3-ylidene]-2-(2-hydroxy-2-methylpropoxy)-5-(trifluoromethyl)benzamide Sodium t-butoxide (0.15 g, 1.6 mmol) was added to a solution of Example 81D (70 mg, 0.78 mmol) in THF (1 mL). After 10 minutes, a solution of Example 125A (0.15 g, 0.4 mmol) in THF (1 mL) was added and the mixture stirred for 3 hours. The reaction was partitioned between dichloromethane with and saturated NaHCO$_3$. The organic extract was washed with water and brine, dried with MgSO$_4$, filtered, and concentrated. The residue was purified by chromatography (SiO$_2$, hexane:EtOAc:MeOH:Et$_3$N (8:8:1:0.2)) then recrystallized from EtOAc and hexanes to afford the title compound (0.1 g, 0.22 mmol, 56% yield). $^1$H NMR (300 MHz, Methanol-d$_4$) δ ppm 0.94 (t, J=7.5 Hz, 3H), 1.27 (s, 6H), 1.46 (s, 9H), 1.70-1.82 (m, 2H), 3.96 (s, 5H), 4.26-4.33 (m, 2H), 6.77 (s, 1H), 7.18 (d, J=8.5 Hz, 1H), 7.61 (dd, J=8.5, 2.0 Hz, 1H), 7.77 (d, J=2.0 Hz, 1H); MS (DCI/NH$_3$) m/z 456.1 (M+H)$^+$.

Example 126

N-[(3E)-5-tert-butyl-1-methyl-2-propyl-1,2-dihydro-3H-pyrazol-3-ylidene]-2-{[(2S)-5-oxopyrrolidin-2-yl]methoxy}-5-(trifluoromethyl)benzamide Sodium hydride (50 mg, 60% dispersion in mineral oil, 1.25 mmol) was added to a solution of (S)-5-(hydroxymethyl)pyrrolidin-2-one (72 mg, 0.62 mmol) in dimethylformamide (0.5 mL). After 10 minutes a solution of Example 125A (0.12 g, 0.31 mmol) in dimethylformamide (1.0 mL) was added and the mixture stirred for 3 hours. The reaction mixture was partitioned between EtOAc (15 mL) and saturated NaHCO$_3$ (1 mL). The organic extract was washed with water and brine, dried with MgSO$_4$, filtered and concentrated. The residue was purified by chromatography (hexanes:EtOAc:MeOH:Et$_3$N (4:4:1:0.2) to afford the title compound (50 mg, 0.10 mmol, 33% yield). $^1$H NMR (500 MHz, Pyridine-d$_5$) δ ppm 0.76 (t, J=7.5 Hz, 3H), 1.16 (s, 9H), 1.57-1.64 (m, 2H), 1.64-1.69 (m, 1H), 1.95-2.03 (m, 1H), 2.27 (ddd, J=16.9, 9.7, 7.3 Hz, 1H), 2.37-2.45 (m, 1H), 3.71 (s, 3H), 3.88 (t, J=9.3 Hz, 1H), 4.05-4.12 (m, 1H), 4.31 (t, J=7.3 Hz, 2H), 4.38 (dd, J=9.6, 3.5 Hz, 1H), 7.17 (d, J=8.5 Hz, 1H), 7.43 (s, 1H), 7.64 (dd, J=8.5, 2.1 Hz, 1H), 8.53 (d, J=2.1 Hz, 1H), 9.25 (s, 1H); MS (ESI$^+$) m/z 481.2 [M+H]$^+$. Anal. calculated for C$_{24}$H$_{31}$F$_3$N$_4$O$_3$: C, 59.99; H, 6.50; N, 11.66. Found: C, 59.81; H, 6.45; N, 11.52.

Example 127

N-[(3E)-5-tert-butyl-2-(cyclopentylmethyl)-1-methyl-1,2-dihydro-3H-pyrazol-3-ylidene]-5-cyano-2-(2-hydroxy-2-methylpropoxy)benzamide Example 127A cyclopentylmethyl 4-methylbenzenesulfonate To a mixture of cyclopentylmethanol (8.7 g, 87 mmol) and 4-(dimethylamino)pyridine (0.5 g, 4.3 mmol) in dichloromethane (30 mL) and pyridine (30 mL) was added 4-methylbenzene-1-sulfonyl chloride (16.6 g, 87 mmol). The mixture was stirred at ambient temperature for 20 hours then diluted with 2 N aqueous HCl and extracted with dichloromethane (3×10 mL). The combined organic extracts were dried with NaSO$_4$, concentrated and the filtered thru a silica plug using hexanes:EtOAc (3:1) to afford the title compound (16.5 g, 64.9 mmol, 76% yield). $^1$H NMR (300 MHz, CDCl$_3$) δ ppm 1.12-1.27 (m, 2H), 1.47-1.61 (m, 4H), 1.64-1.78 (m, 2H), 2.12-2.30 (m, 1H), 2.45 (s, 3H), 3.90 (d, J=7.1 Hz, 2H), 7.32-7.36 (m, 2H), 7.76-7.81 (m, 2H); MS (DCI/NH$_3$) m/z 272.1 (M+NH$_4$)$^+$.

Example 127B 3-tert-butyl-1-(cyclopentylmethyl)-1H-pyrazol-5-amine

Hydrazine hydrate (4.3 mL, 88 mmol) was added to a solution of Example 127A (15.0 g, 59.0 mmol) in absolute EtOH (60 mL). The mixture was heated at 85° C. for 20 hours. After cooling to ambient temperature, 4,4-dimethyl-3-oxopentanenitrile (11.1 g, 88 mmol) was added and the mixture was heated at 85° C. for an additional 4 hours. The mixture was cooled to ambient temperature and concentrated. The residue was partitioned between dichloromethane (50 mL) and saturated aqueous NaHCO$_3$. The aqueous phase was extracted with dichloromethane (3×10 mL). The combined organic extracts were dried with MgSO$_4$, filtered and concentrated. The residue was purified by chromatography (SiO$_2$, 25% EtOAc/Hexanes) to afford the title compound (5.5 g, 24.9 mmol, 42% yield). $^1$H NMR (300 MHz, Methanol-d$_4$) δ ppm 1.22 (s, 9H), 1.25-1.38 (m, 2H), 1.47-1.73 (m, 6H), 2.28-2.48 (m, 1H), 3.79 (d, J=7.8 Hz, 2H), 5.32 (s, 1H); MS (DCI/NH$_3$) m/z 222.2 (M+H)$^+$.

Example 127C

N-[3-tert-butyl-1-(cyclopentylmethyl)-1H-pyrazol-5-yl]-2,2,2-trifluoroacetamide

Trifluoroacetic anhydride (3.2 mL, 22.6 mmol) was added to a 0° C. solution of Example 127B (5.0 g, 22.6 mmol) and triethylamine (9.5 mL, 67.8 mmol) in dichloromethane (15 mL). The cooling bath was removed and the mixture was stirred at ambient temperature for 2 hours then concentrated under reduced pressure. The residue purified by chromatography (SiO$_2$, 10% EtOAc/hexanes) to afford the title compound (4.5 g, 14.2 mmol, 63% yield). $^1$H NMR (300 MHz, Methanol-d$_4$) δ ppm 1.16-1.28 (m, 3H), 1.28 (s, 9H), 1.53-1.68 (m, 6H), 2.27-2.41 (m, 1H), 3.89 (d, J=7.5 Hz, 2H), 6.15 (s, 1H); MS (DCI/NH$_3$) m/z 318.1 (M+H)$^+$.

Example 127D

N-[(3E)-5-tert-butyl-2-(cyclopentylmethyl)-1-methyl-1,2-dihydro-3H-pyrazol-3-ylidene]-2,2,2-trifluoroacetamide Dimethylsulfate (4.1 mL, 42.5 mmol) was added to a solution of Example 127C (4.5 g, 14.2 mmol) in toluene (15 mL) at room temperature and then the mixture was heated at 90° C. for 72 hours. The mixture was cooled to ambient temperature and concentrated under reduced pressure. The residue was purified by chromatography (SiO$_2$, hexanes:EtOAc:MeOH: Et$_3$N (4:4:1:0.2)) to afford the title compound (2.8 g, 8.3 mmol, 59% yield). $^1$H NMR (300 MHz, Methanol-d$_4$) δ ppm 1.27-1.41 (m, 2H), 1.45 (s, 9H), 1.51-1.68 (m, 4H), 1.68-1.77 (m, 2H), 2.28-2.43 (m, 1H), 3.98 (s, 3H), 4.31 (d, J=7.8 Hz, 2H), 6.74 (s, 1H); LCMS (APCI) 332.1 m/z [M+H]$^+$.

Example 127E 5-tert-butyl-2-(cyclopentylmethyl)-1-methyl-1,2-dihydro-3H-pyrazol-3-imine A solution of sodium hydroxide (1.7 g, 41.5 mmol) in water (2 mL) was added to a solution of Example 127D (2.75 g, 8.3 mmol) in MeOH (10 mL) and the mixture stirred at 50° C. for 3 hours. After cooling to ambient temperature, the mixture was concentrated under reduced pressure and the residue was partitioned between dichloromethane and water. The aqueous phase was extracted with dichloromethane (3×10 mL). The combined organic extracts were concentrated and the residue crystallized from MeOH and EtOAc to afford the title compound (1.9 g, 8.1 mmol, 97% yield). $^1$H NMR (300 MHz, Methanol-$d_4$) δ ppm 1.23-1.37 (m, 2H), 1.41 (s, 9H), 1.53-1.64 (m, 2H), 1.64-1.78 (m, 4H), 2.17-2.44 (m, 1H), 3.34 (s, 1H), 3.80 (s, 3H), 4.12 (d, J=7.5 Hz, 2H), 5.75 (s, 1H); MS (ESI$^+$) m/z 236 [M+H]$^+$.

Example 127F

N-[(3E)-5-tert-butyl-2-(cyclopentylmethyl)-1-methyl-1,2-dihydro-3H-pyrazol-3-ylidene]-5-cyano-2-fluorobenzamide A solution of oxalyl chloride (2.4 mL, 2 M in $CH_2Cl_2$) was added to a solution of Example 102B (0.26 g, 1.6 mmol) in $CH_2Cl_2$ (1.0 mL) followed by dimethylformamide (10 μL). The mixture was stirred at ambient temperature for 1 hour. The mixture was concentrated and the residue was twice dissolved and concentrated from toluene (5 mL) to afford the acid chloride. A solution of Example 127E (0.37 g, 1.6 mmol) in THF (3 mL) was added to the acid chloride followed by triethylamine (1.3 mL, 9.5 mmol). The mixture was stirred at ambient temperature for 4 hours then partitioned between EtOAc (15 mL) and saturated $NaHCO_3$ (1 mL). The organic extract was washed with water and brine, dried with $MgSO_4$, filtered and concentrated. The residue was purified by chromatography ($SiO_2$, Solvent A=hexane:EtOAc:Et$_3$N (2:2:0.2), Solvent B=hexane:EtOAc:MeOH:Et$_3$N (2:2:1:0.2), 100% solvent A for 150 mL then 25% solvent B/75% solvent A for 300 mL.) to afford the title compound (0.25 g, 0.65 mmol, 42% yield). $^1$H NMR (500 MHz, Pyridine-$d_5$) δ ppm 1.17 (s, 9H), 1.34-1.43 (m, 4H), 1.47-1.54 (m, 9H), 1.57-1.65 (m, 2H), 2.24-2.37 (m, 1H), 3.77 (s, 3H), 4.20 (s, 2H), 4.33 (d, J=7.3 Hz, 2H), 7.24 (d, J=8.5 Hz, 1H), 7.37 (s, 1H), 7.69 (dd, J=8.5, 2.4 Hz, 1H), 8.62 (d, J=2.1 Hz, 1H); MS (ESI$^+$) m/z 383.1 [M+H]$^+$.

Example 127G

N-[(3E)-5-tert-butyl-2-(cyclopentylmethyl)-1-methyl-1,2-dihydro-3H-pyrazol-3-ylidene]-5-cyano-2-(2-hydroxy-2-methylpropoxy)benzamide Sodium t-butoxide (0.25 g, 2.6 mmol) was added to a solution of Example 81D (0.12 g, 1.4 mmol) in THF (2.0 mL). After 10 minutes, Example 127F (0.25 g, 0.65 mmol) was added and the reaction mixture was stirred at ambient temperature for 2 hours. The reaction mixture was partitioned between EtOAc (15 mL) and saturated $NaHCO_3$ (1 mL). The organic extract was washed with water and brine, dried with $MgSO_4$, filtered and concentrated. The residue was purified by chromatography ($SiO_2$, Solvent A=hexane:EtOAc:Et$_3$N (2:2:0.2), Solvent B=hexane:EtOAc:MeOH:Et$_3$N (2:2:1:0.2), 100% solvent A to 50% solvent B/solvent A gradient over 600 mL) then recrystallized from EtOAc and hexanes to afford the title compound (0.17 g, 0.38 mmol, 58% yield). $^1$H NMR (300 MHz, Methanol-$d_4$) δ ppm 1.27 (s, 6H), 1.32-1.44 (m, 2H), 1.46 (s, 9H), 1.57-1.72 (m, 6H), 2.30-2.43 (m, 1H), 3.95 (s, 2H), 3.96 (s, 3H), 4.28 (d, J=7.8 Hz, 2H), 6.80 (s, 1H), 7.18 (d, J=8.5 Hz, 1H), 7.68 (dd, J=8.6, 2.2 Hz, 1H), 7.80 (d, J=2.0 Hz, 1H); MS (ESI$^+$) m/z 453.1 [M+H]$^+$. Anal. calculated for $C_{26}H_{36}N_4O_3$: C, 69.00; H, 8.02; N, 12.38. Found: C, 69.10; H, 7.96; N, 12.24.

Example 128

5-bromo-N-{(3E)-5-tert-butyl-1-methyl-2-[(2R)-tetrahydrofuran-2-ylmethyl]-1,2-dihydro-3H-pyrazol-3-ylidene}-2-(2-hydroxy-2-methylpropoxy)benzamide

Example 128A 5-bromo-N-{(3E)-5-tert-butyl-1-methyl-2-[(2R)-tetrahydrofuran-2-ylmethyl]-1,2-dihydro-3H-pyrazol-3-ylidene}-2-fluorobenzamide The title compound was prepared and isolated in 64% yield using procedure as described in Example 121A, substituting 2-fluoro-5-bromobenzoic acid for 2-fluoro-5-nitrobenzoic acid. $^1$H NMR (300 MHz, CDCl$_3$) δ ppm 1.42 (s, 9H) 1.72-1.81 (m, 2H) 1.83-1.89 (m, 1H) 1.98-2.10 (m, 1H) 3.68-3.81 (m, 2H) 3.88 (s, 3H) 4.18-2.24 (m, 1H) 4.30-4.39 (m, 1H) 4.51-4.58 (m, 1H) 6.92 (dd, J=10.17, 8.82 Hz, 1H) 7.06 (s, 1H) 7.38 (ddd, J=8.65, 4.24, 2.71 Hz, 1H) 8.12 (dd, J=6.44, 2.71 Hz, 1H); MS (DCI/NH$_3$) m/z 438 (M+H)$^+$.

Example 128B 5-bromo-N-{(3E)-5-tert-butyl-1-methyl-2-[(2R)-tetrahydrofuran-2-ylmethyl]-1,2-dihydro-3H-pyrazol-3-ylidene}-2-(2-hydroxy-2-methylpropoxy)benzamide The title compound was prepared and isolated in 38% yield as described in Example 1F, substituting Example 128A for Example 1E, and Example 81D for (R)-(tetrahydrofuran-2-yl)methanol. $^1$H NMR (300 MHz, CDCl$_3$) δ ppm 1.26 (s, 6H) 1.41 (s, 9H) 1.65-1.77 (m, 2H) 1.81-1.90 (m, 1H) 1.96-2.07 (m, 1H) 3.66-3.79 (m, 2H) 3.86 (s, 3H) 3.97 (s, 2H) 4.09-4.20 (m, 1H) 4.23-4.35 (m, 1H) 4.47-4.55 (m, 1H) 6.81-6.84 (m, 1H) 6.98 (s, 1H) 7.33-7.36 (m, 1H) 7.90-7.91 (m, 1H); MS (DCI/NH$_3$) m/z 509 (M+H)$^+$. Anal. Calcd for $C_{24}H_{34}BrN_3O_4 \cdot 0.8H_2O$: C, 55.13; H, 6.86; N, 8.04. Found: C, 55.12; H, 6.76; N, 7.98.

Example 129

N-[(3E)-5-tert-butyl-2-(cyclobutylmethyl)-1-methyl-1,2-dihydro-3H-pyrazol-3-ylidene]-2-(2-hydroxy-2-methylpropoxy)-5-methylbenzamide

Example 129A

N-[(3E)-5-tert-butyl-2-(cyclobutylmethyl)-1-methyl-1,2-dihydro-3H-pyrazol-3-ylidene]-2-fluoro-5-methylbenzamide To a solution of Example 113C (0.30 g, 1.4 mmol) and Et$_3$N (0.56 mL, 4.1 mmol) in THF (10 mL) was added 2-fluoro-5-methylbenzoyl chloride (0.23 g, 1.4 mmol). The mixture was stirred at ambient temperature for 4 hours then partitioned between saturated aqueous $NaHCO_3$ (10 mL) and EtOAc (10 mL). The layers were separated and the aqueous phase was extracted EtOAc (3×10 mL). The combined organic extracts were dried over $Na_2SO_4$, filtered, and concentrated under reduced pressure. Purification by column chromatography ($SiO_2$, 50% hexanes in EtOAc to 100% EtOAc to 9:1:0.1 EtOAc:MeOH:$Et_3N$) afforded the title compound (0.24 g, 0.67 mmol, 50% yield). MS ($ESI^+$) m/z 358 $(M+H)^+$.

Example 129B

N-[(3E)-5-tert-butyl-2-(cyclobutylmethyl)-1-methyl-1,2-dihydro-3H-pyrazol-3-ylidene]-2-(2-hydroxy-2-methylpropoxy)-5-methylbenzamide To a solution of Example 81D (0.091 g, 1.0 mmol) in THF (10 mL) at 0° C. was added potassium tert-butoxide (0.23 g, 2.0 mmol). The mixture was allowed to warm to ambient temperature and was stirred for 30 minutes then Example 129A (0.24 g, 0.67 mmol) was added. The mixture was stirred for 2 hours then warmed to 55° C. and stirred for 96 hours. The mixture was quenched with saturated aqueous $NaHCO_3$ (10 mL) and was diluted with EtOAc (10 mL). The layers were separated and the aqueous phase was extracted with EtOAc (3×5 mL). The combined organic extracts were dried over anhydrous $Na_2SO_4$, filtered and concentrated under reduced pressure. Purification by column chromatography ($SiO_2$, 50% hexanes/EtOAc then 100% EtOAc then 9:1:0.1 EtOAc:MeOH:$Et_3N$) afforded the title compound (20 mg, 0.047 mmol, 7% yield). $^1H$ NMR (300 MHz, $CD_3OD$) δ ppm 1.25 (s, 6H) 1.45 (s, 9H) 1.83-1.93 (m, 4H) 1.97-2.06 (m, 2H) 2.29 (s, 3H) 2.67-2.81 (m, 1H) 3.88 (s, 2H) 3.93 (s, 3H) 4.40 (d, J=7.1 Hz, 2H) 6.74 (s, 1H) 6.93 (d, J=8.1 Hz, 1H) 7.10-7.20 (m, 1H) 7.30-7.39 (m, 1H); MS ($DCI/NH_3$) m/z 428 $(M+H)^+$.

Example 130

2-[2-(acetylamino)ethoxy]-N-[(3E)-5-tert-butyl-2-(cyclobutylmethyl)-1-methyl-1,2-dihydro-3H-pyrazol-3-ylidene]-5-(trifluoromethyl)benzamide To a solution of N-acetylethanolamine (0.18 mL, 1.9 mmol) in THF (7 mL) at 0° C. was added potassium tert-butoxide (0.22 g, 1.9 mmol). The ice bath was removed and the mixture was stirred for 45 minutes then a solution of Example 86D (0.40 g, 0.97 mmol) in THF (100 mL) was added. The mixture was stirred for 2 hours then partitioned between saturated aqueous $NaHCO_3$ (10 mL) and EtOAc (10 mL). The layers were separated and the aqueous phase was extracted with EtOAc (3×5 mL). The combined organic extracts were dried over anhydrous $Na_2SO_4$, filtered and concentrated under reduced pressure. Purification by column chromatography ($SiO_2$, 50% hexanes/EtOAc then 100% EtOAc then 9:1:0.1 EtOAc:MeOH:$Et_3N$) afforded the title compound (0.27 g, 0.55 mmol, 56% yield). $^1H$ NMR (300 MHz, $CD_3OD$) δ ppm 1.46 (s, 9H) 1.88-1.98 (m, 4H) 1.95 (s, 3H) 2.02-2.10 (m, 2H) 2.69-2.85 (m, 1H) 3.58 (t, J=5.1 Hz, 2H) 3.93 (s, 3H) 4.18 (t, J=5.3 Hz, 2H) 4.43 (d, J=7.1 Hz, 2H) 6.83 (s, 1H) 7.20 (d, J=8.8 Hz, 1H) 7.62 (dd, J=8.8, 2.0 Hz, 1H) 7.86 (d, J=2.4 Hz, 1H); MS ($ESI^+$) m/z 495 $(M+H)^+$; Anal. calculated for $C_{25}H_{33}F_3N_4O_3$: Calc: C, 60.72; H, 6.73; N, 11.33. Found: C, 60.75; H, 6.84; N, 11.42.

Example 131

5-(aminosulfonyl)-N-[(3E)-5-tert-butyl-2-(cyclobutylmethyl)-1-methyl-1,2-dihydro-3H-pyrazol-3-ylidene]-2-(2-hydroxy-2-methylpropoxy)benzamide

Example 131A 5-(aminosulfonyl)-N-[(3E)-5-tert-butyl-2-(cyclobutylmethyl)-1-methyl-1,2-dihydro-3H-pyrazol-3-ylidene]-2-fluorobenzamide To a solution of Example 113C (0.43 g, 1.9 mmol) and 2-fluoro-5-sulfamoylbenzoic acid (Enamine, 0.47 g, 2.1 mmol) in THF (10 mL) was added $Et_3N$ (0.68 mL, 4.9 mmol) followed by diethyl cyanophosphonate (0.44 mL, 2.9 mmol). The mixture was stirred at ambient temperature for 2 hours then concentrated under reduced pressure. Purification by column chromatography ($SiO_2$, 50% hexanes/EtOAc to 100% EtOAc to 9:1:0.1 EtOAc:MeOH:$Et_3N$) afforded the title compound (0.26 g, 0.62 mmol, 32% yield). MS (DCI/$NH_3$) m/z 423 $(M+H)^+$.

Example 131B 5-(aminosulfonyl)-N-[(3E)-5-tert-butyl-2-(cyclobutylmethyl)-1-methyl-1,2-dihydro-3H-pyrazol-3-ylidene]-2-(2-hydroxy-2-methylpropoxy)benzamide To a solution of Example 81D (0.083 g, 0.92 mmol) in THF (10 mL) at 0° C. was added potassium tert-butoxide (0.21 g, 1.8 mmol). The mixture was allowed to warm to ambient temperature and was stirred for 30 minutes then Example 131A (0.26 g, 0.62 mmol) was added. The mixture was stirred for 2 hours then partitioned between saturated aqueous $NaHCO_3$ (10 mL) and EtOAc (10 mL). The layers were separated and the aqueous phase was extracted with EtOAc (3×10 mL). The combined organic extracts were dried over anhydrous $Na_2SO_4$, filtered and concentrated under reduced pressure. Purification by column chromatography ($SiO_2$, 50% hexanes/EtOAc then 100% EtOAc then 9:1:0.1 EtOAc:MeOH:$Et_3N$) afforded the title compound (0.20 g, 0.41 mmol, 66% yield). $^1H$ NMR (300 MHz, $CD_3OD$) δ ppm 1.28 (s, 6H) 1.46 (s, 9H) 1.81-1.95 (m, 4H) 1.97-2.07 (m, 2H) 2.66-2.83 (m, 1H) 3.93 (s, 3H) 3.97 (s, 2H) 4.41 (d, J=7.1 Hz, 2H) 6.78 (s, 1H) 7.17 (d, J=8.8 Hz, 1H) 7.86 (dd, J=8.6, 2.5 Hz, 1H) 8.08 (d, J=2.4 Hz, 1H); MS ($ESI^+$) m/z 493 $(M+H)^+$; Anal. calculated for $C_{24}H_{36}N_4O_5S \cdot 0.3H_2O$: Calc: C, 58.88; H, 7.41; N, 11.25. Found: C, 57.81; H, 7.47; N, 11.12.

Example 132 methyl 3-[({(3E)-5-tert-butyl-1-methyl-2-[(2R)-tetrahydrofuran-2-ylmethyl]-1,2-dihydro-3H-pyrazol-3-ylidene}amino)carbonyl]-4-(2-hydroxy-2-methylpropoxy)benzoate In a 50 mL pressure bottle, to a solution of 128B (180 mg, 0.354 mmol) in MeOH (5 mL) was added to $PdCl_2(dppf) \cdot 2CH_2Cl_2$ (13 mg, 0.018 mmol) and triethylamine (0.099 mL, 0.71 mmol). The mixture was pressurized with carbon monoxide (60 psi), and stirred for 4 hours at 100° C. The reaction mixture was concentrated, diluted with EtOAc, and filtered. The filtrate was concentrated and the residue purified by column chromatography using an Analogix® Intelliflash280™ ($SiO_2$, 15-100% solvent B in hexane, solvent B=5% triethyl amine, 10% MeOH in ethyl acetate) to afford the title compound (58 mg, 50%). $^1$H NMR (300 MHz, CDCl$_3$) δ ppm 1.28 (s, 6H) 1.42 (s, 9H) 1.71-1.87 (m, 3H) 1.99-2.13 (m, 1H) 3.67-3.79 (m, 2H) 3.87 (s, 6H) 4.04 (s, 2H) 4.13-4.22 (m, 1H) 4.27-4.39 (m, 1H) 4.48-4.58 (m, 1H) 6.96 (d, J=8.48 Hz, 1H) 6.99 (s, 1H) 7.97 (dd, J=8.48, 2.03 Hz, 1H) 8.51 (d, J=2.03 Hz, 1H); MS (DCI/NH$_3$) m/z 488 (M+H)$^+$.

Example 133

N-[(3E)-5-tert-butyl-2-(cyclobutylmethyl)-1-methyl-1,2-dihydro-3H-pyrazol-3-ylidene]-2-[3-(methylthio)propoxy]-5-(trifluoromethyl)benzamide To a solution of methionol (0.19 mL, 1.8 mmol) in THF (7 mL) was added potassium tert-butoxide (0.41 g, 3.7 mmol). The mixture was stirred at ambient temperature for 15 minutes, then a solution of Example 86D (0.50 g, 1.2 mmol) in THF (5 mL) was added. The mixture was stirred for 2 h then partitioned between saturated aqueous NaHCO$_3$ (10 mL) and EtOAc (10 mL). The layers were separated and the aqueous phase was extracted with EtOAc (3×5 mL). The combined organic extracts were dried over anhydrous Na$_2$SO$_4$, filtered and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (0.55 g, 1.1 mmol, 91% yield). $^1$H NMR (300 MHz, CDCl$_3$) δ ppm 1.42 (s, 9H) 1.85-1.95 (m, 4H) 1.99-2.19 (m, 5H) 2.08 (s, 3H) 2.68 (t, J=7.1 Hz, 2H) 3.71 (s, 3H) 4.19 (t, J=5.4 Hz, 2H) 4.32 (d, J=6.1 Hz, 2H) 6.98 (d, J=8.5 Hz, 1H) 7.02 (s, 1H) 7.50 (dd, J=8.0, 1.5 Hz, 1H) 7.98 (d, J=2.0 Hz, 1H); MS (ESI$^+$) m/z 498 (M+H)$^+$; Anal. calculated for C$_{25}$H$_{34}$F$_3$N$_3$O$_2$S: Calc: C, 60.34; H, 6.89; N, 8.44. Found: C, 60.43; H, 6.91; N, 8.42.

Example 134

N-[(3E)-5-tert-butyl-2-(cyclobutylmethyl)-1-methyl-1,2-dihydro-3H-pyrazol-3-ylidene]-2-[3-(methylsulfonyl)propoxy]-5-(trifluoromethyl)benzamide To a solution of Example 133 (0.43 g, 0.86 mmol) in CH$_2$Cl$_2$ (7 mL) was added 3-chloroperbenzoic acid (0.58 g, 2.6 mmol) portionwise over 5 min. The mixture was stirred at ambient temperature for 90 minutes then the mixture was quenched with saturated aqueous NaHCO$_3$ (5 mL) and extracted with CH$_2$Cl$_2$ (10 mL). The aqueous phase was extracted with CH$_2$Cl$_2$ (3×5 mL). The combined organic extracts were dried over anhydrous Na$_2$SO$_4$ and concentrated under reduced pressure. Purification by column chromatography (SiO$_2$, 50% hexanes/EtOAc to 100% EtOAc to 9:1:0.1 EtOAc:MeOH:Et$_3$N) afforded the title compound (0.33 g, 0.62 mmol, 72% yield). $^1$H NMR (300 MHz, CDCl$_3$) δ ppm 1.43 (s, 9H) 1.83-1.95 (m, 4H) 1.99-2.07 (m, 2H) 2.27-2.41 (m, 2H) 2.57-2.72 (m, 1H) 2.89 (s, 3H) 3.35-3.46 (m, 2H) 3.72 (s, 3H) 4.22 (t, J=5.8 Hz, 2H) 4.33 (d, J=7.1 Hz, 2H) 6.95 (d, J=8.5 Hz, 1H) 7.00 (s, 1H) 7.51 (dd, J=8.6, 1.5 Hz, 1H) 8.00 (d, J=2.0 Hz, 1H); MS (ESI$^+$) m/z 530 (M+H)$^+$; Anal. calculated for C$_{25}$H$_{34}$F$_3$N$_3$O$_4$S: Calc: C, 56.70; H, 6.47; N, 7.93. Found: C, 56.78; H, 6.43; N, 8.01.

Example 135

N-[(3E)-5-tert-butyl-1-methyl-2-(4,4,4-trifluorobutyl)-1,2-dihydro-3H-pyrazol-3-ylidene]-2-(2-hydroxy-2-methylpropoxy)-5-(trifluoromethyl)benzamide Example 135A 4,4,4-trifluorobutyl 4-methylbenzenesulfonate To a solution of 4,4,4-trifluorobutan-1-ol (5.0 g, 39.0 mmol) in CH$_2$Cl$_2$ (30 mL) and pyridine (20 mL) was added 4-(dimethylamino)pyridine (0.24 g, 2.0 mmol) followed by p-toluenesulfonyl chloride (7.4 g, 39.0 mmol). The mixture was allowed to stir at ambient temperature for 20 hours then was quenched with 5% aqueous HCl (20 mL) and the layers were separated. The aqueous phase was extracted with CH$_2$Cl$_2$ (3×5 mL). The combined organic extracts were dried over Na$_2$SO$_4$, filtered and concentrated under reduced pressure. Purification by column chromatography (SiO$_2$, 75% hexanes in EtOAc) afforded the title compound (5.0 g, 17.7 mmol, 45% yield). $^1$H NMR (300 MHz, CDCl$_3$) δ ppm 1.86-1.98 (m, 2H) 2.06-2.24 (m, 2H) 2.46 (s, 3H) 4.09 (t, J=5.9 Hz, 2H) 7.37 (d, J=7.8 Hz, 2H) 7.79 (d, J=8.5 Hz, 2H).

Example 135B 3-tert-butyl-1-(4,4,4-trifluorobutyl)-1H-pyrazol-5-amine

To a solution of Example 135A (5 g, 17.7 mmol) in EtOH (50 mL) was added hydrazine hydrate (1.1 mL, 23.0 mmol). The mixture was warmed to reflux (85° C.) and was allowed to stir for 20 hours. The mixture was cooled to ambient temperature then 4,4-dimethyl-3-oxopentanenitrile (2.9 g, 23.0 mmol) was added and the mixture was again warmed to reflux (85° C.) and stirred for 6 hours. After cooling to ambient temperature, the mixture was concentrated under reduced pressure and the residue was dissolved in CH$_2$Cl$_2$ (100 mL) and saturated aqueous NaHCO$_3$ (50 mL) was added slowly. The layers were separated and the aqueous phase was extracted with CH$_2$Cl$_2$ (3×10 mL). The combined organic extracts were dried over Na$_2$SO$_4$, filtered and concentrated under reduced pressure. Purification by column chromatography (SiO$_2$, 50% hexanes in EtOAc to 100% EtOAc to 9:1:0.1 EtOAc:MeOH:Et$_3$N) afforded the title compound (2.0 g, 8.1 mmol, 46% yield). MS (ESI$^+$) m/z 250 (M+H)$^+$.

Example 135C

N-[3-tert-butyl-1-(4,4,4-trifluorobutyl)-1H-pyrazol-5-yl]-2-fluoro-5-(trifluoromethyl)benzamide To a solution of Example 135B (2.0 g, 8.1 mmol) and Et$_3$N (3.4 mL, 24.3 mmol) in THF (40 mL) was added 2-fluoro-5-(trifluoromethyl)benzoyl chloride (1.2 mL, 8.1 mmol). The mixture was allowed to stir at ambient temperature for 3 h then partitioned between saturated aqueous NaHCO$_3$ (10 mL) and EtOAc (10 mL). The layers were separated and the aqueous phase was extracted EtOAc (3×10 mL). The combined organic extracts were dried over anhydrous Na$_2$SO$_4$, filtered and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (2.9 g, 6.5 mmol, 80% yield). MS (ESI$^+$) m/z 440 (M+H)$^+$.

Example 135D

N-[(3E)-5-tert-butyl-1-methyl-2-(4,4,4-trifluorobutyl)-1,2-dihydro-3H-pyrazol-3-ylidene]-2-fluoro-5-(trifluoromethyl)benzamide To a solution of Example 135C (1.7 g, 3.9 mmol) in toluene (15 mL) was added methyl trifluoromethanesulfonate (0.64 mL, 5.8 mmol). The mixture was warmed to 100° C. and stirred for 20 hours, cooled to ambient temperature and diluted with water (20 mL) and acetone (50 mL). This solution was allowed to stir for 30 minutes then concentrated NH$_4$OH (10 mL) was added. The mixture was stirred for 30 minutes then partially concentrated under reduced pressure. The mixture was diluted with EtOAc (30 mL) and brine (10 mL) and the layers were separated. The aqueous phase was extracted with EtOAc (3×5 mL). The combined organic extracts were dried over anhydrous Na$_2$SO$_4$, filtered and concentrated under reduced pressure. Purification by column chromatography (SiO$_2$, 80% hexanes/EtOAc to 100% EtOAc to 10% MeOH in EtOAc) afforded the title compound (1.3 g, 2.9 mmol, 74% yield). MS (ESI$^+$) m/z 454 (M+H)$^+$.

Example 135E

N-[(3E)-5-tert-butyl-1-methyl-2-(4,4,4-trifluorobutyl)-1,2-dihydro-3H-pyrazol-3-ylidene]-2-(2-hydroxy-2-methylpropoxy)-5-(trifluoromethyl)benzamide To a solution of Example 81D (0.15 g, 1.7 mmol) in THF (10 mL) at 0° C. was added potassium tert-butoxide (0.37 g, 3.3 mmol). The ice bath was removed and the mixture was stirred for 45 minutes then Example 135D (0.50 g, 1.1 mmol) was added. The mixture was stirred for 2 h then partitioned between saturated aqueous NaHCO$_3$ (10 mL) and EtOAc (10 mL). The layers were separated and the aqueous phase was extracted with EtOAc (3×5 mL). The combined organic extracts were dried over anhydrous Na$_2$SO$_4$, filtered and concentrated under reduced pressure. Purification by column chromatography (SiO$_2$, 50% hexanes/EtOAc then 100% EtOAc then 9:1:0.1 EtOAc:MeOH:Et$_3$N) afforded the title compound (0.45 g, 0.86 mmol, 78% yield). $^1$H NMR (300 MHz, CDCl$_3$) δ ppm 1.28 (s, 6H) 1.43 (s, 9H) 1.89-2.04 (m, 2H) 2.09-2.33 (m, 2H) 3.75 (s, 3H) 4.02 (s, 2H) 4.34 (t, J=7.3 Hz, 2H) 5.99 (s, 1H) 7.00 (d, J=9.5 Hz, 1H) 7.02 (s, 1H) 7.53 (dd, J=8.6, 1.9 Hz, 1H) 8.07 (d, J=2.0 Hz, 1H); MS (DCI/NH$_3$) m/z 524 (M+H)$^+$; Anal. calculated for C$_{24}$H$_{31}$F$_6$N$_3$O$_3$: Calc: C, 55.06; H, 5.97; N, 8.03. Found: C, 55.00; H, 6.02; N, 8.01.

Example 136

N-[(3E)-2-butyl-5-tert-butyl-1-methyl-1,2-dihydro-3H-pyrazol-3-ylidene]-2-[2-hydroxypropyl)thio]-5-(trifluoromethyl)benzamide A mixture of Example 81C (400 mg, 1 mmol), 1-mercaptopropan-2-ol (277 mg, 3 mmol) and potassium carbonate (415 mg, 3 mmol) in DMF (10 mL) was heated at 50° C. for 16 hours. The mixture was then poured into water and extracted with ethyl acetate. The acetate layer was washed with brine, dried with MgSO$_4$, filtered, and concentrated under reduced pressure. Purification by chromatography afforded 320 mg of the title compound. $^1$H NMR (300 MHz, DMSO-d$_6$) δ ppm 0.91 (t, J=7.3 Hz, 3H), 1.15-1.24 (m, 3H), 1.27-1.44 (m, 11H), 1.54-1.79 (m, 2H), 2.68-3.07 (m, 2H), 3.76-3.94 (m, 4H), 4.27-4.45 (m, 2H), 4.94 (d, J=4.8 Hz, 1H), 6.83 (s, 1H), 7.42-7.52 (m, 1H), 7.54-7.66 (m, 1H), 8.24 (d, J=1.6 Hz, 1H). MS (DCI/NH$_3$) m/z 472 (M+H)$^+$. Anal. calculated for C$_{23}$H$_{32}$F$_3$N$_3$O$_2$S: C, 58.58; H, 6.84; N, 8.91. Found: C, 58.57; H, 6.96; N, 8.77.

Example 137

N-[(3E)-2-butyl-5-tert-butyl-1-methyl-1,2-dihydro-3H-pyrazol-3-ylidene]-2-[(2-hydroxy-2-methylpropyl)thio]-5-(trifluoromethyl)benzamide

Example 137A

S-2-hydroxy-2-methylpropyl ethanethioate

To a mixture of 1-chloro-2-methylpropan-2-ol (2.2 g, 20.26 mmol) and potassium ethanethioate (6.94 g, 60.8 mmol) in DMF (20 mL) was added 100 mg of sodium bromide and the resulting mixture was heated at 50° C. for 18 hours. The mixture was then poured into water and extracted with EtOAc. The acetate layer was washed with water, brine, dried with MgSO$_4$ and concentrated under reduced pressure to provide 3.4 g of the title compound.

Example 137B 1-mercapto-2-methylpropan-2-ol

A mixture of Example 137A (2.9 g, 19.57 mmol) and 1 N aqueous potassium hydroxide (41 mL, 41 mmol) in MeOH (40 mL) was stirred at room temperature for 10 hours. The methanol was removed under reduced pressure and the residue was acidified to pH 4 and then brought to pH 8 by the addition of aqueous NaHCO$_3$. The solution was extracted with EtOAc to afford 2.15 g of the title compound.

Example 137C

N-[(3E)-2-butyl-5-tert-butyl-1-methyl-1,2-dihydro-3H-pyrazol-3-ylidene]-2-[(2-hydroxy-2-methylpropyl)thio]-5-(trifluoromethyl)benzamide A mixture of Example 81C (400 mg, 1 mmol), 1-mercapto-2-methylpropan-2-ol (213 mg, 2 mmol) and potassium tert-butoxide (225 mg, 2 mmol) in dimethylacetamide (10 mL) was heated at 100° C. for 12 hours. The mixture was then poured into water and extracted with ethyl acetate. The acetate layer was washed with brine, dried with MgSO$_4$, filtered, and concentrated under reduced pressure. Purification by chromatography (SiO$_2$, eluant: EtOAc-MeOH 9:1) afforded 125 mg of the title compound. $^1$H NMR (300 MHz, DMSO-D$_6$) δ ppm 0.90 (t, J=7.3 Hz, 3H), 1.25 (s, 6H), 1.31-1.42 (m, 11H), 1.58-1.81 (m, 2H), 2.95 (s, 2H), 3.87 (s, 3H), 4.30-4.43 (m, 2H), 4.70 (s, 1H), 6.84 (s, 1H), 7.40-7.65 (m, 2H), 8.21 (d, J=2.0 Hz, 1H). MS (ESI$^+$) m/z 486 (M+H)$^+$. Anal. calculated for C$_{24}$H$_{34}$F$_3$N$_3$O$_2$S: C, 59.36; H, 7.06; N, 8.65. Found: C, 59.27; H, 6.74; N, 8.40.

Example 138

N-[(3E)-2-butyl-5-tert-butyl-1-methyl-1,2-dihydro-3H-pyrazol-3-ylidene]-2-(2-hydroxy-2-methylpropoxy)-5-nitrobenzamide

Example 138A (E)-N-(5-tert-butyl-2-butyl-1-methyl-1H-pyrazol-3(2H)-ylidene)-2-fluoro-5-nitrobenzamide The title compound was prepared as described in Example 27G substituting Example 108C for Example 27F and 2-fluoro-5-nitrobenzoyl chloride for 2-fluoro-5-(trifluoromethyl)benzoyl chloride. $^1$H NMR (300 MHz, CDCl$_3$) δ ppm 0.99 (t, J=7.34 Hz, 3H), 1.43 (s, 9H), 1.37-1.49 (m, 2H), 1.66-1.78 (m, 2H), 4.29-4.38 (m, 2H), 7.09 (s, 1H), 7.17 (t, J=9.32 Hz, 1H), 8.19 (dt, J=9.02, 3.42 Hz, 1H), 8.97 (dd, J=6.54, 2.97 Hz, 1H); MS (DCI/NH$_3$) m/z 377 (M+H)$^+$.

Example 138B

N-[(3E)-2-butyl-5-tert-butyl-1-methyl-1,2-dihydro-3H-pyrazol-3-ylidene]-2-(2-hydroxy-2-methylpropoxy)-5-nitrobenzamide The title compound was prepared as described in Example 81E substituting Example 138A for Example 81C. $^1$H NMR (300 MHz, CDCl$_3$) δ ppm 0.98 (t, J=7.14 Hz, 3H), 1.23 (s, 6H), 1.43 (s, 9H), 1.58 (s, 2H) 1.62-1.75 (m, 2H), 1.81-2.02 (m, 2H), 3.78 (s, 3H), 4.06 (s, 2H), 4.25-4.33 (m, 2H), 6.99 (t, J=4.36 Hz, 2H), 8.17 (dd, J=8.92, 2.97 Hz, 1H), 8.75 (d, J=3.17 Hz, 1H); MS (ESI$^+$) m/z 447 (M+H)$^+$, 445 (M−H)$^−$.

Example 139

N-[(3E)-5-tert-butyl-2-(cyclopropylmethyl)-1-methyl-1,2-dihydro-3H-pyrazol-3-ylidene]-5-cyano-2-(2-hydroxy-2-methylpropoxy)benzamide Example 139A N-[(3E)-5-tert-butyl-2-(cyclopropylmethyl)-1-methyl-1,2-dihydro-3H-pyrazol-3-ylidene]-5-cyano-2-fluorobenzamide The title compound was prepared according as described in Example 27G in 83% yield, substituting 5-cyano-2-fluorobenzoyl chloride for 2-fluoro-5-(trifluoromethyl)benzoyl chloride. $^1$H NMR (300 MHz, DMSO-d$_6$) δ ppm 0.40-0.57 (m, 4H), 1.12-1.28 (m, 1H), 1.39 (s, 9H), 3.94 (s, 3H), 4.24 (d, J=7.12 Hz, 2H), 6.83 (s, 1H), 7.38 (dd, J=10.17, 8.48 Hz, 1H), 7.82-7.91 (m, 1H), 8.15 (dd, J=6.95, 2.20 Hz, 1H); MS (ESI$^+$) m/z 355 (M+H)$^+$, 353 (M−H)$^−$.

Example 139B

N-[(3E)-5-tert-butyl-2-(cyclopropylmethyl)-1-methyl-1,2-dihydro-3H-pyrazol-3-ylidene]-5-cyano-2-(2-hydroxy-2-methylpropoxy)benzamide The title compound was prepared as described in Example 81E substituting Example 139A for Example 81C. $^1$H NMR (300 MHz, DMSO-d$_6$) δ ppm 0.37-0.56 (m, 4H), 1.14 (s, 6H), 1.15-1.25 (m, J=7.12, 7.12 Hz, 1H), 1.39 (s, 9H), 3.88 (s, 2H), 3.92 (s, 3H), 4.20 (d, J=7.12 Hz, 2H), 5.28 (s, 1H), 6.76 (s, 1H), 7.18 (d, J=8.82 Hz, 1H), 7.71 (dd, J=8.48, 2.37 Hz, 1H), 7.79 (d, J=2.37 Hz, 1H); MS (ESI$^+$) m/z 425 (M+H)$^+$, 423 (M−H)$^−$.

Example 140

2-[(2-amino-2-oxoethyl)thio]-N-[(3E)-2-butyl-5-tert-butyl-1-methyl-1,2-dihydro-3H-pyrazol-3-ylidene]-5-(trifluoromethyl)benzamide A mixture of Example 81C (400 mg, 1 mmol), 2-mercaptoacetamide (183 mg, 2 mmol) and potassium carbonate (277 mg, 2 mmol) in DMA (10 mL) was heated at 50° C. for 14 hours. The mixture was then poured into water and extracted with ethyl acetate. The acetate layer was washed with brine, dried with MgSO$_4$, filtered, and concentrated under reduced pressure. Purification by chromatography (SiO$_2$, EtOAc-MeOH: 9:1) afforded 235 mg of the title compound. $^1$H NMR (300 MHz, DMSO-d$_6$) δ ppm 0.81-1.02 (m, 3H), 1.27-1.44 (m, 11H), 1.56-1.78 (m, 2H), 3.55 (s, 2H), 3.88 (s, 3H), 4.27-4.50 (m, 2H), 6.83 (s, 1H), 7.12 (s, 1H), 7.41-7.73 (m, 3H), 8.32 (d, J=2.0 Hz, 1H). MS (ESI$^+$) m/z 471 (M+H)$^+$. Anal. calculated for C$_{22}$H$_{29}$F$_3$N$_4$O$_2$S.0.25; H$_2$O: C, 55.62; H, 6.26; N, 11.79. Found: C, 55.46; H, 6.32; N, 11.50.

Example 141 tert-butyl 2-({[(2Z)-3-butyl-5-tert-butyl-1,3,4-thiadiazol-2(3H)-ylidene]amino}carbonyl)-4-(trifluoromethyl)phenoxycarbamate A mixture of Example 7B (121 mg, 0.3 mmol), tert-butyl hydroxycarbamate (44 mg, 0.33 mmol) and 1N solution of potassium tert-butoxide in THF (0.3 mL, 0.3 mmol) were combined in THF (10 mL) and the mixture was stirred at room temperature for 1 hour. Acetic acid was added to adjust the acidity to pH 5 and the mixture was concentrated under reduced pressure. The residue was partitioned between EtOAc and water. The organic extract was washed with brine, dried with MgSO$_4$ and concentrated under reduced pressure. The residue was purified by chromatography (SiO$_2$, hexane-EtOAc: 2:1) to afford 100 mg of the title compound. $^1$H NMR (300 MHz, DMSO-d$_6$) δ ppm 0.92 (t, J=7.3 Hz, 3H), 1.25-1.53 (m, 20H), 1.72-1.89 (m, 2H), 4.38 (t, J=7.1 Hz, 2H), 7.46 (d, J=9.1 Hz, 1H), 7.85 (dd, J=8.7, 2.4 Hz, 1H), 8.19 (d, J=2.4 Hz, 1H), 11.03 (s, 1H). MS (ESL) m/z 517 (M+H)$^+$.

Example 142

2-[(tert-butylamino)oxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of Example 1E (170 mg, 0.4 mmol) and N-tert-butylhydroxylamine hydrochloride (Aldrich, 100 mg, 0.8 mmol) in THF (25 mL) was added dropwise 1N potassium tert-butoxide in THF (0.6 mL, 0.6 mmol) and the mixture was stirred at room temperature for 24 hours. The mixture was then concentrated under reduced pressure and the residue was partitioned between EtOAc and water. The ethyl acetate layer was washed with brine, dried with MgSO$_4$, filtered, and concentrated under reduced pressure. The residue was purified by chromatography (SiO$_2$, EtOAc-MeOH: 12:1) to afford 150 mg of the title compound. $^1$H NMR (300 MHz, DMSO-d$_6$) δ ppm 1.09 (s, 9H), 1.39 (s, 9H), 1.55-2.02 (m, 4H), 3.56-3.66 (m, 1H), 3.70-3.81 (m, 1H), 3.88 (s, 3H), 4.09-4.22 (m, 1H), 4.36 (d, J=5.6 Hz, 2H), 6.80 (s, 1H), 7.08 (s, 1H), 7.45-7.81 (m, 3H); MS (DCI/NH$_3$) m/z 497 (M+H)$^+$. Anal. calculated for C$_{25}$H$_{35}$F$_3$N$_4$O$_3$.0.5H$_2$O: C, 59.39; H, 7.18; N, 11.08. Found: C, 59.35; H, 7.28; N, 10.55.

Example 143

N-[(2Z)-3-butyl-5-tert-butyl-1,3,4-thiadiazol-2(3H)-ylidene]-2-[2-(4-fluorobenzoyl)hydrazino]-5-(trifluoromethyl)benzamide The title compound was prepared as described in Example 191, substituting isonicotinohydrazide with 4-fluorobenzohydrazide. $^1$H NMR (300 MHz, DMSO-d$_6$) δ 0.93 (t, 3H), 1.29-1.48 (m, 11H), 1.78-1.91 (m, 2H), 4.43 (t, J=7.3 Hz, 2H), 7.15 (d, J=8.8 Hz, 1H), 7.32-7.44 (m, 2H), 7.69 (dd, J=9.0, 2.2 Hz, 1H), 7.95-8.08 (m, 2H), 8.56 (d, J=2.0 Hz, 1H), 10.41 (s, 1H), 10.84 (s, 1H); MS (ESI$^+$) m/z 538 (M+H)$^+$.

Example 144

N-[(2Z)-3-butyl-5-tert-butyl-1,3,4-thiadiazol-2(3H)-ylidene]-2-[(isopropylamino)oxy]-5-(trifluoromethyl)benzamide To a solution of Example 7B (807 mg, 2 mmol) and N-isopropylhydroxylamine (300 mg, 4 mmol) in THF (20 mL) at 0° C. was added 1N potassium tert-butoxide (2.5 mL, 2.5 mmol) and the resulting mixture was stirred at 0 to 5° C. for 1 hour. After acetic acid was added to adjust the acidity to pH 5, the volatiles were removed under reduced pressure. The residue was treated with saturated aqueous NaHCO$_3$ and extracted with EtOAc. The organic extract was washed with brine, dried with MgSO$_4$ and concentrated under reduced pressure. The residue was purified by chromatography (hexanes-CH$_2$Cl$_2$ 2:1) to afford 120 mg of the title compound. $^1$H NMR (300 MHz, DMSO-d$_6$) δ ppm 0.92 (t, J=7.3 Hz, 3H), 1.06 (d, J=6.3 Hz, 6H), 1.23-1.43 (m, 11H), 1.69-1.92 (m, 2H), 3.25-3.31 (m, 1H), 4.36 (t, J=7.1 Hz, 2H), 7.63 (d, J=5.6 Hz, 1H), 7.78 (s, 2H), 8.12 (s, 1H); MS (DCI/NH$_3$) m/z 459 (M+H)$^+$. Anal. calculated for C$_{21}$H$_{29}$F$_3$N$_4$O$_2$S: C, 55.01; H, 6.37; N, 12.22. Found: C, 55.17; H, 6.37; N, 11.87.

Example 145

2-[(tert-butylamino)oxy]-N-[(2Z)-3-butyl-5-(1-methylcyclopropyl)-1,3,4-thiadiazol-2(3H)-ylidene]-5-(trifluoromethyl)benzamide

Example 145A 2-fluoro-N-(5-(1-methylcyclopropyl)-1,3,4-thiadiazol-2-yl)-5-(trifluoromethyl)benzamide The title compound was prepared as described in Example 7A substituting 541-methylcyclopropyl)-1,3,4-thiadiazol-2-amine (WO2009048936) for 5-tert-butyl-1,3,4-thiadiazol-2-amine. MS (DCI/NH$_3$) m/z 346 (M+H)$^+$.

Example 145B (Z)—N-(3-butyl-5-(1-methylcyclopropyl)-1,3,4-thiadiazol-2(3H)-ylidene)-2-fluoro-5-(trifluoromethyl)benzamide The title compound was prepared as described in Example 7B substituting Example 145A for Example 7A. MS (DCI/NH$_3$) m/z 402 (M+H)$^+$.

Example 145C

2-[(tert-butylamino)oxy]-N-[(2Z)-3-butyl-5-(1-methylcyclopropyl)-1,3,4-thiadiazol-2(3H)-ylidene]-5-(trifluoromethyl)benzamide The title compound was prepared using the procedure as described in Example 34 substituting Example 145B for Example 7B. $^1$H NMR (500 MHz, chloroform-d) δ ppm 0.94-1.02 (m, 4H) 1.20 (s, 3H) 1.21 (s, 9H) 1.35-1.45 (m, 2H) 1.57 (s, 3H) 1.79-1.99 (m, 2H) 4.37 (t, J=7.17 Hz, 2H) 5.71 (s, 1H) 7.59 (dd, J=8.85, 2.44 Hz, 1H) 7.80 (d, J=8.85 Hz, 1H) 8.32 (d, J=1.83 Hz, 1H); MS (DCI/NH$_3$) m/z 471 (M+H)$^+$.

Example 146

2-[(tert-butylamino)oxy]-N-[(3E)-5-tert-butyl-2-(cyclopropylmethyl)-1-methyl-1,2-dihydro-3H-pyrazol-3-ylidene]-5-(trifluoromethyl)benzamide The title compound was prepared as described in Example 46 in 90% yield, substituting N-tert-butylhydroxyamine (prepared from commercially available t-butylhydroxylamine acetate (Aldrich) by adding saturated sodium bicarbonate solution and extracting free base with ethyl ether) for pyrazin-2-ylmethanol. $^1$H NMR (300 MHz, DMSO-d$_6$) δ ppm 0.36-0.52 (m, 4H), 1.09 (s, 9H), 1.13-1.25 (m, 1H), 1.39 (s, 9H), 3.90 (s, 3H), 4.18 (d, J=6.78 Hz, 2H), 6.79 (s, 1H), 7.06 (s, 1H), 7.46-7.55 (m, 1H), 7.59-7.72 (m, 2H); MS (ESI) m/z 467 (M+H)$^+$, 465 (M−H)$^−$.

Example 147

2-[(tert-butylamino)oxy]-N-[(2Z)-5-tert-butyl-3-(tetrahydro-2H-pyran-2-ylmethyl)-1,3,4-thiadiazol-2(3H)-ylidene]-5-(trifluoromethyl)benzamide

Example 147A (tetrahydro-2H-pyran-2-yl)methyl 4-methylbenzenesulfonate

The title compound was prepared as described in Example 114A, substituting cyclopentylmethanol with (tetrahydro-2H-pyran-2-yl)methanol.

Example 147B

N-[(2Z)-5-tert-butyl-3-(tetrahydro-2H-pyran-2-ylmethyl)-1,3,4-thiadiazol-2(3H)-ylidene]-2-fluoro-5-(trifluoromethyl)benzamide A mixture of Example 7A (1.5 g, 4.32 mmol), Example 147A (2.34 g, 8.64 mmol), potassium carbonate (1.19 g, 8.64 mmol), tetrabutylammonium iodide (20 mg, 06 mmol), tetrabutylammonium hydrogen sulfate (20 mg, 0.05 mmol) and tetraethylammonium iodide (20 mg, 0.08 mmol) in toluene (50 mL) was heated at reflux for 14 hours. The mixture was washed with water, brine, dried with MgSO$_4$, filtered, and concentrated under reduced pressure. The residue was purified by chromatography to afford 480 mg of the title compound. MS (DCI/NH$_3$) m/z 446 (M+H)$^+$.

Example 147C

2-[(tert-butylamino)oxy]-N-[(2Z)-5-tert-butyl-3-(tetrahydro-2H-pyran-2-ylmethyl)-1,3,4-thiadiazol-2(3H)-ylidene]-5-(trifluoromethyl)benzamide A mixture of Example 147B (445 mg, 1 mmol), N-tert-butylhydroxylamine (prepared from commercially available N-tert-butylhydroxylamine acetate (Aldrich) by adding saturated sodium bicarbonate solution and extracting free base with ethyl ether, 178 mg, 2 mmol) and 1N potassium tert butoxide in THF (1.5 mL, 1.5 mmol) in THF (15 mL) was stirred at 40° C. for 30 hours. The mixture was concentrated under reduced pressure and the residue was dissolved in EtOAc, washed with water, brine, dried with MgSO$_4$, filtered, and concentrated under reduced pressure. The residue was purified by chromatography (SiO$_2$, Hexanes-Et$_2$O: 4:1) to afford 75 mg of the title compound. $^1$H NMR (300 MHz, DMSO-d$_6$) δ ppm 1.08-1.17 (m, 9H), 1.29-1.51 (m, 14H), 1.62 (d, J=12.9 Hz, 1H), 1.79 (s, 1H), 3.78-3.91 (m, 2H), 4.22 (dd, J=13.7, 4.2 Hz, 1H), 4.51 (dd, J=13.7, 8.3 Hz, 1H), 7.34 (s, 1H), 7.72-7.86 (m, 2H), 8.12 (s, 1H); MS (ESI$^+$) m/z 515 (M+H)$^+$. Anal. calculated for C$_{24}$H$_{33}$F$_3$N$_4$O$_3$S: C, 56.02; H, 6.46; N, 10.89. Found: C, 56.11; H, 6.64; N, 10.94.

Example 148

N-[(2Z)-3-butyl-5-tert-butyl-1,3,4-thiadiazol-2(3H)-ylidene]-2-[(E)-tert-butyldiazenyl]-5-(trifluoromethyl)benzamide A mixture of Example 7B (807 mg, 2 mmol), tert-butylhydrazine hydrochloride (374 mg, 3 mmol) and potassium carbonate (550 mg, 4 mmol) in DMF (30 mL) was heated at reflux at 50° C. for 14 hours. The mixture was then poured into water and extracted with EtOAc. The acetate layer was washed with water, brine, dried with MgSO$_4$, filtered, and concentrated under reduced pressure. The residue was purified by chromatography (SiO$_2$, hexane-Et$_2$O: 9:1) to afford 340 mg of the title compound. $^1$H NMR (300 MHz, DMSO-d$_6$) δ ppm 0.82-0.99 (m, 3H), 1.21-1.47 (m, 20H), 1.72-1.91 (m, 2H), 4.33 (t, J=7.1 Hz, 2H), 7.27 (d, J=8.1 Hz, 1H), 7.94 (dd, J=8.1, 1.7 Hz, 1H), 8.21 (d, J=1.7 Hz, 1H); MS (DCI/NH$_3$) m/z 470 (M+H)$^+$. Anal. calculated for C$_{22}$H$_{30}$F$_3$N$_5$OS: C, 56.27; H, 6.44; N, 14.91. Found: C, 56.49; H, 6.59; N, 14.57.

Example 149

2-[(tert-butylamino)oxy]-N-[(3E)-2-butyl-5-tert-butyl-1-methyl-1,2-dihydro-3H-pyrazol-3-ylidene]-5-(trifluoromethyl)benzamide To a solution of Example 81C (0.45 g, 1.1 mmol) and N-(tert-butyl)hydroxylamine hydrochloride (0.28 g, 2.3 mmol) in THF (20 mL) was added potassium tert-butoxide (0.19 g, 1.7 mmol). The mixture was warmed to 40° C. and stirred for 18 hours then additional potassium tert-butoxide was added (0.40 g). The mixture was stirred for an additional 1 hour then partitioned between saturated aqueous NaHCO$_3$ (10 mL) and EtOAc (10 mL). The layers were separated and the aqueous phase was extracted with EtOAc (3×10 mL). The combined organic extracts were dried over anhydrous Na$_2$SO$_4$, filtered, and concentrated. Purification by column chromatography (SiO$_2$, 50% hexanes/EtOAc then 100% EtOAc then 9:1:0.1 EtOAc:MeOH:Et$_3$N) afforded the title compound (0.41 g, 0.88 mmol, 78% yield). $^1$H NMR (300 MHz, CDCl$_3$) δ ppm 0.96 (t, J=7.3 Hz, 3H) 1.20 (s, 9H) 1.34-1.43 (m, 2H) 1.42 (s, 9H) 1.64-1.72 (m, 2H) 3.72 (s, 3H) 4.27 (dd, J=7.5 Hz, 2H) 5.75 (s, 1H) 7.01 (s, 1H) 7.46 (dd, J=8.6, 1.9 Hz, 1H) 7.67 (d, J=8.8 Hz, 1H) 8.10 (d, J=2.0 Hz, 1H); MS (DCI/NH$_3$) m/z 469 (M+H)$^+$; Anal. calculated for C$_{24}$H$_{35}$F$_3$N$_4$O$_2$: Calc: C, 61.52; H, 7.53; N, 11.96. Found: C, 61.18; H, 7.26; N, 11.92.

Example 150

N-[(2Z)-3-butyl-5-tert-butyl-1,3,4-thiadiazol-2(3H)-ylidene]-5-(trifluoromethyl)-2-({[(1E)-1,2,2-trimethylpropylidene]amino}oxy)benzamide A mixture of Example 7B (680 mg, 1.69 mmol), (E)-3,3-dimethylbutan-2-one oxime (388 mg, 3.37 mmol) and 1N solution of potassium tert-butoxide (2.5 mL, 2.5 mmol) in THF (20 mL) was stirred at room temperature for 0.5 hour. The mixture was then concentrated under reduced pressure and the residue was partitioned between water and EtOAc. The acetate layer was washed with water, brine, dried with MgSO$_4$, filtered, and concentrated under reduced pressure. The residue was purified by chromatography (SiO$_2$, hexane-Et$_2$O: 9:1) to afford 700 mg of the title compound. $^1$H NMR (300 MHz, DMSO-d$_6$) δ ppm 0.92 (t, J=7.3 Hz, 3H), 1.16-1.21 (m, 9H), 1.24-1.44 (m, 11H), 1.74-1.88 (m, 2H), 2.10 (s, 3H), 4.36 (t, J=7.1 Hz, 2H), 7.69 (d, J=8.7 Hz, 1H), 7.82 (d, J=2.4 Hz, 1H), 8.24 (d, J=2.0 Hz, 1H); MS (DCI/NH$_3$) m/z 499 (M+H)$^+$.

Example 151

2-[(tert-butylamino)oxy]-N-[(2Z)-5-tert-butyl-3-(3-cyanopropyl)-1,3,4-thiadiazol-2(3H)-ylidene]-5-(trifluoromethyl)benzamide Example 151A (Z)—N-(5-tert-butyl-3-(3-cyanopropyl)-1,3,4-thiadiazol-2(3H)-ylidene)-2-fluoro-5-(trifluoromethyl)benzamide A mixture of Example 7A (400 mg, 1.15 mmol), potassium carbonate (318 mg, 2.30 mmol) and 4-bromobutanenitrile (170 mg, 1.15 mmol) in toluene (8 mL) and dioxane (2 mL) was treated with tetrabutylammonium hydrogensulfate (2.74 mg, 8.06 µmol), tetrabutylammonium iodide (2.98 mg, 8.06 µmol) and tetraethylammonium iodide (296 mg, 1.152 mmol) and the resulting mixture was heated at reflux for 7 hours. The mixture was washed with water, brine, dried with MgSO$_4$, filtered, and concentrated under reduced pressure to give the title compound.

Example 151B

2-[(tert-butylamino)oxy]-N-[(2Z)-5-tert-butyl-3-(3-cyanopropyl)-1,3,4-thiadiazol-2(3H)-ylidene]-5-(trifluoromethyl)benzamide To a solution of N-tert-butylhydroxylamine (133 mg, 1.50 mmol) (prepared from commercially available N-tert-butylhydroxylamine acetate (Aldrich) by adding saturated sodium bicarbonate solution and extracting the free base with ethyl ether) in anhydrous THF (10 mL) was added sodium hydride (53.9 mg, 1.35 mmol). The mixture was stirred at 0° C. for 20 min. A solution of Example 151A (310 mg, 0.75 mmol) in THF (4 mL) was added and the mixture was stirred at 22° C. for 5 hours. The solvent was removed under reduced pressure and the residue was partitioned between water and ethyl acetate. The organic layer was washed with brine, dried with MgSO$_4$ and concentrated under reduced pressure. The residue was purified by chromatography on SiO$_2$ using an Analogix® Intelliflash280™ (Hexanes-EtOAc: 0-50% gradient) to give the title compound. $^1$H NMR (300 MHz, CDCl$_3$) δ ppm 1.22 (s, 9H), 1.42 (s, 9H), 2.23-2.37 (m, 2H), 2.48 (t, J=7.1 Hz, 2H), 4.54 (t, J=6.5 Hz, 2H), 5.75 (s, 1H), 7.61 (dd, J=8.7, 2.4 Hz, 1H), 7.83 (d, J=8.7 Hz, 1H), 8.28 (d, J=2.4 Hz, 1H); MS (ESI) m/z 484 (M+H)$^+$.

Example 152

2-[(tert-butylamino)oxy]-N-[(2Z)-5-tert-butyl-3-isobutyl-1,3,4-thiadiazol-2(3H)-ylidene]-5-(trifluoromethyl)benzamide

Example 152A (Z)—N-(5-tert-butyl-3-isobutyl-1,3,4-thiadiazol-2(3H)-ylidene)-2-fluoro-5-(trifluoromethyl)benzamide The title compound was prepared as described in Example 151A, substituting 1-bromo-2-methylpropane for 4-bromobutanenitrile. LC/MS m/z 404 (M+H)$^+$.

Example 152B

2-[(tert-butylamino)oxy]-N-[(2Z)-5-tert-butyl-3-isobutyl-1,3,4-thiadiazol-2(3H)-ylidene]-5-(trifluoromethyl)benzamide The title compound was prepared as described in Example 151B, substituting Example 152A for Example 151A. $^1$H NMR (300 MHz, CDCl$_3$) δ ppm 0.97 (d, J=6.8 Hz, 6H), 1.22 (s, 9H), 1.42 (s, 9H), 2.30-2.46 (m, 1H), 4.22 (d, J=7.1 Hz, 2H), 5.70 (s, 1H), 7.59 (dd, J=8.6, 2.2 Hz, 1H), 7.80 (d, J=8.8 Hz, 1H), 8.31 (d, J=2.4 Hz, 1H); MS (ESI) m/z 473 (M+H)$^+$.

Example 153

2-[(tert-butylamino)oxy]-N-[(2Z)-5-tert-butyl-3-[(2R)-tetrahydrofuran-2-ylmethyl]-1,3,4-thiadiazol-2(3H)-ylidene]-5-(trifluoromethyl)benzamide

Example 153A

N-[(2Z)-5-tert-butyl-3-[(2R)-tetrahydrofuran-2-ylmethyl]-1,3,4-thiadiazol-2(3H)-ylidene]-2-fluoro-5-(trifluoromethyl)benzamide The title compound was prepared as described in Example 1D, substituting Example 69C for Example 1C. LC/MS m/z 432 (M+H)$^+$.

Example 153B

2-[(tert-butylamino)oxy]-N-[(2Z)-5-tert-butyl-3-[(2R)-tetrahydrofuran-2-ylmethyl]-1,3,4-thiadiazol-2(3H)-ylidene]-5-(trifluoromethyl)benzamide To a solution of N-tert-butylhydroxylamine (145 mg, 1.62 mmol) (prepared from commercially available N-tert-butylhydroxylamine acetate (Aldrich) by adding saturated sodium bicarbonate solution and extracting the free base with ethyl ether) in anhydrous THF (10 mL) was added sodium hydride (58.4 mg, 1.46 mmol). The mixture was stirred at 0° C. for 20 minutes. A solution of Example 153A (350 mg, 0.81 mmol) in THF (4 mL) was added and the mixture was stirred at 0° C. for 3 hours. The solvent was removed under reduced pressure and the residue was partitioned between water and ethyl acetate. The organic layer was washed with brine, dried with MgSO$_4$, filtered, and concentrated under reduced pressure. The residue was purified by chromatography on SiO$_2$ using an Analogix® Intelliflash280™ (Hexanes-EtOAc: 0-50% gradient) to give the title compound. $^1$H NMR (300 MHz, CDCl$_3$) δ ppm 1.22 (s, 9H), 1.42 (s, 9H), 1.74-1.89 (m, 1H), 1.88-2.08 (m, 3H), 3.74-3.84 (m, 1H), 3.89-4.00 (m, 1H), 4.29 (dd, J=12.0, 4.7 Hz, 1H), 4.45-4.63 (m, 2H), 5.73 (s, 1H), 7.59 (dd, J=8.8, 3.1 Hz, 1H), 7.80 (d, J=8.8 Hz, 1H), 8.33 (d, J=2.4 Hz, 1H); MS (ESI) m/z 501 (M+H)$^+$.

Example 154

2-[(acetylamino)oxy]-N-[(2Z)-3-butyl-5-tert-butyl-1,3,4-thiadiazol-2(3H)-ylidene]-5-(trifluoromethyl)benzamide To a solution of N-hydroxyacetamide (130 mg, 1.74 mmol) in anhydrous THF (10 mL) was added sodium hydride (55.5 mg, 1.39 mmol). The reaction was stirred at 0° C. for 20 minutes. A solution of Example 7B (280 mg, 0.70 mmol) in THF (4 mL) was added to the reaction mixture and the reaction was stirred at 30° C. for 8 hours. The solvent was removed under reduced pressure and the residue was partitioned between water and ethyl acetate. The organic layer was washed with brine, dried with MgSO$_4$, filtered, and concentrated under reduced pressure. The residue was purified by chromatography on SiO$_2$ using an Analogix® Intelliflash280™ (Hexanes-EtOAc: 0-50% gradient) to give the title compound. $^1$H NMR (300 MHz, CDCl$_3$) δ ppm 0.92 (t, J=7.3 Hz, 3H), 1.24-1.37 (m, 2H), 1.37-1.43 (m, 9H), 1.75-1.89 (m, 2H), 1.96 (s, 3H), 4.37 (t, J=7.1 Hz, 2H), 7.39 (d, J=8.5 Hz, 1H), 7.83 (d, J=8.5 Hz, 1H), 8.21 (d, J=2.0 Hz, 1H), 11.90 (s, 1H); MS (ESI) m/z 459 (M+H)$^+$.

Example 155

2-[(tert-butylamino)oxy]-N-[(3E)-5-tert-butyl-2-(cyclobutylmethyl)-1-methyl-1,2-dihydro-3H-pyrazol-3-ylidene]-5-(trifluoromethyl)benzamide To a solution of Example 86D (0.52 g, 1.3 mmol) and N-(tert-butyl)hydroxylamine hydrochloride (Aldrich, 0.32 g, 2.5 mmol) in THF (10 mL) was added potassium tert-butoxide (0.57 g, 5.1 mmol). The mixture was allowed to stir at ambient temperature for 16 hours then partitioned between saturated aqueous NaHCO$_3$ (10 mL) and EtOAc (10 mL). The layers were separated and the aqueous phase was extracted with EtOAc (3×10 mL). The combined organic extracts were dried over anhydrous Na$_2$SO$_4$, filtered, and concentrated. Purification by column chromatography (SiO$_2$, 50% hexanes/EtOAc then 100% EtOAc then 9:1:0.1 EtOAc:MeOH:Et$_3$N) afforded the title compound (0.10 g, 0.21 mmol, 16% yield). $^1$H NMR (300 MHz, CDCl$_3$) δ ppm 1.20 (s, 9H) 1.41 (s, 9H) 1.84-1.99 (m, 4H) 1.98-2.07 (m, 2H) 2.58-2.76 (m, 1H) 3.69 (s, 3H) 4.33 (d, J=7.1 Hz, 2H) 5.76 (s, 1H) 7.02 (s, 1H) 7.46 (dd, J=8.6, 1.9 Hz, 1H) 7.68 (d, J=8.8 Hz, 1H) 8.12 (d, J=2.4 Hz, 1H); MS (DCI/NH$_3$) m/z 481 (M+H)$^+$. Anal. calculated for C$_{25}$H$_{35}$F$_3$N$_4$O$_2$: Calc: C, 62.48; H, 7.34; N, 11.66. Found: C, 62.19; H, 7.12; N, 11.48.

Example 156

2-[(tert-butylamino)oxy]-N-[(3E)-5-tert-butyl-1-methyl-2-(3,3,3-trifluoropropyl)-1,2-dihydro-3H-pyrazol-3-ylidene]-5-(trifluoromethyl)benzamide To a solution of N-(tert-butyl)hydroxylamine hydrochloride (Aldrich, 0.29 g, 2.3 mmol) and a solution of Example 87D (0.51 g, 1.2 mmol) in THF (10 mL) was added potassium tert-butoxide (0.65 g, 5.8 mmol). The mixture was warmed to 40° C. for 16 hours then partitioned between saturated aqueous NaHCO$_3$ (10 mL) and EtOAc (10 mL). The layers were separated and the aqueous phase was extracted with EtOAc (3×10 mL). The combined organic extracts were dried over anhydrous $Na_2SO_4$, filtered, and concentrated. Purification via column chromatography ($SiO_2$, 50% hexanes/EtOAc then 100% EtOAc then 9:1:0.1 EtOAc:MeOH:$Et_3N$) afforded the title compound (0.32 g, 0.63 mmol, 54% yield). $^1H$ NMR (300 MHz, $CDCl_3$) δ ppm 1.19 (s, 9H) 1.42 (s, 9H) 2.55-2.73 (m, 2H) 3.71 (s, 3H) 4.46 (t, J=7.1 Hz, 2H) 5.70 (s, 1H) 7.02 (s, 1H) 7.49 (dd, J=8.7, 2.4 Hz, 1H) 7.71 (d, J=8.7 Hz, 1H) 8.09 (d, J=2.4 Hz, 1H); MS (DCI/$NH_3$) m/z 509 (M+H)$^+$. Anal. calculated for $C_{23}H_{30}F_6N_4O_2$: Calc: C, 54.33; H, 5.95; N, 11.02. Found: C, 54.39; H, 5.79; N, 11.01.

Example 157

2-[(tert-butylamino)oxy]-N-[(2E)-1-butyl-4-tert-butylpyridin-2(1H)-ylidene]-5-(trifluoromethyl)benzamide The title compound was prepared as described in Example 92C substituting N-tert-butylhydroxylamine (prepared from commercially available N—N-tert-butylhydroxylamine acetate (Aldrich) by adding saturated sodium bicarbonate solution and extracting free base with ethyl ether) for Example 81D. $^1H$ NMR (500 MHz, chloroform-d) δ ppm 0.96 (t, J=7.32 Hz, 3H) 1.19 (s, 9H) 1.30 (s, 9H) 1.36-1.44 (m, 2H) 1.78-1.88 (m, 2H) 4.12-4.30 (m, 2H) 5.80 (s, 1H) 6.58 (dd, J=7.02, 2.14 Hz, 1H) 7.42-7.48 (m, 1H) 7.51 (dd, J=8.70, 1.98 Hz, 1H) 7.69 (d, J=8.85 Hz, 1H) 8.12 (d, J=2.14 Hz, 1H) 8.23 (d, J=2.14 Hz, 1H); MS (DCI/$NH_3$) m/z 466 (M+H)$^+$.

Example 158

2-[(tert-butylamino)oxy]-N-[(2Z)-5-tert-butyl-3-(2-methoxyethyl)-1,3,4-thiadiazol-2(3H)-ylidene]-5-(trifluoromethyl)benzamide

Example 158A

N-[(2Z)-5-tert-butyl-3-(2-methoxyethyl)-1,3,4-thiadiazol-2(3H)-ylidene]-2-fluoro-5-(trifluoromethyl)benzamide The title compound was prepared as described in Example 7B substituting 1-bromo-2-methoxyethane for 1-iodobutane.

Example 158B

2-[(tert-butylamino)oxy]-N-[(2Z)-5-tert-butyl-3-(2-methoxyethyl)-1,3,4-thiadiazol-2(3H)-ylidene]-5-(trifluoromethyl)benzamide The title compound was prepared as described in Example 34 substituting Example 158A for Example 7B. $^1H$ NMR (300 MHz, DMSO-$d_6$) δ ppm 1.07-1.16 (m, 9H), 1.39 (s, 9H), 3.22-3.29 (m, 3H), 3.80 (t, J=5.4 Hz, 2H), 4.53 (t, J=5.4 Hz, 2H), 7.34 (s, 1H), 7.67-7.89 (m, 2H), 8.12 (d, J=2.4 Hz, 1H). MS (DCI) m/z 475 (M+H)$^+$. Anal. calculated for $C_{21}H_{29}F_3N_4O_3S$ C, 53.15; H, 6.16; N, 11.81. Found C, 52.97; H, 6.12; N, 11.53.

Example 159

N-[(3E)-2-butyl-5-tert-butyl-1-methyl-1,2-dihydro-3H-pyrazol-3-ylidene]-2-[(isopropylamino)oxy]-5-(trifluoromethyl)benzamide To a solution of Example 81C (0.51 g, 1.3 mmol) and N-isopropylhydroxylamine hydrochloride (0.29 g, 2.6 mmol) in THF (20 mL) was added potassium tert-butoxide (0.43 g, 3.8 mmol). The mixture was warmed to 40° C. for 18 hours then concentrated under reduced pressure. Purification by column chromatography ($SiO_2$, 50% hexanes/EtOAc then 100% EtOAc then 9:1:0.1 EtOAc:MeOH:$Et_3N$) afforded the title compound (0.11 g, 0.24 mmol, 19% yield). $^1H$ NMR (300 MHz, $CDCl_3$) δ ppm 0.97 (t, J=7.3 Hz, 3H) 1.11 (d, J=6.4 Hz, 6H) 1.33-1.49 (m, 2H) 1.42 (s, 9H) 1.63-1.73 (m, 2H) 3.43-3.59 (m, 1H) 3.75 (s, 3H) 4.28 (dd, J=7.1 Hz, 2H) 6.06 (s, 1H) 7.08 (s, 1H) 7.48 (dd, J=8.6, 1.9 Hz, 1H) 7.68 (d, J=8.8 Hz, 1H) 8.14 (d, J=2.0 Hz, 1H); MS (DCI/$NH_3$) m/z 455 (M+H)$^+$. Anal. calculated for $C_{23}H_{33}F_3N_4O_2$: Calc: C, 60.78; H, 7.32; N, 12.33. Found: C, 60.87; H, 7.37; N, 12.16.

Example 160

2-[(tert-butylamino)oxy]-N-[(2E)-1-butyl-5-tert-butylpyridin-2(1H)-ylidene]-5-(trifluoromethyl)benzamide

Example 160A 5-tert-butyl-1-butylpyridin-2(1H)-imine

The title compound was prepared as described in Example 92A substituting 5-tert-butylpyridin-2-amine for 4-tert-butylpyridin-2-amine. MS (DCI/$NH_3$) m/z 207 (M+H)$^+$.

Example 160B

N-[(2E)-1-butyl-5-tert-butylpyridin-2(1H)-ylidene]-2-fluoro-5-(trifluoromethyl)benzamide The title compound was prepared as described in Example 92B substituting Example 160A for Example 92A. MS (DCI/$NH_3$) m/z 397 (M+H)$^+$.

Example 160C

2-[(tert-butylamino)oxy]-N-[(2E)-1-butyl-5-tert-butylpyridin-2(1H)-ylidene]-5-(trifluoromethyl)benzamide The title compound was prepared as described in Example 92C substituting Example 160B for Example 92B. $^1H$ NMR (500 MHz, chloroform-d) δ ppm 0.97 (t, J=7.32 Hz, 3H) 1.20 (s, 9H) 1.29 (s, 9H) 1.35-1.48 (m, 2H) 1.75-1.94 (m, 2H) 4.16-4.30 (m, 2H) 5.80 (s, 1H) 7.37 (d, J=2.44 Hz, 1H) 7.51 (dd, J=8.70, 1.98 Hz, 1H) 7.57-7.75 (m, 2H) 8.14 (d, J=2.44 Hz, 1H) 8.25 (d, J=9.46 Hz, 1H); MS (DCI/$NH_3$) m/z 466 (M+H)$^+$.

Example 161

2-[(tert-butylamino)oxy]-N-{(3E)-5-tert-butyl-1-methyl-2-[(2R)-tetrahydrofuran-2-ylmethyl]-1,2-dihydro-3H-pyrazol-3-ylidene}-5-cyanobenzamide A mixture of N-tert-butylhydroxylamine (prepared from commercially available N-tert-butylhydroxylamine hydrochloride (Aldrich) by adding saturated sodium bicarbonate solution and extracting free base with ethyl ether) (0.2 g, 1.6 mmol) and sodium tert-butoxide (0.46 g, 4.7 mmol) in THF (2 mL) was stirred for 10 minutes. A solution of Example 90A (0.2 g, 0.5 mmol) in THF (0.5 mL) was added and the mixture stirred for 1 hour. The reaction mixture was partitioned between EtOAc (15 mL) and saturated $NaHCO_3$ (1 mL). The organic extract was washed with water and brine, dried with MgSO$_4$, filtered and concentrated. The residue was purified by chromatography (SiO$_2$, hexane:EtOAc:Et$_3$N (1:3:0.2) isocratic for 600 mL.) then recrystallized from EtOAc and hexanes to afford the title compound (0.12 g, 0.27 mmol, 51% yield). $^1$H NMR (500 MHz, Pyridine-d$_5$) δ ppm 1.16 (s, 9H), 1.31 (s, 9H), 1.50-1.59 (m, 2H), 1.60-1.68 (m, 1H), 1.71-1.79 (m, 1H), 3.53-3.59 (m, 1H), 3.67-3.73 (m, 1H), 3.79 (s, 3H), 4.21 (qd, J=6.7, 3.1 Hz, 1H), 4.38 (dd, J=15.1, 6.6 Hz, 1H), 4.60 (dd, J=15.3, 3.1 Hz, 1H), 7.38 (s, 1H), 7.65 (dd, J=8.7, 2.3 Hz, 1H), 7.96 (d, J=8.5 Hz, 1H), 8.54 (d, J=2.1 Hz, 1H); MS (DCI/NH$_3$) m/z 454.4 (M+H)$^+$. Anal. calculated for C$_{25}$H$_{35}$N$_5$O$_3$: C, 66.20; H, 7.78; N, 15.44. Found: C, 66.06; H, 7.78; N, 15.52.

Example 162

2-[(tert-butylamino)oxy]-N-[(2Z)-3-butyl-5-tert-butyl-1,3,4-thiadiazol-2(3H)-ylidene]-5-chlorobenzamide Example 162A (E)-N'-(5-tert-butyl-1,3,4-thiadiazol-2-yl)-N,N-dimethylformimidamide A mixture of 5-tert-butyl-1,3,4-thiadiazol-2-amine (Aldrich) (10.0 g, 63.6 mmol) and 1,1-dimethoxy-N,N-dimethylmethanamine (26.3 mL, 197 mmol) in 200 mL of toluene was heated at 100° C. for 12 hours. The mixture was cooled to room temperature and hexane was added. The solid was collected by filtration (hexane wash) to afford the title compound.

Example 162B (E)-5-tert-butyl-3-butyl-2-((dimethylamino)methyleneamino)-1,3,4-thiadiazol-3-ium bromide To a suspension of Example 162A (1.00 g, 4.71 mmol) in toluene (10 mL) was added 1-bromobutane (0.56 mL, 5.18 mmol). The mixture was heated at 100° C. for 12 hours, then cooled to ambient temperature and diluted with hexanes. The solid was collected by filtration (hexane wash) to afford the title compound. $^1$H NMR (300 MHz, DMSO-d$_6$) δ ppm 0.91 (t, J=7.5 Hz, 3H), 1.23-1.36 (m, 2H), 1.39 (s, 9H), 1.70-1.84 (m, 2H), 3.22 (s, 6H), 4.29 (t, J=7.1 Hz, 2H), 8.54 (s, 1H).

Example 162C 5-tert-butyl-3-butyl-1,3,4-thiadiazol-2(3H)-imine

A solution of Example 162B (4 g, 11.45 mmol) in 1N HCl (12.6 mL) was heated at 65° C. for 12 hours. The mixture was cooled at room temperature and extracted with ether (2×20 mL). The aqueous phase was neutralized to pH 7 with concentrated ammonia and extracted with ether (2×25 mL). The combined organic extracts were dried over MgSO$_4$, filtered, and concentrated under reduced pressure. The residue was purified by chromatography on SiO$_2$ using an Analogix® Intelliflash280™ (Hexanes-EtOAc: 0-80%) to give the title compound. LC/MS m/z 214 (M+H)$^+$.

Example 162D (Z)—N-(5-tert-butyl-3-butyl-1,3,4-thiadiazol-2(3H)-ylidene)-5-chloro-2-fluorobenzamide To a mixture of Example 162C (250 mg, 1.17 mmol), 1H-benzo[d][1,2,3]triazol-1-ol hydrate (179 mg, 1.17 mmol), N$_1$-((ethylimino)methylene)-N$_3$,N$_3$-dimethylpropane-1,3-diamine hydrochloride (225 mg, 1.17 mmol), 5-chloro-2-fluorobenzoic acid (205 mg, 1.17 mmol) in 8 mL of THF was added triethylamine (163 µL, 1.17 mmol). The mixture was heated at 70° C. for 12 hours then cooled to ambient temperature and diluted with ethyl acetate and aqueous NaHCO$_3$. The organic extract was concentrated and the residue was purified by chromatography on SiO$_2$ using an Analogix® Intelliflash280™ (Hex-EtOAc, 0 to 30% gradient) to give the title compound. LC/MS m/z 369 (M+H)$^+$.

Example 162E

2-[(tert-butylamino)oxy]-N-[(2Z)-3-butyl-5-tert-butyl-1,3,4-thiadiazol-2(3H)-ylidene]-5-chlorobenzamide The title compound was prepared as described in Example 34, substituting Example 162D for Example 7B. $^1$H NMR (300 MHz, CDCl$_3$) δ ppm 6 ppm 0.99 (t, J=7.3 Hz, 3H), 1.20 (s, 9H), 1.33-1.40 (m, 2H), 1.41 (s, 9H), 1.80-1.95 (m, 2H), 4.39 (t, J=7.1 Hz, 2H), 5.73 (s, 1H), 7.30 (dd, J=9.1, 2.8 Hz, 1H), 7.61 (d, J=8.7 Hz, 1H), 8.00 (d, J=2.8 Hz, 1H); MS (ESI) m/z 440 (M+H)$^+$.

Example 163

2-[(tert-butylamino)oxy]-N-[(2Z)-5-tert-butyl-3-(cyclopropylmethyl)-1,3,4-thiadiazol-2(3H)-ylidene]-5-(trifluoromethyl)benzamide Example 163A N-[(2Z)-5-tert-butyl-3-(cyclopropylmethyl)-1,3,4-thiadiazol-2(3H)-ylidene]-2-fluoro-5-(trifluoromethyl)benzamide The title compound was prepared as described in Example 151A, substituting bromomethyl)cyclopropane for 4-bromobutanenitrile. LC/MS m/z 402 (M+H)$^+$.

Example 163B

2-[(tert-butylamino)oxy]-N-[(2Z)-5-tert-butyl-3-(cyclopropylmethyl)-1,3,4-thiadiazol-2(3H)-ylidene]-5-(trifluoromethyl)benzamide The title compound was prepared as described in Example 151B, substituting Example 163A for Example 151A. $^1$H NMR (300 MHz, CDCl$_3$) δ ppm 0.45-0.53 (m, 2H), 0.53-0.62 (m, 2H), 1.22 (s, 9H), 1.33-1.41 (m, 1H), 1.43 (s, 9H), 4.26 (d, J=7.1 Hz, 2H), 5.70 (s, 1H), 7.59 (dd, J=8.8, 2.4 Hz, 1H), 7.80 (d, J=8.8 Hz, 1H), 8.27 (d, J=2.4 Hz, 1H); MS (ESI) m/z 471 (M+H)$^+$.

Example 164

2-[(tert-butylamino)oxy]-N-[(2Z)-5-tert-butyl-3-(4,4,4-trifluorobutyl)-1,3,4-thiadiazol-2(3H)-ylidene]-5-(trifluoromethyl)benzamide

Example 164A

N-[(2Z)-5-tert-butyl-3-(4,4,4-trifluorobutyl)-1,3,4-thiadiazol-2(3H)-ylidene]-2-fluoro-5-(trifluoromethyl)benzamide The title compound was prepared as described in Example 151A by substituting 4-bromo-1,1,1-trifluorobutane for 4-bromobutanenitrile. LC/MS m/z 458 (M+H)$^+$.

Example 164B

2-[(tert-butylamino)oxy]-N-[(2Z)-5-tert-butyl-3-(4,4,4-trifluorobutyl)-1,3,4-thiadiazol-2(3H)-ylidene]-5-(trifluoromethyl)benzamide The title compound was prepared as described in Example 151B, substituting Example 164A for Example 151A. $^1$H NMR (300 MHz, CDCl$_3$) δ ppm 1.22 (s, 9H), 1.42 (s, 9H), 2.13-2.27 (m, 4H), 4.42-4.52 (m, 2H), 5.70 (s, 1H), 7.61 (dd, J=8.8, 3.1 Hz, 1H), 7.82 (d, J=8.8 Hz, 1H), 8.29 (d, J=2.0 Hz, 1H); MS (ESI) m/z 527 (M+H)$^+$.

Example 165

2-[(tert-butylamino)oxy]-N-[(2Z)-5-tert-butyl-3-(cyclobutylmethyl)-1,3,4-thiadiazol-2(3H)-ylidene]-5-(trifluoromethyl)benzamide

Example 165A

N-[(2Z)-5-tert-butyl-3-(cyclobutylmethyl)-1,3,4-thiadiazol-2(3H)-ylidene]-2-fluoro-5-(trifluoromethyl)benzamide The title compound was prepared as described in Example 151A by substituting (bromomethyl)cyclobutane for 4-bromobutanenitrile LC/MS m/z 416 (M+H)$^+$.

Example 165B

2-[(tert-butylamino)oxy]-N-[(2Z)-5-tert-butyl-3-(cyclobutylmethyl)-1,3,4-thiadiazol-2(3H)-ylidene]-5-(trifluoromethyl)benzamide The title compound was prepared as described in Example 151B, substituting Example 165A for Example 151A. $^1$H NMR (300 MHz, CDCl$_3$) δ ppm 1.22 (s, 9H), 1.41 (s, 9H), 1.85-1.98 (m, 4H), 2.01-2.15 (m, 2H), 2.84-3.01 (m, 1H), 4.42 (d, J=7.1 Hz, 2H), 5.70 (s, 1H), 7.59 (dd, J=8.7, 1.6 Hz, 1H), 7.80 (d, J=8.7 Hz, 1H), 8.31 (d, J=2.0 Hz, 1H); MS (ESI) m/z 485 (M+H)$^+$.

Example 166

2-({[1-amino-2,2-dimethylpropylidene]amino}oxy)-N-[(2Z)-3-butyl-5-tert-butyl-1,3,4-thiadiazol-2(3H)-ylidene]-5-(trifluoromethyl)benzamide A mixture of Example 7B (202 mg, 0.5 mmol), (E)-N'-hydroxypivalimidamide (58.2 mg, 0.5 mmol) and potassium carbonate (69.2 mg, 0.5 mmol) in DMSO (30 mL) was heated at 100° C. for 16 hours. The mixture was then poured into water and extracted with EtOAc. The acetate layer was washed with water, brine, dried with MgSO$_4$, filtered, and concentrated under reduced pressure. The residue was purified by chromatography (SiO$_2$, hexane-Et$_2$O: 1:1) to afford 160 mg of the title compound. $^1$H NMR (300 MHz, DMSO-d$_6$) δ ppm 0.94 (t, J=7.3 Hz, 3H), 1.19-1.27 (m, 9H), 1.30-1.47 (m, 11H), 1.78-1.91 (m, 2H), 4.39 (t, J=7.1 Hz, 2H), 6.33 (s, 2H), 7.66-7.91 (m, 2H), 8.38 (d, J=2.4 Hz, 1H); MS (DCI/NH$_3$) m/z 500 (M+H)$^+$. Anal. calculated for C$_{23}$H$_{32}$F$_3$N$_5$O$_2$S: C, 55.29; H, 6.46; N, 14.02. Found: C, 55.66; H, 6.25; N, 13.77.

Example 167

N-[(2Z)-3-butyl-5-tert-butyl-1,3,4-thiadiazol-2(3H)-ylidene]-2-{[(1-methylethylidene)amino]oxy}-5-(trifluoromethyl)benzamide The title compound was isolated as a side product of the procedure described in Example 144. $^1$H NMR (300 MHz, DMSO-d$_6$) δ ppm 0.92 (t, J=7.3 Hz, 3H), 1.28-1.45 (m, 11H), 1.73-1.89 (m, 2H), 2.03 (s, 3H), 2.14 (s, 3H), 4.37 (t, J=7.1 Hz, 2H), 7.69 (s, 1H), 7.78-7.91 (m, 1H), 8.27 (d, J=2.0 Hz, 1H). MS (DCI/NH$_3$) m/z 537 (M+H)$^+$.

Example 168

2-[(tert-butylamino)oxy]-N-{(3E)-5-tert-butyl-1-methyl-2-[(2R)-tetrahydrofuran-2-ylmethyl]-1,2-dihydro-3H-pyrazol-3-ylidene}-5-chlorobenzamide A mixture of N-tert-butylhydroxylamine (prepared from commercially available N-tert-butylhydroxylamine hydrochloride (Aldrich) by adding saturated sodium bicarbonate solution and extracting free base with ethyl ether) (0.29 g, 2.3 mmol) and sodium tert-butoxide (0.66 g, 6.9 mmol) in THF (1.5 mL) was stirred for 10 minutes. A solution of Example 89G (0.3 g, 0.76 mmol) in THF (1.5 mL) was added and the mixture stirred for 20 hours at 35° C. The reaction mixture was partitioned between EtOAc (15 mL) and saturated NaHCO$_3$ (1 mL). The organic extract was washed with water and brine, dried with MgSO$_4$, filtered and concentrated. The residue was purified by chromatography (SiO$_2$, CH$_2$Cl$_2$: EtOAc Et$_3$N (1:1:0.05)) and then recrystallized from EtOAc and hexanes to afford the title compound (0.19 g, 0.41 mmol, 54% yield). $^1$H NMR (500 MHz, Pyridine-d$_5$) δ ppm 1.15 (s, 9H), 1.31 (s, 9H), 1.50-1.59 (m, 2H), 1.60-1.69 (m, 1H), 1.72-1.79 (m, 1H), 3.53-3.59 (m, 1H), 3.68-3.73 (m, 1H), 4.20 (qd, J=6.6, 3.2 Hz, 1H), 4.37 (dd, J=15.0, 6.4 Hz, 1H), 4.58 (dd, J=15.1, 3.2 Hz, 1H), 7.20 (s, 1H), 7.38 (dd, J=8.8, 2.7 Hz, 1H), 7.46 (s, 1H), 7.82 (d, J=8.8 Hz, 1H), 8.26 (d, J=2.7 Hz, 1H); MS (DCI/NH$_3$) m/z 463.3 (M+H)$^+$. Anal. calculated for C$_{24}$H$_{35}$ClN$_4$O$_3$: C, 62.26; H, 7.62; N, 12.10. Found: C, 62.33; H, 7.87; N, 12.20.

Example 169

N-[(2Z)-3-butyl-5-tert-butyl-1,3,4-thiadiazol-2(3H)-ylidene]-2-{[(2,2-dimethylpropanoyl)amino]oxy}-5-(trifluoromethyl)benzamide The title compound was prepared as described in Example 34 substituting N-hydroxypivalamide for N-tert-butylhydroxylamine. $^1$H NMR (500 MHz, chloroform-d) δ ppm 1.00 (t, J=7.48 Hz, 3H) 1.28 (s, 9H) 1.36-1.44 (m, 2H) 1.43 (s, 9H)

1.83-2.00 (m, 2H) 4.43 (t, J=7.17 Hz, 2H) 7.70 (t, J=8.09 Hz, 2H) 8.47 (s, 1H) 10.79 (s, 1H) MS (DCI/NH$_3$) m/z 501 (M+H)$^+$.

Example 170

2-[(tert-butylamino)oxy]-N-[(2Z)-3-butyl-5-tert-butyl-1,3,4-thiadiazol-2(3H)-ylidene]-4-(trifluoromethyl)benzamide

Example 170A (Z)—N-(5-tert-butyl-3-butyl-1,3,4-thiadiazol-2(3H)-ylidene)-2-fluoro-4-(trifluoromethyl)benzamide The title compound was prepared as described in Example 162D substituting 2-fluoro-4-(trifluoromethyl)benzoic acid for 5-chloro-2-fluorobenzoic acid. MS (DCI/NH$_3$) m/z 404 (M+H)$^+$.

Example 170B

2-[(tert-butylamino)oxy]-N-[(2Z)-3-butyl-5-tert-butyl-1,3,4-thiadiazol-2(3H)-ylidene]-4-(trifluoromethyl)benzamide The title compound was prepared as described in Example 34, substituting Example 170A for Example 7B. $^1$H NMR $^1$H NMR (500 MHz, chloroform-d) δ ppm 0.97 (t, J=7.32 Hz, 3H) 1.23 (s, 9H) 1.33-1.41 (m, 2H) 1.43 (s, 9H) 1.81-1.93 (m, 2H) 4.39 (t, J=7.17 Hz, 2H) 7.20 (d, J=8.24 Hz, 1H) 7.96 (s, 1H) 8.04 (d, J=7.93 Hz, 1H); MS (DCI/NH$_3$) m/z 473 (M+H)$^+$.

Example 171

N-[(2Z)-3-butyl-5-tert-butyl-1,3,4-thiadiazol-2(3H)-ylidene]-2-[(dimethylamino)oxy]-5-(trifluoromethyl)benzamide To a solution of Example 7B (403 mg, 1 mmol) and N,N-dimethylhydroxylamine (122 mg, 2 mmol) in THF (15 mL) at room temperature was added 1N potassium tert-butoxide (1.5 mL, 1.5 mmol) and the resulting mixture was stirred at room temperature for 1 hour. After acetic acid was added to pH 5, the volatiles were removed under reduced pressure. The residue was treated with saturated aqueous NaHCO$_3$ and extracted with EtOAc. The organic extract was washed with brine, dried with MgSO$_4$, filtered, and concentrated under reduced pressure. The residue was purified by chromatography (SiO$_2$, Hexanes-Et$_2$O: 3:1) to afford 150 mg of the title compound. $^1$H NMR (300 MHz, DMSO-d$_6$) δ ppm 0.92 (t, J=7.3 Hz, 3H), 1.17-1.33 (m, 2H), 1.33-1.43 (m, 9H), 1.76-1.90 (m, 2H), 2.78 (s, 6H), 4.37 (t, J=7.1 Hz, 2H), 7.62-7.74 (m, 1H), 7.74-7.92 (m, 1H), 8.13 (d, J=2.7 Hz, 1H); MS (DCI/NH$_3$) m/z 445 (M+H)$^+$. Anal. calculated for C$_{20}$H$_{27}$F$_3$N$_4$O$_2$S: C, 54.04; H, 6.12; N, 12.60. Found: C, 54.24; H, 6.27; N, 12.42.

Example 172

N-[(2Z)-3-butyl-5-tert-butyl-1,3,4-thiadiazol-2(3H)-ylidene]-5-(trifluoromethyl)-2-({[2,2,2-trifluoro-1-methylethylidene]amino}oxy)benzamide The title compound was prepared as described in Example 34 by substituting (E)-1,1,1-trifluoropropan-2-one oxime for N-tert-butylhydroxyamine. $^1$H NMR (300 MHz, CDCl$_3$) δ ppm 0.99 (t, J=7.34 Hz, 3H), 1.33-1.40 (m, 2H), 1.43 (s, 9H), 1.90 (t, J=7.34 Hz, 2H), 2.37 (s, 3H), 4.40 (t, J=7.34 Hz, 2H), 7.68 (s, 2H), 8.43 (s, 1H); MS (ESI) m/z 511 (M+H)$^+$, 509 (M−H)$^−$.

Example 173

N-[(2Z)-3-butyl-5-tert-butyl-1,3,4-thiadiazol-2(3H)-ylidene]-2-(2-tert-butylhydrazino)-5-(trifluoromethyl)benzamide A solution of Example 7B (432 mg, 1.07 mmol) and tert-butylhydrazine (283 mg, 3.2 mmol) in toluene (15 mL) was heated at reflux for 24 hours. The resulting mixture was cooled to ambient temperature, and concentrated under reduced pressure. The residue was purified by silica gel chromatography (Hexane-CH$_2$Cl$_2$: 3:1) to afford 115 mg of the title compound. $^1$H NMR (300 MHz, DMSO-d$_6$) δ ppm 0.88-0.99 (m, 3H), 1.08 (s, 9H), 1.32-1.47 (m, 11H), 1.77-1.96 (m, 2H), 4.40 (t, J=7.1 Hz, 2H), 4.68 (s, 1H), 7.50-7.65 (m, 2H), 8.55 (d, J=2.0 Hz, 1H), 9.81 (s, 1H). MS (DCI/NH$_3$) m/z 472 (M+H)$^+$; Anal. calculated for C$_{22}$H$_{32}$F$_3$N$_5$OS: C, 56.03; H, 6.84; N, 14.85. Found: C, 56.13; H, 6.76; N, 14.76.

Example 174

2-[(tert-butylamino)oxy]-N-[(2Z)-5-tert-butyl-3-(4-fluorobutyl)-1,3,4-thiadiazol-2(3H)-ylidene]-5-(trifluoromethyl)benzamide

Example 174A (Z)—N-(5-tert-butyl-3-(4-fluorobutyl)-1,3,4-thiadiazol-2(3H)-ylidene)-2-fluoro-5-(trifluoromethyl)benzamide The title compound was prepared as described in Example 7B substituting 1-bromo-4-fluorobutane for 1-iodobutane. MS (DCI/NH$_3$) m/z 422 (M+H)$^+$.

Example 174B

2-[(tert-butylamino)oxy]-N-[(2Z)-5-tert-butyl-3-(4-fluorobutyl)-1,3,4-thiadiazol-2(3H)-ylidene]-5-(trifluoromethyl)benzamide To a solution of N-tert-butylhydroxylamine (prepared from commercially available N-tert-butylhydroxylamine acetate (Aldrich) by adding saturated sodium bicarbonate solution and extracting free base with ethyl ether) (85 mg, 0.95 mmol) in anhydrous THF (5 mL) was added a 1N solution of potassium tert-butoxide in THF (712 µL, 0.71 mmol). The mixture was stirred at room temperature for 20 minutes then cooled to 0° C. and Example 174A (200 mg, 0.475 mmol) was added. The reaction mixture was stirred at 0° C. for 30 min. The solvent was removed under reduced pressure and the residue was partitioned between water and ethyl acetate. The organic layer was washed with brine, dried with MgSO$_4$, filtered, and concentrated under reduced pressure. The residue was purified by silica gel chromatography (hexane:diethyl ether=17:3) to provide 27 mg of the title compound (12%). $^1$H NMR (500 MHz, chloroform-d) δ ppm 1.22 (s, 9H) 1.42 (s, 9H) 1.68-1.85 (m, 2H) 2.01-2.11 (m, 2H) 4.39-4.50 (m, 3H) 4.56 (t, J=5.80 Hz, 1H) 5.71 (s, 1H) 7.60

(dd, J=8.85, 2.14 Hz, 1H) 7.81 (d, J=8.85 Hz, 1H) 8.30 (d, J=2.44 Hz, 1H); MS (DCI/NH₃) m/z 491 (M+H)⁺.

Example 175

2-({[1-amino-2-methylpropylidene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166, replacing (E)-N'-hydroxypivalimidamide with (E)-N'-hydroxyisobutyrimidamide. ¹H NMR (300 MHz, DMSO-d₆) δ ppm 0.88-0.99 (m, 3H), 1.17 (t, J=7.0 Hz, 6H), 1.25-1.43 (m, 11H), 1.75-1.92 (m, 2H), 2.51-2.56 (m, 1H), 4.38 (t, J=7.1 Hz, 2H), 6.32 (s, 2H), 7.68-7.76 (m, 1H), 7.78-7.83 (m, 1H), 8.37 (d, J=2.4 Hz, 1H); MS (DCI/NH₃) m/z 486 (M+H)⁺. Anal. calculated for C₂₂H₃₀F₃N₅O₂S: C, 54.42; H, 6.23; N, 14.42. Found: C, 54.44; H, 5.91; N, 13.38.

Example 176 ethyl amino{[2-({[(2Z)-3-butyl-5-tert-butyl-1,3,4-thiadiazol-2(3H)-ylidene]amino}carbonyl)-4-(trifluoromethyl)phenoxy]imino}acetate The title compound was prepared as described in Example 166, replacing (E)-N'-hydroxypivalimidamide with (E)-ethyl 2-amino-2-(hydroxyimino)acetate except that the reaction mixture was heated at 50° C. for 5 hours. ¹H NMR (300 MHz, DMSO-d₆) δ ppm 0.88-0.99 (m, 3H), 1.25-1.36 (m, 5H), 1.41 (s, 9H), 1.76-1.91 (m, 2H), 4.22-4.49 (m, 4H), 6.80 (d, 2H), 7.75 (d, J=8.8 Hz, 1H), 7.89 (dd, J=9.5, 2.4 Hz, 1H), 8.40 (d, J=2.4 Hz, 1H). MS (DCI/NH₃) m/z 516 (M+H)⁺. Anal. calculated for C₂₂H₂₈F₃N₅O₄S: C, 51.25; H, 5.47; N, 13.58. Found: C, 51.40; H, 5.32; N, 13.25.

Example 177

2-[(tert-butylamino)oxy]-N-[(2Z)-5-tert-butyl-3-(oxetan-2-ylmethyl)-1,3,4-thiadiazol-2(3H)-ylidene]-5-(trifluoromethyl)benzamide The title compound was prepared as described in Example 34, substituting Example 96A for Example 7B. ¹H NMR (500 MHz, chloroform-d) δ ppm 1.18-1.26 (m, 9H) 1.38-1.46 (m, 9H) 2.60-2.70 (m, 1H) 2.73-2.85 (m, 1H) 4.55-4.65 (m, 2H) 4.66-4.73 (m, 1H) 4.80 (dd, J=13.73, 6.10 Hz, 1H) 5.19-5.43 (m, 1H) 7.60 (dd, J=8.85, 2.14 Hz, 1H) 7.80 (d, J=8.85 Hz, 1H) 8.31 (d, J=2.14 Hz, 1H); MS (DCI/NH₃) m/z 487 (M+H)⁺.

Example 178

N-{(3E)-5-tert-butyl-1-methyl-2-[(2R)-tetrahydrofuran-2-ylmethyl]-1,2-dihydro-3H-pyrazol-3-ylidene}-5-(trifluoromethyl)-2-({[(1E)-2,2,2-trifluoro-1-methylethylidene]amino}oxy)benzamide The title compound was prepared according to the procedure described in Example 1E, substituting (E)-1,1,1-trifluoropropan-2-one oxime for (R)-(tetrahydrofuran-2-yl)methanol. ¹H NMR (300 MHz, DMSO-d₆) δ ppm 1.41 (s, 9H) 1.60-2.14 (m, 4H) 3.66 (q, J=7.40 Hz, 1H) 3.75-3.85 (m, 1H) 4.02 (s, 3H) 4.17-4.30 (m, 1H) 4.39-4.47 (m, 2H) 5.68 (s, 1H) 5.75 (s, 1H) 6.93 (s, 1H) 7.64 (d, J=2.38 Hz, 1H) 8.01 (d, J=2.38 Hz, 1H) 17.65 (s, 1H); MS (ESI) m/z 535 (M+H)⁺, 533 (M−H)⁻.

Example 179

N-[(3E)-5-tert-butyl-2-(cyclopropylmethyl)-1-methyl-1,2-dihydro-3H-pyrazol-3-ylidene]-5-trifluoromethyl-2-({[(1E)-2,2,2-trifluoro-1-methylethylidene]amino}oxy)benzamide The title compound was prepared as described in Example 46, substituting (E)-1,1,1-trifluoropropan-2-one oxime for pyrazin-2-ylmethanol. ¹H NMR (300 MHz, DMSO-d₆) δ ppm 0.32-0.68 (m, 4H) 1.42 (s, 1H) 1.42 (s, 9H) 4.04 (s, 3H) 4.30 (d, J=7.12 Hz, 2H) 5.67 (s, 2H) 5.75 (s, 1H) 6.95 (s, 1H) 7.66 (d, J=2.71 Hz, 1H) 8.00 (d, J=2.37 Hz, 1H), 17.67 (s, 1H); MS (ESI) m/z 505 (M+H)⁺, 503 (M−H)⁻.

Example 180

N-[(2Z)-3-butyl-5-tert-butyl-1,3,4-thiadiazol-2(3H)-ylidene]-2-({[(1E)-1-methyl-2-oxopropylidene]amino}oxy)-5-(trifluoromethyl)benzamide The title compound was prepared as described in Example 7C, substituting (E)-3-(hydroxyimino)butan-2-one for (1-methylpiperidin-2-yl)methanol. ¹H NMR (300 MHz, DMSO-d₆) δ ppm 0.92 (t, J=7.34 Hz, 3H) 1.23-1.36 (m, 2H) 1.39 (s, 9H) 1.75-1.87 (m, 2H) 2.15 (s, 3H) 2.44 (s, 3H) 4.37 (t, J=6.94 Hz, 2H) 7.82-7.99 (m, 2H) 8.31 (d, J=1.98 Hz, 1H); MS (ESI) m/z 485 (M+H)⁺.

Example 181 tert-butyl 2-[2-({[(2Z)-3-butyl-5-tert-butyl-1,3,4-thiadiazol-2(3H)-ylidene]amino}carbonyl)-4-(trifluoromethyl)phenyl]hydrazinecarboxylate A mixture of Example 7B (404 mg, 1 mmol) and tert-butyl hydrazinecarboxylate (411 mg, 2 mmol) in pyridine (15 mL) was heated at reflux for 18 hours. The resulting mixture was cooled to ambient temperature and concentrated under reduced pressure. The residue was dissolved in EtOAc, washed with water, brine, dried with MgSO₄, filtered, and concentrated under reduced pressure. The residue was purified by silica gel chromatography and eluted with CH₂Cl₂ to afford 200 mg of the title compound. ¹H NMR (300 MHz, DMSO-d₆) δ ppm 0.85-1.00 (m, 3H), 1.26-1.49 (m, 20H), 1.75-1.90 (m, 2H), 4.40 (t, J=7.1 Hz, 2H), 7.03 (d, J=8.7 Hz, 1H), 7.71 (dd, J=9.1, 2.0 Hz, 1H), 8.53 (d, J=2.0 Hz, 1H), 9.26 (s, 1H), 9.98 (s, 1H); MS (DCI/NH₃) m/z 516 (M+H)⁺. Anal. calculated for C₂₃H₃₂F₃N₅O₃S: C, 53.58; H, 6.26; N, 13.58. Found: C, 53.68; H, 6.24; N, 13.52.

Example 182

2-({[amino(4-fluorophenyl)methylene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-4-fluoro-N'-hydroxybenzimidamide, and with the exception that the reaction mixture was heated at 75° C. for 0.5 hour. ¹H NMR (300 MHz, DMSO-d₆) δ ppm 0.94 (t, J=7.3 Hz, 3H), 1.31-1.38 (m, J=7.1 Hz, 2H), 1.38-1.43 (m, 9H), 1.76-1.93 (m, 2H), 4.40 (t, J=6.9 Hz, 2H), 6.90 (s, 2H), 7.35 (t, J=8.7 Hz, 2H), 7.79-7.94 (m, 4H), 8.42 (s, 1H); MS (DCI/NH₃) m/z 538

Example 183

N-[(2Z)-3-butyl-5-tert-butyl-1,3,4-thiadiazol-2(3H)-ylidene]-2-(2-pyridin-2-ylhydrazino)-5-(trifluoromethyl)benzamide The title compound was prepared as described in Example 181, replacing tert-butyl hydrazinecarboxylate with 2-hydrazinylpyridine. $^1$H NMR (300 MHz, DMSO-d$_6$) δ ppm 0.87 (t, J=7.5 Hz, 3H), 1.27-1.35 (m, 2H), 1.36-1.43 (m, 9H), 1.73-1.90 (m, 2H), 4.39 (t, J=7.3 Hz, 2H), 6.62 (d, J=8.1 Hz, 1H), 6.73 (dd, J=6.8, 5.4 Hz, 1H), 7.13 (d, J=8.8 Hz, 1H), 7.54 (s, 1H), 7.64 (dd, J=8.8, 2.0 Hz, 1H), 8.08 (d, J=3.7 Hz, 1H), 8.55 (d, J=2.0 Hz, 1H), 8.68 (s, 1H), 10.21 (s, 1H); MS (DCI/NH$_3$) m/z 493 (M+H)$^+$.

Example 184 tert-butyl 2-[2-({[2Z)-3-butyl-5-tert-butyl-1,3,4-thiadiazol-2(3H)-ylidene]amino}carbonyl)-4-(trifluoromethyl)phenyl]-1,2-dimethylhydrazinecarboxylate To a mixture of Example 181 (118 mg, 0.23 mmol) and iodomethane (130 mg, 0.92 mmol) in THF (20 mL) was added a 1N solution of potassium tert-butoxide in THF (0.46 mL, 0.46 mmol) and the mixture was heated at reflux for 12 hours. The mixture was then cooled to ambient temperature and concentrated under reduced pressure. The residue was partitioned between water and EtOAc. The organic layer was washed with brine, dried with MgSO$_4$, filtered, and concentrated under reduced pressure. The residue was purified by silica gel chromatography and eluted with 4:1 hexanes-Et$_2$O to afford 75 mg of the title compound. $^1$H NMR (300 MHz, DMSO-d$_6$) δ ppm 0.84-0.97 (m, 3H), 1.10-1.32 (m, 11H), 1.37-1.46 (m, 9H), 1.70-1.85 (m, 2H), 2.81 (s, 3H), 2.96 (s, 3H), 4.26 (s, 2H), 6.91 (d, J=8.8 Hz, 1H), 7.47 (s, 1H), 7.60 (dd, J=8.6, 1.9 Hz, 1H); MS (DCI/NH$_3$) m/z 544 (M+H)$^+$.

Example 185

2-({[1-amino ethylidene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-N'-hydroxyacetimidamide. $^1$H NMR (300 MHz, DMSO-d$_6$) δ ppm 0.92 (q, J=7.8 Hz, 3H), 1.25-1.48 (m, 11H), 1.74-1.93 (m, 5H), 4.38 (t, J=7.1 Hz, 2H), 6.18 (s, 1H), 6.78 (s, 1H), 7.64-7.88 (m, 2H), 8.38 (d, J=2.4 Hz, 1H); MS (DCI/NH$_3$) m/z 458 (M+H)$^+$. Anal. calculated for C$_{20}$H$_{26}$F$_3$N$_5$O$_2$S: C, 52.50; H, 5.73; N, 15.31. Found: C, 52.57; H, 5.72; N, 15.19.

Example 186

2-({[1-aminopropylidene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-N'-hydroxypropionimidamide. $^1$H NMR (300 MHz, DMSO-d$_6$) δ ppm 0.94 (t, J=7.3 Hz, 3H), 1.10-1.21 (m, 3H), 1.28-1.37 (m, 2H), 1.36-1.44 (m, 9H), 1.75-1.90 (m, 2H), 2.21 (q, J=7.5 Hz, 2H), 4.38 (t, J=7.1 Hz, 2H), 6.00-6.73 (m, 2H), 7.63-7.93 (m, 2H), 8.37 (d, J=2.4 Hz, 1H); MS (DCI/NH$_3$) m/z 472 (M+H)$^+$. Anal. calculated for C$_{21}$H$_{28}$F$_3$N$_5$O$_2$S: C, 53.49; H, 5.99; N, 14.95. Found: C, 53.49; H, 5.99; N, 14.57.

Example 187

N-[(2Z)-3-butyl-5-tert-butyl-1,3,4-thiadiazol-2(3H)-ylidene]-2-[2-(1-methylethylidene)hydrazino]-5-(trifluoromethyl)benzamide The title compound was prepared as described in Example 148 by replacing tert-butyl hydrazine hydrochloride with isopropylhydrazine hydrochloride. $^1$H NMR (300 MHz, DMSO-D$_6$) δ ppm 0.96 (t, J=7.3 Hz, 3H), 1.27-1.50 (m, 11H), 1.76-1.92 (m, 2H), 2.03 (d, J=15.9 Hz, 6H), 4.42 (t, J=7.0 Hz, 2H), 7.68 (s, 2H), 8.65 (s, 1H), 11.68 (s, 1H); MS (DCI/NH$_3$) m/z 456 (M+H)$^+$. Anal. calculated for C$_{21}$H$_{28}$F$_3$N$_5$OS: C, 55.37; H, 6.20; N, 15.37. Found: C, 55.48; H, 6.03; N, 14.80.

Example 188

2-({[amino(cyclopropyl)methylene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-N'-hydroxycyclopropanecarboximidamide. $^1$H NMR (300 MHz, DMSO-d$_6$) δ ppm 0.76-0.87 (m, 4H), 0.94 (t, J=7.3 Hz, 3H), 1.26-1.44 (m, 11H), 1.50-1.63 (m, 1H), 1.74-1.91 (m, 2H), 4.38 (t, J=7.1 Hz, 2H), 6.31 (s, 2H), 7.64-7.75 (m, 1H), 7.76-7.87 (m, 1H), 8.37 (d, J=2.4 Hz, 1H); MS (DCI/NH$_3$) m/z 484 (M+H)$^+$. Anal. calculated for C$_{22}$H$_{28}$F$_3$N$_5$O$_2$S: C, 54.65; H, 5.84; N, 14.48. Found: C, 54.59; H, 5.74; N, 14.20.

Example 189

2-{[azepan-2-ylideneamino]oxy}-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-azepan-2-one oxime. $^1$H NMR (300 MHz, DMSO-d$_6$) δ ppm 0.93 (t, J=7.3 Hz, 3H), 1.28-1.46 (m, 11H), 1.51-1.72 (m, 8H), 1.76-1.91 (m, 2H), 2.33-2.44 (m, 2H), 4.38 (t, J=7.1 Hz, 2H), 6.75 (t, 1H), 7.63-7.87 (m, 2H), 8.33 (d, J=2.0 Hz, 1H); MS (DCI/NH$_3$) m/z 512 (M+H)$^+$.

Example 190

N-[(2Z)-3-butyl-5-tert-butyl-1,3,4-thiadiazol-2(3H)-ylidene]-2-[(cyclopentylideneamino)oxy]-5-(trifluoromethyl)benzamide The title compound was prepared as described in Example 7C, substituting cyclopentanone oxime for (1-methylpiperidin-2-yl)methanol. $^1$H NMR (300 MHz, CDCl$_3$) δ ppm 0.99 (t, J=7.29 Hz, 3H) 1.32-1.48 (m, 11H) 1.74-1.95 (m, 6H) 2.46-2.58 (m, 2H) 2.72-2.84 (m, 2H) 4.33-4.45 (m, 2H) 7.56-7.71 (m, 2H) 8.38 (d, J=2.37 Hz, 1H); MS (ESI) m/z 483 (M+H)$^+$, 481 (M−H)$^−$.

(M+H)$^+$. Anal. calculated for C$_{25}$H$_{27}$F$_4$N$_5$O$_2$S: C, 55.86; H, 5.06; N, 13.03. Found: C, 56.07; H, 4.82; N, 12.89.

Example 191

N-[(2Z)-3-butyl-5-tert-butyl-1,3,4-thiadiazol-2(3H)-ylidene]-2-(2-isonicotinoylhydrazino)-5-(trifluoromethyl)benzamide A solution of Example 7B (360 mg, 0.89 mmol) and isonicotinohydrazide (245 mg, 1.79 mmol) and sodium bicarbonate (150 mg, 1.79 mmol) in DMA (10 mL) was heated at reflux at 100° C. for 15 hours. The resulting mixture was cooled to ambient temperature and poured into water and extracted with EtOAc. The acetate layer was washed with water, brine, dried with $MgSO_4$, filtered, and concentrated under reduced pressure. The residue was purified by silica gel chromatography and eluted with EtOAc to afford 350 mg of the title compound. $^1$H NMR (300 MHz, DMSO-$d_6$) δ ppm 0.92 (t, 3H), 1.26-1.47 (m, 11H), 1.77-1.97 (m, 2H), 4.44 (t, J=7.1 Hz, 2H), 7.17 (d, J=8.8 Hz, 1H), 7.64-7.72 (m, 1H), 7.83-7.91 (m, 2H), 8.57 (d, J=1.7 Hz, 1H), 8.73-8.85 (m, 2H), 10.47 (s, 1H), 11.11 (s, 1H). MS (DCI/$NH_3$) m/z 521 $(M+H)^+$. Anal. calculated for $C_{24}H_{27}F_3N_6O_2S$: C, 55.37; H, 5.23; N, 16.14. Found: C, 55.41; H, 5.21; N, 15.91.

Example 192 methyl 2-[2-({[(2Z)-3-butyl-5-tert-butyl-1,3,4-thiadiazol-2(3H)-ylidene]amino}carbonyl)-4-(trifluoromethyl)phenyl]hydrazinecarboxylate The title compound was prepared as described in Example 181 by replacing tert butyl hydrazinecarboxylate with methyl hydrazinecarboxylate. $^1$H NMR (300 MHz, DMSO-$d_6$) δ ppm 0.93 (t, 3H), 1.24-1.46 (m, 11H), 1.75-1.93 (m, 2H), 3.64 (s, 3H), 4.40 (t, J=7.1 Hz, 2H), 7.04 (d, J=8.8 Hz, 1H), 7.70 (dd, J=8.8, 2.4 Hz, 1H), 8.54 (d, J=1.7 Hz, 1H), 9.51 (s, 1H), 10.04 (s, 1H); MS (DCI/$NH_3$) m/z 474 $(M+H)^+$.

Example 193

N-[(2Z)-3-butyl-5-tert-butyl-1,3,4-thiadiazol-2(3H)-ylidene]-2-[2-(2,2-dimethylpropanoyl)hydrazino]-5-(trifluoromethyl)benzamide The title compound was prepared as described in Example 181 by replacing tert butyl hydrazinecarboxylate with pivalohydrazide. $^1$H NMR (300 MHz, DMSO-$d_6$) δ ppm 0.94 (t, J=7.3 Hz, 3H), 1.21 (s, 9H), 1.34-1.46 (m, 11H), 1.75-1.92 (m, 2H), 4.41 (t, J=7.3 Hz, 2H), 6.98 (d, J=8.7 Hz, 1H), 7.70 (dd, J=8.7, 2.4 Hz, 1H), 8.52 (d, J=1.6 Hz, 1H), 9.94 (s, 1H), 10.13 (s, 1H); MS (DCI/$NH_3$) m/z 500 $(M+H)^+$.

Example 194

N-[(3E)-2-butyl-5-tert-butyl-1-methyl-1,2-dihydro-3H-pyrazol-3-ylidene]-5-(trifluoromethyl)-2-({[(1E)-2,2,2-trifluoro-1-methylethylidene]amino}oxy)benzamide The title compound was prepared as described in Example 81E substituting (E)-1,1,1-trifluoropropan-2-one oxime for Example 81D. $^1$H NMR (300 MHz, DMSO-$d_6$) δ ppm 0.93 (t, J=7.34 Hz, 3H) 1.32-1.39 (m, 2H) 1.41 (s, 9H) 1.67-1.82 (m, 2H) 4.00 (s, 3H) 4.33 (t, J=7.54 Hz, 2H) 5.63 (s, 2H) 5.77 (s, 1H) 6.92 (s, 1H) 7.66 (d, J=2.38 Hz, 1H) 8.01 (d, J=2.38 Hz, 1H) 17.75 (s, 1H); MS (ESI) m/z 507 $(M+H)^+$, 505 $(M-H)^-$.

Example 195

2-[(tert-butylamino)oxy]-N-[(3E)-2-(cyclopentylmethyl)-5-isopropyl-1-methyl-1,2-dihydro-3H-pyrazol-3-ylidene]-5-(trifluoromethyl)benzamide To a mixture Example 114F (206 mg, 0.5 mmol) and N-tert-butylhydroxylamine (prepared from commercially available N-tert-butylhydroxylamine acetate (Aldrich) by adding saturated sodium bicarbonate solution and extracting free base with ethyl ether) (67 mg, 0.75 mmol) in anhydrous THF (15 mL) was added 1N potassium tert-butoxide in THF (1.35 mL, 1.35 mmol). The mixture was stirred at room temperature for 2 hours then acetic acid was added (pH 5). The mixture was concentrated under reduced pressure. The residue was diluted with saturated aqueous $NaHCO_3$ and extracted with EtOAc. The ethyl acetate layer was washed with water, brine, dried with anhydrous $MgSO_4$, filtered, and concentrated under reduced pressure. The residue was purified by silica gel chromatography and eluted with 9:1 EtOAc-MeOH to afford 100 mg of the title compound. $^1$H NMR (300 MHz, DMSO-$d_6$) δ ppm 1.09 (s, 9H), 1.24 (d, J=6.7 Hz, 6H), 1.31-1.72 (m, 8H), 2.27-2.40 (m, 1H), 3.00-3.15 (m, 1H), 3.73 (s, 3H), 4.18 (d, J=7.9 Hz, 2H), 6.77 (s, 1H), 7.06 (s, 1H), 7.46-7.57 (m, 1H), 7.60-7.70 (m, 1H), 7.77 (d, J=1.6 Hz, 1H); MS (DCI/$NH_3$) m/z 481 $(M+H)^+$. Anal. calculated for $C_{25}H_{35}F_3N_4O_2 \cdot 0.5H_2O$: C, 61.33; H, 7.41; N, 11.44. Found: C, 61.35; H, 7.48; N, 11.04.

Example 196

2-({[amino(pyridin-2-yl)methylene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-N'-hydroxypicolinimidamide. $^1$H NMR (300 MHz, DMSO-$d_6$) δ ppm 0.93 (t, 3H), 1.23-1.46 (m, 11H), 1.80-1.93 (m, 2H), 4.40 (t, J=7.1 Hz, 2H), 6.37 (s, 1H), 7.21 (s, 1H), 7.52-7.64 (m, 1H), 7.83-8.02 (m, 3H), 8.09 (d, J=8.1 Hz, 1H), 8.43 (d, J=2.4 Hz, 1H), 8.70 (d, J=5.1 Hz, 1H); MS (DCI/$NH_3$) m/z 521 $(M+H)^+$. Anal. calculated for $C_{24}H_{27}F_3N_6O_2S$: C, 55.37; H, 5.23; N, 16.14. Found: C, 55.51; H, 5.13; N, 15.97.

Example 197

N-[(2Z)-3-butyl-5-tert-butyl-1,3,4-thiadiazol-2(3H)-ylidene]-2-[2-(pyridin-3-ylcarbonyl)hydrazino]-5-(trifluoromethyl)benzamide The title compound was prepared as described in Example 191 by replacing isonicotinohydrazide with nicotinohydrazide. $^1$H NMR (300 MHz, DMSO-$d_6$) δ ppm 0.91 (t, 3H), 1.30-1.37 (m, 2H), 1.41 (s, 9H), 1.81-1.92 (m, 2H), 4.44 (t, J=7.1 Hz, 2H), 7.20 (d, J=8.7 Hz, 1H), 7.59 (dd, J=7.9, 5.2 Hz, 1H), 7.70 (dd, J=8.7, 2.4 Hz, 1H), 8.23-8.35 (m, 1H), 8.57 (d, J=2.0 Hz, 1H), 8.79 (dd, J=4.8, 1.6 Hz, 1H), 9.12 (d, J=1.6 Hz, 1H), 10.45 (s, 1H), 11.01 (s, 1H); MS (DCI/$NH_3$) m/z 521 $(M+H)^+$. Anal. calculated for $C_{24}H_{27}F_3N_6O_2S$: C, 55.37; H, 5.23; N, 16.14. Found: C, 55.46; H, 5.00; N, 15.77.

Example 198

N-[(3E)-2-butyl-5-tert-butyl-1-methyl-1,2-dihydro-3H-pyrazol-3-ylidene]-2-[2-(2,2-dimethylpropanoyl)hydrazino]-5-(trifluoromethyl)benzamide To a 20-ml vial were added Example 81C (240 mg, 0.600 mmol), solid potassium carbonate (Aldrich, 166 mg, 1.20 mmol), and pyridine (6 mL). Solid pivalohydrazide (Acros, 139 mg, 2.00 mmol) was added and the resulting slurry was stirred at 60-80° C. for 5 days. After cooling to room temperature, water (10 mL) was added and the mixture was extracted with dichloromethane (3×10 mL). The combined organic extracts were dried over sodium sulfate, filtered, and concentrated by rotary evaporator to give a brown oil. Flash chromatography (silica gel, 1-5% methanol in dichloromethane) afforded 59.2 mg (20%) of a white solid. $^1$H NMR (DMSO-d$_6$) δ 0.91 (t, J=7.3 Hz, 3H), 1.20 (s, 9H), 1.28-1.41 (m, 2H), 1.39 (s, 9H), 1.57-1.68 (m, 2H), 3.89 (s, 3H), 4.28 (t, J=7.5 Hz, 2H), 6.83 (d, J=8.3 Hz, 1H), 6.87 (s, 1H), 7.49 (dd, J=8.5, 2.2 Hz, 1H), 8.36 (d, J=2.4 Hz, 1H), 9.76 (d, J=2.0 Hz, 1H), 11.1 (d, J=2.4 Hz, 1H). MS (ESI$^+$) m/z 496 (M+H)$^+$.

Example 199

N-[(3E)-2-butyl-5-tert-butyl-1-methyl-1,2-dihydro-3H-pyrazol-3-ylidene]-2-[2-(pyridin-3-ylcarbonyl)hydrazino]-5-(trifluoromethyl)benzamide The title compound was prepared as described in Example 198 substituting nicotinohydrazide for pivalohydrazide. $^1$H NMR (DMSO-d$_6$) δ 0.82 (t, J=7.3 Hz, 3H), 1.24-1.36 (m, 2H), 1.39 (s, 9H), 1.59-1.70 (m, 2H), 3.90 (s, 3H), 4.31 (t, J=7.7 Hz, 2H), 6.90 (s, 1H), 7.03 (d, j=8.7 Hz, 1H), 7.51 (dd, J=8.7, 2.0 Hz, 1H), 7.59 (dd, J=7.9, 4.8 Hz, 1H), 8.25-8.29 (m, 1H), 8.41 (d, j=2.0 Hz, 1H), 8.78 (dd, J=4.8, 1.6 Hz, 1H), 9.10 (d, J=2.0 Hz, 1H), 10.85 (s, 1H), 11.59 (s, 1H); MS (ESI$^+$) m/z 517 (M+H)$^+$. Anal. calcd. for C$_{26}$H$_{31}$F$_3$N$_6$O$_2$: C, 60.45; H, 6.05; N, 16.27. Found: C, 59.63; H, 6.04; N, 15.89.

Example 200

N-[(3E)-2-butyl-5-tert-butyl-1-methyl-1,2-dihydro-3H-pyrazol-3-ylidene]-2-(2-isonicotinoylhydrazino)-5-(trifluoromethyl)benzamide The title compound was prepared as described in Example 198 substituting isonicotinodrazide for pivalohydrazide. $^1$H NMR (DMSO-d$_6$) δ 0.82 (t, J=7.5 Hz, 3H), 1.24-1.36 (m, 2H), 1.39 (s, 9H), 1.59-1.69 (m, 2H), 3.90 (s, 3H), 4.30 (t, J=7.5 Hz, 2H), 6.89 (s, 1H), 7.00 (d, J=8.8 Hz, 1H), 7.51 (dd, J=8.8, 2.4 Hz, 1H), 7.84 (d, J=6.1 Hz, 2H), 8.41 (d, J=2.0 Hz, 1H), 8.79 (d, J=6.1 Hz, 2H), 10.96 (s, 1H), 11.62 (s, 1H); MS (ESI$^+$) m/z 517 (M+H)$^+$. Anal. calcd. for C$_{26}$H$_{31}$F$_3$N$_6$O$_2$: C, 60.45; H, 6.05; N, 16.27. Found: C, 60.50; H, 6.11; N, 16.79.

Example 201

2-[2-({[(2Z)-3-butyl-5-tert-butyl-1,3,4-thiadiazol-2(3H)-ylidene]amino}carbonyl)-4-(trifluoromethyl)phenyl]hydrazinecarboxamide The title compound was prepared as described in Example 191 by replacing isonicotinohydrazide with hydrazinecarboxamide. $^1$H NMR (300 MHz, DMSO-d$_6$) δ ppm 0.94 (t, J=7.3 Hz, 3H), 1.26-1.45 (m, 11H), 1.77-1.90 (m, 2H), 4.40 (t, J=7.1 Hz, 2H), 6.12 (s, 2H), 7.07 (d, J=8.7 Hz, 1H), 7.70 (dd, J=8.9, 1.8 Hz, 1H), 7.70 (dd, J=8.9, 1.8 Hz, 1H), 8.53 (s, 1H), 9.94 (s, 1H); MS (DCI/NH$_3$) m/z 459 (M+H)$^+$.

Example 202

2-(2-benzylhydrazino)-N-[(2Z)-3-butyl-5-tert-butyl-1,3,4-thiadiazol-2(3H)-ylidene]-5-(trifluoromethyl)benzamide A mixture of Example 7B (404 mg, 1 mmol), benzylhydrazine hydrochloride (317 mg, 2 mmol) and sodium bicarbonate (336 mg, 4 mmol) in DMSO (15 mL) was heated at reflux for 12 hours. The resulting mixture was poured into water and extracted with EtOAc. The ethyl acetate layer was washed with water, brine, dried with MgSO$_4$, filtered, and concentrated under reduced pressure. The residue was purified by silica gel chromatography and eluted with 2:1 hexane-Et$_2$O to afford 50 mg of product. $^1$H NMR (300 MHz, DMSO-d$_6$) δ ppm 0.94 (t, J=7.3 Hz, 3H), 1.24-1.50 (m, 11H), 1.74-1.90 (m, 2H), 3.92 (d, J=5.8 Hz, 2H), 4.32 (t, J=7.1 Hz, 2H), 5.40 (s, 1H), 7.23-7.43 (m, 5H), 7.49-7.64 (m, 2H), 8.49 (s, 1H), 9.68 (s, 1H); MS (DCI/NH$_3$) m/z 506 (M+H)$^+$.

Example 203

2-({[amino(pyridin-4-yl)methylene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-N'-hydroxyisonicotinimidamide. $^1$H NMR (300 MHz, DMSO-d$_6$) δ ppm 0.93 (t, J=7.5 Hz, 3H), 1.27-1.47 (m, 11H), 1.74-1.93 (m, 2H), 4.40 (t, J=7.1 Hz, 2H), 7.04 (s, 2H), 7.76-7.84 (m, 2H), 7.87 (s, 2H), 8.41 (s, 1H), 8.65-8.78 (m, 2H); MS (DCI/NH$_3$) m/z 521 (M+H)$^+$.

Example 204

2-({[amino(pyridin-3-yl)methylene]amino}oxy)-N-[(2Z)-3-butyl-5-tert-butyl-1,3,4-thiadiazol-2(3H)-ylidene]-5-(trifluoromethyl)benzamide The title compound was prepared as described in Example 166 by replacing (E)-N'-hydroxypivalimidamide with (E)-N'-hydroxynicotinimidamide. $^1$H NMR (300 MHz, DMSO-d$_6$) δ ppm 0.94 (t, J=7.3 Hz, 3H), 1.28-1.48 (m, 11H), 1.78-1.96 (m, 2H), 4.40 (t, J=7.1 Hz, 2H), 6.87-7.14 (m, 2H), 7.50-7.59 (m, 1H), 7.78-7.93 (m, 2H), 8.12-8.26 (m, 1H), 8.41 (d, J=2.0 Hz, 1H), 8.72 (dd, J=4.7, 1.7 Hz, 1H), 9.00 (d, J=1.4 Hz, 1H); MS (DCI/NH$_3$) m/z 521 (M+H)$^+$.

Example 205 tert-butyl (2E)-1-[2-({[(2Z)-3-butyl-5-tert-butyl-1,3,4-thiadiazol-2(3H)-ylidene]amino}carbonyl)-4-(trifluoromethyl)phenyl]-2-[(6-methylpyridin-2-yl)methylene]hydrazinecarboxylate Example 205A (E)-tert-butyl 2-((6-methylpyridin-2-yl)methylene)hydrazinecarboxylate and (Z)-tert-butyl 2-((6-methylpyridin-2-yl)methylene)hydrazinecarboxylate A mixture of 6-methylpicolinaldehyde (1.21 g, 10 mmol), tert butyl hydrazinecarboxylate (1.32 g, 10 mmol) and acetic acid (0.57 mL, 10 mmol) in dioxane (20 mL) was stirred at room temperature for 12 hours. The mixture was then concentrated under reduced pressure, treated with saturated aqueous NaHCO$_3$ to pH 8 and extracted with ethyl acetate. The acetate layer was washed with brine, dried with MgSO$_4$, filtered, and concentrated under reduced pressure. The residue was purified by silica gel chromatography and eluted with 2:1 CH$_2$Cl$_2$-EtOAc to afford 2 g of (E)-isomer and 260 mg of (Z)-isomer of the title compound. Data for (E)-isomer: $^1$H NMR (300 MHz, DMSO-d$_6$) δ ppm 1.48 (s, 9H), 2.46 (s, 3H), 7.21 (d, J=7.5 Hz, 1H), 7.55-7.79 (m, 2H), 7.98 (s, 1H), 11.08 (s, 1H); MS (ESI$^+$) m/z 236 (M+H)$^+$. Data for (Z)-isomer: $^1$H NMR (300 MHz, DMSO-d$_6$) δ ppm 1.48 (s, 9H), 2.55 (s, 3H), 7.32-7.44 (m, 2H), 7.49 (d, J=7.9 Hz, 1H), 7.93 (t, J=7.7 Hz, 1H), 13.97 (s, 1H); MS (ESI$^+$) m/z 236 (M+H)$^+$.

Example 205B tert-butyl (2E)-1-[2-({[(2Z)-3-butyl-5-tert-butyl-1,3,4-thiadiazol-2(3H)-ylidene]amino}carbonyl)-4-(trifluoromethyl)phenyl]-2-[(6-methylpyridin-2-yl)methylene]hydrazinecarboxylate To a mixture of (E)-isomer of Example 205A (196 mg, 0.83 mmol) and Example 7B (280 mg, 0.69 mmol) in anhydrous DMSO (15 mL) was added solid potassium tert-butoxide (90 mg, 0.8 mmol) and the resulting mixture was stirred at 90° C. for 14 hours. Water was added and the mixture was extracted with EtOAc. The ethyl acetate layer was washed with water, brine, dried with anhydrous MgSO$_4$, filtered, and concentrated under reduced pressure. The residue was purified by silica gel chromatography and eluted with 1:1 hexanes-Et$_2$O to afford 140 mg of the title compound. $^1$H NMR (300 MHz, DMSO-d$_6$) δ ppm 0.65 (t, J=7.3 Hz, 3H), 0.97-1.10 (m, 2H), 1.22-1.28 (m, 9H), 1.34 (s, 9H), 1.47-1.58 (m, 2H), 2.38 (s, 3H), 4.19-4.35 (m, 2H), 7.13 (s, 1H), 7.23 (dd, J=6.3, 2.4 Hz, 1H), 7.63 (d, J=8.3 Hz, 1H), 7.74-7.82 (m, 2H), 8.09 (dd, J=8.3, 2.4 Hz, 1H), 8.44 (d, J=2.0 Hz, 1H). MS (ESI$^+$) m/z 619 (M+H)$^+$.

Example 206

N-[(2Z)-3-butyl-5-tert-butyl-1,3,4-thiadiazol-2(3H)-ylidene]-2-{(2E)-2-[(6-methylpyridin-2-yl)methylene]hydrazino}-5-(trifluoromethyl)benzamide A solution of Example 205B (120 mg, 0.19 mmol) in CH$_2$Cl$_2$ (5 mL) was treated with trifluoroacetic acid (0.15 mL, 1.9 mmol) at room temperature for 3 hours. The mixture was then concentrated under reduced pressure. The residue was treated with saturated aqueous NaHCO$_3$ and extracted with EtOAc. The ethyl acetate layer was washed with water, brine, dried with anhydrous MgSO$_4$, filtered, and concentrated under reduced pressure. The residue was purified by silica gel chromatography and eluted with 1:1 hexanes-Et$_2$O to afford 60 mg of the title compound. $^1$H NMR (300 MHz, DMSO-d$_6$) δ ppm 0.95 (t, J=7.5 Hz, 3H), 1.29-1.48 (m, 11H), 1.77-1.96 (m, 2H), 2.43-2.56 (m, 3H), 4.46 (t, J=7.3 Hz, 2H), 7.23 (d, J=6.8 Hz, 1H), 7.65-8.00 (m, 4H), 8.15 (s, 1H), 8.59 (d, J=1.7 Hz, 1H), 12.29 (s, 1H); MS (ESI$^+$) m/z 519 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:

1. A compound according to formula (I), or a pharmaceutically acceptable salt thereof

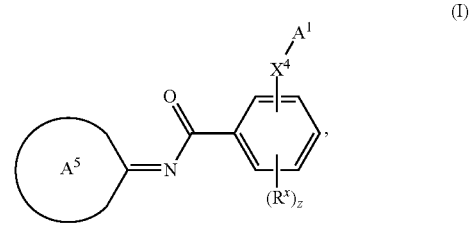

wherein
X$^4$ is O, S, S(O), S(O)$_2$, or N(R$^{bx}$); wherein R$^{bX}$ is hydrogen, alkyl, haloalkyl, alkoxyalkyl, —C(O)O(alkyl), monocyclic cycloalkyl, —(CR$^{1c}$R$^{1d}$)$_{q3}$-(monocyclic cycloalkyl), or haloalkoxyalkyl; and
A$^1$ is —N(R$^b$)C(O)R$^a$, —N(R$^b$)C(O)OR$^d$, —N(R$^b$)C(O)N(R$^b$)(R$^c$), —N(R$^b$)(R$^c$), or —N═C(R$^p$)(R$^q$); or
X$^4$ and A$^1$ together is N═N(R$^{cx}$);
each occurrence of R$^a$ and R$^c$, are each independently hydrogen, alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;
R$^b$, at each occurrence, is each independently hydrogen, alkyl, haloalkyl, alkoxyalkyl, monocyclic cycloalkyl, —(CR$^{1c}$R$^{1d}$)$_{q3}$-(monocyclic cycloalkyl), or haloalkoxyalkyl;
R$^d$, at each occurrence, is each independently alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;
R$^{cx}$ is alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;
R$^p$ is hydrogen, alkyl, haloalkyl, —(CR$^{1a}$R$^{1b}$)$_{q3}$-A$^3$, —C(O)OR$^d$, —C(O)R$^d$, G$^{1d}$, or —(CR$^{1a}$R$^{1b}$)$_{q3}$-G$^{1d}$;
R$^q$ is hydrogen, alkyl, haloalkyl, —N(R$^b$)(R$^c$), —(CR$^{1a}$R$^{1b}$)$_{q3}$-A$^3$, G$^{1d}$, or —(CR$^{1a}$R$^{1b}$)$_{q3}$-G$^{1d}$; or
R$^p$ and R$^q$, together with the carbon atom to which they are attached, form a monocyclic 5-, 6-, 7-, or 8-membered ring, optionally substituted with 1, 2, 3, 4, or 5 substituents independently selected from the group consisting of oxo, alkyl, haloalkyl, and halogen;
A$^3$ is C(O)R$^h$, —S(O)$_2$R$^e$, —C(O)N(R$^h$)$_2$, —C(S)N(R$^h$)$_2$, —S(O)$_2$N(R$^h$)$_2$, —C(═NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N(R$^h$)$_2$, —CN, —OR$^h$, or —N(R$^h$)$_2$;
A$^5$ represents formula (a),

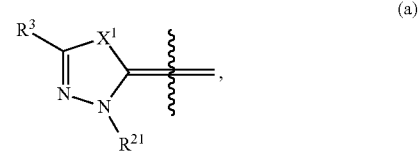

G$^{1d}$, at each occurrence, is independently a monocyclic heterocycle, a monocyclic heteroaryl, a phenyl, a monocyclic cycloalkyl, or a monocyclic cycloalkenyl;

wherein $G^{1d}$ is optionally substituted with 1, 2, 3, or 4 substituents independently selected from the group consisting of —N(R$^h$)$_2$, —CN, oxo, alkyl, haloalkyl, alkoxy, haloalkoxy, halogen, and OH;

R$^e$, at each occurrence, is independently C$_1$-C$_4$ alkyl, C$_1$-C$_4$ haloalkyl, monocyclic cycloalkyl, monocyclic heterocycle, or —(CR$^{1c}$R$^{1d}$)$_{q3}$-(monocyclic cycloalkyl);

R$^h$, at each occurrence, is independently hydrogen, C$_1$-C$_4$ alkyl, C$_1$-C$_4$ haloalkyl, monocyclic cycloalkyl, or —(CR$^{1c}$R$^{1d}$)$_{q3}$-(monocyclic cycloalkyl);

R$^{21}$ is alkyl, alkenyl, alkynyl, haloalkyl, —(CR$^{2a}$R$^{2b}$)$_{q4}$—OH, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q4}$—O-G$^{2a}$, —(CR$^{2a}$R$^{2b}$)$_{q4}$—O—(CR$^{2c}$R$^{2d}$)$_{q3}$-G$^{2a}$, —(CR$^{2a}$R$^{2b}$)$_{q5}$—C(O)—R$^a$, —(CR$^{2a}$R$^{2b}$)$_{q5}$—C(=N—OR$^f$)R$^a$, —(CR$^{2a}$R$^{2b}$)$_{q5}$—SO$_2$—R$^d$, —(CR$^{2a}$R$^{2b}$)$_{q5}$-G$^{2b}$, —(CR$^{2a}$R$^{2b}$)$_{q5}$—C(O)N(R$^b$)(R$^c$), or —(CR$^{2a}$R$^{2b}$)$_{q5}$—CN;

R$^f$, at each occurrence, is independently hydrogen, C$_1$-C$_4$ alkyl, C$_1$-C$_4$ haloalkyl, —(CR$^{1c}$R$^{1d}$)$_{q3}$—OR$^h$, monocyclic heterocycle, monocyclic cycloalkyl, or —(CR$^{1c}$R$^{1d}$)-(monocyclic cycloalkyl);

each occurrence of G$^{2a}$ is independently cycloalkyl, heterocycle, aryl, or heteroaryl;

G$^{2b}$ is a monocyclic ring selected from the group consisting of cycloalkyl, cycloalkenyl, thienyl, phenyl, furanyl, oxazolyl, isoxazolyl, oxadiazolyl, and heterocycle; wherein the heterocycle contains zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; each ring G$^{2b}$ is optionally fused with a monocyclic ring selected from the group consisting of benzo, cycloalkyl, cycloalkenyl, heterocycle and heteroaryl;

each occurrence of G$^{2a}$ and G$^{2b}$ are each independently unsubstituted or substituted with 1, 2, 3, 4, 5, or 6 substituents independently selected from the group consisting of oxo, alkyl, halogen, —OH, alkoxy, haloalkoxy, and haloalkyl;

X$^1$ is S;

R$^3$ is G$^3$, hydrogen, alkyl, alkenyl, alkynyl, —NO$_2$, —CN, halogen, —OR$^h$, —N(R$^h$)$_2$, —C(O)R$^h$, —C(O)O(R$^h$), haloalkyl, —(CR$^{3a}$R$^{3b}$)$_{q6}$—OR$^h$, —(CR$^{3a}$R$^{3b}$)$_{q6}$—N(R$^h$)$_2$, —(CR$^{3a}$R$^{3b}$)$_{q6}$—C(O)R$^h$, or —(CR$^{3a}$R$^{3b}$)$_{q6}$—C(O)O(R$^h$);

G$^3$, at each occurrence, is independently cycloalkyl, cycloalkenyl, aryl, heterocycle, or heteroaryl, wherein each G$^3$ is independently unsubstituted or substituted with 1, 2, 3 or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, =N—CN, =N—OR$^h$, —CN, oxo, —OR$^h$, —OC(O)R$^h$, —OC(O)N(R$^h$)$_2$, —S(O)$_2$R$^e$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^h$, —N(R$^h$)S(O)$_2$R$^e$, —N(R$^h$)C(O)O(R$^e$), and —N(R$^h$)C(O)N(R$^h$)$_2$;

R$^{1a}$, at each occurrence, is independently hydrogen, halogen, C$_1$-C$_4$ alkyl, or C$_1$-C$_4$ haloalkyl;

R$^{1b}$, at each occurrence, is independently hydrogen, halogen, C$_1$-C$_4$ alkyl, C$_2$-C$_4$ alkenyl, C$_1$-C$_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$;

R$^{1c}$, R$^{1d}$, R$^{2a}$, R$^{2b}$, R$^{2c}$, R$^{2d}$, R$^{3a}$ and R$^{3b}$, at each occurrence, are each independently hydrogen, halogen, C$_1$-C$_4$ alkyl, or C$_1$-C$_4$ haloalkyl;

R$^x$ at each occurrence, is each independently G$^{1d}$, C$_1$-C$_4$ alkyl, C$_2$-C$_4$ alkenyl, C$_2$-C$_4$ alkynyl, halogen, C$_1$-C$_4$ haloalkyl, NO$_2$, —CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, or —(CR$^{1c}$R$^{1d}$)$_{q3}$—CN;

q4, at each occurrence, is independently 2, 3, 4, or 5;

q3, at each occurrence, is 1, 2 or, 3;

q5 and q6, at each occurrence, are each independently 1, 2, 3, 4, 5, or 6;

z is 0, 1, 2, 3, or 4; and the monocyclic cycloalkyl and the monocyclic heterocycle, as a substituent or as part of a substituent, of R$^{bx}$, R$^b$, R$^e$, R$^f$, and R$^h$, are each independently unsubstituted or substituted with 1, 2, 3, or 4 substituents independently selected from the group consisting of oxo, C$_1$-C$_4$ alkyl, halogen, OH, C$_1$-C$_4$ alkoxy, C$_1$-C$_4$ haloalkoxy, and C$_1$-C$_4$ haloalkyl;

with the proviso that when

X$^4$ is S(O)$_2$, and

R$^{21}$ is alkyl, alkynyl, haloalkyl, —(CR$^{2a}$R$^{2b}$)$_{q4}$—O-alkyl, —(CR$^{2a}$R$^{2b}$)$_{q4}$—OH, —(CR$^{2a}$R$^{2b}$)$_{q5}$—C(O)-(monocyclic heterocycle), —(CR$^{2a}$R$^{2b}$)$_{q5}$—C(O)N(R$^b$)(R$^c$), —(CR$^{2a}$R$^{2b}$)$_{q5}$—CN, or —(CR$^{2a}$R$^{2b}$)$_{q5}$-G$^{2b}$ wherein G$^{2b}$ is monocyclic cycloalkyl or phenyl;

then A$^1$ is not N(H)$_2$, N(H)(alkyl), or N(alkyl)$_2$.

2. The compound according to claim 1 or a pharmaceutically acceptable salt thereof, wherein A$^1$ is —N(R$^b$)(R$^c$).

3. The compound according to claim 1 or a pharmaceutically acceptable salt thereof, wherein X$^4$ is O or N(R$^{bx}$); and R$^{bx}$ is hydrogen, alkyl, or —C(O)O(alkyl).

4. The compound according to claim 3 or a pharmaceutically acceptable salt thereof, wherein R$^{21}$ is alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

5. The compound according to claim 4 or a pharmaceutically acceptable salt thereof, wherein A$^1$ is —N(R$^b$)(R$^c$).

6. The compound according to claim 4 or a pharmaceutically acceptable salt thereof, wherein A$^1$ is —N(R$^b$)C(O)R$^a$, —N(R$^b$)C(O)OR$^d$, —N(R$^b$)C(O)N(R$^b$)(R$^c$), or —N=C(R$^p$)(R$^q$).

7. The compound according to claim 1 or a pharmaceutically acceptable salt thereof, wherein X$^4$ and A$^1$ together is N=N(R$^{cx}$); and R$^{21}$ is alkyl, alkenyl, alkynyl, haloalkyl, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q5}$-G$^{2b}$, or —(CR$^{2a}$R$^{2b}$)$_{q5}$—CN.

8. The compound according to claim 1 or a pharmaceutically acceptable salt thereof, selected from the group consisting of 2-[(tert-butylamino)oxy]-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-{(2Z)-2-[(6-methylpyridin-2-yl)methylene]hydrazino}-5-(trifluoromethyl)benzamide;

tert-butyl 2-({[(2Z)-3-butyl-5-tert-butyl-1,3,4-thiadiazol-2(3H)-ylidene]amino}carbonyl)-4-(trifluoromethyl)phenoxycarbamate;

N-[(2Z)-3-butyl-5-tert-butyl-1,3,4-thiadiazol-2(3H)-ylidene]-2-[2-(4-fluorobenzoyl)hydrazino]-5-(trifluoromethyl)benzamide;

N-[(2Z)-3-butyl-5-tert-butyl-1,3,4-thiadiazol-2(3H)-ylidene]-2-[(isopropylamino)oxy]-5-(trifluoromethyl)benzamide;

2-[(tert-butylamino)oxy]-N-[(2Z)-3-butyl-5-(1-methylcyclopropyl)-1,3,4-thiadiazol-2(3H)-ylidene]-5-(trifluoromethyl)benzamide;

2-[(tert-butylamino)oxy]-N-[(2Z)-5-tert-butyl-3-(tetrahydro-2H-pyran-2-ylmethyl)-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[(E)-tert-butyldiazenyl]-5-(trifluoromethyl)benzamide;

N-[(2Z)-3-butyl-5-tert-butyl-1,3,4-thiadiazol-2(3H)-ylidene]-5-(trifluoromethyl)-2-({[(1E)-1,2,2-trimethylpropylidene]amino}oxy)benzamide;

2-[(tert-butylamino)oxy]-N-[(2Z)-5-tert-butyl-3-(3-cyanopropyl)-1,3,4-thiadiazol-2(3H)-ylidene]-5-(trifluoromethyl)benzamide;

2-[(tert-butylamino)oxy]-N-[(2Z)-5-tert-butyl-3-isobutyl-1,3,4-thiadiazol-2(3H)-ylidene]-5-(trifluoromethyl)benzamide;

2-[(tert-butylamino)oxy]-N-[(2Z)-5-tert-butyl-3-[(2R)-tetrahydrofuran-2-ylmethyl]-1,3,4-thiadiazol-2(3H)-ylidene]-5-(trifluoromethyl)benzamide;

2-[(acetylamino)oxy]-N-[(2Z)-3-butyl-5-tert-butyl-1,3,4-thiadiazol-2(3H)-ylidene]-5-(trifluoromethyl)benzamide;

2-[(tert-butylamino)oxy]-N-[(2Z)-5-tert-butyl-3-(2-methoxyethyl)-1,3,4-thiadiazol-2(3H)-ylidene]-5-(trifluoromethyl)benzamide;

2-[(tert-butylamino)oxy]-N-[(2Z)-3-butyl-5-tert-butyl-1,3,4-thiadiazol-2(3H)-ylidene]-5-chlorobenzamide;

2-[(tert-butylamino)oxy]-N-[(2Z)-5-tert-butyl-3-(cyclopropylmethyl)-1,3,4-thiadiazol-2(3H)-ylidene]-5-(trifluoromethyl)benzamide;

2-[(tert-butylamino)oxy]-N-[(2Z)-5-tert-butyl-3-(4,4,4-trifluorobutyl)-1,3,4-thiadiazol-2(3H)-ylidene]-5-(trifluoromethyl)benzamide;

2-[(tert-butylamino)oxy]-N-[(2Z)-5-tert-butyl-3-(cyclobutylmethyl)-1,3,4-thiadiazol-2(3H)-ylidene]-5-(trifluoromethyl)benzamide;

2-({[1-amino-2,2-dimethylpropylidene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-{[(1-methylethylidene)amino]oxy}-5-(trifluoromethyl)benzamide;

N-[(2Z)-3-butyl-5-tert-butyl-1,3,4-thiadiazol-2(3H)-ylidene]-2-{[(2,2-dimethylpropanoyl)amino]oxy}-5-(trifluoromethyl)benzamide;

2-[(tert-butylamino)oxy]-N-[(2Z)-3-butyl-5-tert-butyl-1,3,4-thiadiazol-2(3H)-ylidene]-4-(trifluoromethyl)benzamide;

N-[(2Z)-3-butyl-5-tert-butyl-1,3,4-thiadiazol-2(3H)-ylidene]-2-[(dimethylamino)oxy]-5-(trifluoromethyl)benzamide;

N-[(2Z)-3-butyl-5-tert-butyl-1,3,4-thiadiazol-2(3H)-ylidene]-5-(trifluoromethyl)-2-({[2,2,2-trifluoro-1-methylethylidene]amino}oxy)benzamide;

N-[(2Z)-3-butyl-5-tert-butyl-1,3,4-thiadiazol-2(3H)-ylidene]-2-(2-tert-butylhydrazino)-5-(trifluoromethyl)benzamide;

2-[(tert-butylamino)oxy]-N-[(2Z)-5-tert-butyl-3-(4-fluorobutyl)-1,3,4-thiadiazol-2(3H)-ylidene]-5-(trifluoromethyl)benzamide;

2-({[1-amino-2-methylpropylidene]amino}oxy)-N-[(2Z)-3-butyl-5-tert-butyl-1,3,4-thiadiazol-2(3H)-ylidene]-5-(trifluoromethyl)benzamide;

ethyl amino {[2-({[(2Z)-3-butyl-5-tert-butyl-1,3,4-thiadiazol-2(3H)-ylidene]amino}carbonyl)-4-(trifluoromethyl)phenoxy]imino}acetate;

2-[(tert-butylamino)oxy]-N-[(2Z)-5-tert-butyl-3-(oxetan-2-ylmethyl)-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-({[(1E)-1-methyl-2-oxopropylidene]amino}oxy)-5-(trifluoromethyl)benzamide;

tert-butyl 2-[2-({[(2Z)-3-butyl-5-tert-butyl-1,3,4-thiadiazol-2(3H)-ylidene]amino}carbonyl)-4-(trifluoromethyl)phenyl]hydrazinecarboxylate;

2-({[amino(4-fluorophenyl)methylene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-(2-pyridin-2-ylhydrazino)-5-(trifluoromethyl)benzamide;

tert-butyl 2-[2-({[(2Z)-3-butyl-5-tert-butyl-1,3,4-thiadiazol-2(3H)-ylidene]amino}carbonyl)-4-(trifluoromethyl)phenyl]-1,2-dimethylhydrazinecarboxylate;

2-({[1-amino ethylidene]amino}oxy)-N-[(2Z)-3-butyl-5-tert-butyl-1,3,4-thiadiazol-2(3H)-ylidene]-5-(trifluoromethyl)benzamide;

2-({[1-aminopropylidene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[2-(1-methylethylidene)hydrazino]-5-(trifluoromethyl)benzamide;

2-({[amino(cyclopropyl)methylene]amino}oxy)-N-[(2Z)-3-butyl-5-tert-butyl-1,3,4-thiadiazol-2(3H)-ylidene]-5-(trifluoromethyl)benzamide;

2-{[azepan-2-ylideneamino]oxy}-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[(cyclopentylideneamino)oxy]-5-(trifluoromethyl)benzamide;

N-[(2Z)-3-butyl-5-tert-butyl-1,3,4-thiadiazol-2(3H)-ylidene]-2-(2-isonicotinoylhydrazino)-5-(trifluoromethyl)benzamide;

methyl 2-[2-({[(2Z)-3-butyl-5-tert-butyl-1,3,4-thiadiazol-2(3H)-ylidene]amino}carbonyl)-4-(trifluoromethyl)phenyl]hydrazinecarboxylate;

N-[(2Z)-3-butyl-5-tert-butyl-1,3,4-thiadiazol-2(3H)-ylidene]-2-[2-(2,2-dimethylpropanoyl)hydrazino]-5-(trifluoromethyl)benzamide;

2-({[amino(pyridin-2-yl)methylene]amino}oxy)-N-[(2Z)-3-butyl-5-tert-butyl-1,3,4-thiadiazol-2(3H)-ylidene]-5-(trifluoromethyl)benzamide;

N-[(2Z)-3-butyl-5-tert-butyl-1,3,4-thiadiazol-2(3H)-ylidene]-2-[2-(pyridin-3-ylcarbonyl)hydrazino]-5-(trifluoromethyl)benzamide;

2-[2-({[(2Z)-3-butyl-5-tert-butyl-1,3,4-thiadiazol-2(3H)-ylidene]amino}carbonyl)-4-(trifluoromethyl)phenyl]hydrazinecarboxamide;

2-(2-benzylhydrazino)-N-[(2Z)-3-butyl-5-tert-butyl-1,3,4-thiadiazol-2(3H)-ylidene]-5-(trifluoromethyl)benzamide;

2-({[amino(pyridin-4-yl)methylene]amino}oxy)-N-[(2Z)-3-butyl-5-tert-butyl-1,3,4-thiadiazol-2(3H)-ylidene]-5-(trifluoromethyl)benzamide;

2-({[amino(pyridin-3-yl)methylene]amino}oxy)-N-[(2Z)-3-butyl-5-tert-butyl-1,3,4-thiadiazol-2(3H)-ylidene]-5-(trifluoromethyl)benzamide;

tert-butyl (2E)-1-[2-({[(2Z)-3-butyl-5-tert-butyl-1,3,4-thiadiazol-2(3H)-ylidene]amino}carbonyl)-4-(trifluoromethyl)phenyl]-2-[(6-methylpyridin-2-yl)methylene]hydrazinecarboxylate; and N-[(2Z)-3-butyl-5-tert-butyl-1,3,4-thiadiazol-2(3H)-ylidene]-2-{(2E)-2-[(6-methylpyridin-2-yl)methylene]hydrazino}-5-(trifluoromethyl)benzamide.

9. A pharmaceutical composition comprising a therapeutically effective amount of a compound of formula (I) according to claim 1 or a pharmaceutically acceptable salt thereof, in combination with a pharmaceutically acceptable carrier.

\* \* \* \* \*